US012509497B2

(12) United States Patent
Diener et al.

(10) Patent No.: US 12,509,497 B2
(45) Date of Patent: Dec. 30, 2025

(54) RELAXIN-2 FUSION PROTEIN ANALOGS AND METHODS OF USING SAME

(71) Applicant: TECTONIC OPERATING COMPANY, INC., Watertown, MA (US)

(72) Inventors: John Diener, Watertown, MA (US); Andrew Kruse, Watertown, MA (US); Franz Gruswitz, Watertown, MA (US)

(73) Assignee: Tectonic Operating Company, Inc., Watertown, MA (US)

( * ) Notice: Subject to any disclaimer, the term of this patent is extended or adjusted under 35 U.S.C. 154(b) by 164 days.

(21) Appl. No.: 18/054,596

(22) Filed: Nov. 11, 2022

(65) Prior Publication Data

US 2023/0340058 A1 Oct. 26, 2023

Related U.S. Application Data

(60) Provisional application No. 63/263,917, filed on Nov. 11, 2021.

(51) Int. Cl.
*C07K 14/64* (2006.01)
*A61P 43/00* (2006.01)
*C12N 15/63* (2006.01)

(52) U.S. Cl.
CPC .............. *C07K 14/64* (2013.01); *A61P 43/00* (2018.01); *C12N 15/63* (2013.01); *C07K 2319/30* (2013.01)

(58) Field of Classification Search
None
See application file for complete search history.

(56) References Cited

U.S. PATENT DOCUMENTS 8,389,475 B2 3/2013 Park et al.
8,445,635 B2 5/2013 Medin et al.
8,735,539 B2 5/2014 Kraynov et al.
9,056,922 B2 6/2015 Bathgate et al.
9,381,231 B2 7/2016 Conrad
9,382,305 B2 7/2016 Wilmen et al.
9,434,780 B2 9/2016 Forssmann et al.
9,561,261 B2 2/2017 Garvin et al.
9,907,833 B2 3/2018 Conrad
10,081,662 B2 9/2018 Bathgate et al.
10,226,512 B2 3/2019 Dschietzig
10,253,083 B2 4/2019 Kraynov et al.
10,266,578 B2 4/2019 Dubowchik et al.
10,286,078 B2 5/2019 Shen et al.
10,842,851 B2 11/2020 Dschietzig
10,961,295 B2 3/2021 Duclos et al.
10,988,523 B2 4/2021 Brasseur et al.
10,988,524 B2 4/2021 Illiano et al.
11,192,931 B2 12/2021 Hao et al.
11,344,607 B2 5/2022 Garvin et al.
11,439,685 B2 9/2022 Grinstaff et al.
11,723,957 B2 8/2023 Nazarian et al.
12,264,188 B2 * 4/2025 Diener ...................... A61P 9/00
2011/0243942 A1 10/2011 Wang
2011/0245469 A1 10/2011 Wang
2014/0148390 A1 5/2014 Haupts et al.
2015/0299294 A1 10/2015 Dooper et al.
2016/0244482 A1 8/2016 Elliott
2016/0296632 A1 10/2016 Chipman
2016/0326562 A1 11/2016 Kopetzki et al.
2021/0275642 A1 9/2021 Schwartzman et al.
2021/0380655 A1 12/2021 Grinstaff et al.
2022/0017591 A1 1/2022 Sermadiras et al.
2022/0275042 A1 9/2022 Verdino et al.
2022/0289809 A1 9/2022 Schwartzman et al.
2023/0174610 A1 6/2023 Kruse et al.

FOREIGN PATENT DOCUMENTS

EP 0251615 B1 12/1992
EP 3522911 B1 12/2021
WO 2012031327 A1 3/2012
WO 2013004607 A1 1/2013
WO 2013177529 A1 11/2013
WO 2014040008 A1 3/2014
WO 2015038938 A1 3/2015
WO 2015073727 A1 5/2015
WO 2016144968 A1 9/2016
WO 2017100540 A2 6/2017
WO 2017201340 A2 11/2017
WO 2018023170 A1 2/2018
WO 2018068047 A1 4/2018
WO 2018138170 A1 8/2018
WO WO-2018148419 A1 * 8/2018 ............. A61K 38/18

(Continued)

OTHER PUBLICATIONS

Chen et al.. "The pharmacokinetics of recombinant human relaxin in nonpregnant women after intravenous, intravaginal, and intracervical administration," Pharm Res. 1993 10(6): 834-8 doi: 10.1023/a:1018901009062.
Bathgate et al., "The relaxin receptor as a therapeutic target—perspectives from evolution and drug targeting", Pharmacology & Therapeutics, Jul. 2018, 187:114-132.
Bogzil et al., "Relaxin-induced changes in renal sodium excretion in the anesthetized male rat", Am J Physiol Regul Integr Comp Physiol., Jan. 2005, 288:R322-R328.
Choi et al., "Interpretation of Non-Clinical Data for Prediction of Human Pharmacokinetic Parameters: In Vitro-In Vivo Extrapolation and Allometric Scaling", Pharmaceutics, 2019, 11(4):168, pp. 1-33.
Wilhelmi et al., "Serelaxin alleviates cardiac fibrosis through inhibiting endothelial-to-mesenchymal transition via RXFP1", Theranostics, 2020, 10(9):3905-3924.

(Continued)

*Primary Examiner* — Sudhakar Katakam
*Assistant Examiner* — Zachary J Miknis
(74) *Attorney, Agent, or Firm* — COOLEY LLP

(57) ABSTRACT

The present disclosure provides relaxin-2 fusion protein analogs with enhanced in vivo half-life and methods for making the same. Also disclosed herein are methods of treating relaxin-2-associated disorders or diseases using the relaxin-2 fusion protein analogs described herein.

12 Claims, No Drawings

Specification includes a Sequence Listing.

(56) References Cited

FOREIGN PATENT DOCUMENTS

| | | | |
|---|---|---|---|
| WO | 2021094626 | A1 | 5/2021 |
| WO | 2021226439 | A2 | 11/2021 |
| WO | 2021255127 | A1 | 12/2021 |
| WO | 2022037469 | A1 | 2/2022 |
| WO | 2022147897 | A1 | 7/2022 |
| WO | 2023028008 | A2 | 3/2023 |
| WO | 2023041845 | A1 | 3/2023 |
| WO | 2023056044 | A1 | 4/2023 |
| WO | 2023086913 | A2 | 5/2023 |
| WO | 2023111112 | A1 | 6/2023 |
| WO | 2023216981 | A1 | 11/2023 |
| WO | 2024047130 | A1 | 3/2024 |

OTHER PUBLICATIONS

Dschietzig et al., "First Clinical Experience with Intravenous Recombinant Human Relaxin in Compensated Heart Failure", Annals of the New York Academy of Sciences, 2009, 1160:387-392.

Erlandson et al., "Engineering and characterization of a long half-life relaxin receptor RXFP1 agonist" , BioRxiv, Apr. 19, 2022, pp. 1-23.

Hossain et al., "The Minimal Active Structure of Human Relaxin-2", The Journal of Biological Chemistry, Oct. 28, 2011, 286(43): 37555-37565.

Humbert et al., "2022 ESC/ERS Guidelines for the diagnosis and treatment of pulmonary hypertension", European Heart Journal, 2022, 43(38):3618-3731.

Ibe et al. "Combined pre- and post-capillary pulmonary hypertension: The clinical implications for patients with heart failure", PLOS One, 2021, 16(3):e0247987, pp. 1-14.

Yang et al., "ML290, an Allosteric Relaxin-RXFP1 Agonist, Attenuates Experimental Pulmonary Hypertension", Am J Respir Crit Care Med., 2018, 197:A4626.

Leo et al., "Vascular actions of relaxin: nitric oxide and beyond", British Journal of Pharmacology, 2017, 174(10):1002-1014.

Lteif et al., "Therapeutic Challenges and Emerging Treatment Targets for Pulmonary Hypertension in Left Heart Disease", Journal of the American Heart Association, Jun. 1, 2021, 10(11):e020633, pp. 1-19.

Mandras et al., "Pulmonary Hypertension: A Brief Guide for Clinicians", Mayo Clin Proc., Sep. 2020, 95(9):1978-1988.

Martin et al., "Relaxin Inhibits Ventricular Arrhythmia and Asystole in Rats With Pulmonary Arterial Hypertension", Frontiers in Cardiovascular Medicine, Jul. 2021, 8:668222, pp. 1-11.

Metra et al., "Effects of Serelaxin in Patients with Acute Heart Failure", N Engl J Med., Aug. 22, 2019, 381(8):716-726.

Moore et al., "Diverse Regulation of Cardiac Expression of Relaxin Receptor by alpha1- and beta1- Adrenoceptors", Cardiovasc Drugs Ther., May 23, 2014, 28(3):221-228.

Yung et al. "ML290, an Allosteric Agonist of RXFP1, Attenuates Experimental Pulmonary Hypertension", Circulation, 2018, 138(suppl1):Abstract 16555.

Ponikowski et al., "A randomized, double-blind, placebo-controlled, multicentre study to assess haemodynamic effects of serelaxin in patients with acute heart failure", European Heart Journal , 2014, 35(7):431-441.

Samuel et al., "The Relaxin Gene-Knockout Mouse: A Model of Progressive Fibrosis", Ann N Y Acad Sci., 2005, 1041(1):173-181.

Schiffner et al., "Effects of human relaxin-2 (serelaxin) on hypoxic pulmonary vasoconstriction during acute hypoxia in a sheep model", Hypoxia, 2018, 6:11-22.

Snowdon et al., "Serelaxin as a potential treatment for renal dysfunction in cirrhosis: Preclinical evaluation and results of a randomized phase 2 trial", PLoS Med., 2017, 14(2):e1002248, pp. 1-29.

Teerlink et al., "Effects of serelaxin in patients admitted for acute heart failure: A meta-analysis", European Journal of Heart Failure, 2020, 22(2):315-329.

Teerlink et al., "Serelaxin, recombinant human relaxin-2, for treatment of acute heart failure (RELAX-AHF): A randomised, placebo-controlled trial", Lancet, Jan. 5, 2013, 381(9860):29-39.

Thenappan, "Pulmonary Hypertension Due to Left Heart Disease-Combine or Not Combined? DPG In or Out? A Practical Approach to the Patient With Suspected Left Heart Disease", Advances in Pulmonary Hypertension, 2019, 18(3):87-91.

Tozzi et al., "Recombinant human relaxin reduces hypoxic pulmonary hypertension in the rat", Pulmonary Pharmacology & Therapeutics, 2005, 18(5):346-353.

UniProt Accession No. Q163I7, "Hypothetical protein", National Center for Biotechnology Information, Oct. 31, 2006, 1 page.

Vachiery et al., "Pulmonary hypertension due to left heart disease", Eur Respir J., 2019, 53(1):1801897, pp. 1-12.

Vasilenko et al., "Growth-Promoting Effects of Relaxin and Related Compositional Changes in the Uterus, Cervix, and Vagina of the Rat", Endocrinology, 1987, 120(4):1370-1376.

Vasilenko et al., "Uterine Growth-Promoting Effects of Relaxin: A Morphometric and Histological Analysis", Biology of Reproduction, 1986, 35(4):987-995.

"Chain B, Relaxin B Chain", Haugaard-Kedstrom et al., GenBank Accession No. 2MV1_B. Dec. 1, 2020: <https://www.ncbi.nlm.nih.gov/protein/753536198/>.

"Relaxin precursor, partial [Gorilla gorilla]", Evans et al., GenBank Accession No. CAA81742.1. Jul. 26, 2016.: <https://www.ncbi.nlm.nih.gov/protein/CAA81742.1/>.

"Chain A, IG GAMMA-1 Chain C Region", Silva-Martin et al., GenBank Accession No. 4CDH_A. Dec. 1, 2020.: <https://www.ncbi.nlm.nih.gov/protein/4CDH_A>.

"Immunoglobulin heavy chain constant region G1m17,1,1422, partial [Homo sapiens]", Goetze et al., GenBank Accession No. AEO21920.1. Jul. 25, 2016: <https://www.ncbi.nlm.nih.gov/protein/AEO21920.1>.

PCT International Search Report and Written Opinion from PCT/US2022/079681, dated May 3, 2023.

Ahmad et al., "Heart Failure with Preserved Ejection Fraction: Many Emperors with Many Clothes," JACC Heart Failure, 2020;8(3):185-187.

Al-Omary et al., "Pulmonary Hypertension Due to Left Heart Disease: Diagnosis, Pathophysiology, and Therapy," Hypertension, 2020;75(6):1397-1408.

Bani et al., "Relaxin activates the L-arginine-nitric oxide pathway in vascular smooth muscle cells in culture," Hypertension, 1998;(6):1240-1247.

Barilli et al., "Structural and Hemodynamic Changes of the Right Ventricle in PH-HFpEF," Int J Mol Sci, 2022;23(9):4554:1-12.

Bartsch et al., "Phosphodiesterase 4 Inhibition Synergizes with Relaxin Signaling to Promote Decidualization of Human Endometrial Stromal Cells," The Journal of Clinical Endocrinology & Metabolism, 2004;89(1):324-334.

Beck, "RELAX-AHF-2 Results on Serelaxin in Acute Heart Failure Published," Medscape, Aug. 21, 2019 (retrieved Mar. 3, 2023);1-2.

Belyavskiy et al., "Phosphodiesterase 5 inhibitor sildenafil in patients with heart failure with preserved ejection fraction and combined pre- and postcapillary pulmonary hypertension: a randomized open-label pilot study," BMC Cardiovasc Disord, 2020;20(1):408, pp. 1-15.

Bumbaca et al., "Physiochemical and biochemical factors influencing the pharmacokinetics of antibody therapeutics," AAPS J, 2012;14(3):554-558.

Committee for Medicinal Products for Human Use (CHMP), "Reasanz: European Public Assessment Report," European Medicines Agency, EMA/303748/2014, 2014;1-112.

Conrad and Shroff, "Effects of relaxin on arterial dilation, remodeling, and mechanical properties," Curr Hypertens Rep, 2011;13(6):409-420.

Dachs et al., "Riociguat in Pulmonary Hypertension and Heart Failure with Preserved Ejection Fraction: the haemoDYNAMIC trial," European Heart Journal, 2022;43:3402-3413.

Dahlke et al., "Safety and tolerability of serelaxin, a recombinant human relaxin-2 in development for the treatment of acute heart failure, in healthy Japanese volunteers and a comparison of

(56) References Cited

OTHER PUBLICATIONS pharmacokinetics and pharmacodynamics in healthy Japanese and Caucasian populations," The Journal of Clinical Pharmacology, 2014;55(4):415-422.
Del Buono et al., "Primary and Secondary Diastolic Dysfunction in Heart Failure with Preserved Ejection Fraction," The American Journal of Cardiology, 2018;00:1-10.
Delcroix et al., "Long-Term Outcome of Patients With Chronic Thromboembolic Pulmonary Hypertension: Results From an International Prospective Registry," Circulation, 2016;133(9):859- 871.
Dschietzig and Salama, "Relaxin-2 for heart failure with preserved ejection fraction: a comment on the termination of a phase-II trial investigating the relaxin-2 analogue, LY3540378," Global Cardiology, 2024;4:1-3.
Dschietzig et al., "Relaxin, a pregnancy hormone, is a functional endothelin-1 antagonist: attenuation of endothelin-1-mediated vasoconstriction by stimulation of endothelin type-B receptor expression via ERK-1/2 and nuclear factor-kappaB," Circ Res, 2003;92(1):32-40.
Duarte et al., "Endothelial nitric oxide synthase genotype is associated with pulmonary hypertension severity in left heart failure patients," Pulm Circ, 2018;8(2):2045894018773049:1-8.
Erlandson et al., "The relaxin receptor RXFP1 signals through a mechanism of autoinhibition," bioRxiv, Jan. 2022;1-36.
Failli et al., "Relaxin up-regulates inducible nitric oxide synthase expression and nitric oxide generation in rat coronary endothelial cells," FASEB J, 2002;16(2):252-254.
Galiè et al., "2015 ESC/ERS Guidelines for the diagnosis and treatment of pulmonary hypertension: The Joint Task Force for the Diagnosis and Treatment of Pulmonary Hypertension of the European Society of Cardiology (ESC) and the European Respiratory Society (ERS): Endorsed by: Association for European Paediatric and Congenital Cardiology (AEPC), International Society for Heart and Lung Transplantation (ISHLT)," Eur Heart J, 2016;37(1):67-119.
Garcia-Morales et al., "The CAMP effectors PKA and Epac activate endothelial NO synthase through PI3K/Akt pathway in human endothelial cells," Biochemical Pharmacology, 2017;145:94-101.
Ghofrani et al., "Riociguat for the treatment of chronic thromboembolic pulmonary hypertension," N Engl J Med, 2013;369(4):319-29.
Guazzi et al., "Pulmonary Hypertension in Heart Failure With Preserved Ejection Fraction a Target of Phosphodiesterase-5 Inhibition in a 1-Year Study," Circulation, 2011;124:164-174.
Heeg et al., "The antifibrotic effects of relaxin in human renal fibroblasts are mediated in part by inhibition of the Smad2 pathway," Kidney Int, 2005;68(1):96-109.
Hisaw, "Experimental relaxation of the pubic ligament of the guinea pig," Proceedings of the Society for Experimental Biology and Medicine, 1926;23(8):661-663.
Hoeper et al., "Pulmonary hypertension in heart failure with preserved ejection fraction: a plea for proper phenotyping and further research," Eur Heart J, 2017;38(38):2869-2873.
Hsu and Tedford, "Will we be singing a different tune on combined post- and pre-capillary pulmonary hypertension?," Eur Respir J, 2018;51:1702589:1-3.
Huang et al., "Activation of Relaxin Family Receptor 1 from Different Mammalian Species by Relaxin Peptide and small-molecule agonist ML290," Frontiers in Endocrinology, 2015;6(128)1-12.
Humbert et al., "Sotatercept for the Treatment of Pulmonary Arterial Hypertension," N Engl J Med, 2021;384(13):1204-1215.
Igawa et al., "Reduced elimination of IgG antibodies by engineering the variable region," Protein Eng Des Sel, 2010;23(5):385-392.
Jang et al., "Pulmonary Hypertension in Heart Failure," Int J Heart Fail, 2021;3(3):147-159.
Jelinic et al., "Peptide hormone relaxin: from bench to bedside," Am J Physiol Regul Integr Comp Physiol, 2018;314(6):R753-R760.
Kamath, "Translational pharmacokinetics and pharmacodynamics of monoclonal antibodies," Drug Discov Today Technol, 2016;21-22:75-83.
Khanna et al., "Recombinant Human Relaxin in the Treatment of Systemic Sclerosis With Diffuse Cutaneous Involvement: A Randomized, Double-Blind, Placebo-Controlled Trial," Arthritis & Rheumatism, 2009;60(4):1102-1111.
Kim et al., "Biased Relaxin-RXFP1 Agonist ML290 Attenuates the Development of Pulmonary Hypertension," Poster session presented at: Dartmouth Geisel School of Medicine, Feb. 1, 2022, Hanover, New Hampshire, USA.
Kraft et al., "Heparin chromatography as an in vitro predictor for antibody clearance rate through pinocytosis," MAbs, 2020;12(1):1683432.
Lang et al., "Chronic Thromboembolic Disease and Chronic Thromboembolic Pulmonary Hypertension," Clin Chest Med, 2021;42(1):81-90.
Lapinskas et al., "Serelaxin Improves Regional Myocardial Function in Experimental Heart Failure: An In Vivo Cardiac Magnetic Resonance Study," J Am Heart Assoc, 2020;9(3):e013702, 1-12.
Li et al., "Framework selection can influence pharmacokinetics of a humanized therapeutic antibody through differences in molecule charge," MAbs, 2014;6(5):1255-1264.
Liu, "Pharmacokinetics of monoclonal antibodies and Fc-fusion proteins," Protein Cell, 2018;9(1):15-32.
Madani et al., "Pulmonary endarterectomy: recent changes in a single institution's experience of more than 2,700 patients," Ann Thorac Surg, 2012;94(1):97-103, discussion 103.
Maggioni et al., "Efficacy and safety of serelaxin when added to standard of care in patients with acute heart failure: results from a PROBE study, RELAX-AHF-EU," Eur J Heart Fail, 2019;21(3):322-333.
Maron et al., "Cardiopulmonary Hemodynamics in Pulmonary Hypertension and Heart Failure: JACC Review Topic of the Week," J Am Coll Cardiol, 2020;76(22):2671-2681.
Martin et al., "Relaxin reverses inflammatory and immune signals in aged hearts," PLoS One, 2018;13(1):e0190935:1-17.
Mease et al., "Biomarkers for nonclinical infusion reactions in marketed biotherapeutics and considerations for study design," Current Opinion in Toxicology, 2017;4:1-15.
Moles and Grafton, "Pulmonary Hypertension in Heart Failure with Preserved Ejection Fraction," Cardiol Clin, 2022;40(4):533-540.
Nogueira-Ferreira et al., "Exploring the monocrotaline animal model for the study of pulmonary arterial hypertension: A network approach," Pulmonary Pharmacology & Therapeutics, 2015;35:8-16.
Ogawa and Ono, "Modulation of cyclic AMP and autoregulation of renal blood flow, analysed by the use of forskolin and 1 -methyl-3-isobutylxanthine," J. Pharm. Pharmacol, 1988;40:207-209.
Palazzini et al., "Pulmonary hypertension due to left heart disease: analysis of survival according to the haemodynamic classification of the 2015 ESC/ERS guidelines and insights for future changes," Eur J Heart Fail, 2017;20(2):248-255.
Pfeffer et al., "Heart Failure with Preserved Ejection Fraction: In Perspective," Circ. Res, 2019;124:1598-1617.
Pinar et al., "Relaxin Can Mediate Its Anti-Fibrotic Effects by Targeting the Myofibroblast NLRP3 Inflammasome at the Level of Caspase-1," Front Pharmacol, 2020;11:1201:1-14.
Ranchoux et al., "Metabolic Syndrome Exacerbates Pulmonary Hypertension due to Left Heart Disease," Circ Res, 2019;125(4):449-466.
Rodriquez, "International Search Report and Written Opinion for PCT Patent Application No. PCT/US2021/031260," Jan. 13, 2022;1-12.
Rojko et al., "Formation, Clearance, Deposition, Pathogenicity, and Identification of Biopharmaceutical-related Immune Complexes: Review and Case Studies," Toxicol Pathol, 2014;42(4):725-764.
Samuel et al., "Relaxin regulates collagen overproduction associated with experimental progressive renal fibrosis," Ann N Y Acad Sci, 2005;1041:182-184.
Samuel et al., "Relaxin modulates cardiac fibroblast proliferation, differentiation, and collagen production and reverses cardiac fibrosis in vivo," Endocrinology, May 2004;145(9):4125-4133.
Samuel et al., "Serelaxin is a more efficacious antifibrotic than enalapril in an experimental model of heart disease," Hypertension, 2014;64(2):315-322.

(56) References Cited

OTHER PUBLICATIONS

Sato et al., "Evaluating the Efficacy, Safety, and Tolerability of Serelaxin When Added to Standard Therapy in Asian Patients With Acute Heart Failure: Design and Rationale of RELAX-AHF-ASIA Trial," J Card Fail, 2017;23(1):63-71.
Satoh et al., "Metabolic Syndrome Mediates ROS-miR-193b-NFYA-Dependent Downregulation of Soluble Guanylate Cyclase and Contributes to Exercise-Induced Pulmonary Hypertension in Heart Failure With Preserved Ejection Fraction," Circulation, 2021;144(8):615-637.
Shah and Pfeffer, "The many faces of heart failure with preserved ejection fraction," Nat. Rev. Cardiol. Advanced online publication, 2012;1-2.
Shuai et al., "Relaxin-2 improves diastolic function of pressure-overloaded rats via phospholamban by activating Akt," Int J Cardiol, 2016;218:305-311.
Sun et al., "Human Relaxin-2 Fusion Protein Treatment Prevents and Reverses Isoproterenol-Induced Hypertrophy and Fibrosis in Mouse Heart," J Am Heart Assoc, 2019; 8(24):e013465:1-16.
Tectonic Therapeutic, "Corporate Presentation," Apr. 2021; slides 1-10.
Tectonic Therapeutic, "Corporate Presentation," Jan. 2022; slides 1-21.
Tectonic Therapeutic, "Corporate Presentation," Sep. 2022; slides 1-23.
Tectonic Therapeutic, "Transforming the Discovery of GPCR-Targeted Therapies," Nov. 2022; slides 1-29.
Thenappan et al., "Clinical Characteristics of Pulmonary Hypertension in Patients With Heart Failure and Preserved Ejection Fracti," Circ Heart Fail, 2011;4(3):257-265.
Wu et al., "The role of inflammation in a rat model of chronic thromboembolic pulmonary hypertension induced by carrageenan," Ann Transl Med, 2020;8(7):492:1-14.
Yang et al., "Abstract 16068: Biased Relaxin-RXFP1 Agonist ML290 Attenuates the Development of Pulmonary Hypertension," Circulation, 2019;140(Suppl_1):A16068:1 page.
Chen et al., "Fusion Protein Linkers: Property, Design and Functionality," Adv Drug Deliv Rev., 2013;65(10): 1357-1369.
Righetti, "Determination of the isoelectric point of proteins by capillary isoelectric focusing," Journal of Chromatography A, 2004;1037(1-2):491-499 (Abstract only).

* cited by examiner

SEQUENCE LISTING

```
Sequence total quantity: 225
SEQ ID NO: 1            moltype = AA  length = 29
FEATURE                 Location/Qualifiers
source                  1..29
                        mol_type = protein
                        organism = synthetic construct
SEQUENCE: 1
DSWMEEVIKL CGRELVRAQI AICGMSTWS                                29

SEQ ID NO: 2            moltype = AA  length = 24
FEATURE                 Location/Qualifiers
source                  1..24
                        mol_type = protein
                        organism = synthetic construct
SEQUENCE: 2
QLYSALANKC CHVGCTKRSL ARFC                                     24

SEQ ID NO: 3            moltype = AA  length = 27
FEATURE                 Location/Qualifiers
source                  1..27
                        mol_type = protein
                        organism = synthetic construct
VARIANT                 4
                        note = can be methionine, lysine, or glutamine
VARIANT                 25
                        note = can be methionine or lysine
SEQUENCE: 3
DSWXEEVIKL CGRELVRAQI AICGXST                                  27

SEQ ID NO: 4            moltype = AA  length = 25
FEATURE                 Location/Qualifiers
```

```
source                 1..25
                       mol_type = protein
                       organism = synthetic construct
VARIANT                1
                       note = can be arginine or absent (e.g., no amino acid)
VARIANT                3
                       note = can be leucine or aspartic acid
VARIANT                23
                       note = can be arginine, glutamine, or glutamate
SEQUENCE: 4
XQXYSALANK CCHVGCTKRS LAXFC                                          25

SEQ ID NO: 5           moltype = AA  length = 27
FEATURE                Location/Qualifiers
source                 1..27
                       mol_type = protein
                       organism = synthetic construct
SEQUENCE: 5
DSWKEEVIKL CGRELVRAQI AICGKST                                        27

SEQ ID NO: 6           moltype = AA  length = 27
FEATURE                Location/Qualifiers
source                 1..27
                       mol_type = protein
                       organism = synthetic construct
SEQUENCE: 6
DSWMEEVIKL CGRELVRAQI AICGKST                                        27

SEQ ID NO: 7           moltype = AA  length = 27
FEATURE                Location/Qualifiers
source                 1..27
                       mol_type = protein
                       organism = synthetic construct
SEQUENCE: 7
DSWQEEVIKL CGRELVRAQI AICGKST                                        27

SEQ ID NO: 8           moltype = AA  length = 25
FEATURE                Location/Qualifiers
source                 1..25
                       mol_type = protein
                       organism = synthetic construct
SEQUENCE: 8
RQLYSALANK CCHVGCTKRS LARFC                                          25

SEQ ID NO: 9           moltype = AA  length = 24
FEATURE                Location/Qualifiers
source                 1..24
                       mol_type = protein
                       organism = synthetic construct
SEQUENCE: 9
QLYSALANKC CHVGCTKRSL ARFC                                           24

SEQ ID NO: 10          moltype = AA  length = 25
FEATURE                Location/Qualifiers
source                 1..25
                       mol_type = protein
                       organism = synthetic construct
SEQUENCE: 10
RQLYSALANK CCHVGCTKRS LAQFC                                          25

SEQ ID NO: 11          moltype = AA  length = 25
FEATURE                Location/Qualifiers
source                 1..25
                       mol_type = protein
                       organism = synthetic construct
SEQUENCE: 11
RQLYSALANK CCHVGCTKRS LAEFC                                          25

SEQ ID NO: 12          moltype = AA  length = 25
FEATURE                Location/Qualifiers
source                 1..25
                       mol_type = protein
                       organism = synthetic construct
SEQUENCE: 12
RQDYSALANK CCHVGCTKRS LAQFC                                          25

SEQ ID NO: 13          moltype = AA  length = 25
FEATURE                Location/Qualifiers
source                 1..25
```

```
                        mol_type = protein
                        organism = synthetic construct
SEQUENCE: 13
RQDYSALANK CCHVGCTKRS LARFC                                             25

SEQ ID NO: 14           moltype = AA  length = 4
FEATURE                 Location/Qualifiers
source                  1..4
                        mol_type = protein
                        organism = synthetic construct
SEQUENCE: 14
GGGE                                                                    4

SEQ ID NO: 15           moltype = AA  length = 4
FEATURE                 Location/Qualifiers
source                  1..4
                        mol_type = protein
                        organism = synthetic construct
SEQUENCE: 15
GEGE                                                                    4

SEQ ID NO: 16           moltype = AA  length = 4
FEATURE                 Location/Qualifiers
source                  1..4
                        mol_type = protein
                        organism = synthetic construct
SEQUENCE: 16
GGEG                                                                    4

SEQ ID NO: 17           moltype = AA  length = 4
FEATURE                 Location/Qualifiers
source                  1..4
                        mol_type = protein
                        organism = synthetic construct
SEQUENCE: 17
GEGG                                                                    4

SEQ ID NO: 18           moltype = AA  length = 4
FEATURE                 Location/Qualifiers
source                  1..4
                        mol_type = protein
                        organism = synthetic construct
SEQUENCE: 18
GGEE                                                                    4

SEQ ID NO: 19           moltype = AA  length = 13
FEATURE                 Location/Qualifiers
source                  1..13
                        mol_type = protein
                        organism = synthetic construct
SEQUENCE: 19
GGGEGGGEGG GEG                                                          13

SEQ ID NO: 20           moltype = AA  length = 15
FEATURE                 Location/Qualifiers
source                  1..15
                        mol_type = protein
                        organism = synthetic construct
SEQUENCE: 20
GGGEGGGEGG GEGGG                                                        15

SEQ ID NO: 21           moltype = AA  length = 13
FEATURE                 Location/Qualifiers
source                  1..13
                        mol_type = protein
                        organism = synthetic construct
SEQUENCE: 21
GEGGGEEGGG EGG                                                          13

SEQ ID NO: 22           moltype = AA  length = 13
FEATURE                 Location/Qualifiers
source                  1..13
                        mol_type = protein
                        organism = synthetic construct
SEQUENCE: 22
GGGEEGGGEE GGG                                                          13

SEQ ID NO: 23           moltype = AA  length = 13
FEATURE                 Location/Qualifiers
```

```
source                 1..13
                       mol_type = protein
                       organism = synthetic construct
SEQUENCE: 23
GGEGEGGEGE GGS                                                         13

SEQ ID NO: 24          moltype = AA  length = 12
FEATURE                Location/Qualifiers
source                 1..12
                       mol_type = protein
                       organism = synthetic construct
SEQUENCE: 24
GGGEGGGEGG GE                                                          12

SEQ ID NO: 25          moltype = AA  length = 65
FEATURE                Location/Qualifiers
source                 1..65
                       mol_type = protein
                       organism = synthetic construct
SEQUENCE: 25
DSWKEEVIKL CGRELVRAQI AICGKSTGGG EGGGEGGGEG RQLYSALANK CCHVGCTKRS  60
LARFC                                                              65

SEQ ID NO: 26          moltype = AA  length = 66
FEATURE                Location/Qualifiers
source                 1..66
                       mol_type = protein
                       organism = synthetic construct
SEQUENCE: 26
DSWKEEVIKL CGRELVRAQI AICGKSTGGG EGGGEGGGEG GGQLYSALAN KCCHVGCTKR  60
SLARFC                                                             66

SEQ ID NO: 27          moltype = AA  length = 65
FEATURE                Location/Qualifiers
source                 1..65
                       mol_type = protein
                       organism = synthetic construct
SEQUENCE: 27
DSWMEEVIKL CGRELVRAQI AICGKSTGGG EGGGEGGGEG RQLYSALANK CCHVGCTKRS  60
LARFC                                                              65

SEQ ID NO: 28          moltype = AA  length = 65
FEATURE                Location/Qualifiers
source                 1..65
                       mol_type = protein
                       organism = synthetic construct
SEQUENCE: 28
DSWQEEVIKL CGRELVRAQI AICGKSTGGG EGGGEGGGEG RQLYSALANK CCHVGCTKRS  60
LARFC                                                              65

SEQ ID NO: 29          moltype = AA  length = 66
FEATURE                Location/Qualifiers
source                 1..66
                       mol_type = protein
                       organism = synthetic construct
SEQUENCE: 29
DSWMEEVIKL CGRELVRAQI AICGKSTGGG EGGGEGGGEG GGQLYSALAN KCCHVGCTKR  60
SLARFC                                                             66

SEQ ID NO: 30          moltype = AA  length = 66
FEATURE                Location/Qualifiers
source                 1..66
                       mol_type = protein
                       organism = synthetic construct
SEQUENCE: 30
DSWQEEVIKL CGRELVRAQI AICGKSTGGG EGGGEGGGEG GGQLYSALAN KCCHVGCTKR  60
SLARFC                                                             66

SEQ ID NO: 31          moltype = AA  length = 65
FEATURE                Location/Qualifiers
source                 1..65
                       mol_type = protein
                       organism = synthetic construct
SEQUENCE: 31
DSWMEEVIKL CGRELVRAQI AICGKSTGGE GGGEEGGGEG GQLYSALANK CCHVGCTKRS  60
LARFC                                                              65

SEQ ID NO: 32          moltype = AA  length = 65
FEATURE                Location/Qualifiers
```

-continued

```
source                  1..65
                        mol_type = protein
                        organism = synthetic construct
SEQUENCE: 32
DSWQEEVIKL CGRELVRAQI AICGKSTGGE GGGEEGGGEG GQLYSALANK CCHVGCTKRS  60
LARFC                                                              65

SEQ ID NO: 33           moltype = AA  length = 65
FEATURE                 Location/Qualifiers
source                  1..65
                        mol_type = protein
                        organism = synthetic construct
SEQUENCE: 33
DSWMEEVIKL CGRELVRAQI AICGKSTGGE GGGEEGGGEG GQLYSALANK CCHVGCTKRS  60
LARFC                                                              65

SEQ ID NO: 34           moltype = AA  length = 65
FEATURE                 Location/Qualifiers
source                  1..65
                        mol_type = protein
                        organism = synthetic construct
SEQUENCE: 34
DSWQEEVIKL CGRELVRAQI AICGKSTGGE GGGEEGGGEG GQLYSALANK CCHVGCTKRS  60
LARFC                                                              65

SEQ ID NO: 35           moltype = AA  length = 65
FEATURE                 Location/Qualifiers
source                  1..65
                        mol_type = protein
                        organism = synthetic construct
SEQUENCE: 35
DSWQEEVIKL CGRELVRAQI AICGKSTGGG EGGGEGGGEG RQLYSALANK CCHVGCTKRS  60
LAQFC                                                              65

SEQ ID NO: 36           moltype = AA  length = 65
FEATURE                 Location/Qualifiers
source                  1..65
                        mol_type = protein
                        organism = synthetic construct
SEQUENCE: 36
DSWQEEVIKL CGRELVRAQI AICGKSTGGG EGGGEGGGEG RQLYSALANK CCHVGCTKRS  60
LARFC                                                              65

SEQ ID NO: 37           moltype = AA  length = 65
FEATURE                 Location/Qualifiers
source                  1..65
                        mol_type = protein
                        organism = synthetic construct
SEQUENCE: 37
DSWQEEVIKL CGRELVRAQI AICGKSTGGG EGGGEGGGEG RQLYSALANK CCHVGCTKRS  60
LAQFC                                                              65

SEQ ID NO: 38           moltype = AA  length = 65
FEATURE                 Location/Qualifiers
source                  1..65
                        mol_type = protein
                        organism = synthetic construct
SEQUENCE: 38
DSWQEEVIKL CGRELVRAQI AICGKSTGGG EEGGGEEGGG RQLYSALANK CCHVGCTKRS  60
LARFC                                                              65

SEQ ID NO: 39           moltype = AA  length = 65
FEATURE                 Location/Qualifiers
source                  1..65
                        mol_type = protein
                        organism = synthetic construct
SEQUENCE: 39
DSWQEEVIKL CGRELVRAQI AICGKSTGGG EEGGGEEGGG RQLYSALANK CCHVGCTKRS  60
LAQFC                                                              65

SEQ ID NO: 40           moltype = AA  length = 65
FEATURE                 Location/Qualifiers
source                  1..65
                        mol_type = protein
                        organism = synthetic construct
SEQUENCE: 40
DSWQEEVIKL CGRELVRAQI AICGKSTGGG EEGGGEEGGG RQLYSALANK CCHVGCTKRS  60
LARFC                                                              65
```

```
SEQ ID NO: 41          moltype = AA  length = 65
FEATURE                Location/Qualifiers
source                 1..65
                       mol_type = protein
                       organism = synthetic construct
SEQUENCE: 41
DSWQEEVIKL CGRELVRAQI AICGKSTGGG EEGGGEEGGG RQLYSALANK CCHVGCTKRS  60
LAQFC                                                              65

SEQ ID NO: 42          moltype = AA  length = 65
FEATURE                Location/Qualifiers
source                 1..65
                       mol_type = protein
                       organism = synthetic construct
SEQUENCE: 42
DSWQEEVIKL CGRELVRAQI AICGKSTGGG EGGGEGGGEG RQDYSALANK CCHVGCTKRS  60
LAQFC                                                              65

SEQ ID NO: 43          moltype = AA  length = 65
FEATURE                Location/Qualifiers
source                 1..65
                       mol_type = protein
                       organism = synthetic construct
SEQUENCE: 43
DSWQEEVIKL CGRELVRAQI AICGKSTGGG EGGGEGGGEG RQDYSALANK CCHVGCTKRS  60
LARFC                                                              65

SEQ ID NO: 44          moltype = AA  length = 65
FEATURE                Location/Qualifiers
source                 1..65
                       mol_type = protein
                       organism = synthetic construct
SEQUENCE: 44
DSWQEEVIKL CGRELVRAQI AICGKSTGGG EGGGEGGGEG RQDYSALANK CCHVGCTKRS  60
LAQFC                                                              65

SEQ ID NO: 45          moltype = AA  length = 65
FEATURE                Location/Qualifiers
source                 1..65
                       mol_type = protein
                       organism = synthetic construct
SEQUENCE: 45
DSWQEEVIKL CGRELVRAQI AICGKSTGGE GEGGEGEGGS RQLYSALANK CCHVGCTKRS  60
LAQFC                                                              65

SEQ ID NO: 46          moltype = AA  length = 65
FEATURE                Location/Qualifiers
source                 1..65
                       mol_type = protein
                       organism = synthetic construct
SEQUENCE: 46
DSWQEEVIKL CGRELVRAQI AICGKSTGGE GEGGEGEGGS RQLYSALANK CCHVGCTKRS  60
LARFC                                                              65

SEQ ID NO: 47          moltype = AA  length = 65
FEATURE                Location/Qualifiers
source                 1..65
                       mol_type = protein
                       organism = synthetic construct
SEQUENCE: 47
DSWQEEVIKL CGRELVRAQI AICGKSTGGE GEGGEGEGGS RQLYSALANK CCHVGCTKRS  60
LAQFC                                                              65

SEQ ID NO: 48          moltype = AA  length = 65
FEATURE                Location/Qualifiers
source                 1..65
                       mol_type = protein
                       organism = synthetic construct
SEQUENCE: 48
DSWQEEVIKL CGRELVRAQI AICGKSTGGE GEGGEGEGGS RQDYSALANK CCHVGCTKRS  60
LAQFC                                                              65

SEQ ID NO: 49          moltype = AA  length = 227
FEATURE                Location/Qualifiers
source                 1..227
                       mol_type = protein
                       organism = synthetic construct
SEQUENCE: 49
DKTHTCPPCP APELLGGPSV FLFPPKPKDT LMISRTPEVT CVVVDVSHED PEVKFNWYVD  60
```

```
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 50          moltype = AA  length = 227
FEATURE                Location/Qualifiers
source                 1..227
                       mol_type = protein
                       organism = synthetic construct
SEQUENCE: 50
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 51          moltype = AA  length = 227
FEATURE                Location/Qualifiers
source                 1..227
                       mol_type = protein
                       organism = synthetic construct
SEQUENCE: 51
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 52          moltype = AA  length = 227
FEATURE                Location/Qualifiers
source                 1..227
                       mol_type = protein
                       organism = synthetic construct
SEQUENCE: 52
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGK                227

SEQ ID NO: 53          moltype = AA  length = 295
FEATURE                Location/Qualifiers
source                 1..295
                       mol_type = protein
                       organism = synthetic construct
SEQUENCE: 53
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWKEEVIKL  240
CGRELVRAQI AICGKSTGGG EGGGEGGGEG RQLYSALANK CCHVGCTKRS LARFC       295

SEQ ID NO: 54          moltype = AA  length = 296
FEATURE                Location/Qualifiers
source                 1..296
                       mol_type = protein
                       organism = synthetic construct
SEQUENCE: 54
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWKEEVIKL  240
CGRELVRAQI AICGKSTGGG EGGGEGGGEG GGQLYSALAN KCCHVGCTKR SLARFC      296

SEQ ID NO: 55          moltype = AA  length = 295
FEATURE                Location/Qualifiers
source                 1..295
                       mol_type = protein
                       organism = synthetic construct
SEQUENCE: 55
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWMEEVIKL  240
CGRELVRAQI AICGKSTGGG EGGGEGGGEG RQLYSALANK CCHVGCTKRS LARFC       295

SEQ ID NO: 56          moltype = AA  length = 295
FEATURE                Location/Qualifiers
source                 1..295
                       mol_type = protein
                       organism = synthetic construct
SEQUENCE: 56
```

```
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWQEEVIKL  240
CGRELVRAQI AICGKSTGGG EGGGEGGGEG RQLYSALANK CCHVGCTKRS LARFC       295

SEQ ID NO: 57          moltype = AA  length = 295
FEATURE                Location/Qualifiers
source                 1..295
                       mol_type = protein
                       organism = synthetic construct
SEQUENCE: 57
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGG EGGGEGGGEG RQLYSALANK CCHVGCTKRS LARFC       295

SEQ ID NO: 58          moltype = AA  length = 296
FEATURE                Location/Qualifiers
source                 1..296
                       mol_type = protein
                       organism = synthetic construct
SEQUENCE: 58
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWMEEVIKL  240
CGRELVRAQI AICGKSTGGG EGGGEGGGEG GGQLYSALAN KCCHVGCTKR SLARFC      296

SEQ ID NO: 59          moltype = AA  length = 296
FEATURE                Location/Qualifiers
source                 1..296
                       mol_type = protein
                       organism = synthetic construct
SEQUENCE: 59
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWQEEVIKL  240
CGRELVRAQI AICGKSTGGG EGGGEGGGEG GGQLYSALAN KCCHVGCTKR SLARFC      296

SEQ ID NO: 60          moltype = AA  length = 296
FEATURE                Location/Qualifiers
source                 1..296
                       mol_type = protein
                       organism = synthetic construct
SEQUENCE: 60
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGG EGGGEGGGEG GGQLYSALAN KCCHVGCTKR SLARFC      296

SEQ ID NO: 61          moltype = AA  length = 295
FEATURE                Location/Qualifiers
source                 1..295
                       mol_type = protein
                       organism = synthetic construct
SEQUENCE: 61
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWMEEVIKL  240
CGRELVRAQI AICGKSTGGE GGGEEGGGEG GQLYSALANK CCHVGCTKRS LARFC       295

SEQ ID NO: 62          moltype = AA  length = 295
FEATURE                Location/Qualifiers
source                 1..295
                       mol_type = protein
                       organism = synthetic construct
SEQUENCE: 62
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWQEEVIKL  240
CGRELVRAQI AICGKSTGGE GGGEEGGGEG GQLYSALANK CCHVGCTKRS LARFC       295

SEQ ID NO: 63          moltype = AA  length = 294
```

-continued

```
FEATURE                Location/Qualifiers
source                 1..294
                       mol_type = protein
                       organism = synthetic construct
SEQUENCE: 63
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGSD SWMEEVIKLC  240
GRELVRAQIA ICGKSTGGEG GGEEGGGEGG QLYSALANKC CHVGCTKRSL ARFC        294

SEQ ID NO: 64          moltype = AA  length = 294
FEATURE                Location/Qualifiers
source                 1..294
                       mol_type = protein
                       organism = synthetic construct
SEQUENCE: 64
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGSD SWQEEVIKLC  240
GRELVRAQIA ICGKSTGGEG GGEEGGGEGG QLYSALANKC CHVGCTKRSL ARFC        294

SEQ ID NO: 65          moltype = AA  length = 295
FEATURE                Location/Qualifiers
source                 1..295
                       mol_type = protein
                       organism = synthetic construct
SEQUENCE: 65
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWQEEVIKL  240
CGRELVRAQI AICGKSTGGG EGGGEGGGEG RQLYSALANK CCHVGCTKRS LAQFC       295

SEQ ID NO: 66          moltype = AA  length = 295
FEATURE                Location/Qualifiers
source                 1..295
                       mol_type = protein
                       organism = synthetic construct
SEQUENCE: 66
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGG EGGGEGGGEG RQLYSALANK CCHVGCTKRS LAQFC       295

SEQ ID NO: 67          moltype = AA  length = 294
FEATURE                Location/Qualifiers
source                 1..294
                       mol_type = protein
                       organism = synthetic construct
SEQUENCE: 67
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGSD SWQEEVIKLC  240
GRELVRAQIA ICGKSTGGGE GGGEGGGEGR QLYSALANKC CHVGCTKRSL ARFC        294

SEQ ID NO: 68          moltype = AA  length = 294
FEATURE                Location/Qualifiers
source                 1..294
                       mol_type = protein
                       organism = synthetic construct
SEQUENCE: 68
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGGE GGGEGGGEGR QLYSALANKC CHVGCTKRSL ARFC        294

SEQ ID NO: 69          moltype = AA  length = 294
FEATURE                Location/Qualifiers
source                 1..294
                       mol_type = protein
                       organism = synthetic construct
SEQUENCE: 69
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
```

```
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGSD SWQEEVIKLC  240
GRELVRAQIA ICGKSTGGGE GGGEGGGEGR QLYSALANKC CHVGCTKRSL AQFC        294

SEQ ID NO: 70          moltype = AA  length = 294
FEATURE                Location/Qualifiers
source                 1..294
                       mol_type = protein
                       organism = synthetic construct
SEQUENCE: 70
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGGE GGGEGGGEGR QLYSALANKC CHVGCTKRSL AQFC        294

SEQ ID NO: 71          moltype = AA  length = 295
FEATURE                Location/Qualifiers
source                 1..295
                       mol_type = protein
                       organism = synthetic construct
SEQUENCE: 71
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWQEEVIKL  240
CGRELVRAQI AICGKSTGGG EEGGGEEGGG RQLYSALANK CCHVGCTKRS LARFC       295

SEQ ID NO: 72          moltype = AA  length = 295
FEATURE                Location/Qualifiers
source                 1..295
                       mol_type = protein
                       organism = synthetic construct
SEQUENCE: 72
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGG EEGGGEEGGG RQLYSALANK CCHVGCTKRS LARFC       295

SEQ ID NO: 73          moltype = AA  length = 295
FEATURE                Location/Qualifiers
source                 1..295
                       mol_type = protein
                       organism = synthetic construct
SEQUENCE: 73
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWQEEVIKL  240
CGRELVRAQI AICGKSTGGG EEGGGEEGGG RQLYSALANK CCHVGCTKRS LAQFC       295

SEQ ID NO: 74          moltype = AA  length = 295
FEATURE                Location/Qualifiers
source                 1..295
                       mol_type = protein
                       organism = synthetic construct
SEQUENCE: 74
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGG EEGGGEEGGG RQLYSALANK CCHVGCTKRS LAQFC       295

SEQ ID NO: 75          moltype = AA  length = 294
FEATURE                Location/Qualifiers
source                 1..294
                       mol_type = protein
                       organism = synthetic construct
SEQUENCE: 75
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGSD SWQEEVIKLC  240
GRELVRAQIA ICGKSTGGGE EGGGEEGGGR QLYSALANKC CHVGCTKRSL ARFC        294

SEQ ID NO: 76          moltype = AA  length = 294
FEATURE                Location/Qualifiers
source                 1..294
```

```
                        mol_type = protein
                        organism = synthetic construct
SEQUENCE: 76
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGGE EGGGEEGGGR QLYSALANKC CHVGCTKRSL ARFC        294

SEQ ID NO: 77           moltype = AA  length = 294
FEATURE                 Location/Qualifiers
source                  1..294
                        mol_type = protein
                        organism = synthetic construct
SEQUENCE: 77
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGGGSD SWQEEVIKLC  240
GRELVRAQIA ICGKSTGGGE EGGGEEGGGR QLYSALANKC CHVGCTKRSL AQFC        294

SEQ ID NO: 78           moltype = AA  length = 294
FEATURE                 Location/Qualifiers
source                  1..294
                        mol_type = protein
                        organism = synthetic construct
SEQUENCE: 78
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGGE EGGGEEGGGR QLYSALANKC CHVGCTKRSL AQFC        294

SEQ ID NO: 79           moltype = AA  length = 295
FEATURE                 Location/Qualifiers
source                  1..295
                        mol_type = protein
                        organism = synthetic construct
SEQUENCE: 79
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGG EGGGEGGGEG RQDYSALANK CCHVGCTKRS LAQFC       295

SEQ ID NO: 80           moltype = AA  length = 294
FEATURE                 Location/Qualifiers
source                  1..294
                        mol_type = protein
                        organism = synthetic construct
SEQUENCE: 80
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGGE GGGEGGGEGR QDYSALANKC CHVGCTKRSL ARFC        294

SEQ ID NO: 81           moltype = AA  length = 294
FEATURE                 Location/Qualifiers
source                  1..294
                        mol_type = protein
                        organism = synthetic construct
SEQUENCE: 81
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGGE GGGEGGGEGR QDYSALANKC CHVGCTKRSL AQFC        294

SEQ ID NO: 82           moltype = AA  length = 295
FEATURE                 Location/Qualifiers
source                  1..295
                        mol_type = protein
                        organism = synthetic construct
SEQUENCE: 82
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
```

```
CGRELVRAQI AICGKSTGGE GEGGEGEGGS RQLYSALANK CCHVGCTKRS LAQFC       295

SEQ ID NO: 83          moltype = AA  length = 294
FEATURE                Location/Qualifiers
source                 1..294
                       mol_type = protein
                       organism = synthetic construct
SEQUENCE: 83
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGEG EGGEGEGGSR QLYSALANKC CHVGCTKRSL ARFC        294

SEQ ID NO: 84          moltype = AA  length = 294
FEATURE                Location/Qualifiers
source                 1..294
                       mol_type = protein
                       organism = synthetic construct
SEQUENCE: 84
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGEG EGGEGEGGSR QLYSALANKC CHVGCTKRSL AQFC        294

SEQ ID NO: 85          moltype = AA  length = 295
FEATURE                Location/Qualifiers
source                 1..295
                       mol_type = protein
                       organism = synthetic construct
SEQUENCE: 85
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGE GEGGEGEGGS RQDYSALANK CCHVGCTKRS LAQFC       295

SEQ ID NO: 86          moltype = AA  length = 315
FEATURE                Location/Qualifiers
source                 1..315
                       mol_type = protein
                       organism = synthetic construct
SEQUENCE: 86
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWKEEVIKL CGRELVRAQI AICGKSTGGG EGGGEGGGEG RQLYSALANK  300
CCHVGCTKRS LARFC                                                   315

SEQ ID NO: 87          moltype = AA  length = 316
FEATURE                Location/Qualifiers
source                 1..316
                       mol_type = protein
                       organism = synthetic construct
SEQUENCE: 87
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWKEEVIKL CGRELVRAQI AICGKSTGGG EGGGEGGGEG GGQLYSALAN  300
KCCHVGCTKR SLARFC                                                  316

SEQ ID NO: 88          moltype = AA  length = 315
FEATURE                Location/Qualifiers
source                 1..315
                       mol_type = protein
                       organism = synthetic construct
SEQUENCE: 88
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWMEEVIKL CGRELVRAQI AICGKSTGGG EGGGEGGGEG RQLYSALANK  300
CCHVGCTKRS LARFC                                                   315

SEQ ID NO: 89          moltype = AA  length = 315
FEATURE                Location/Qualifiers
```

```
source                  1..315
                        mol_type = protein
                        organism = synthetic construct
SEQUENCE: 89
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWQEEVIKL CGRELVRAQI AICGKSTGGG EGGGEGGGEG RQLYSALANK  300
CCHVGCTKRS LARFC                                                   315

SEQ ID NO: 90           moltype = AA  length = 315
FEATURE                 Location/Qualifiers
source                  1..315
                        mol_type = protein
                        organism = synthetic construct
SEQUENCE: 90
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGG EGGGEGGGEG RQLYSALANK  300
CCHVGCTKRS LARFC                                                   315

SEQ ID NO: 91           moltype = AA  length = 316
FEATURE                 Location/Qualifiers
source                  1..316
                        mol_type = protein
                        organism = synthetic construct
SEQUENCE: 91
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWMEEVIKL CGRELVRAQI AICGKSTGGG EGGGEGGGEG GGQLYSALAN  300
KCCHVGCTKR SLARFC                                                  316

SEQ ID NO: 92           moltype = AA  length = 316
FEATURE                 Location/Qualifiers
source                  1..316
                        mol_type = protein
                        organism = synthetic construct
SEQUENCE: 92
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWQEEVIKL CGRELVRAQI AICGKSTGGG EGGGEGGGEG GGQLYSALAN  300
KCCHVGCTKR SLARFC                                                  316

SEQ ID NO: 93           moltype = AA  length = 316
FEATURE                 Location/Qualifiers
source                  1..316
                        mol_type = protein
                        organism = synthetic construct
SEQUENCE: 93
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGG EGGGEGGGEG GGQLYSALAN  300
KCCHVGCTKR SLARFC                                                  316

SEQ ID NO: 94           moltype = AA  length = 315
FEATURE                 Location/Qualifiers
source                  1..315
                        mol_type = protein
                        organism = synthetic construct
SEQUENCE: 94
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWMEEVIKL CGRELVRAQI AICGKSTGGE GGGEEGGGEG GQLYSALANK  300
CCHVGCTKRS LARFC                                                   315

SEQ ID NO: 95           moltype = AA  length = 315
FEATURE                 Location/Qualifiers
source                  1..315
```

```
                        mol_type = protein
                        organism = synthetic construct
SEQUENCE: 95
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWQEEVIKL CGRELVRAQI AICGKSTGGE GGGEEGGGEG GQLYSALANK  300
CCHVGCTKRS LARFC                                                   315

SEQ ID NO: 96           moltype = AA  length = 314
FEATURE                 Location/Qualifiers
source                  1..314
                        mol_type = protein
                        organism = synthetic construct
SEQUENCE: 96
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGGGSD SWMEEVIKLC GRELVRAQIA ICGKSTGGEG GGEEGGGEGG QLYSALANKC  300
CHVGCTKRSL ARFC                                                    314

SEQ ID NO: 97           moltype = AA  length = 314
FEATURE                 Location/Qualifiers
source                  1..314
                        mol_type = protein
                        organism = synthetic construct
SEQUENCE: 97
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGGGSD SWQEEVIKLC GRELVRAQIA ICGKSTGGEG GGEEGGGEGG QLYSALANKC  300
CHVGCTKRSL ARFC                                                    314

SEQ ID NO: 98           moltype = AA  length = 315
FEATURE                 Location/Qualifiers
source                  1..315
                        mol_type = protein
                        organism = synthetic construct
SEQUENCE: 98
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWQEEVIKL CGRELVRAQI AICGKSTGGG EGGGEGGGEG RQLYSALANK  300
CCHVGCTKRS LAQFC                                                   315

SEQ ID NO: 99           moltype = AA  length = 315
FEATURE                 Location/Qualifiers
source                  1..315
                        mol_type = protein
                        organism = synthetic construct
SEQUENCE: 99
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGG EGGGEGGGEG RQLYSALANK  300
CCHVGCTKRS LAQFC                                                   315

SEQ ID NO: 100          moltype = AA  length = 314
FEATURE                 Location/Qualifiers
source                  1..314
                        mol_type = protein
                        organism = synthetic construct
SEQUENCE: 100
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGGGSD SWQEEVIKLC GRELVRAQIA ICGKSTGGGE GGGEGGGEGR QLYSALANKC  300
CHVGCTKRSL ARFC                                                    314

SEQ ID NO: 101          moltype = AA  length = 314
FEATURE                 Location/Qualifiers
source                  1..314
                        mol_type = protein
```

```
                         organism = synthetic construct
SEQUENCE: 101
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGGE GGGEGGGEGR QLYSALANKC  300
CHVGCTKRSL ARFC                                                    314

SEQ ID NO: 102           moltype = AA  length = 314
FEATURE                  Location/Qualifiers
source                   1..314
                         mol_type = protein
                         organism = synthetic construct
SEQUENCE: 102
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGGGSD SWQEEVIKLC GRELVRAQIA ICGKSTGGGE GGGEGGGEGR QLYSALANKC  300
CHVGCTKRSL AQFC                                                    314

SEQ ID NO: 103           moltype = AA  length = 314
FEATURE                  Location/Qualifiers
source                   1..314
                         mol_type = protein
                         organism = synthetic construct
SEQUENCE: 103
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGGE GGGEGGGEGR QLYSALANKC  300
CHVGCTKRSL AQFC                                                    314

SEQ ID NO: 104           moltype = AA  length = 315
FEATURE                  Location/Qualifiers
source                   1..315
                         mol_type = protein
                         organism = synthetic construct
SEQUENCE: 104
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWQEEVIKL CGRELVRAQI AICGKSTGGG EEGGGEEGGG RQLYSALANK  300
CCHVGCTKRS LARFC                                                   315

SEQ ID NO: 105           moltype = AA  length = 315
FEATURE                  Location/Qualifiers
source                   1..315
                         mol_type = protein
                         organism = synthetic construct
SEQUENCE: 105
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGG EEGGGEEGGG RQLYSALANK  300
CCHVGCTKRS LARFC                                                   315

SEQ ID NO: 106           moltype = AA  length = 315
FEATURE                  Location/Qualifiers
source                   1..315
                         mol_type = protein
                         organism = synthetic construct
SEQUENCE: 106
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGS DSWQEEVIKL CGRELVRAQI AICGKSTGGG EEGGGEEGGG RQLYSALANK  300
CCHVGCTKRS LAQFC                                                   315

SEQ ID NO: 107           moltype = AA  length = 315
FEATURE                  Location/Qualifiers
source                   1..315
                         mol_type = protein
                         organism = synthetic construct
```

```
SEQUENCE: 107
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGG EEGGGEEGGG RQLYSALANK  300
CCHVGCTKRS LAQFC                                                   315

SEQ ID NO: 108          moltype = AA  length = 314
FEATURE                 Location/Qualifiers
source                  1..314
                        mol_type = protein
                        organism = synthetic construct
SEQUENCE: 108
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGGGSD SWQEEVIKLC GRELVRAQIA ICGKSTGGGE EGGGEEGGGR QLYSALANKC  300
CHVGCTKRSL ARFC                                                    314

SEQ ID NO: 109          moltype = AA  length = 314
FEATURE                 Location/Qualifiers
source                  1..314
                        mol_type = protein
                        organism = synthetic construct
SEQUENCE: 109
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGGE EGGGEEGGGR QLYSALANKC  300
CHVGCTKRSL ARFC                                                    314

SEQ ID NO: 110          moltype = AA  length = 314
FEATURE                 Location/Qualifiers
source                  1..314
                        mol_type = protein
                        organism = synthetic construct
SEQUENCE: 110
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGGGSD SWQEEVIKLC GRELVRAQIA ICGKSTGGGE EGGGEEGGGR QLYSALANKC  300
CHVGCTKRSL AQFC                                                    314

SEQ ID NO: 111          moltype = AA  length = 314
FEATURE                 Location/Qualifiers
source                  1..314
                        mol_type = protein
                        organism = synthetic construct
SEQUENCE: 111
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGGE EGGGEEGGGR QLYSALANKC  300
CHVGCTKRSL AQFC                                                    314

SEQ ID NO: 112          moltype = AA  length = 315
FEATURE                 Location/Qualifiers
source                  1..315
                        mol_type = protein
                        organism = synthetic construct
SEQUENCE: 112
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGG EGGGEGGGEG RQDYSALANK  300
CCHVGCTKRS LAQFC                                                   315

SEQ ID NO: 113          moltype = AA  length = 314
FEATURE                 Location/Qualifiers
source                  1..314
                        mol_type = protein
                        organism = synthetic construct
SEQUENCE: 113
```

```
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGGE GGGEGGGEGR QDYSALANKC  300
CHVGCTKRSL ARFC                                                    314

SEQ ID NO: 114         moltype = AA  length = 314
FEATURE                Location/Qualifiers
source                 1..314
                       mol_type = protein
                       organism = synthetic construct
SEQUENCE: 114
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGGE GGGEGGGEGR QDYSALANKC  300
CHVGCTKRSL AQFC                                                    314

SEQ ID NO: 115         moltype = AA  length = 315
FEATURE                Location/Qualifiers
source                 1..315
                       mol_type = protein
                       organism = synthetic construct
SEQUENCE: 115
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGE GEGGEGEGGS RQLYSALANK  300
CCHVGCTKRS LAQFC                                                   315

SEQ ID NO: 116         moltype = AA  length = 314
FEATURE                Location/Qualifiers
source                 1..314
                       mol_type = protein
                       organism = synthetic construct
SEQUENCE: 116
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGEG EGGEGEGGSR QLYSALANKC  300
CHVGCTKRSL ARFC                                                    314

SEQ ID NO: 117         moltype = AA  length = 314
FEATURE                Location/Qualifiers
source                 1..314
                       mol_type = protein
                       organism = synthetic construct
SEQUENCE: 117
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGEG EGGEGEGGSR QLYSALANKC  300
CHVGCTKRSL AQFC                                                    314

SEQ ID NO: 118         moltype = AA  length = 315
FEATURE                Location/Qualifiers
source                 1..315
                       mol_type = protein
                       organism = synthetic construct
SEQUENCE: 118
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGE GEGGEGEGGS RQDYSALANK  300
CCHVGCTKRS LAQFC                                                   315

SEQ ID NO: 119         moltype = DNA  length = 885
FEATURE                Location/Qualifiers
source                 1..885
                       mol_type = other DNA
                       organism = synthetic construct
SEQUENCE: 119
gataaaacac acacgtgtcc cccctgcccg gctccagagg cggctggtgg tcccagcgta  60
```

```
ttcttgtttc ctcccaaacc taaggatacg ctcatgatat cccgcacccc agaagttacg  120
tgtgtagtcg tcgacgtcag tcacgaagat ccagaggtca aatttaactg gtatgtcgac  180
ggagtagagg tccacaatgc gaaaaccaag cccagagaag agcagtacaa ctccacgtat  240
cgcgtcgtct ccgtcctcac cgtactccat caagattggc tgaatgggaa agagtataaa  300
tgcaaagtat ctaacaaggc tctgccagct ccgatagaaa agactatatc aaaggccaag  360
gggcagccaa gggagcctca agtctatact ttgcccccat ctcgggatga gcttacgaaa  420
aaccaggtca gccttacctg tcttgttaaa ggtttttatc cgagtgacat cgcagtggaa  480
tgggaatcta atggtcaacc tgaaaacaat tacaaaacca caccgccagt attggacagc  540
gatggtagtt tttttcttta ctcaaaactg actgtagata aaagcagatg gcagcagggc  600
aatgtctttt catgtagcgt tatgcatgag gctcttcaca accactatac ccaaaagtca  660
ttgtctctta gtcccggaaa gggcggaagt gattcttgga aggaggaggt aatcaagttg  720
tgcgggcgag agttggtacg ggcacagatc gcgatatgcg gaaaatccac aggtgggggc  780
gaaggaggag gtgagggtgg aggtgaagga cgacagttgt attccgcctt ggcaaacaag  840
tgttgccatg tgggttgcac aaaacgcagt cttgcccgct tctgt                   885

SEQ ID NO: 120         moltype = DNA  length = 888
FEATURE                Location/Qualifiers
source                 1..888
                       mol_type = other DNA
                       organism = synthetic construct
SEQUENCE: 120
gataagacac atacatgccc tccctgtccg gctccagagg cagccggggg tccatcagtc  60
ttcctttttc cgcctaaacc taaggataca ctgatgatct ctcgaacacc ggaggtcact  120
tgtgttgtcg ttgacgtatc acatgaggat cccgaagtaa agttcaactg gtatgtcgat  180
ggtgtggagg ttcataatgc taaaactaaa ccacgggagg agcaatataa ttccacatat  240
agggtcgtga gcgtgttgac ggtgcttcat caagactggc ttaatgggaa ggaatataaa  300
tgcaaagtgt caaataaagc acttcctgcg ccaatcgaga aaacaattag taaggcaaag  360
gggcagccgc gagaacctca ggtgtacacc ttgccgcctt ctagagacga gctcacaaag  420
aaccaagttt ccctgacttg cctcgttaag ggtgttttatc cgtccgatat agccgtggag  480
tgggagtcaa acggccaacc ggaaaataat tacaaaacga cacccccagt attggatagt  540
gacggctctt ttttccttta ttctaagctg actgtggaca aaagccgctg gcagcagggc  600
aatgtctttt catgcagcgt aatgcatgaa gccctgcaca accactacac gcaaaaatcc  660
ctttccttgt cacccggcaa gggcggctct gactcctgga aagaggaagt tataaaactc  720
tgtggccgag aacttgttcg agctcaaatc gcgatttgtg gtaagtcaac gggtgggggc  780
gaaggtggag gcgagggtgg gggagaagga ggaggccagt tgtactcagc tcttgcaaat  840
aagtgttgcc acgttggttg tacgaagcgg agccttgctc gcttctgc                888

SEQ ID NO: 121         moltype = DNA  length = 885
FEATURE                Location/Qualifiers
source                 1..885
                       mol_type = other DNA
                       organism = synthetic construct
SEQUENCE: 121
gacaaaacac atacttgtcc gccttgcccg gcacccgaag cggccggcgg acccagtgtc  60
tttctcttcc cacccaaacc gaaagacact ctgatgattt ccaggacgcc tgaagtgacc  120
tgcgttgtag ttgatgtatc acacgaggat cccgaggtca agttcaattg gtatgtagat  180
ggggtggagg tccataatgc aaagacgaag ccacgggagg aacagtacaa ctctacgtac  240
agagttgtca gtgttttgac cgtccttcat caggattggc tgaacggtaa agaatataaa  300
tgcaaggtta gcaataaagc tttgcccgcc cctatagaga aaacgatcag taaggcgaag  360
gggcagccta gggaacccca ggtatatacc ttgccgccaa gtcgagatga gctgacgaag  420
aaccaagtga gtctgacatg cctcgtgaag ggcttctatc cgagcgatat cgctgtcgaa  480
tgggagagca atgggcagcc tgagaataac tataaaacaa cgccacccgt cctcgactcc  540
gatggctcat tcttcctgta cagtaaactt acagtagata agagtagatg gcagcagggt  600
aacgtcttta gttgctccgt gatgcacgag gcattgcaca atcattacac tcaaaaatct  660
ctgtccctga gtccgggcaa aggcggttca gatagctgga tggaggaggt cataaagctt  720
tgtggacgag aactcgttcg cgcccagata gctatttgtg ggaaatcaac cgggggtgga  780
gaaggtggcg gagaaggggg aggcgaaggg cgccaactgt attctgcatt ggctaataag  840
tgctgtcacg taggatgtac aaaaaggtct ctggcgagat tctgc                   885

SEQ ID NO: 122         moltype = DNA  length = 885
FEATURE                Location/Qualifiers
source                 1..885
                       mol_type = other DNA
                       organism = synthetic construct
SEQUENCE: 122
gacaagacgc acacttgtcc accttgccct gcgccggaag ctgctggagg ccccagtgtc  60
tttttgttcc cgcccaaacc gaaggacact ttgatgataa gtcgcacgcc cgaggttacc  120
tgtgtggttg tcgatgtctc acacgaagat ccggaggtga agtttaattg gtatgtagat  180
ggcgtggagg ttcataacgc caaaacgaaa cccagagaag aacaatataa cagtacatat  240
cgagtagtat ccgttctcac tgtcctgcat caagactggt tgaacgggaa ggaatataag  300
tgcaaggtga gcaataaagc actcccggcc ccaatcgaaa agaccatcag caaagcgaag  360
gggcaacctc gagaacccca ggtatatacg ctcccccccta gtcgggatga acttactaaa  420
aatcaggtta gcctcacttg ccttgttaaa gggttctatc ccagtgatat tgccgtcgaa  480
tgggaatcaa acgggcagcc ggaaaataac tacaagacaa cccctcctgt gctcgatagc  540
gatggctctt ttttcctcta cagcaaactt accgttgata agagccggtg gcaacaaggt  600
aatgttttct cctgctccgt tatgcatgaa gcactccata accattatac ccaaaaaagc  660
ctgtcactta gtccgggtaa aggaggtagt gattcttggc aggaggaggt aatcaaactt  720
tgtgggaggg agctggtacg agctcagatt gctatatgtg gaaaaagcac gggcggagga  780
gaaggaggtg gcgaaggcgg gggtgaaggt cggcaactct actccgctct cgctaataag  840
```

```
tgctgccacg tcgggtgtac gaagcgctcc ctggcgcgat tctgc                  885

SEQ ID NO: 123          moltype = DNA  length = 885
FEATURE                 Location/Qualifiers
source                  1..885
                        mol_type = other DNA
                        organism = synthetic construct
SEQUENCE: 123
gataaaacgc acacgtgtcc gccctgccca gcgcctgaag ccgcaggcgg gccgtccgtc  60
ttcctctttc ctccaaaacc caaagacaca cttatgatca gtaggacccc agaggtaacc  120
tgcgtcgtgg tcgacgtttc ccatgaagac ccagaggtca agttcaactg gtacgtcgac  180
ggtgtcgaag tacataatgc taaaacgaag cctcgggaag agcagtacaa ctctacctac  240
cgcgtcgttt ccgtactcac cgtacttcac caggactggc ttaacggtaa agagtataaa  300
tgcaaagtat ctaataaggc tctcgccgcg ccgattgaga agacaatttc aaaggccaag  360
gggcagccgc gggagcccca agtgtatacc ttgcccccgt cccgagatga gctgactaaa  420
aaccaagtaa gcttgacttg cttggtcaaa ggcttctacc cttccgatat agctgtcgaa  480
tgggagtcaa atggccaacc agagaacaat tataaaacta cacccccggt cttggattct  540
gatggctcat tttttctcta ttctaaactg accgtggata agtctcgctg gcagcaaggt  600
aacgtgttca gttgctctgt tcttcacgaa gcactgcaca gtcattacac tcagaagagt  660
cttagcctga gccctggtaa agggggttct gattcctggc aggaggaagt aataaaactc  720
tgtggccggg agttggtacg ggcgcagatt gcgatatgcg gtaagagcac cggcggaggc  780
gaaggcggtg gggaaggagg aggagaaggg agacaactct attccgcatt ggcaaataag  840
tgctgccacg tcgggtgtac caaacgatcc cttgcacggt tctgt                  885

SEQ ID NO: 124          moltype = DNA  length = 888
FEATURE                 Location/Qualifiers
source                  1..888
                        mol_type = other DNA
                        organism = synthetic construct
SEQUENCE: 124
gataagaccc atacgtgccc cccttgccct gcgcctgagg cagcgggtgg cccatcagtc  60
tttttgttcc cgcccaagcc aaaggacacc ctcatgatta gtagaacacc ggaggttacg  120
tgcgtcgtag tggatgtcag ccacgaggat cccgaggtta agtttaactg gtacgttgat  180
ggggttgagg tccataatgc gaagactaag ccgagagagg aacagtacaa ttccacgtat  240
agagttgtct ctgtactgac tgtgctgcat caagattggc ttaacggtaa ggagtacaag  300
tgcaaagtct ctaataaggc tcttcctgca cccattgaga aaactataag caaagcaaaa  360
ggtcaacctc gcgaacctca ggtgtacaca ctgccaccct ctagggacga gcttaccaaa  420
aatcaagtat ctcttacctg ccttgtgaaa gggttttatc cctcagatat tgcggttgag  480
tgggagtcta acggacaacc tgagaacaac tataagacta ctcccccggt gcttgattca  540
gacgggagtt tttttttgta tagcaaactt accgtcgaca aaagccggtg gcaacagggc  600
aatgtattca gttgttctgt aatgcatgaa gctttgcata atcattacac ccaaaagagt  660
ctttccctgt ctcctggaaa agggggggtca gactcctgga tggaggaggt gatcaaactg  720
tgtgggagag agctcgtccg ggctcagata gctatatgcg gcaagtctac gggtgggggga  780
gagggcggag gagagggcgg tggagaagga ggcggccaac tctacagcgc tctggccaat  840
aaatgttgtc atgtcgggtg tactaagcgc tcactggcac gcttttgc               888

SEQ ID NO: 125          moltype = DNA  length = 888
FEATURE                 Location/Qualifiers
source                  1..888
                        mol_type = other DNA
                        organism = synthetic construct
SEQUENCE: 125
gacaagacgc atacatgccc gccatgcccg gcccccgaag ctgctggggg accatccgta  60
ttcctcttcc ctcccaaacc aaaagacacg ttgatgataa gtagaacacc agaggtaacg  120
tgcgtggttg tcgatgtttc ccacgaagat ccggaggtaa aattcaattg gtatgtagat  180
ggggtggaag tgcacaatgc caaaacaaag ccgcgagaag aacaatacaa tagtacttac  240
cgggttgtga gcgtgctcac ggtgttgcac caagactggc tcaacggcaa ggaatacaag  300
tgcaaagtat ctaataaagc tctgcctgcg ccgatagaga agaccatcag taaggccaaa  360
gggcagcccc gagagccgca agtttacact cttcctccga gcagagatga attgaccaag  420
aaccaagtaa gtttgacgtg cctggtgaag ggcttctacc cctcagacat tgcggtggag  480
tgggaaagta atggtcaacc ggaaaacaac tacaagacca cgccgcccgt cctcgactcc  540
gatgggtctt tctttcttta ttcaaagttg acagtagata agtcaaggtg gcagcaaggt  600
aacgtgttta gttgtagtgt aatgcacgag gccctgcata atcattatac ccaaaagagt  660
ttgagcctct caccaggaaa aggcggatca gacagctggc aggaggaggt aattaaattg  720
tgtggacggg agttggtcag ggcgcaaata gccatctgcg gtaagagcac gggtggagga  780
gagggtggag gggaaggtgg gggagaaggc ggcgggcagc tctattctgc actcgccaac  840
aagtgttgtc acgtcggatg cacaaagaga tctcttgctc gattctgc               888

SEQ ID NO: 126          moltype = DNA  length = 888
FEATURE                 Location/Qualifiers
source                  1..888
                        mol_type = other DNA
                        organism = synthetic construct
SEQUENCE: 126
gacaaaacac acacctgtcc gccttgcccg gctcctgaag ccgcgggtgg ccctagtgtg  60
tttttgtttc cgccgaaacc taaggatacc ctcatgataa gccggacgcc cgaggttacc  120
tgtgtcgtgg tcgatgttag tcatgaggat ccagaagtca agtttaattg gtacgtcgac  180
ggcgttgaag tccacaatgc aaaaactaaa ccgcgagaag aacagtacaa ctccacctac  240
agagttgtct cagttttgac agttctccat caggattggc tcaatggaaa ggaatataag  300
```

```
tgcaaggtca gcaataaagc gcttgccgcc cctatagaga agaccattag caaggcgaaa  360
ggacagcccc gcgagcccca ggtctatacg ctgcctccta gcagagatga gctcacgaaa  420
aatcaggtca gcttgacatg cttggtgaag ggcttctacc ccagtgacat cgcagttgaa  480
tgggagagca acggccaacc tgagaacaac tacaaaacaa cgccccccggt tcttgacagc  540
gatgggtcct tctttcttta ctctaagctt acagttgata aaagcaggtg gcagcagggg  600
aatgtgttct catgttccgt actgcatgag gctctgcatt ctcactacac ccaaaaaagc  660
cttagcctga gccccggtaa gggaggtagt gactcatggc aagaggaagt gattaagctc  720
tgcggccggg agttggtgag agcccaaatc gccatttgcg gtaaaagtac cggagggggc  780
gagggaggag gcgaaggtgg aggtgaagga ggtggacagt tgtactcagc tcttgcaaat  840
aaatgttgtc atgttggttg cacgaaaaga tctcttgcga ggttctgt              888

SEQ ID NO: 127         moltype = DNA  length = 885
FEATURE                Location/Qualifiers
source                 1..885
                       mol_type = other DNA
                       organism = synthetic construct
SEQUENCE: 127
gataagacgc atacttgtcc accgtgcccc gcaccggaag cggctggtgg tccatcagtt  60
tttctgttcc caccgaaacc taaggacacg ttgatgatat cacggacacc agaggttacg  120
tgcgtagtgg tggatgtgag ccacgaggat ccagaagtta aatttaattg gtacgtagat  180
ggagtggagg ttcataatgc gaagacaaag cctcgcgagg aacagtataa ttccacctat  240
cgcgtcgtat ctgtgcttac ggtacttcac caagactggt tgaacggtaa ggaatataaa  300
tgcaaggttt ccaataaagc acttcctgcg ccaattgaga agacaatatc caaagctaaa  360
ggtcaaccca gggaaccgca agtctacact ctccccccgt ctcgcgatga attgacgaag  420
aaccaggtta gtctcacctg cctggtcaag ggttttaccc cctctgacat agctgtagaa  480
tgggagtcta atggacagcc agagaacaat tacaaaacga cccccccggt cctcgattct  540
gatgggagtt tttttcttta ttcaaaattg actgtcgata agtcaagatg gcaacagggt  600
aacgtatttt cttgcagtgt tatgcatgaa gcattgcaca accactatac acaaaaatca  660
ttgagtttga gtcccggtaa aggggggaagc gactcatgga tggaagaagt aatcaagctg  720
tgcgggcgag agcttgtgcg agctcagata gcaatctgtg gtaagtctac aggtggagag  780
ggtggcggtg aagaaggcgg gggagaggga ggccagcttt attctgccct ggctaacaag  840
tgctgtcacg ttggatgcac gaagcgctcc ctggcccgat tctgc                 885

SEQ ID NO: 128         moltype = DNA  length = 885
FEATURE                Location/Qualifiers
source                 1..885
                       mol_type = other DNA
                       organism = synthetic construct
SEQUENCE: 128
gataagacgc atacttgtcc cccatgtccc gctccggaag ccgctggcgg cccctccgtt  60
tttctgttcc cgccgaaacc gaaagacacc ctgatgatat cacgcactcc cgaggtcact  120
tgcgtggtag tcgatgttag tcatgaagat cctgaggtca aattcaattg gtatgtagat  180
ggcgttgagg tacacaacgc gaagacaaaa ccccgagaag aacagtataa ctcaacctac  240
cgcgtagttt cagttcttac cgtactgcac caagactggt tgaacggtaa agagtacaaa  300
tgtaaagtca gcaataaagc tttgccagca cctatcgaaa aaaccatcag taaggccaag  360
ggtcaaccca gggagccgca agtgtacact cttcccccta gcagggatga attgaccaag  420
aatcaggtct ctttgacgtg cctcgttaag ggtttctatc ccagcgatat agccgtagaa  480
tgggagtcta acggtcagcc agaaaataac tataagacaa ccccgcctgt tttggattcc  540
gacggctctt tttttctcta ctctaagttg accgttgata agagcagatg gcagcaggga  600
aacgtatttt cttgttccgt gatgcacgaa gccctgcaca atcactatac gcaaaagtct  660
ctgagcttga gtccgggtaa aggcggttct gactcctggc aggaggaagt cataaaactc  720
tgcggaagag agctcgtaag ggcgcaaatc gctatttgtg gtaagagcac cggtggggaa  780
ggaggcggtg aagagggtgg cggcgagggt gggcaattgt attccgcgct tgccaataaa  840
tgttgtcacg taggctgcac aaagcgaagt ctcgctaggt tctgc                 885

SEQ ID NO: 129         moltype = DNA  length = 882
FEATURE                Location/Qualifiers
source                 1..882
                       mol_type = other DNA
                       organism = synthetic construct
SEQUENCE: 129
gacaagaccc acacatgtcc cccgtgtccg gcaccagaag cagcgggggg accgtcagta  60
ttcttgtttc caccgaagcc caaagacaca ttgatgattt cacgaactcc tgaagttacc  120
tgtgtggttg tagatgtatc acacgaagac ccagaagtca aattcaattg gtatgtcgac  180
ggggttgaag ttcacaatgc gaagacgaag ccccgggagg aacagtacaa cagcacgtac  240
agggttgtga gcgttcttac tgtattgcac caggattggc tcaacggcaa ggagtataaa  300
tgtaaagttt ctaataaggc tcttcctgcc ccaattgaaa agacgatatc taaagcgaag  360
ggccaaccac gggaacctca ggtgtacaca cttccgccta gcagggatga gttgaccaag  420
aatcaagtct ctttgacgtg cctggtcaag gggttttacc catcagatat cgccgtcgaa  480
tgggagtcaa acggacaacc cgaaaataac tataaaacta ctccaccagt tctggatagc  540
gacggctcat tttttctgta ttcaaagctc actgtagaca agtctaggtg gcagcagggt  600
aatgtcttct cctgctcagt aatgcatgag gctcttcaca accactatac tcaaaagagc  660
ctttccctgt cacctggcgg tggaagcgac tcatggatgg aggaggtaat aaagctctgc  720
ggaagagaac tggtacgcgc acaaatcgca atttgtggta agagtactgg cggggaagga  780
ggtggggaag aagggggcgg tgagggcgga cagctctatt ctgcacttgc aaacaaatgt  840
tgccacgtgg gatgtactaa gcgaagcctt gcaagattct gc                    882

SEQ ID NO: 130         moltype = DNA  length = 882
FEATURE                Location/Qualifiers
```

```
source                  1..882
                        mol_type = other DNA
                        organism = synthetic construct
SEQUENCE: 130
gataaaaccc acacatgccc tccatgccct gctccagagg ccgccggtgg gccatcagtt  60
ttcttgtttc cgcctaaacc aaaggacacg cttatgatct ccaggacccc cgaagttacg  120
tgtgtggtgg ttgatgttag tcacgaggac ccggaagtca agttcaactg gtacgttgat  180
ggtgtagagg tgcacaatgc aaagacgaag ccacgcgaag aacaatacaa cagcacatat  240
cgagttgtga gcgtactcac ggtactgcat caggactggc tgaacggtaa agaatacaaa  300
tgtaaagtct ccaataaggc acttcctgcg ccgatagaaa aaacgatcag taaggccaag  360
ggccaacccc gagaaccaca ggtatatacg ctcccaccgt cacgagacga gttgacaaaa  420
aatcaggtct ccctgacttg cctcgtgaaa ggtttttatc cctcagatat tgctgttgag  480
tgggaaagca atgggcagcc agagaataat tataagacga ctcctccggt tttggattcc  540
gacggtagtt ttttcttgta tagtaagctt actgtagaca agtcaagatg gcaacaaggt  600
aatgtgttct cttgctcagt tatgcatgaa gctcttcata accattacac gcaaaagagt  660
ctcagtctga gccccggtgg cggtagcgac agttggcagg aagaggtgat taagttgtgc  720
ggtcgcgagc tcgttcgggc ccaaattgca atctgcggaa aatctacggg cggagagggc  780
gggggtgagg agggtggggg tgaaggtggg cagctctata gcgcccttgc gaataaatgt  840
tgtcacgtcg gatgcacaaa gaggtccctc gccaggttct gc                    882

SEQ ID NO: 131          moltype = DNA  length = 885
FEATURE                 Location/Qualifiers
source                  1..885
                        mol_type = other DNA
                        organism = synthetic construct
SEQUENCE: 131
gataagaccc acacttgccc cccttgccct gcccccgaag cggccggagg tccttcagta  60
tttttgtttc caccgaaacc caaagatact ttgatgatat caagaactcc tgaagtcacc  120
tgcgtggtag ttgacgtatc tcatgaggat cccgaggtga agttcaattg gtacgtcgat  180
ggcgtcgagg ttcataacgc taagactaag ccgagggaag agcaatataa ttccacttat  240
agggtggtgt ccgtcttgac tgttttgcac caggattggt tgaacgggaa agagtacaaa  300
tgtaaggtga gtaataaagc tttggctgct cccatcgaaa agacaataag caaggccaag  360
gggcaacctc gggagccgca ggtgtacacc cttcctccca gtagagacga actgacaaaa  420
aaccaggtgt ccctgacctg ccttgtgaag ggttttaccc cgagcgacat agcggttgaa  480
tgggagagca acgggcaacc cgagaacaac tacaaaacta caccgcctgt cctggactcc  540
gatggaagct tcttcctcta ctccaaactg accgtggaca aaagcagatg gcaacaagga  600
aacgtattct catgctcagt aatgcacgaa gcattgcaca atcactacac ccaaaagtcc  660
ctctcactct cccctggtaa gggcggatca gactcatggc aagaggaggt aattaagttg  720
tgcgggaggg agctcgtccg cgcgcaaata gccatttgtg gcaagtccac tggaggaggc  780
gagggtggag gagagggtgg tggggagggc aggcaactct acagtgcgct cgccaataaa  840
tgctgccatg ttgggtgcac gaagcgcagt ctcgcacaat tctgc                 885

SEQ ID NO: 132          moltype = DNA  length = 885
FEATURE                 Location/Qualifiers
source                  1..885
                        mol_type = other DNA
                        organism = synthetic construct
SEQUENCE: 132
gataagaccc acacgtgtcc tccatgtccg gcaccggagg ctgctggcgg gccttctgta  60
ttcctcttcc cacccaagcc aaaagacaca ttgatgatat caaggacgcc ggaagtcacc  120
tgtgttgttg tggacgtttc ccatgaagac ccagaggtaa aattcaattg gtatgtggac  180
ggcgtagagg ttcacaacgc caaaaccaaa ccccgagagg aacagtataa tagcacatat  240
cgagtagtat ctgttctcac agtgctccat caagactggc ttaatggtaa agagtataaa  300
tgcaaagttt ccaataaagc cctcgctgca ccgatcgaga agacaatcag taaagcgaag  360
ggccagcctc gggaaccgca ggtgtatact cttccaccct caagagacga gctcactaaa  420
aaccaagttt cattgacatg cctcgtcaaa ggtttctacc catcagacat cgcggtcgaa  480
tgggaaagta atgggcagcc ggaaaacaac tataaaacga cgccgcccgt cttggattct  540
gatggttcat tttttcttta ctctaaattg accgtcgata aaagtaggtg gcaacaagga  600
aatgtttttt cctgctccgt cctgcatgaa gcgttgcaca gtcactatac ccagaagagt  660
ctttctttgt cacccggaaa aggcggttca gattcatggc aggaagaagt aattaaactc  720
tgtggccgcg agcttgttag ggcgcagata gccatatgtg gtaaaagcac cggaggaggt  780
gaaggcggag gcgaaggagg tggggaagga agacaattgt attctgcact tgcaaataaa  840
tgctgtcatg tggggtgcac gaaacgcagt cttgcacaat tttgt                 885

SEQ ID NO: 133          moltype = DNA  length = 882
FEATURE                 Location/Qualifiers
source                  1..882
                        mol_type = other DNA
                        organism = synthetic construct
SEQUENCE: 133
gacaaaaccc atacctgccc cccttgccct gcaccagaag cggcgggagg acctagcgtt  60
tttctttttc ctccgaaacc gaaagatacc ctcatgatat caagaacacc tgaggttact  120
tgcgttgtcg tggacgtgag tcacgaagac cccgaggtga agttcaactg gtatgtagat  180
ggagtggagg tccataatgc aaaaacgaaa ccgagagaag aacaatacaa ctctacatat  240
cgagtcgtgt cagtactcac ggttttgcat caagattggc tgaacggtaa ggagtacaag  300
tgtaaggtta gcaacaaggc tctcgcggcg ccgatagaaa agactataag taaagcaaaa  360
ggccagccca gagaacctca agtttacact ctgcctccca gcagagatga actgactaaa  420
aatcaggttt cattgacctg tctcgtcaag ggtttttatc caagcgacat agcagttgaa  480
tgggaaagca acggtcaacc agaaaataat tacaaaacca ctccaccagt cttggactct  540
```

```
gacggatcct tctttctcta ttcaaaattg acggtggata aatctaggtg gcagcaaggc  600
aacgtcttct cttgtagcgt tatgcatgag gcgctgcaca accactacac acaaaagtct  660
cttagtttga gcccgggcgg cggaagcgac tcttggcaag aggaagtgat aaaactctgt  720
ggtcgagaat tggtacgcgc gcagatcgct atctgcggca agtccacagg gggaggggaa  780
ggtggcgggg aaggtggtgg cgagggcagg cagttgtata gtgcacttgc caacaagtgc  840
tgccatgtgg ggtgcaccaa gcgcagtttg gcacggttct gc                     882

SEQ ID NO: 134          moltype = DNA  length = 882
FEATURE                 Location/Qualifiers
source                  1..882
                        mol_type = other DNA
                        organism = synthetic construct
SEQUENCE: 134
gataaaactc acacttgtcc cccgtgtccg gcaccagaag ccgcaggagg gccatctgtc  60
tttctttttc ccccaaaacc caaggataca ctgatgatct cccgcactcc cgaagttact  120
tgtgtcgtag tagacgtttc tcacgaggac ccagaggtga aattcaattg gtatgttgac  180
ggagtagagg tgcataatgc caagacaaag ccccgagagg aacaatacaa ttcaacctac  240
agagtagtgt ccgttcttac ggttctccat caggattggc tcaacggtaa ggaatataag  300
tgcaaggtaa gcaacaaagc gctggccgca cccattgaga aaaccatttc aaaagctaaa  360
ggccaacccc gcgaaccaca agtttatact ctccccccaa gtcgcgatga acttacaaaa  420
aatcaagtct cattgacgtg cttggtcaaa ggcttctacc cgagcgatat cgctgttgaa  480
tgggagtcta atggacaacc ggaaaataac tataaaacta cacccccagt cctcgattca  540
gacggcagct tcttcctgta ttcaaaactg acggttgaca aatcacgctg gcaacaggt  600
aacgtttttt cctgtagcgt tcttcatgaa gccttgcaca gtcactacac ccagaagtcc  660
cttagcttgt cacctggcgg gggttcagac tcttggcagg aggaggtaat caaactgtgc  720
ggaagagaac tggtgagggc tcagattgca atttgtggga agagcacggg tggcggtgaa  780
ggaggtggcg agggcggagg agaggggagg caactctaca gtgcgttggc taataaatgc  840
tgtcacgtcg gctgtactaa gagaagcctc gccagatttt gc                     882

SEQ ID NO: 135          moltype = DNA  length = 882
FEATURE                 Location/Qualifiers
source                  1..882
                        mol_type = other DNA
                        organism = synthetic construct
SEQUENCE: 135
gacaagacgc atacttgccc tccgtgccct gcaccagaag ccgctggtgg cccatctgtg  60
tttttgttcc cccctaagcc aaaagacaca ttgatgattt cacgaactcc agaagtgact  120
tgcgtagttg ttgacgtatc acacgaagac cccgaggtta aatttaattg gtatgtggac  180
ggggtcgagg tgcataacgc caaaaccaaa ccccgggagg aacaatataa ctctacgtat  240
cgggtcgtat ctgtgttgac cgtccttcac caagattggt tgaacggcaa ggaatataag  300
tgtaaagtgt ctaataaagc attggctgcc ccgatagaaa agacgatctc taaagccaag  360
ggccaaccca gagagcctca agtatatact ctcccaccga gtcgagatga gctcactaag  420
aaccaggtgt cactcacgtg tctggttaaa ggattttacc ctagtgatat agccgtcgag  480
tgggaatcaa atgggcagcc ggagaataac tataagacca cgcctccagt tctcgattcc  540
gatggtagct tttcctttta ctctaaactt acggtcgaca agtccaggtg gcaacagggc  600
aatgtatttt cttgctccgt catgcacgag gctttgcaca accattacac gcaaaagtca  660
ctgtccctgt ctcctggagg cggttctgac agttggcagg aggaggtaat caaattgtgt  720
gggcgggagt tggttagggc gcaaattgct atttgcggca aaagtactgg gggcggtgaa  780
ggcggaggcg agggaggagg agaaggtcga caactgtatt ctgccttggc gaacaaatgc  840
tgtcacgtcg gctgtacgaa acggtctttg gcccagtttt gt                     882

SEQ ID NO: 136          moltype = DNA  length = 882
FEATURE                 Location/Qualifiers
source                  1..882
                        mol_type = other DNA
                        organism = synthetic construct
SEQUENCE: 136
gataagacac acacttgtcc gccatgccct gcgccggaag cggcgggagg accgtccgtt  60
ttcctgttcc ctcccaaacc caaagacacg ttgatgatta gtcgcacgcc agaagttacg  120
tgcgttgtcg tagatgtatc ccacgaagac cccgaggtga agttcaattg gtatgtagat  180
ggggtggagg tccataacgc taagaccaaa ccacgcgagg aacaatataa ttctacgtac  240
cgcgtagtga gcgttctcac agttcttcac caggattggc ttaacggcaa ggagtataag  300
tgtaaggtgt ctaataaggc cttggctgcc ccgatcgaaa aaacgataag taaagcaaag  360
ggtcaaccta gagaacccca agtgtacact ctcccgccat cacgggatga attgactaag  420
aaccaagtgt cactcacgtg tcttgtaaag ggcttctacc catccgatat agccgttgag  480
tgggaatcca atggtcagcc agagaacaac tataagacaa ctccgcccgt acttgatagt  540
gacggttcct ttttccttta cagtaaattg acggtagata agtctcgctg gcagcaagga  600
aacgtctttt cttgttcagt gcttcatgag gcgcttcact cacactatac tcagaagagt  660
ttgagtttgt ctccaggtgg aggcagcgac tcatggcaag aggaagtaat caaactgtgt  720
ggtcgcgaat tggtacgagc acagatcgcg atctgcggga aatcaacagg tggcggcgaa  780
ggcggcgggg aaggcggcgg cgaaggtagg caactttact cagcccttgc gaacaaatgt  840
tgccacgtag gctgtactaa gagaagtctc gcccagtttt gc                     882

SEQ ID NO: 137          moltype = DNA  length = 885
FEATURE                 Location/Qualifiers
source                  1..885
                        mol_type = other DNA
                        organism = synthetic construct
SEQUENCE: 137
```

```
gacaagactc atacctgccc cccttgtcca gcaccagaag cagctggcgg gccaagcgtg  60
ttcctgtttc cacctaagcc caaagatacg ttgatgatca gccgcacccc ggaagtaacc  120
tgtgtagtag tagatgtgtc ccacgaagac cccgaagtaa agtttaattg gtacgtcgat  180
ggtgtcgaag tacataacgc taaaacgaag ccccgagaag agcagtacaa cagtacttac  240
agagtagttt ctgttcttac agtgctgcat caggattggc tgaacgggaa ggagtataaa  300
tgtaaagtct caaacaaggc acttgcggca ccaatagaga agacaatatc taaggccaaa  360
gggcagccta gagagccaca agtatatacg ctgcccccca gcagggacga gctgacaaag  420
aaccaagtgt cactgacctg ccttgttaag ggcttctatc cgagtgatat tgctgttgaa  480
tgggaaagta acggacagcc ggagaacaac tataaaacta ctccacccgt gttggatagt  540
gacggtagct tttttctgta ctccaagttg acggtagaca aaagtcggtg gcagcagggg  600
aacgtatttt cttgttctgt catgcacgaa gctcttcaca atcactatac gcagaagtcc  660
ctctctctct ctcctgggaa gggtggttcc gacagctggc aggaggaggt cattaaactg  720
tgtggtagag agctggtacg ggctcaaatt gcaatttgtg gtaagagtac tggcggtggc  780
gaggaagggg gtggggagga gggcggaggt aggcagctct actctgctct cgccaacaag  840
tgttgtcacg tcgggtgtac taaaagatca cttgcccgct tttgt  885

SEQ ID NO: 138          moltype = DNA  length = 885
FEATURE                 Location/Qualifiers
source                  1..885
                        mol_type = other DNA
                        organism = synthetic construct
SEQUENCE: 138
gacaaaacac atacatgccc gccgtgtccg gcgcctgaag cagcaggagg ccccagtgta  60
ttccttttcc ctccaaagcc aaaagatacg ttgatgatat ctaggacacc tgaggttacc  120
tgcgtcgtag tggacgtatc ccacgaagac ccagaagtca agtttaactg gtatgtggac  180
ggagtggagg tacacaatgc aaagacaaag ccgcgagagg aacaatataa ttccacctat  240
agagtcgtgt cagtccttac ggtcttgcac caggactggc tcaatggtaa ggagtataag  300
tgcaaagtat caaacaaagc tctcgcagcg cccatcgaaa agaccatcag caaagctaag  360
ggccagccaa gagagcctca agtgtacacg ttgccgcctt caagggacga gctcactaaa  420
aatcaggtat cacttacgtg tcttgtcaaa gggttttatc cttccgacat cgcggttgaa  480
tgggagagca atggacagcc ggagaataat tataaaacga cgccgccggt ccttgacagc  540
gatggttcat tttcctttta ctcaaagctg acggttgata agtctaggtg gcagcagggg  600
aacgtctttt cctgtagtgt acttcatgag gcgctccatt ctcattacac tcagaagtca  660
ctgagccttt cacccggcaa aggtggatca gactcctggc aagaagaggt aatcaaactc  720
tgtgggaggg aactcgttcg agcccagatt gcaatctgtg ggaaaagcac aggcggaggg  780
gaagaagggg gtggcgaaga aggtgggggc aggcagctct attcagctct tgccaacaaa  840
tgctgtcatg taggctgcac aaagcgatca ctggcgagat tctgt  885

SEQ ID NO: 139          moltype = DNA  length = 885
FEATURE                 Location/Qualifiers
source                  1..885
                        mol_type = other DNA
                        organism = synthetic construct
SEQUENCE: 139
gataaaactc atacttgccc accctgcccg gctcccgagg cagcaggtgg accctcagta  60
tttttgttcc ctccgaaacc taaagataca cttatgatta gccggacccc tgaggtaacg  120
tgtgtggtgg ttgacgtaag tcatgaagat ccagaagtaa agtttaactg gtacgtagac  180
ggtgtggagg tacataatgc gaagacaaaa ccacgagagg aacagtataa ctctacctac  240
cgcgtagtaa gcgtacttac tgtgctccac caagactggc ttaacgggaa agagtataag  300
tgtaaagtca gtaataaagc actggccgcc ccgatcgaaa aaacaatcag caaggccaaa  360
ggacaaccaa gggagcctca ggtctatact cttcccccga gtagggatga gcttaccaag  420
aaccaggtgt ctctgacatg ccttgtcaag ggattttacc cgagtgacat agccgtagaa  480
tgggagtcaa acggccaacc tgaaaacaac tataagacca cgcctcccgt actcgactca  540
gatggaagct tttcctcta tagcaagctg accgtcgaca aaagtaggtg gcaacaggga  600
aacgtcttta gttgttccgt catgcacgaa gctttgcata accattacac ccagaagagt  660
ctttcccttt cccctggcaa ggggggctcc gactcctggc aagaggaagt aatcaaactg  720
tgtgggcgcg agcttgtccg cgcgcaaata gccatttgcg gaaaaagtac tggaggagga  780
gaggaaggcg gcggcgagga aggtgggggc aggcagctgt acagtgcctt ggctaacaag  840
tgctgccatg tcggctgtac gaaaaggtct cttgctcaat tctgt  885

SEQ ID NO: 140          moltype = DNA  length = 885
FEATURE                 Location/Qualifiers
source                  1..885
                        mol_type = other DNA
                        organism = synthetic construct
SEQUENCE: 140
gataagacac atacctgtcc accctgccca gcacctgaag ctgcaggcgg ccccagcgta  60
ttcctgtttc ctccgaagcc gaaagacaca cttatgattt cccggacgcc tgaggtaact  120
tgcgtcgtag tagatgtgtc tcacgaagac cccgaggtga aattcaactg gtacgttgat  180
ggtgtggaag ttcataatgc gaaaactaaa ccacgagagg agcaatataa ctcaacttat  240
agagttgtga gcgtcttgac ggtactgcac caggactggc tgaatggcaa agagtacaaa  300
tgcaaagtct caaataaggc gttggcggct cccatagaga aaactatcag caaagccaag  360
ggtcaacctc gggagccaca agtgtatact cttccgccta gtcgcgacga gctcacaaag  420
aatcaggtga gtcttacttg tttggttaag ggtttctacc ccagtgacat tgcggtcgag  480
tgggaaagta acggacagcc tgaaaacaac tataaaacaa cgcctccagt actcgattca  540
gatggttcat tctttcttta ttccaaactc acagtcgaca agagtagatg gcaacaaggg  600
aacgtgttta gctgtagcgt actccatgag gcactccact ctcactatac ccaaaagtct  660
ctcagcttgt cacccggaaa aggcggttct gacagttggc aagaggaagt gattaaattg  720
tgtgggcggg aacttgtgag ggctcaaatc gcgatttgcg gcaagtccac tggtggcggc  780
```

```
gaggaaggag gaggtgaaga aggaggaggt aggcaactgt attcagcgtt ggcgaataaa  840
tgctgccatg ttggatgtac taaacggagc cttgctcagt tctgc                  885

SEQ ID NO: 141         moltype = DNA  length = 882
FEATURE                Location/Qualifiers
source                 1..882
                       mol_type = other DNA
                       organism = synthetic construct
SEQUENCE: 141
gataaaacgc atacttgccc tccttgcccg gcacctgaag ctgccggagg tccttccgtg  60
ttcctgttcc cacctaagcc aaaagacaca cttatgattt ctcgcacacc agaagtaacg  120
tgcgtcgtag ttgacgtctc ccatgaagac ccggaggtaa aatttaattg gtacgtcgac  180
ggggtagaag ttcataacgc aaagactaaa ccacgagaag agcaatacaa ctctacatac  240
agagtagtaa gcgttctcac cgttcttcat caagattggc tcaacggaaa ggagtataag  300
tgtaaggtgt ccaataaagc gttggccgca ccaatcgaaa agaccataag caaagccaaa  360
ggccaacccc gcgaaccgca ggtgtacaca cttcccccgt ccagggatga attgacaaaa  420
aaccaagttt ccctcacgtg tctcgtcaag ggattctacc cgagtgatat cgcagttgaa  480
tgggaaagca atggtcagcc cgagaataac tacaagacta ctccccctgt gttggactca  540
gacggctcat tcttcctcta cagtaagttg actgtggaca aaagtcggtg gcagcaaggc  600
aatgtcttca gttgtagtgt aatgcatgaa gcactccaca atcattacac ccaaaaatcc  660
ctgagcctgt ccccgggcgg aggttcagat tcatggcagg aggaagttat aaaactgtgc  720
gggcgcgagt tggtgagggc gcagatcgca atctgtggaa agagtacggg aggtggcgaa  780
gagggtggtg gagaagaggg aggaggtcga caactgtatt ccgcgctcgc gaacaagtgt  840
tgccacgttg gctgcaccaa acgaagcctg gctcgatttt gc                     882

SEQ ID NO: 142         moltype = DNA  length = 882
FEATURE                Location/Qualifiers
source                 1..882
                       mol_type = other DNA
                       organism = synthetic construct
SEQUENCE: 142
gacaagacac acacttgtcc accttgcccg gctcccgagg cggcaggagg accaagcgtt  60
tttctgttcc ctcccaaacc aaaggatacg cttatgatct ctcgaacgcc ggaagttact  120
tgcgtagtag ttgatgtctc ccatgaagat cccgaagtga agttcaactg gtatgtagat  180
ggtgtggaag ttcataacgc gaaaaccaaa ccacgcgaag aacagtataa cagtacttat  240
cgggttgttt cagtactcac ggtgctccat caagactggc ttaatggaaa ggagtataaa  300
tgtaaggtaa gtaacaaggc attggcggct cccatcgaga agacaatctc caaagcaaaa  360
gggcaaccac gggagcctca ggtgtatacg ttgccgccca gcagagatga acttactaag  420
aatcaggtga gtctcacttg tctcgtcaag ggcttctatc ccagcgatat agccgtagaa  480
tgggagagta acggtcagcc ggagaacaac tacaaaacaa ccccgcctgt tttggactcc  540
gatgggagtt tttttctcta cagcaaactc acggtagaca aaagcaggtg gcagcagggc  600
aatgttttca gttgctctgt tctccacgaa gccctccact cccactatac tcagaagtct  660
ctgagtctct caccaggggg aggtagcgat agctggcagg aggaagtgat caagttgtgc  720
gggcgcgaac tcgtgcgggc acaaattgct atatgcggta aaagtacggg aggtggagag  780
gagggtggag gtgaagaagg cggtggtaga caattgtata gtgcgctcgc caacaagtgt  840
tgtcatgtcg ggtgtacgaa acggtccttg gcgcggtttt gc                     882

SEQ ID NO: 143         moltype = DNA  length = 882
FEATURE                Location/Qualifiers
source                 1..882
                       mol_type = other DNA
                       organism = synthetic construct
SEQUENCE: 143
gacaagacac atacttgtcc accatgtccc gccccagaag ctgcgggagg accatcagtt  60
tttttgttcc ccccgaaacc gaaggatacc ctcatgataa gtcgaacgcc cgaagtcact  120
tgcgtggtgg ttgatgttag ccacgaggac ccagaagtga agttcaactg gtacgtggac  180
ggggtcgaag ttcataatgc gaaaacaaag cctcgcgagg aacagtacaa ctctacatac  240
agggttgtgt ctgttttgac agtcttgcac caagattggc tcaacgggaa ggaatataag  300
tgtaaggtaa gcaataaagc actggcggcc ccgatcgaaa aaacgatatc caaggccaag  360
ggccagcccc gagagcctca ggtatatact ctgccgccaa gccgggatga actgactaaa  420
aaccaggtct ctttgacttg tcttgtcaag ggattttacc caagtgacat tgcggtagag  480
tgggaaagca acggtcaacc agaaaacaat tacaagacga caccgccggt actcgactca  540
gatggatcct ttttcctgta tagcaagctg acagtggaca agtcccggtg gcagcaaggg  600
aacgtatttt catgcagcgt gatgcatgag gctcttcaca accattacac acagaaaagt  660
ctgtcattga gccctggcgg cgggagcgat tcttggcaag aagaagttat aaaactttgc  720
ggtcgagagc tggttcgggc acaaattgct atctgcggaa aatctacagg aggaggcgag  780
gagggagggg gcgaagaagg cggggggaga cagttgtaca gtgcgctcgc taacaagtgt  840
tgccacgtcg gttgcacaaa gagatccctg gctcaattct gt                     882

SEQ ID NO: 144         moltype = DNA  length = 882
FEATURE                Location/Qualifiers
source                 1..882
                       mol_type = other DNA
                       organism = synthetic construct
SEQUENCE: 144
gataaaactc acacctgtcc cccgtgtccc gcaccagaag cggccggtgg tccctccgtt  60
tttctcttcc ctcctaaacc taaggacaca cttatgatta gcagaactcc agaagttacg  120
tgcgtagtcg ttgacgttag tcatgaagat cctgaggtta agttcaactg gtacgtagac  180
ggagtagagg tccacaacgc caagacgaaa ccccgagaag agcagtataa ttctacctat  240
```

```
cgagttgttt cagtattgac ggtgcttcac caagattggc tgaatggcaa agagtataag  300
tgcaaggtaa gcaacaaagc actcgcggct cctatcgaga aaactatttc caaagctaag  360
ggccagcctc gcgaaccaca agtctatacc ctgccaccga gtcgggacga actcaccaag  420
aaccaagtgt ctcttacttg cctcgttaaa ggtttttatc ccagcgacat agccgtcgaa  480
tgggagtcca atggccaacc tgagaacaac tataaaacta cccctcctgt acttgatagc  540
gacggaagtt ttttcctcta ttcaaaactc acagttgata agtctcgatg gcaacagggc  600
aacgtcttct cttgcagtgt gttgcatgaa gctctgcact ctcattacac acagaagagt  660
ttgtctctca gtccaggtgg cggctcagat agctggcagg aagaagtaat caagttgtgc  720
ggcagggaac tggtaagggc acagatagcc atttgtggaa aatctacggg tggcggtgag  780
gaaggcggcg gagaagaagg gggaggtcgg cagctgtata gtgcactcgc aaacaagtgc  840
tgccatgtcg ggtgcaccaa gcgatccctt gcccagtttt gc                    882

SEQ ID NO: 145         moltype = DNA  length = 885
FEATURE                Location/Qualifiers
source                 1..885
                       mol_type = other DNA
                       organism = synthetic construct
SEQUENCE: 145
gacaaaacgc acacctgtcc accgtgtcct gctccagagg cggccggggg accgtccgtt  60
ttcctttttc ctcccaaacc taaggatacc cttatgatct ctcgcacgcc cgaggttacc  120
tgtgttgtgg ttgacgtgtc ccatgaagac ccggaagtaa aatttaattg gtacgtggac  180
ggggtcgagg ttcataacgc aaagaccaag ccacgagagg agcaatataa ttccacctat  240
cgcgtagtct ccgtcctcac cgtgcttcac caggattggc tcaacgggaa ggaatacaaa  300
tgtaaagtca gtaataaggc tttggcggcc ccgattgaga agactataag taaggctaag  360
ggacagccac gagaaccgca agtttataca ttgccccccct ctagggatga gttgactaag  420
aatcaggtgt cactcacttg tctggtaaaa gggttctacc cgtccgacat cgctgtggaa  480
tgggaaagca atgggcaacc tgaaaataat tataagacaa cccctccggt gcttgatagc  540
gacggatcat tctttctcta ttccaagctt actgtagata agagtcgatg gcaacagggg  600
aacgtattca gttgctctgt tctccatgag gccctgcata gtcactacac ccaaaaaagc  660
cttagtttga gtcccgggaa aggaggctcc gattcttggc aagaagaggt aataaagctg  720
tgtggacgag aacttgtccg agcacaaatt gcgatttgtg gcaaatctac aggaggggga  780
gaaggaggcg gcgaaggggg aggcgagggc aggcaggatt attccgctct ggcgaacaaa  840
tgttgccatg ttggatgcac gaaacgaagc ctggctcagt tttgc                 885

SEQ ID NO: 146         moltype = DNA  length = 882
FEATURE                Location/Qualifiers
source                 1..882
                       mol_type = other DNA
                       organism = synthetic construct
SEQUENCE: 146
gataaaacgc atacctgccc accgtgtcct gcacctgagg ccgctggagg accttccgtc  60
ttcctctttc cacccaagcc gaaagacaca ctcatgatta gtagaactcc agaggtcacg  120
tgtgttgtgg tggacgtcag tcacgaggac cctgaggtta agttcaactg gtacgttgat  180
ggcgtagaag tccacaatgc aaagaccaaa ccgagagagg agcaatataa cagtacatat  240
agggttgtta gcgtacttac tgttttgcat caagactggt tgaatgggaa ggaatataaa  300
tgtaaagtct ccaacaaggc tctggctgca ccaatagaaa aaactatttc taaggcaaag  360
ggtcagccta gagagcctca agtctatacc ttgccaccgt caagagacga gctcactaaa  420
aatcaggtga gcctgacctg tcttgtgaag ggcttttacc cgtcagatat tgccgtggag  480
tgggaatcaa acggtcagcc ggagaataac tacaagacga ccccaccagt actcgatagc  540
gatgggtctt tctttctgta ctccaagctc accgtggaca aatcacgctg gcaacagggc  600
aacgtcttta gttgcagcgt actgcacgag gcactgcaca gccactacac acaaaagagt  660
ctttctctgt ctcccggtgg tggctccgat agttggcagg aagaagtcat aaagctttgt  720
ggaagagagc ttgtacgagc gcagattgca atctgcggga agagcactgg aggaggtgag  780
ggagggggtg agggcggggg cgaaggacgc caggactatt cagcacttgc aaacaaatgc  840
tgccatgtag ggtgtacgaa gcgctcactg gcccggtttt gc                    882

SEQ ID NO: 147         moltype = DNA  length = 882
FEATURE                Location/Qualifiers
source                 1..882
                       mol_type = other DNA
                       organism = synthetic construct
SEQUENCE: 147
gataaaacac atacctgccc cccatgccca gcccccgaag ctgcaggggg gccctctgtt  60
ttccttttc cacccaaacc taaagatact ctgatgatta gtcggactcc ggaagtgact  120
tgcgtcgttg tcgacgtctc tcatgaggat ccagaagtta agtttaactg gtatgtcgac  180
ggggttgagg ttcataatgc aaaaactaaa ccgagagaag aacagtacaa ctctacttat  240
agggttgtca gtgtactgac cgtcctgcac caggattggc ttaacggtaa ggagtataag  300
tgtaaagtgt ccaataaagc ccttgccgca cccatcgaga aaaccatctc caaggcaaaa  360
ggacagccaa gggaaccgca ggtatataca cttccgccaa gccgagacga acttacgaag  420
aaccaggtgt ctctcacgtg tctcgtaaaa gggttttatc ccagcgatat cgcagttgag  480
tgggagagca atgggcagcc agagaataat tataagacaa cccctcccgt gctggattca  540
gacgggagtt tttttcttta ctctaagctg accgtagaca aaagtcgatg gcagcaaggc  600
aacgtctttt cctgctccgt tctccatgaa gcactgcata gccattatac ccagaagtca  660
ctgagcctct ctccaggggg cgggtccgat tcatggcagg aagaggtaat caaactctgt  720
ggacgcgaac tggttcgcgc gcagatagcg atttgcggca aaagcacagg cggtggggaa  780
ggcggtggcg agggcggtgg tgaaggtcga caagattatt ctgctctcgc taacaagtgt  840
tgtcatgtag gatgtactaa aaggagtctt gcgcagttct gt                    882

SEQ ID NO: 148         moltype = DNA  length = 885
```

```
FEATURE                Location/Qualifiers
source                 1..885
                       mol_type = other DNA
                       organism = synthetic construct
SEQUENCE: 148
gataagacgc acacatgccc accctgtcct gcgcctgaag ccgcgggggg acccagcgtt  60
tttctcttcc cgccgaaacc gaaagacaca cttatgatca gccggactcc cgaggttacc  120
tgcgtggtgg tagatgtatc tcacgaggat cccgaggtca aattcaactg gtacgttgat  180
ggggttgaag ttcataatgc caaaacgaag ccaagagaag agcagtataa ctccacatat  240
agagttgttt ccgtcttgac tgttcttcac caagattggc tgaatgggaa ggagtacaaa  300
tgtaaagtta gcaacaaggc actcgccgct cccattgaaa aaactataag caaagctaag  360
ggccaaccgc gcgaaccaca ggtctacacg ttgccgccct ctagggacga actcacgaag  420
aatcaggttt cccttacctg cctcgttaaa ggattctacc cctctgacat agcggttgaa  480
tgggagagca acggtcagcc tgagaacaac tacaaaacga cgcctccggt gttggattcc  540
gacggtagtt ttttcctcta tagtaagctg acagtggata aatctcggtg gcagcaaggg  600
aatgtattct cctgttcagt cctgcatgaa gccctccact cccattatac acagaaatct  660
ctttctctga gtcccggtaa aggtgggagt gactcttggc aggaagaggt aattaagttg  720
tgtggaaggg agctggtaag agcacagatt gccatctgtg gcaaatccac gggcggcgaa  780
ggtgaggggg gtgaggggga agggggtcc agacaactgt attctgctct ggcgaataag  840
tgttgccatg tagggtgcac taaacggtcc ttggcgcagt tctgt               885

SEQ ID NO: 149         moltype = DNA  length = 882
FEATURE                Location/Qualifiers
source                 1..882
                       mol_type = other DNA
                       organism = synthetic construct
SEQUENCE: 149
gataaaactc atacgtgccc accttgcccc gcaccggagg ctgctggagg accctctgtc  60
ttcctgttcc cgccgaagcc taaagacaca ttgatgatca gtcgaacacc ggaagtcacc  120
tgtgtagtgg ttgatgtgag ccatgaggac cctgaagtaa aatttaactg gtatgttgat  180
ggcgtagaag tacacaacgc gaagactaaa ccaagggaag agcaatacaa ctctacctat  240
agggtcgtta gcgtactgac tgtgcttcac caagactggc ttaacgggaa ggagtacaag  300
tgcaaagtga gcaataaggc cctcgccgcg cctatcgaga aaaccatttc caaagccaag  360
ggtcaaccaa gggagcctca ggtttacacc ctgccccctt caagggatga gttgacaaaa  420
aaccaggtaa gtctgacgtg tctcgttaag ggattctacc cgtcagatat cgcggtagag  480
tgggagagca acggtcagcc agaaaataat tacaaaacaa cacctccagt tttggactct  540
gatgggagtt tttttcttta ttctaagttg acagtggata agtcacgctg gcaacagggg  600
aacgtattta gctgctcagt acttcatgaa gcgttgcatt ctcactacac acagaagagc  660
ctctccttga gtcccggagg tggctctgat tcttggcagg aggaggtaat aaaactttgt  720
ggtagagaac tggttcgcgc tcagatagct atttgtggaa aatccactgg cggtgaaggt  780
gaaggtggag aaggagaggg cggaagccgg cagttgtact ctgccctggc taataagtgc  840
tgtcacgtgg gctgcactaa gcggagcttg gcaagatttt gc                    882

SEQ ID NO: 150         moltype = DNA  length = 882
FEATURE                Location/Qualifiers
source                 1..882
                       mol_type = other DNA
                       organism = synthetic construct
SEQUENCE: 150
gataaaactc atacctgtcc accttgtcct gcgcctgagg cagctggagg gcctagcgtg  60
ttcctgttcc cccccaaacc caaagacacg ctcatgatta gccgaacccc tgaagtgacc  120
tgcgttgttg tggacgtaag ccacgaagac cccgaagtta agtttaattg gtacgtcgac  180
ggtgttgagg ttcataacgc gaagactaag ccgagagagg agcaatataa cagcacctac  240
cgcgtagtct cagttcttac cgtgctccac caggactggc ttaacgggaa ggaatacaaa  300
tgcaaagttt ccaacaaagc cttggcagcc ccaatagaga agacaatatc taaggcgaaa  360
ggccaaccgc gggaaccgca agtttatacc ctcccaccga gcagggatga gctgacaaaa  420
aatcaggttt ccctcacttg tctggtcaag ggattttatc cttcagacat agccgttgaa  480
tgggagagta atgggcagcc ggagaataat tacaagacca cccccccggt gttggacagc  540
gacggttcct tctttctcta ttctaaactt accgtcgaca aatcacggtg gcaacaagga  600
aatgtattct catgcagtgt attgcacgaa gctctgcact ctcattacac ccaaaaatcc  660
ctctctctca gccctggcgg tggatctgat tcttggcagg aagaggtgat taaactgtgt  720
gggcgagagc ttgtccgagc tcagatcgct atttgtggca agagtaccgg aggcgagggt  780
gagggaggcg aaggcgaggg cggaagccgg caactctata gcgcactcgc taataaatgt  840
tgtcatgtcg gctgcacgaa gcgctcactg gcgcagttct gc                    882

SEQ ID NO: 151         moltype = DNA  length = 885
FEATURE                Location/Qualifiers
source                 1..885
                       mol_type = other DNA
                       organism = synthetic construct
SEQUENCE: 151
gacaaaacgc atacctgtcc tccatgcccc gctcccgagg ctgccggcgg accaagcgta  60
tttctcttcc cccctaaacc taaagacaca ttgatgataa gtaggacgcc tgaagtaacg  120
tgtgttgtcg ttgatgtaag ccatgaagat cctgaagtaa agtttaattg gtatgttgat  180
ggcgtagaag tacataacgc taagacgaag ccacgggaag agcagtataa ctcaacttac  240
cgcgttgtaa gcgtgcttac cgtcctgcat caggattggc tgaatggtaa ggaatataag  300
tgcaaagtaa gcaacaaagc attggccgca ccaatagaga agacgattag taaagcaaaa  360
ggccagccca gagagccgca ggtttataca cttccaccaa gcagagatga acttacgaag  420
aaccaggtgt ctctgacttg tctggtcaag ggtttctatc cttccgacat tgcagtggag  480
```

```
tgggaaagca atgggcagcc cgaaaacaat tataagacga cacctccagt gttggactca  540
gacggttcct ttttcttgta ttccaaactt acagtggata agtcaaggtg gcagcaaggc  600
aacgtatttt cttgtagtgt tttgcacgaa gccctgcatt cccactatac tcaaaagagc  660
ctcagtctgt ccccaggaaa gggagggagt gacagttggc aagaggaggt aataaaattg  720
tgtggcagag agcttgtgcg cgctcagatc gcaatatgcg ggaaatctac tgggggtgag  780
ggtgagggcg gcgagggaga ggggggcagt cgccaagatt attccgccct tgcgaataag  840
tgttgtcacg tcggatgtac taagagatca ttggctcagt tttgt                   885

SEQ ID NO: 152         moltype = DNA  length = 945
FEATURE                Location/Qualifiers
source                 1..945
                       mol_type = other DNA
                       organism = synthetic construct
SEQUENCE: 152
atggagacgg acactttgct gctttgggta ctgctgcttt gggttcctgg atctactggc  60
gataaaacac acacgtgtcc cccctgcccg gctccagagg cggctggtgg tcccagcgta  120
ttcttgtttc ctcccaaacc taaggatacg ctcatgatat cccgcacccc agaagttacg  180
tgtgtagtcg tcgacgtcag tcacgaagat ccagaggtca aatttaactg gtatgtcgac  240
ggagtagagg tccacaatgc gaaaaccaag cccagagaag agcagtacaa ctccacgtat  300
cgcgtcgtct ccgtcctcac cgtactccat caagattggc tgaatgggaa agagtataaa  360
tgcaaagtat ctaacaaggc tctgccagct ccgatagaaa agactatatc aaaggccaag  420
gggcagccaa gggagcctca agtctatact ttgcccccat ctcgggatga gcttacgaaa  480
aaccaggtca gccttacctg tcttgttaaa ggtttttatc cgagtgacat cgcagtggaa  540
tgggaatcta atggtcaacc tgaaaacaat tacaaaacca caccgccagt attggacagc  600
gatggtagtt tttttcttta ctcaaaactg actgtagata aaagcagatg gcagcagggc  660
aatgtctttt catgtagcgt tatgcatgag gctcttcaca accactatac ccaaaagtca  720
ttgtctctta gtcccggaaa gggcggaagt gattcttgga aggaggaggt aatcaagttg  780
tgcgggcgag agttggtacg ggcacagatc gcgatatgcg gaaaatccac aggtgggggc  840
gaaggaggag gtgagggtgg aggtgaagga cgacagttgt attccgcctt ggcaaacaag  900
tgttgccatg tgggttgcac aaaacgcagt cttgcccgct tctgt                   945

SEQ ID NO: 153         moltype = DNA  length = 948
FEATURE                Location/Qualifiers
source                 1..948
                       mol_type = other DNA
                       organism = synthetic construct
SEQUENCE: 153
atggagaccg atacgctgtt gctgtgggta ttgcttctct gggtgcccgg ctcaactggg  60
gataagacac atacatgccc tccctgtccg gctccagagg cagccggggg tccatcagtc  120
ttcctttttc cgcctaaacc taaggataca ctgatgatct ctcgaacacc ggaggtcact  180
tgtgttgtcg ttgacgtatc acatgaggat cccgaagtaa agttcaactg gtatgtcgat  240
ggtgtggagg ttcataatgc taaaactaaa ccacgggagg agcaatataa ttccacatat  300
agggtcgtga gcgtgttgac ggtgcttcat caagactggc ttaatgggaa ggaatataaa  360
tgcaaagtgt caaataaagc acttcctgcg ccaatcgaga aaacaattag taaggcaaag  420
gggcagccgc gagaacctca ggtgtacacc ttgccgcctt ctagagacga gctcacaaag  480
aaccaagttt ccctgacttg cctcgttaag gggttttatc cgtccgatat agccgtggag  540
tgggagtcaa acggccaacc ggaaaataat tacaaaacga cacccccagt attggatagt  600
gacggctctt ttttccttta ttctaagctg actgtggaca aaagccgctg gcagcagggc  660
aatgtctttt catgcagcgt aatgcatgaa gccctgcaca accactacac gcaaaaatcc  720
ctttccttgt cacccggcaa gggcggctct gactcctgga aagaggaagt tataaaactc  780
tgtggccgag aacttgttcg agctcaaatc gcgatttgtg gtaagtcaac gggtgggggc  840
gaaggtggag gcgagggtgg gggagaagga ggaggccagt tgtactcagc tcttgcaaat  900
aagtgttgcc acgttggttg tacgaagcgg agccttgctc gcttctgc                948

SEQ ID NO: 154         moltype = DNA  length = 945
FEATURE                Location/Qualifiers
source                 1..945
                       mol_type = other DNA
                       organism = synthetic construct
SEQUENCE: 154
atggaaactg atactcttct gctgtgggtc ctgctgctgt gggttccagg atctactgga  60
gacaaaacac atacttgtcc gccttgcccg gcacccgaag cggccggcgg acccagtgtc  120
tttctcttcc cacccaaacc gaaagacact ctgatgattt ccaggacgcc tgaagtgacc  180
tgcgttgtag ttgatgtatc acacgaggat cccgaggtca agttcaattg gtatgtagat  240
ggggtggagg tccataatgc aaagacgaag ccacgggagg aacagtacaa ctctacgtac  300
agagttgtca gtgttttgac cgtccttcat caggattggc tgaacggtaa agaatataaa  360
tgcaaggtta gcaataaagc tttgcccgcc cctatagaga aaacgatcag taaggcgaag  420
gggcagccta gggaacccca ggtatatacc ttgccgccaa gtcgagatga gctgacgaag  480
aaccaagtga gtctgacatg cctcgtgaag ggcttctatc cgagcgatat cgctgtcgaa  540
tgggagagca atgggcagcc tgagaataac tataaaacaa cgccacccgt cctcgactcc  600
gatggctcat tcttcctgta cagtaaactt acagtagata agagtagatg gcagcagggt  660
aacgtcttta gttgctccgt gatgcacgag gcattgcaca atcattacac tcaaaaatct  720
ctgtccctga gtccgggcaa aggcggttca gatagctgga tggaggaggt cataaagctt  780
tgtggacgag aactcgttcg cgcccagata gctatttgtg ggaaatcaac cgggggtgga  840
gaaggtggcg gagaaggggg aggcgaaggg cgccaactgt attctgcatt ggctaataag  900
tgctgtcacg taggatgtac aaaaaggtct ctggcgagat tctgc                   945

SEQ ID NO: 155         moltype = DNA  length = 945
FEATURE                Location/Qualifiers
```

```
source                  1..945
                        mol_type = other DNA
                        organism = synthetic construct
SEQUENCE: 155
atggagaccg acaccctctt gttgtgggtt ctcctcttgt gggtgcccgg cagtactgga  60
gacaagacgc acacttgtcc accttgccct gcgccggaag ctgctggagg ccccagtgtc  120
tttttgttcc cgcccaaacc gaaggacact ttgatgataa gtcgcacgcc cgaggttacc  180
tgtgtggttg tcgatgtctc acacgaagat ccggaggtga agtttaattg gtatgtagat  240
ggcgtggagg ttcataacgc caaaacgaaa cccagagaag aacaatataa cagtacatat  300
cgagtagtat ccgttctcac tgtcctgcat caagactggt tgaacgggaa ggaatataag  360
tgcaaggtga gcaataaagc actcccggcc ccaatcgaaa agaccatcag caaagcgaag  420
gggcaacctc gagaacccca ggtatatacg ctccccccta gtcgggatga acttactaaa  480
aatcaggtta gcctcacttg ccttgttaaa gggttctatc ccagtgatat tgccgtcgaa  540
tgggaatcaa acgggcagcc ggaaaataac tacaagacaa cccctcctgt gctcgatagc  600
gatggctctt ttttcctcta cagcaaactt accgttgata agagccggtg gcaacaaggt  660
aatgttttct cctgctccgt tatgcatgaa gcactccata accattatac ccaaaaaagc  720
ctgtcactta gtccgggtaa aggaggtagt gattcttggc aggaggaggt aatcaaactt  780
tgtgggaggg agctggtacg agctcagatt gctatatgtg gaaaaagcac gggcggagga  840
gaaggaggtg gcgaaggcgg gggtgaaggt cggcaactct actccgctct cgctaataag  900
tgctgccacg tcgggtgtac gaagcgctcc ctggcgcgat tctgc                   945

SEQ ID NO: 156          moltype = DNA  length = 945
FEATURE                 Location/Qualifiers
source                  1..945
                        mol_type = other DNA
                        organism = synthetic construct
SEQUENCE: 156
atggaaacag ataccctcct cctctgggtc cttcttcttt gggtgcctgg ctcaactgga  60
gataaaaacgc acacgtgtcc gccctgccca gcgcctgaag ccgcaggcgg gccgtccgtc  120
ttcctctttc ctccaaaacc caaagacaca cttatgatca gtaggacccc agaggtaacc  180
tgcgtcgtgg tcgacgtttc ccatgaagac ccagaggtca agttcaactg gtacgtcgac  240
ggtgtcgaag tacataatgc taaaacgaag cctcgggaag agcagtacaa ctctacctac  300
cgcgtcgttt ccgtactcac cgtacttcac caggactggc ttaacggtaa agagtataaa  360
tgcaaagtat ctaataaggc tctcgccgcg ccgattgaga agacaatttc aaaggccaag  420
gggcagccgc gggagcccca agtgtatacc ttgcccccgt cccgagatga gctgactaaa  480
aaccaagtaa gcttgacttg cttggtcaaa ggcttctacc cttccgatat agctgtcgaa  540
tgggagtcaa atggccaacc agagaacaat tataaaacta cacccccggt cttggattct  600
gatggctcat tttttctcta ttctaaactg accgtggata agtctcgctg gcagcaaggt  660
aacgtgttca gttgctctgt tcttcacgaa gcactgcaca gtcattacac tcagaagagt  720
cttagcctga gccctggtaa aggggggttct gattcctggc aggaggaagt aataaaactc  780
tgtggccggg agttggtacg ggcgcagatt gcgatatgcg gtaagagcac cggcggaggc  840
gaaggcggtg gggaaggagg aggagaaggg agacaactct attccgcatt ggcaaataag  900
tgctgccacg tcgggtgtac caaacgatcc cttgcacggt tctgt                   945

SEQ ID NO: 157          moltype = DNA  length = 948
FEATURE                 Location/Qualifiers
source                  1..948
                        mol_type = other DNA
                        organism = synthetic construct
SEQUENCE: 157
atggagacgg acaccctcct tctctgggtt ttgctccttt gggtccctgg ttccactgga  60
gataagaccc atacgtgccc cccttgccct gcgcctgagg cagcgggtgg cccatcagtc  120
tttttgttcc cgcccaagcc aaaggacacc ctcatgatta gtagaacacc ggaggttacg  180
tgcgtcgtag tggatgtcag ccacgaggat cccgaggtta agtttaactg gtacgttgat  240
ggggttgagg tccataatgc gaagactaag ccgagagagg aacagtacaa ttccacgtat  300
agagttgtct ctgtactgac tgtgctgcat caagattggc ttaacggtaa ggagtacaag  360
tgcaaagtct ctaataaggc tcttcctgca cccattgaga aaactataag caaagcaaaa  420
ggtcaacctc gcgaacctca ggtgtacaca ctgccaccct ctagggacga gcttaccaaa  480
aatcaagtat ctcttacctg ccttgtgaaa gggttttatc cctcagatat tgcggttgag  540
tgggagtcta acggacaacc tgagaacaac tataagacta ctcccccggt gcttgattca  600
gacgggagtt ttttttgta tagcaaactt accgtcgaca aaagccggtg gcaacagggc  660
aatgtattca gttgttctgt aatgcatgaa gctttgcata atcattacac ccaaaagagt  720
ctttccctgt ctcctggaaa aggggggtca gactcctgga tggaggaggt gatcaaactg  780
tgtgggagag agctcgtccg ggctcagata gctatatgcg gcaagtctac gggtggggga  840
gagggcggag gagagggcgg tggagaagga ggcggccaac tctacagcgc tctggccaat  900
aaatgttgtc atgtcgggtg tactaagcgc tcactggcac gcttttgc                948

SEQ ID NO: 158          moltype = DNA  length = 948
FEATURE                 Location/Qualifiers
source                  1..948
                        mol_type = other DNA
                        organism = synthetic construct
SEQUENCE: 158
atggaaaccg acaccctttt gttgtgggta ttgctgttgt gggttcccgg tagcacgggg  60
gacaagacgc atacatgccc gccatgcccg gcccccgaag ctgctggggg accatccgta  120
ttcctcttcc ctcccaaacc aaaagacacg ttgatgataa gtagaacacc agaggtaacg  180
tgcgtggttg tcgatgtttc ccacgaagat ccggaggtaa aattcaattg gtatgtagat  240
ggggtggaag tgcacaatgc caaaacaaag ccgcgagaag aacaatacaa tagtacttac  300
cgggttgtga gcgtgctcac ggtgttgcac caagactggc tcaacggcaa ggaatacaag  360
```

tgcaaagtat ctaataaagc tctgcctgcg ccgatagaga agaccatcag taaggccaaa 420
gggcagcccc gagagccgca agtttacact cttcctccga gcagagatga attgaccaag 480
aaccaagtaa gtttgacgtg cctggtgaag ggcttctacc cctcagacat tgcggtggag 540
tgggaaagta atggtcaacc ggaaaacaac tacaagacca cgccgcccgt cctcgactcc 600
gatgggtctt tctttcttta ttcaaagttg acagtagata agtcaaggtg gcagcaaggt 660
aacgtgttta gttgtagtgt aatgcacgag gccctgcata atcattatac ccaaaagagt 720
ttgagcctct caccaggaaa aggcggatca gacagctggc aggaggaggt aattaaattg 780
tgtggacggg agttggtcag ggcgcaaata gccatctgcg gtaagagcac gggtggagga 840
gagggtggag gggaaggtgg gggagaaggc ggcgggcagc tctattctgc actcgccaac 900
aagtgttgtc acgtcggatg cacaaagaga tctcttgctc gattctgc 948

SEQ ID NO: 159 moltype = DNA length = 948
FEATURE Location/Qualifiers
source 1..948
mol_type = other DNA
organism = synthetic construct
SEQUENCE: 159
atggagactg atactctttt gttgtgggta ctgctcctgt gggttccagg ctccacagga 60
gacaaaacac acacctgtcc gccttgcccg gctcctgaag ccgcgggtgg ccctagtgtg 120
tttttgtttc cgccgaaacc taaggatacc ctcatgataa gccggacgcc cgaggttacc 180
tgtgtcgtgg tcgatgttag tcatgaggat ccagaagtca agtttaattg gtacgtcgac 240
ggcgttgaag tccacaatgc aaaaactaaa ccgcgagaag aacagtacaa ctccacctac 300
agagttgtct cagttttgac agttctccat caggattggc tcaatggaaa ggaatataag 360
tgcaaggtca gcaataaagc gcttgccgcc cctatagaga agaccattag caaggcgaaa 420
ggacagcccc gcgagcccca ggtctatacg ctgcctccta gcagagatga gctcacgaaa 480
aatcaggtca gcttgacatg cttggtgaag ggcttctacc ccagtgacat cgcagttgaa 540
tgggagagca acggccaacc tgagaacaac tacaaaacaa cgccccccggt tcttgacagc 600
gatgggtcct tctttcttta ctctaagctt acagttgata aaagcaggtg gcagcagggg 660
aatgtgttct catgttccgt actgcatgag gctctgcatt ctcactacac ccaaaaaagc 720
cttagcctga gccccggtaa gggaggtagt gactcatggc aagaggaagt gattaagctc 780
tgcggccggg agttggtgag agcccaaatc gccatttgcg gtaaaagtac cggagggggc 840
gagggaggag gcgaaggtgg aggtgaagga ggtggacagt tgtactcagc tcttgcaaat 900
aaatgttgtc atgttggttg cacgaaaaga tctcttgcga ggttctgt 948

SEQ ID NO: 160 moltype = DNA length = 945
FEATURE Location/Qualifiers
source 1..945
mol_type = other DNA
organism = synthetic construct
SEQUENCE: 160
atggagactg acactctttt gttgtgggtg cttcttctgt gggtacctgg atccactggg 60
gataagacgc atacttgtcc accgtgcccc gcaccggaag cggctggtgg tccatcagtt 120
tttctgttcc caccgaaacc taaggacacg ttgatgatat cacggacacc agaggttacg 180
tgcgtagtgg tggatgtgag ccacgaggat ccagaagtta aatttaattg gtacgtagat 240
ggagtggagg ttcataatgc gaagacaaag cctcgcgagg aacagtataa ttccacctat 300
cgcgtcgtat ctgtgcttac ggtacttcac caagactggt tgaacggtaa ggaatataaa 360
tgcaaggttt ccaataaagc acttcctgcg ccaattgaga agacaatatc caaagctaaa 420
ggtcaaccca gggaaccgca agtctacact ctccccccgt ctcgcgatga attgacgaag 480
aaccaggtta gtctcacctg cctggtcaag ggttttaccc cctctgacat agctgtagaa 540
tgggagtcta atggacagcc agagaacaat tacaaaacga cccccccggt cctcgattct 600
gatgggagtt tttttcttta ttcaaaattg actgtcgata agtcaagatg gcaacagggt 660
aacgtatttt cttgcagtgt tatgcatgaa gcattgcaca accactatac acaaaaatca 720
ttgagtttga gtcccggtaa agggggaagc gactcatgga tggaagaagt aatcaagctg 780
tgcgggcgag agcttgtgcg agctcagata gcaatctgtg gtaagtctac aggtggagag 840
ggtggcggtg aagaaggcgg gggagaggga ggccagcttt attctgccct ggctaacaag 900
tgctgtcacg ttggatgcac gaagcgctcc ctggcccgat tctgc 945

SEQ ID NO: 161 moltype = DNA length = 945
FEATURE Location/Qualifiers
source 1..945
mol_type = other DNA
organism = synthetic construct
SEQUENCE: 161
atggaaaccg atacattgct tttgtgggtc ctccttcttt gggttcctgg ctctacaggc 60
gataagacgc atacttgtcc cccatgtccc gctccggaag ccgctggcgg cccctccgtt 120
tttctgttcc cgccgaaacc gaaagacacc ctgatgatat cacgcactcc cgaggtcact 180
tgcgtggtag tcgatgttag tcatgaagat cctgaggtca aattcaattg gtatgtagat 240
ggcgttgagg tacacaacgc gaagacaaaa ccccgagaag aacagtataa ctcaacctac 300
cgcgtagttt cagttcttac cgtactgcac caagactggt tgaacggtaa agagtacaaa 360
tgtaaagtca gcaataaagc tttgccagca cctatcgaaa aaaccatcag taaggccaag 420
ggtcaaccca gggagccgca agtgtacact cttcccccta gcagggatga attgaccaag 480
aatcaggtct ctttgacgtg cctcgttaag ggtttctatc ccagcgatat agccgtagaa 540
tgggagtcta acggtcagcc agaaaataac tataagacaa ccccgcctgt tttggattcc 600
gacggctctt tttttctcta ctctaagttg accgttgata agagcagatg gcagcaggga 660
aacgtatttt cttgttccgt gatgcacgaa gccctgcaca atcactatac gcaaaagtct 720
ctgagcttga gtccgggtaa aggcggttct gactcctggc aggaggaagt cataaaactc 780
tgcggaagag agctcgtaag ggcgcaaatc gctatttgtg gtaagagcac cggtggggaa 840
ggaggcggtg aagagggtgg cggcgagggt gggcaattgt attccgcgct tgccaataaa 900
tgttgtcacg taggctgcac aaagcgaagt ctcgctaggt tctgc 945

```
SEQ ID NO: 162          moltype = DNA  length = 942
FEATURE                 Location/Qualifiers
source                  1..942
                        mol_type = other DNA
                        organism = synthetic construct
SEQUENCE: 162
atggaaaccg acaccttgct tttgtgggtg ctcttgctgt gggttccggg gagcactggc  60
gacaagaccc acacatgtcc cccgtgtccg gcaccagaag cagcgggggg accgtcagta  120
ttcttgtttc caccgaagcc caaagacaca ttgatgattt cacgaactcc tgaagttacc  180
tgtgtggttg tagatgtatc acacgaagac ccagaagtca aattcaattg gtatgtcgac  240
ggggttgaag ttcacaatgc gaagacgaag ccccgggagg aacagtacaa cagcacgtac  300
agggttgtga gcgttcttac tgtattgcac caggattggc tcaacggcaa ggagtataaa  360
tgtaaagttt ctaataaggc tcttcctgcc ccaattgaaa agacgatatc taaagcgaag  420
ggccaaccac gggaacctca ggtgtacaca cttccgccta gcagggatga gttgaccaag  480
aatcaagtct ctttgacgtg cctggtcaag ggttttacc catcagatat cgccgtcgaa  540
tgggagtcaa acggacaacc cgaaaataac tataaaacta ctccaccagt tctggatagc  600
gacggctcat tttttctgta ttcaaagctc actgtagaca agtctaggtg gcagcagggt  660
aatgtcttct cctgctcagt aatgcatgag gctcttcaca accactatac tcaaaagagc  720
ctttccctgt cacctggcgg tggaagcgac tcatggatgg aggaggtaat aaagctctgc  780
ggaagagaac tggtacgcgc acaaatcgca atttgtggta agagtactgg cggggaagga  840
ggtggggaag aagggggcgg tgagggcgga cagctctatt ctgcacttgc aaacaaatgt  900
tgccacgtgg gatgtactaa gcgaagcctt gcaagattct gc                    942

SEQ ID NO: 163          moltype = DNA  length = 942
FEATURE                 Location/Qualifiers
source                  1..942
                        mol_type = other DNA
                        organism = synthetic construct
SEQUENCE: 163
atggagaccg acacactgtt gctgtgggta ctcctcctgt gggtgccagg aagcacgggc  60
gataaaaccc acacatgccc tccatgccct gctccagagg ccgccggtgg gccatcagtt  120
ttcttgtttc cgcctaaacc aaaggacacg cttatgatct ccaggacccc cgaagttacg  180
tgtgtggtgg ttgatgttag tcacgaggac ccggaagtca agttcaactg gtacgttgat  240
ggtgtagagg tgcacaatgc aaagacgaag ccacgcgaag aacaatacaa cagcacatat  300
cgagttgtga gcgtactcac ggtactgcat caggactggc tgaacggtaa agaatacaaa  360
tgtaaagtct ccaataaggc acttcctgcg ccgatagaaa aaacgatcag taaggccaag  420
ggccaacccc gagaaccaca ggtatatacg ctcccaccgt cacgagacga gttgacaaaa  480
aatcaggtct ccctgacttg cctcgtgaaa ggtttttatc cctcagatat tgctgttgag  540
tgggaaagca atgggcagcc agagaataat tataagacga ctcctccggt tttggattcc  600
gacggtagtt ttttcttgta tagtaagctt actgtagaca agtcaagatg gcaacaaggt  660
aatgtgttct cttgctcagt tatgcatgaa gctcttcata accattacac gcaaaagagt  720
ctcagtctga gccccggtgg cggtagcgac agttggcagg aagaggtgat taagttgtgc  780
ggtcgcgagc tcgttcgggc ccaaattgca atctgcggaa aatctacggg cggagagggc  840
gggggtgagg agggtggggg tgaaggtggg cagctctata gcgcccttgc gaataaatgt  900
tgtcacgtcg gatgcacaaa gaggtccctc gccaggttct gc                    942

SEQ ID NO: 164          moltype = DNA  length = 945
FEATURE                 Location/Qualifiers
source                  1..945
                        mol_type = other DNA
                        organism = synthetic construct
SEQUENCE: 164
atggaaactg acacactgtt gctgtgggtg ctgctccttt gggtacccgg atcaaccggg  60
gataagaccc acacttgccc cccttgccct gcccccgaag cggccggagg tccttcagta  120
tttttgtttc caccgaaacc caaagatact ttgatgatat caagaactcc tgaagtcacc  180
tgcgtggtag ttgacgtatc tcatgaggat cccgaggtga agttcaattg gtacgtcgat  240
ggcgtcgagg ttcataacgc taagactaag ccgagggaag agcaatataa ttccacttat  300
agggtggtgt ccgtcttgac tgttttgcac caggattggt tgaacgggaa agagtacaaa  360
tgtaaggtga gtaataaagc tttggctgct cccatcgaaa agacaataag caaggccaag  420
gggcaacctc gggagccgca ggtgtacacc cttcctccca gtagagacga actgacaaaa  480
aaccaggtgt ccctgacctg ccttgtgaag ggttttacc cgagcgacat agcggttgaa  540
tgggagagca acgggcaacc cgagaacaac tacaaaacta caccgcctgt cctggactcc  600
gatggaagct tcttcctcta ctccaaactg accgtggaca aaagcagatg gcaacaagga  660
aacgtattct catgctcagt aatgcacgaa gcattgcaca atcactacac ccaaaagtcc  720
ctctcactct cccctggtaa gggcggatca gactcatggc aagaggaggt aattaagttg  780
tgcgggaggg agctcgtccg cgcgcaaata gccatttgtg gcaagtccac tggaggaggc  840
gagggtggag gagagggtgg tggggagggc aggcaactct acagtgcgct cgccaataaa  900
tgctgccatg ttgggtgcac gaagcgcagt ctcgcacaat tctgc                 945

SEQ ID NO: 165          moltype = DNA  length = 945
FEATURE                 Location/Qualifiers
source                  1..945
                        mol_type = other DNA
                        organism = synthetic construct
SEQUENCE: 165
atggagaccg acactctgct gctctgggta ctcttgctgt gggtgcctgg gtctactggg  60
gataagaccc acacgtgtcc tccatgtccg gcaccggagg ctgctggcgg gccttctgta  120
ttcctcttcc cacccaagcc aaaagacaca ttgatgatat caaggacgcc ggaagtcacc  180
```

```
tgtgttgttg tggacgtttc ccatgaagac ccagaggtaa aattcaattg gtatgtggac  240
ggcgtagagg ttcacaacgc caaaaccaaa ccccgagagg aacagtataa tagcacatat  300
cgagtagtat ctgttctcac agtgctccat caagactggc ttaatggtaa agagtataaa  360
tgcaaagttt ccaataaagc cctcgctgca ccgatcgaga agacaatcag taaagcgaag  420
ggccagcctc gggaaccgca ggtgtatact cttccaccct caagagacga gctcactaaa  480
aaccaagttt cattgacatg cctcgtcaaa ggtttctacc catcagacat cgcggtcgaa  540
tgggaaagta atgggcagcc ggaaaacaac tataaaacga cgccgcccgt cttggattct  600
gatggttcat tttttcttta ctctaaattg accgtcgata aaagtaggtg gcaacaagga  660
aatgtttttt cctgctccgt cctgcatgaa gcgttgcaca gtcactatac ccagaagagt  720
ctttctttgt cacccggaaa aggcggttca gattcatggc aggaagaagt aattaaactc  780
tgtggccgcg agcttgttag ggcgcagata gccatatgtg gtaaaagcac cggaggaggt  840
gaaggcggag gcgaaggagg tggggaagga agacaattgt attctgcact tgcaaataaa  900
tgctgtcatg tggggtgcac gaaacgcagt cttgcacaat tttgt                  945

SEQ ID NO: 166         moltype = DNA  length = 942
FEATURE                Location/Qualifiers
source                 1..942
                       mol_type = other DNA
                       organism = synthetic construct
SEQUENCE: 166
atggaaaccg atacgctgct tctttgggtt cttctcctct gggttccagg gtccaccggc  60
gacaaaaccc atacctgccc cccttgccct gcaccagaag cggcgggagg acctagcgtt  120
tttctttttc ctccgaaacc gaaagatacc ctcatgatat caagaacacc tgaggttact  180
tgcgttgtcg tggacgtgag tcacgaagac cccgaggtga agttcaactg gtatgtagat  240
ggagtggagg tccataatgc aaaaacgaaa ccgagagaag aacaatacaa ctctacatat  300
cgagtcgtgt cagtactcac ggttttgcat caagattggc tgaacggtaa ggagtacaag  360
tgtaaggtta gcaacaaggc tctcgcggcg ccgatagaaa agactataag taaagcaaaa  420
ggccagccca gagaacctca agtttacact ctgcctccca gcagagatga actgactaaa  480
aatcaggttt cattgacctg tctcgtcaag ggtttttatc caagcgacat agcagttgaa  540
tgggaaagca acggtcaacc agaaaataat tacaaaacca ctccaccagt cttggactct  600
gacggatcct tctttctcta ttcaaaattg acggtggata aatctaggtg gcagcaaggc  660
aacgtcttct cttgtagcgt tatgcatgag gcgctgcaca accactacac acaaaagtct  720
cttagtttga gcccgggcgg cggaagcgac tcttggcaag aggaagtgat aaaactctgt  780
ggtcgagaat tggtacgcgc gcagatcgct atctgcggca agtccacagg gggaggggaa  840
ggtggcgggg aaggtggtgg cgagggcagg cagttgtata gtgcacttgc caacaagtgc  900
tgccatgtgg ggtgcaccaa gcgcagtttg gcacggttct gc                     942

SEQ ID NO: 167         moltype = DNA  length = 942
FEATURE                Location/Qualifiers
source                 1..942
                       mol_type = other DNA
                       organism = synthetic construct
SEQUENCE: 167
atggaaacgg acacccttct gctctgggta ctgctgctct gggttcctgg ttctaccggt  60
gataaaactc acacttgtcc cccgtgtccg gcaccagaag ccgcaggagg gccatctgtc  120
tttctttttc ccccaaaacc caaggataca ctgatgatct cccgcactcc cgaagttact  180
tgtgtcgtag tagacgtttc tcacgaggac ccagaggtga aattcaattg gtatgttgac  240
ggagtagagg tgcataatgc caagacaaag ccccgagagg aacaatacaa ttcaacctac  300
agagtagtgt ccgttcttac ggttctccat caggattggc tcaacggtaa ggaatataag  360
tgcaaggtaa gcaacaaagc gctggccgca cccattgaga aaaccatttc aaaagctaaa  420
ggccaacccc gcgaaccaca agtttatact ctccccccaa gtcgcgatga acttacaaaa  480
aatcaagtct cattgacgtg cttggtcaaa ggcttctacc cgagcgatat cgctgttgaa  540
tgggagtcta atggacaacc ggaaaataac tataaaacta cacccccagt cctcgattca  600
gacggcagct tcttcctgta ttcaaaactg acggttgaca aatcacgctg gcaacagggt  660
aacgtttttt cctgtagcgt tcttcatgaa gccttgcaca gtcactacac ccagaagtcc  720
cttagcttgt cacctggcgg gggttcagac tcttggcagg aggaggtaat caaactgtgc  780
ggaagagaac tggtgagggc tcagattgca atttgtggga agagcacggg tggcggtgaa  840
ggaggtggcg agggcggagg agaggggagg caactctaca gtgcgttggc taataaatgc  900
tgtcacgtcg gctgtactaa gagaagcctc gccagatttt gc                     942

SEQ ID NO: 168         moltype = DNA  length = 942
FEATURE                Location/Qualifiers
source                 1..942
                       mol_type = other DNA
                       organism = synthetic construct
SEQUENCE: 168
atggaaacag atactttgtt gctgtgggta ctcctcctct gggtacctgg gagcaccggg  60
gacaagacgc atacttgccc tccgtgccct gcaccagaag ccgctggtgg cccatctgtg  120
tttttgttcc cccctaagcc aaaagacaca ttgatgattt cacgaactcc agaagtgact  180
tgcgtagttg ttgacgtatc acacgaagac cccgaggtta aatttaattg gtatgtggac  240
ggggtcgagg tgcataacgc caaaaccaaa ccccgggagg aacaatataa ctctacgtat  300
cgggtcgtat ctgtgttgac cgtccttcac caagattggt tgaacggcaa ggaatataag  360
tgtaaagtgt ctaataaagc attggctgcc ccgatagaaa agacgatctc taaagccaag  420
ggccaaccca gagagcctca agtatatact ctcccaccga gtcgagatga gctcactaag  480
aaccaggtgt cactcacgtg tctggttaaa ggattttacc ctagtgatat agccgtcgag  540
tgggaatcaa atgggcagcc ggagaataac tataagacca cgcctccagt tctcgattcc  600
gatggtagct tttcctttta ctctaaactt acggtcgaca agtccaggtg gcaacagggc  660
aatgtatttt cttgctccgt catgcacgag gctttgcaca accattacac gcaaaagtca  720
ctgtccctgt ctcctggagg cggttctgac agttggcagg aggaggtaat caaattgtgt  780
```

```
gggcgggagt tggttagggc gcaaattgct atttgcggca aaagtactgg gggcggtgaa  840
ggcggaggcg agggaggagg agaaggtcga caactgtatt ctgccttggc gaacaaatgc  900
tgtcacgtcg gctgtacgaa acggtctttg gcccagtttt gt                     942

SEQ ID NO: 169         moltype = DNA  length = 942
FEATURE                Location/Qualifiers
source                 1..942
                       mol_type = other DNA
                       organism = synthetic construct
SEQUENCE: 169
atggaaactg acactcttct gttgtgggtc cttctgctgt gggttcctgg ctctactgga  60
gataagacac acacttgtcc gccatgccct gcgccggaag cggcgggagg accgtccgtt  120
ttcctgttcc ctcccaaacc caaagacacg ttgatgatta gtcgcacgcc agaagttacg  180
tgcgttgtcg tagatgtatc ccacgaagac cccgaggtga agttcaattg gtatgtagat  240
ggggtggagg tccataacgc taagaccaaa ccacgcgagg aacaatataa ttctacgtac  300
cgcgtagtga gcgttctcac agttcttcac caggattggc ttaacggcaa ggagtataag  360
tgtaaggtgt ctaataaggc cttggctgcc ccgatcgaaa aaacgataag taaagcaaag  420
ggtcaaccta gagaacccca agtgtacact ctcccgccat cacgggatga attgactaag  480
aaccaagtgt cactcacgtg tcttgtaaag ggcttctacc catccgatat agccgttgag  540
tgggaatcca atggtcagcc agagaacaac tataagacaa ctccgcccgt acttgatagt  600
gacggttcct ttttccttta cagtaaattg acggtagata agtctcgctg gcagcaagga  660
aacgtctttt cttgttcagt gcttcatgag gcgcttcact cacactatac tcagaagagt  720
ttgagtttgt ctccaggtgg aggcagcgac tcatggcaag aggaagtaat caaactgtgt  780
ggtcgcgaat tggtacgagc acagatcgcg atctgcggga aatcaacagg tggcggcgaa  840
ggcggcgggg aaggcggcgg cgaaggtagg caactttact cagcccttgc gaacaaatgt  900
tgccacgtag gctgtactaa gagaagtctc gcccagtttt gc                     942

SEQ ID NO: 170         moltype = DNA  length = 945
FEATURE                Location/Qualifiers
source                 1..945
                       mol_type = other DNA
                       organism = synthetic construct
SEQUENCE: 170
atggagacag ataccccttct gttgtgggtc cttctgcttt gggtgccggg aagtacaggc  60
gacaagactc atacctgccc cccttgtcca gcaccagaag cagctggcgg gccaagcgtg  120
ttcctgtttc cacctaagcc caaagatacg ttgatgatca gccgcacccc ggaagtaacc  180
tgtgtagtag tagatgtgtc ccacgaagac cccgaagtaa agtttaattg gtacgtcgat  240
ggtgtcgaag tacataacgc taaaacgaag ccccgagaag agcagtacaa cagtacttac  300
agagtagttt ctgttcttac agtgctgcat caggattggc tgaacgggaa ggagtataaa  360
tgtaaagtct caaacaaggc acttgcggca ccaatagaga agacaatatc taaggccaaa  420
gggcagccta gagagccaca agtatatacg ctgcccccca gcagggacga gctgacaaag  480
aaccaagtgt cactgacctg ccttgttaag ggcttctatc cgagtgatat tgctgttgaa  540
tgggaaagta acggacagcc ggagaacaac tataaaacta ctccacccgt gttggatagt  600
gacggtagct tttttctgta ctccaagttg acggtagaca aaagtcggtg gcagcagggg  660
aacgtatttt cttgttctgt catgcacgaa gctcttcaca atcactatac gcagaagtcc  720
ctctctctct ctcctgggaa gggtggttcc gacagctggc aggaggaggt cattaaactg  780
tgtggtagag agctggtacg ggctcaaatt gcaatttgtg gtaagagtac tggcggtggc  840
gaggaagggg gtggggagga gggcggaggt aggcagctct actctgctct cgccaacaag  900
tgttgtcacg tcgggtgtac taaaagatca cttgcccgct tttgt                  945

SEQ ID NO: 171         moltype = DNA  length = 945
FEATURE                Location/Qualifiers
source                 1..945
                       mol_type = other DNA
                       organism = synthetic construct
SEQUENCE: 171
atggaaaccg ataccctgct cttgtgggtc ctcctgcttt gggtcccagg ttccacaggc  60
gacaaaacac atacatgccc gccgtgtccg gcgcctgaag cagcaggagg ccccagtgta  120
ttcctttttcc ctccaaagcc aaaagatacg ttgatgatat ctaggacacc tgaggttacc  180
tgcgtcgtag tggacgtatc ccacgaagac ccagaagtca agtttaactg gtatgtggac  240
ggagtggagg tacacaatgc aaagacaaag ccgcgagagg aacaatataa ttccacctat  300
agagtcgtgt cagtccttac ggtcttgcac caggactggc tcaatggtaa ggagtataag  360
tgcaaagtat caaacaaagc tctcgcagcg cccatcgaaa agaccatcag caaagctaag  420
ggccagccaa gagagcctca agtgtacacg ttgccgcctt caagggacga gctcactaaa  480
aatcaggtat cacttacgtg tcttgtcaaa gggttttatc cttccgacat cgcggttgaa  540
tgggagagca atggacagcc ggagaataat tataaaacga cgccgccggt ccttgacagc  600
gatggttcat ttttccttta ctcaaagctg acggttgata agtctaggtg gcagcagggg  660
aacgtctttt cctgtagtgt acttcatgag gcgctccatt ctcattacac tcagaagtca  720
ctgagccttt cacccggcaa aggtggatca gactcctggc aagaagaggt aatcaaactc  780
tgtgggaggg aactcgttcg agcccagatt gcaatctgtg ggaaaagcac aggcggaggg  840
gaagaagggg gtggcgaaga aggtgggggc aggcagctct attcagctct tgccaacaaa  900
tgctgtcatg taggctgcac aaagcgatca ctggcgagat tctgt                  945

SEQ ID NO: 172         moltype = DNA  length = 945
FEATURE                Location/Qualifiers
source                 1..945
                       mol_type = other DNA
                       organism = synthetic construct
SEQUENCE: 172
```

```
atggaaaccg acaccctgct gctctgggtt cttctcctct gggttcccgg ctcaaccgga  60
gataaaactc atacttgccc accctgcccg gctcccgagg cagcaggtgg accctcagta  120
tttttgttcc ctccgaaacc taaagataca cttatgatta gccggacccc tgaggtaacg  180
tgtgtggtgg ttgacgtaag tcatgaagat ccagaagtaa agtttaactg gtacgtagac  240
ggtgtggagg tacataatgc gaagacaaaa ccacgagagg aacagtataa ctctacctac  300
cgcgtagtaa gcgtacttac tgtgctccac caagactggc ttaacgggaa agagtataag  360
tgtaaagtca gtaataaagc actggccgcc ccgatcgaaa aaacaatcag caaggccaaa  420
ggacaaccaa gggagcctca ggtctatact cttcccccga gtagggatga gcttaccaag  480
aaccaggtgt ctctgacatg ccttgtcaag ggattttacc cgagtgacat agccgtagaa  540
tgggagtcaa acggccaacc tgaaaacaac tataagacca cgcctcccgt actcgactca  600
gatggaagct ttttcctcta tagcaagctg accgtcgaca aaagtaggtg gcaacaggga  660
aacgtcttta gttgttccgt catgcacgaa gctttgcata accattacac ccagaagagt  720
ctttcccttt cccctggcaa ggggggctcc gactcctggc aagaggaagt aatcaaactg  780
tgtgggcgcg agcttgtccg cgcgcaaata gccatttgcg gaaaaagtac tggaggagga  840
gaggaaggcg gcggcgagga aggtgggggc aggcagctgt acagtgcctt ggctaacaag  900
tgctgccatg tcggctgtac gaaaaggtct cttgctcaat tctgt                  945

SEQ ID NO: 173          moltype = DNA  length = 945
FEATURE                 Location/Qualifiers
source                  1..945
                        mol_type = other DNA
                        organism = synthetic construct
SEQUENCE: 173
atggaaactg atactcttct cctttgggtg ctcctcctct gggttcccgg gtccacaggc  60
gataagacac atacctgtcc accctgccca gcacctgaag ctgcaggcgg ccccagcgta  120
ttcctgtttc ctccgaagcc gaaagacaca cttatgattt cccggacgcc tgaggtaact  180
tgcgtcgtag tagatgtgtc tcacgaagac cccgaggtga aattcaactg gtacgttgat  240
ggtgtggaag ttcataatgc gaaaactaaa ccacgagagg agcaatataa ctcaacttat  300
agagttgtga gcgtcttgac ggtactgcac caggactggc tgaatggcaa agagtacaaa  360
tgcaaagtct caaataaggc gttggcggct cccatagaga aaactatcag caaagccaag  420
ggtcaacctc gggagccaca agtgtatact cttccgccta gtcgcgacga gctcacaaag  480
aatcaggtga gtcttacttg tttggttaag ggtttctacc ccagtgacat tgcggtcgag  540
tgggaaagta acggacagcc tgaaaacaac tataaaacaa cgcctccagt actcgattca  600
gatggttcat tctttcttta ttccaaactc acagtcgaca agagtagatg gcaacaaggg  660
aacgtgttta gctgtagcgt actccatgag gcactccact ctcactatac ccaaaagtct  720
ctcagcttgt cacccggaaa aggcggttct gacagttggc aagaggaagt gattaaattg  780
tgtgggcggg aacttgtgag ggctcaaatc gcgatttgcg gcaagtccac tggtggcggc  840
gaggaaggag gaggtgaaga aggaggaggt aggcaactgt attcagcgtt ggcgaataaa  900
tgctgccatg ttggatgtac taaacggagc cttgctcagt tctgc                  945

SEQ ID NO: 174          moltype = DNA  length = 942
FEATURE                 Location/Qualifiers
source                  1..942
                        mol_type = other DNA
                        organism = synthetic construct
SEQUENCE: 174
atggaaactg acaccttgtt gctttgggta ttgcttctgt gggttccggg tagcacgggt  60
gataaaacgc atacttgccc tccttgcccg gcacctgaag ctgccggagg tccttccgtg  120
ttcctgttcc cacctaagcc aaaagacaca cttatgattt ctcgcacacc agaagtaacg  180
tgcgtcgtag ttgacgtctc ccatgaagac ccggaggtaa aatttaattg gtacgtcgac  240
ggggtagaag ttcataacgc aaagactaaa ccacgagaag agcaatacaa ctctacatac  300
agagtagtaa gcgttctcac cgttcttcat caagattggc tcaacggaaa ggagtataag  360
tgtaaggtgt ccaataaagc gttggccgca ccaatcgaaa agaccataag caaagccaaa  420
ggccaacccc gcgaaccgca ggtgtacaca cttccccgt ccagggatga attgacaaaa  480
aaccaagttt ccctcacgtg tctcgtcaag ggattctacc cgagtgatat cgcagttgaa  540
tgggaaagca atggtcagcc cgagaataac tacaagacta ctccccctgt gttggactca  600
gacggctcat tcttcctcta cagtaagttg actgtggaca aaagtcggtg gcagcaaggc  660
aatgtcttca gttgtagtgt aatgcatgaa gcactccaca atcattacac ccaaaaatcc  720
ctgagcctgt ccccgggcgg aggttcagat tcatggcagg aggaagttat aaaactgtgc  780
gggcgcgagt tggtgagggc gcagatcgca atctgtggaa agagtacggg aggtggcgaa  840
gagggtggtg gagaagaggg aggaggtcga caactgtatt ccgcgctcgc gaacaagtgt  900
tgccacgttg gctgcaccaa acgaagcctg gctcgatttt gc                     942

SEQ ID NO: 175          moltype = DNA  length = 942
FEATURE                 Location/Qualifiers
source                  1..942
                        mol_type = other DNA
                        organism = synthetic construct
SEQUENCE: 175
atggagactg acacccttct cctctgggtc ctcttgcttt gggtccctgg ctctactggt  60
gacaagacac acacttgtcc accttgcccg gctcccgagg cggcaggagg accaagcgtt  120
tttctgttcc ctcccaaacc aaaggatacg cttatgatct ctcgaacgcc ggaagttact  180
tgcgtagtag ttgatgtctc ccatgaagat cccgaagtga agttcaactg gtatgtagat  240
ggtgtggaag ttcataacgc gaaaaccaaa ccacgcgaag aacagtataa cagtacttat  300
cgggttgttt cagtactcac ggtgctccat caagactggc ttaatggaaa ggagtataaa  360
tgtaaggtaa gtaacaaggc attggcggct cccatcgaga agacaatctc caaagcaaaa  420
gggcaaccac gggagcctca ggtgtatacg ttgccgccca gcagagatga acttactaag  480
aatcaggtga gtctcacttg tctcgtcaag ggcttctatc ccagcgatat agccgtagaa  540
tgggagagta acggtcagcc ggagaacaac tacaaaacaa ccccgcctgt tttggactcc  600
```

```
gatgggagtt tttttctcta cagcaaactc acggtagaca aaagcaggtg gcagcagggc  660
aatgttttca gttgctctgt tctccacgaa gccctccact cccactatac tcagaagtct  720
ctgagtctct caccaggggg aggtagcgat agctggcagg aggaagtgat caagttgtgc  780
gggcgcgaac tcgtgcgggc acaaattgct atatgcggta aaagtacggg aggtggagag  840
gagggtggag gtgaagaagg cggtggtaga caattgtata gtgcgctcgc caacaagtgt  900
tgtcatgtcg ggtgtacgaa acggtccttg gcgcggtttt gc                    942

SEQ ID NO: 176         moltype = DNA  length = 942
FEATURE                Location/Qualifiers
source                 1..942
                       mol_type = other DNA
                       organism = synthetic construct
SEQUENCE: 176
atggaaactg acacacttct tctgtgggta ctcttgttgt gggttccggg ctcaacgggt  60
gacaagacac atacttgtcc accatgtccc gccccagaag ctgcgggagg accatcagtt  120
tttttgttcc ccccgaaacc gaaggatacc ctcatgataa gtcgaacgcc cgaagtcact  180
tgcgtggtgg ttgatgttag ccacgaggac ccagaagtga agttcaactg gtacgtggac  240
ggggtcgaag ttcataatgc gaaaacaaag cctcgcgagg aacagtacaa ctctacatac  300
agggttgtgt ctgttttgac agtcttgcac caagattggc tcaacgggaa ggaatataag  360
tgtaaggtaa gcaataaagc actggcggcc ccgatcgaaa aaacgatatc caaggccaag  420
ggccagcccc gagagcctca ggtatatact ctgccgccaa gccgggatga actgactaaa  480
aaccaggtct ctttgacttg tcttgtcaag ggattttacc caagtgacat tgcggtagag  540
tgggaaagca acggtcaacc agaaaacaat tacaagacga caccgccggt actcgactca  600
gatggatcct ttttcctgta tagcaagctg acagtggaca agtcccggtg gcagcaaggg  660
aacgtatttt catgcagcgt gatgcatgag gctcttcaca accattacac acagaaaagt  720
ctgtcattga gccctggcgg cgggagcgat tcttggcaag aagaagttat aaaactttgc  780
ggtcgagagc tggttcgggc acaaattgct atctgcggaa aatctacagg aggaggcgag  840
gagggagggg gcgaagaagg cggggggaga cagttgtaca gtgcgctcgc taacaagtgt  900
tgccacgtcg gttgcacaaa gagatccctg gctcaattct gt                    942

SEQ ID NO: 177         moltype = DNA  length = 942
FEATURE                Location/Qualifiers
source                 1..942
                       mol_type = other DNA
                       organism = synthetic construct
SEQUENCE: 177
atggagacag atactctctt gctgtgggtg ctgctcttgt gggttcctgg aagtaccggt  60
gataaaactc acacctgtcc cccgtgtccc gcaccagaag cggccggtgg tccctccgtt  120
tttctcttcc ctcctaaacc taaggacaca cttatgatta gcagaactcc agaagttacg  180
tgcgtagtcg ttgacgttag tcatgaagat cctgaggtta agttcaactg gtacgtagac  240
ggagtagagg tccacaacgc caagacgaaa ccccgagaag agcagtataa ttctacctat  300
cgagttgttt cagtattgac ggtgcttcac caagattggc tgaatggcaa agagtataag  360
tgcaaggtaa gcaacaaagc actcgcggct cctatcgaga aaactatttc caaagctaag  420
ggccagcctc gcgaaccaca agtctatacc ctgccaccga gtcgggacga actcaccaag  480
aaccaagtgt ctcttacttg cctcgttaaa ggtttttatc ccagcgacat agccgtcgaa  540
tgggagtcca atggccaacc tgagaacaac tataaaacta cccctcctgt acttgatagc  600
gacggaagtt ttttcctcta ttcaaaactc acagttgata agtctcgatg gcaacagggc  660
aacgtcttct cttgcagtgt gttgcatgaa gctctgcact ctcattacac acagaagagt  720
ttgtctctca gtccaggtgg cggctcagat agctggcagg aagaagtaat caagttgtgc  780
ggcagggaac tggtaagggc acagatagcc atttgtggaa aatctacggg tggcggtgag  840
gaaggcggcg gagaagaagg gggaggtcgg cagctgtata gtgcactcgc aaacaagtgc  900
tgccatgtcg ggtgcaccaa gcgatccctt gcccagtttt gc                    942

SEQ ID NO: 178         moltype = DNA  length = 945
FEATURE                Location/Qualifiers
source                 1..945
                       mol_type = other DNA
                       organism = synthetic construct
SEQUENCE: 178
atggaaactg atacgctcct cctttgggtt cttctcctct gggtacccgg aagcactggt  60
gacaaaacgc acacctgtcc accgtgtcct gctccagagg cggccggggg accgtccgtt  120
ttcctttttc ctcccaaacc taaggatacc cttatgatct ctcgcacgcc cgaggttacc  180
tgtgttgtgg ttgacgtgtc ccatgaagac ccggaagtaa aatttaattg gtacgtggac  240
ggggtcgagg ttcataacgc aaagaccaag ccacgagagg agcaatataa ttccacctat  300
cgcgtagtct ccgtcctcac cgtgcttcac caggattggc tcaacgggaa ggaatacaaa  360
tgtaaagtca gtaataaggc tttggcggcc ccgattgaga agactataag taaggctaag  420
ggacagccac gagaaccgca agtttataca ttgccccccct ctagggatga gttgactaag  480
aatcaggtgt cactcacttg tctggtaaaa gggttctacc cgtccgacat cgctgtggaa  540
tgggaaagca atgggcaacc tgaaaataat tataagacaa cccctccggt gcttgatagc  600
gacggatcat tctttctcta ttccaagctt actgtagata agagtcgatg gcaacagggg  660
aacgtattca gttgctctgt tctccatgag gccctgcata gtcactacac ccaaaaaagc  720
cttagtttga gtcccgggaa aggaggctcc gattcttggc aagaagaggt aataaagctg  780
tgtggacgag aacttgtccg agcacaaatt gcgatttgtg gcaaatctac aggaggggga  840
gaaggaggcg gcgaaggggg aggcgagggc aggcaggatt attccgctct ggcgaacaaa  900
tgttgccatg ttggatgcac gaaacgaagc ctggctcagt tttgc                 945

SEQ ID NO: 179         moltype = DNA  length = 942
FEATURE                Location/Qualifiers
source                 1..942
```

```
                         mol_type = other DNA
                         organism = synthetic construct
SEQUENCE: 179
atggaaaccg acaccctcct cctttgggta cttcttctct gggttccggg tagtacagga  60
gataaaacgc atacctgccc accgtgtcct gcacctgagg ccgctggagg accttccgtc  120
ttcctctttc cacccaagcc gaaagacaca ctcatgatta gtagaactcc agaggtcacg  180
tgtgttgtgg tggacgtcag tcacgaggac cctgaggtta agttcaactg gtacgttgat  240
ggcgtagaag tccacaatgc aaagaccaaa ccgagagagg agcaatataa cagtacatat  300
agggttgtta gcgtacttac tgttttgcat caagactggt tgaatgggaa ggaatataaa  360
tgtaaagtct ccaacaaggc tctggctgca ccaatagaaa aaactatttc taaggcaaag  420
ggtcagccta gagagcctca agtctatacc ttgccaccgt caagagacga gctcactaaa  480
aatcaggtga gcctgacctg tcttgtgaag ggcttttacc cgtcagatat tgccgtggag  540
tgggaatcaa acggtcagcc ggagaataac tacaagacga ccccaccagt actcgatagc  600
gatgggtctt tctttctgta ctccaagctc accgtggaca aatcacgctg gcaacagggc  660
aacgtcttta gttgcagcgt actgcacgag gcactgcaca gccactacac acaaaagagt  720
ctttctctgt ctcccggtgg tggctccgat agttggcagg aagaagtcat aaagctttgt  780
ggaagagagc ttgtacgagc gcagattgca atctgcggga agagcactgg aggaggtgag  840
ggagggggtg agggcggggg cgaaggacgc caggactatt cagcacttgc aaacaaatgc  900
tgccatgtag ggtgtacgaa gcgctcactg gcccggtttt gc                    942

SEQ ID NO: 180           moltype = DNA  length = 942
FEATURE                  Location/Qualifiers
source                   1..942
                         mol_type = other DNA
                         organism = synthetic construct
SEQUENCE: 180
atggagaccg acactttgct gctttgggtg ttgctgctgt gggtccccgg tagtacggga  60
gataaaacac atacctgccc cccatgccca gcccccgaag ctgcaggggg gccctctgtt  120
ttccttttc cacccaaacc taaagatact ctgatgatta gtcggactcc ggaagtgact  180
tgcgtcgttg tcgacgtctc tcatgaggat ccagaagtta agtttaactg gtatgtcgac  240
ggggttgagg ttcataatgc aaaaactaaa ccgagagaag aacagtacaa ctctacttat  300
agggttgtca gtgtactgac cgtcctgcac caggattggc ttaacggtaa ggagtataag  360
tgtaaagtgt ccaataaagc ccttgccgca cccatcgaga aaccatctc caaggcaaaa  420
ggacagccaa gggaaccgca ggtatataca cttccgccaa gccgagacga acttacgaag  480
aaccaggtgt ctctcacgtg tctcgtaaaa gggttttatc ccagcgatat cgcagttgag  540
tgggagagca atgggcagcc agagaataat tataagacaa cccctcccgt gctggattca  600
gacgggagtt tttttcttta ctctaagctg accgtagaca aaagtcgatg gcagcaaggc  660
aacgtctttt cctgctccgt tctccatgaa gcactgcata gccattatac ccagaagtca  720
ctgagcctct ctccaggggg cggtccgat tcatggcagg aagaggtaat caaactctgt  780
ggacgcgaac tggttcgcgc gcagatagcg atttgcggca aaagcacagg cggtggggaa  840
ggcggtggcg agggcggtgg tgaaggtcga caagattatt ctgctctcgc taacaagtgt  900
tgtcatgtag gatgtactaa aaggagtctt gcgcagttct gt                    942

SEQ ID NO: 181           moltype = DNA  length = 945
FEATURE                  Location/Qualifiers
source                   1..945
                         mol_type = other DNA
                         organism = synthetic construct
SEQUENCE: 181
atggagacgg acactcttct cctgtgggtt ctcctcttgt gggttccagg atctaccggc  60
gataagacgc acacatgccc accctgtcct gcgcctgaag ccgcgggggg acccagcgtt  120
tttctcttcc cgccgaaacc gaaagacaca cttatgatca gccggactcc cgaggttacc  180
tgcgtggtgg tagatgtatc tcacgaggat cccgaggtca aattcaactg gtacgttgat  240
ggggttgaag ttcataatgc caaaacgaag ccaagagaag agcagtataa ctccacatat  300
agagttgttt ccgtcttgac tgttcttcac caagattggc tgaatgggaa ggagtacaaa  360
tgtaaagtta gcaacaaggc actcgccgct cccattgaaa aaactataag caaagctaag  420
ggccaaccgc gcgaaccaca ggtctacacg ttgccgccct ctagggacga actcacgaag  480
aatcaggttt cccttacctg cctcgttaaa ggattctacc cctctgacat agcggttgaa  540
tgggagagca acggtcagcc tgagaacaac tacaaaacga cgcctccggt gttggattcc  600
gacggtagtt ttttcctcta tagtaagctg acagtggata aatctcggtg gcagcaaggg  660
aatgtattct cctgttcagt cctgcatgaa gccctccact cccattatac acagaaatct  720
ctttctctga gtcccggtaa aggtgggagt gactcttggc aggaagaggt aattaagttg  780
tgtggaaggg agctggtaag agcacagatt gccatctgtg gcaaatccac gggcggcgaa  840
ggtgaggggg gtgaggggga agggggtcc agacaactgt attctgctct ggcgaataag  900
tgttgccatg tagggtgcac taaacggtcc ttggcgcagt tctgt                 945

SEQ ID NO: 182           moltype = DNA  length = 942
FEATURE                  Location/Qualifiers
source                   1..942
                         mol_type = other DNA
                         organism = synthetic construct
SEQUENCE: 182
atggagactg acacactgct cctctgggtc cttttgctct gggttccggg gtccaccggt  60
gataaaactc atacgtgccc accttgcccc gcaccggagg ctgctggagg accctctgtc  120
ttcctgttcc cgccgaagcc taaagacaca ttgatgatca gtcgaacacc ggaagtcacc  180
tgtgtagtgg ttgatgtgag ccatgaggac cctgaagtaa aatttaactg gtatgttgat  240
ggcgtagaag tacacaacgc gaagactaaa ccaagggaag agcaatacaa ctctacctat  300
agggtcgtta gcgtactgac tgtgcttcac caagactggc ttaacgggaa ggagtacaag  360
tgcaaagtga gcaataaggc cctcgccgcg cctatcgaga aaaccatttc caaagccaag  420
```

```
ggtcaaccaa gggagcctca ggtttacacc ctgccccctt caagggatga gttgacaaaa  480
aaccaggtaa gtctgacgtg tctcgttaag ggattctacc cgtcagatat cgcggtagag  540
tgggagagca acggtcagcc agaaaataat tacaaaacaa cacctccagt tttggactct  600
gatgggagtt tttttcttta ttctaagttg acagtggata agtcacgctg gcaacagggg  660
aacgtattta gctgctcagt acttcatgaa gcgttgcatt ctcactacac acagaagagc  720
ctctccttga gtcccggagg tggctctgat tcttggcagg aggaggtaat aaaactttgt  780
ggtagagaac tggttcgcgc tcagatagct atttgtggaa aatccactgg cggtgaaggt  840
gaaggtggag aaggagaggg cggaagccgg cagttgtact ctgccctggc taataagtgc  900
tgtcacgtgg gctgcactaa gcggagcttg gcaagatttt gc                    942

SEQ ID NO: 183         moltype = DNA  length = 942
FEATURE                Location/Qualifiers
source                 1..942
                       mol_type = other DNA
                       organism = synthetic construct
SEQUENCE: 183
atggaaaccg acacgctgct gctgtgggtg ctgttgttgt gggttccagg ctcaactggc  60
gataaaactc atacctgtcc accttgtcct gcgcctgagg cagctggagg gcctagcgtg  120
ttcctgttcc cccccaaacc caaagacacg ctcatgatta gccgaacccc tgaagtgacc  180
tgcgttgttg tggacgtaag ccacgaagac cccgaagtta agtttaattg gtacgtcgac  240
ggtgttgagg ttcataacgc gaagactaag ccgagagagg agcaatataa cagcacctac  300
cgcgtagtct cagttcttac cgtgctccac caggactggc ttaacgggaa ggaatacaaa  360
tgcaaagttt ccaacaaagc cttggcagcc ccaatagaga agacaatatc taaggcgaaa  420
ggccaaccgc gggaaccgca agtttatacc ctcccaccga gcagggatga gctgacaaaa  480
aatcaggttt ccctcacttg tctggtcaag ggattttatc cttcagacat agccgttgaa  540
tgggagagta atgggcagcc ggagaataat tacaagacca ccccccggt gttggacagc  600
gacggttcct tctttctcta ttctaaactt accgtcgaca aatcacggtg gcaacaagga  660
aatgtattct catgcagtgt attgcacgaa gctctgcact ctcattacac ccaaaaatcc  720
ctctctctca gccctggcgg tggatctgat tcttggcagg aagaggtgat taaactgtgt  780
gggcgagagc ttgtccgagc tcagatcgct atttgtggca agagtaccgg aggcgagggt  840
gagggaggcg aaggcgaggg cggaagccgg caactctata gcgcactcgc taataaatgt  900
tgtcatgtcg gctgcacgaa gcgctcactg gcgcagttct gc                    942

SEQ ID NO: 184         moltype = DNA  length = 945
FEATURE                Location/Qualifiers
source                 1..945
                       mol_type = other DNA
                       organism = synthetic construct
SEQUENCE: 184
atggagacgg acacactgct cttgtgggta ctgctccttt gggtgccagg aagtacagga  60
gacaaaacgc atacctgtcc tccatgcccc gctcccgagg ctgccggcgg accaagcgta  120
tttctcttcc cccctaaacc taaagacaca ttgatgataa gtaggacgcc tgaagtaacg  180
tgtgttgtcg ttgatgtaag ccatgaagat cctgaagtaa agtttaattg gtatgttgat  240
ggcgtagaag tacataacgc taagacgaag ccacgggaag agcagtataa ctcaacttac  300
cgcgttgtaa gcgtgcttac cgtcctgcat caggattggc tgaatggtaa ggaatataag  360
tgcaaagtaa gcaacaaagc attggccgca ccaatagaga agacgattag taaagcaaaa  420
ggccagccca gagagccgca ggtttataca cttccaccaa gcagagatga acttacgaag  480
aaccaggtgt ctctgacttg tctggtcaag ggtttctatc cttccgacat tgcagtggag  540
tgggaaagca atgggcagcc cgaaaacaat tataagacga cacctccagt gttggactca  600
gacggttcct ttttcttgta ttccaaactt acagtggata agtcaaggtg gcagcaaggc  660
aacgtatttt cttgtagtgt tttgcacgaa gccctgcatt cccactatac tcaaaagagc  720
ctcagtctgt ccccaggaaa gggagggagt gacagttggc aagaggaggt aataaaattg  780
tgtggcagag agcttgtgcg cgctcagatc gcaatatgcg ggaaatctac tgggggtgag  840
ggtgagggcg gcgagggaga gggggcagt cgccaagatt attccgccct tgcgaataag  900
tgttgtcacg tcggatgtac taagagatca ttggctcagt tttgt                 945

SEQ ID NO: 185         moltype = DNA  length = 36
FEATURE                Location/Qualifiers
source                 1..36
                       mol_type = other DNA
                       organism = synthetic construct
SEQUENCE: 185
acgggaccga tccagcctcc ggactctaga gccacc                           36

SEQ ID NO: 186         moltype = DNA  length = 36
FEATURE                Location/Qualifiers
source                 1..36
                       mol_type = other DNA
                       organism = synthetic construct
SEQUENCE: 186
tgataaaccg gttagtaatg agtttgatat ctcgac                           36

SEQ ID NO: 187         moltype = AA  length = 29
FEATURE                Location/Qualifiers
source                 1..29
                       mol_type = protein
                       organism = synthetic construct
SEQUENCE: 187
DSWKEEVIKL CGRELVRAQI AICGKSTAS                                   29
```

```
SEQ ID NO: 188         moltype = AA  length = 29
FEATURE                Location/Qualifiers
source                 1..29
                       mol_type = protein
                       organism = synthetic construct
SEQUENCE: 188
DSWKEEVIKL CGRELVRAQI AICGKSTWS                                    29

SEQ ID NO: 189         moltype = AA  length = 29
FEATURE                Location/Qualifiers
source                 1..29
                       mol_type = protein
                       organism = synthetic construct
SEQUENCE: 189
DSWMEEVIKL CGRELVRAQI AICGKSTAS                                    29

SEQ ID NO: 190         moltype = AA  length = 29
FEATURE                Location/Qualifiers
source                 1..29
                       mol_type = protein
                       organism = synthetic construct
SEQUENCE: 190
DSWMEEVIKL CGRELVRAQI AICGKSTWS                                    29

SEQ ID NO: 191         moltype = AA  length = 295
FEATURE                Location/Qualifiers
source                 1..295
                       mol_type = protein
                       organism = synthetic construct
SEQUENCE: 191
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWKEEVIKL  240
CGRELVRAQI AICGKSTASD AAGANANAGA RQLYSALANK CCHVGCTKRS LAQFC       295

SEQ ID NO: 192         moltype = AA  length = 295
FEATURE                Location/Qualifiers
source                 1..295
                       mol_type = protein
                       organism = synthetic construct
SEQUENCE: 192
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGS DSWKEEVIKL  240
CGRELVRAQI AICGKSTASD AAGANANAGA RQLYSALANK CCHVGCTKRS LAEFC       295

SEQ ID NO: 193         moltype =   length =
SEQUENCE: 193
000

SEQ ID NO: 194         moltype = AA  length = 20
FEATURE                Location/Qualifiers
source                 1..20
                       mol_type = protein
                       organism = synthetic construct
SEQUENCE: 194
METDTLLLWV LLLWVPGSTG                                              20

SEQ ID NO: 195         moltype =   length =
SEQUENCE: 195
000

SEQ ID NO: 196         moltype =   length =
SEQUENCE: 196
000

SEQ ID NO: 197         moltype =   length =
SEQUENCE: 197
000

SEQ ID NO: 198         moltype =   length =
SEQUENCE: 198
000

SEQ ID NO: 199         moltype =   length =
SEQUENCE: 199
```

```
000

SEQ ID NO: 200          moltype = AA  length = 226
FEATURE                 Location/Qualifiers
source                  1..226
                        mol_type = protein
                        organism = synthetic construct
SEQUENCE: 200
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 201          moltype = AA  length = 226
FEATURE                 Location/Qualifiers
source                  1..226
                        mol_type = protein
                        organism = synthetic construct
SEQUENCE: 201
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 202          moltype = AA  length = 226
FEATURE                 Location/Qualifiers
source                  1..226
                        mol_type = protein
                        organism = synthetic construct
SEQUENCE: 202
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPG                 226

SEQ ID NO: 203          moltype = AA  length = 226
FEATURE                 Location/Qualifiers
source                  1..226
                        mol_type = protein
                        organism = synthetic construct
SEQUENCE: 203
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPG                 226

SEQ ID NO: 204          moltype = AA  length = 295
FEATURE                 Location/Qualifiers
source                  1..295
                        mol_type = protein
                        organism = synthetic construct
SEQUENCE: 204
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWKEEVIKL  240
CGRELVRAQI AICGKSTGGG EGGGEGGGEG RQLYSALANK CCHVGCTKRS LARFC       295

SEQ ID NO: 205          moltype = AA  length = 296
FEATURE                 Location/Qualifiers
source                  1..296
                        mol_type = protein
                        organism = synthetic construct
SEQUENCE: 205
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWKEEVIKL  240
CGRELVRAQI AICGKSTGGG EGGGEGGGEG GGQLYSALAN KCCHVGCTKR SLARFC      296

SEQ ID NO: 206          moltype = AA  length = 295
FEATURE                 Location/Qualifiers
source                  1..295
                        mol_type = protein
                        organism = synthetic construct
SEQUENCE: 206
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
```

```
DGSFFLYSKL TVDKSRWQQG NVFSCSVLHE ALHSHYTQKS LSLSPGKGGS DSWMEEVIKL  240
CGRELVRAQI AICGKSTGGG EGGGEGGGEG RQLYSALANK CCHVGCTKRS LARFC       295

SEQ ID NO: 207          moltype = AA  length = 296
FEATURE                 Location/Qualifiers
source                  1..296
                        mol_type = protein
                        organism = synthetic construct
SEQUENCE: 207
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWMEEVIKL  240
CGRELVRAQI AICGKSTGGG EGGGEGGGEG GGQLYSALAN KCCHVGCTKR SLARFC      296

SEQ ID NO: 208          moltype = AA  length = 295
FEATURE                 Location/Qualifiers
source                  1..295
                        mol_type = protein
                        organism = synthetic construct
SEQUENCE: 208
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWMEEVIKL  240
CGRELVRAQI AICGKSTGGE GGGEEGGGEG GQLYSALANK CCHVGCTKRS LARFC       295

SEQ ID NO: 209          moltype = AA  length = 295
FEATURE                 Location/Qualifiers
source                  1..295
                        mol_type = protein
                        organism = synthetic construct
SEQUENCE: 209
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWQEEVIKL  240
CGRELVRAQI AICGKSTGGE GGGEEGGGEG GQLYSALANK CCHVGCTKRS LARFC       295

SEQ ID NO: 210          moltype = AA  length = 294
FEATURE                 Location/Qualifiers
source                  1..294
                        mol_type = protein
                        organism = synthetic construct
SEQUENCE: 210
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWMEEVIKLC  240
GRELVRAQIA ICGKSTGGEG GGEEGGGEGG QLYSALANKC CHVGCTKRSL ARFC        294

SEQ ID NO: 211          moltype = AA  length = 294
FEATURE                 Location/Qualifiers
source                  1..294
                        mol_type = protein
                        organism = synthetic construct
SEQUENCE: 211
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGGGSD SWQEEVIKLC  240
GRELVRAQIA ICGKSTGGEG GGEEGGGEGG QLYSALANKC CHVGCTKRSL ARFC        294

SEQ ID NO: 212          moltype = AA  length = 295
FEATURE                 Location/Qualifiers
source                  1..295
                        mol_type = protein
                        organism = synthetic construct
SEQUENCE: 212
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWKEEVIKL  240
CGRELVRAQI AICGKSTASD AAGANANAGA RQLYSALANK CCHVGCTKRS LAQFC       295

SEQ ID NO: 213          moltype = AA  length = 295
FEATURE                 Location/Qualifiers
source                  1..295
                        mol_type = protein
```

```
                         organism = synthetic construct
SEQUENCE: 213
DKTHTCPPCP APEAAGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALAA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVLHE ALHSHYTQKS LSLSPGKGGS DSWKEEVIKL  240
CGRELVRAQI AICGKSTASD AAGANANAGA RQLYSALANK CCHVGCTKRS LAEFC       295

SEQ ID NO: 214           moltype = AA  length = 315
FEATURE                  Location/Qualifiers
source                   1..315
                         mol_type = protein
                         organism = synthetic construct
SEQUENCE: 214
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWKEEVIKL CGRELVRAQI AICGKSTGGG EGGGEGGGEG RQLYSALANK  300
CCHVGCTKRS LARFC                                                   315

SEQ ID NO: 215           moltype = AA  length = 316
FEATURE                  Location/Qualifiers
source                   1..316
                         mol_type = protein
                         organism = synthetic construct
SEQUENCE: 215
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWKEEVIKL CGRELVRAQI AICGKSTGGG EGGGEGGGEG GGQLYSALAN  300
KCCHVGCTKR SLARFC                                                  316

SEQ ID NO: 216           moltype = AA  length = 315
FEATURE                  Location/Qualifiers
source                   1..315
                         mol_type = protein
                         organism = synthetic construct
SEQUENCE: 216
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWMEEVIKL CGRELVRAQI AICGKSTGGG EGGGEGGGEG RQLYSALANK  300
CCHVGCTKRS LARFC                                                   315

SEQ ID NO: 217           moltype = AA  length = 316
FEATURE                  Location/Qualifiers
source                   1..316
                         mol_type = protein
                         organism = synthetic construct
SEQUENCE: 217
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWMEEVIKL CGRELVRAQI AICGKSTGGG EGGGEGGGEG GGQLYSALAN  300
KCCHVGCTKR SLARFC                                                  316

SEQ ID NO: 218           moltype = AA  length = 315
FEATURE                  Location/Qualifiers
source                   1..315
                         mol_type = protein
                         organism = synthetic construct
SEQUENCE: 218
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWMEEVIKL CGRELVRAQI AICGKSTGGE GGGEEGGGEG GQLYSALANK  300
CCHVGCTKRS LARFC                                                   315

SEQ ID NO: 219           moltype = AA  length = 315
FEATURE                  Location/Qualifiers
source                   1..315
                         mol_type = protein
                         organism = synthetic construct
SEQUENCE: 219
```

```
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWQEEVIKL CGRELVRAQI AICGKSTGGE GGGEEGGEG GQLYSALANK  300
CCHVGCTKRS LARFC                                                  315

SEQ ID NO: 220         moltype = AA  length = 314
FEATURE                Location/Qualifiers
source                 1..314
                       mol_type = protein
                       organism = synthetic construct
SEQUENCE: 220
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWMEEVIKLC GRELVRAQIA ICGKSTGGEG GGEEGGGEGG QLYSALANKC  300
CHVGCTKRSL ARFC                                                   314

SEQ ID NO: 221         moltype = AA  length = 314
FEATURE                Location/Qualifiers
source                 1..314
                       mol_type = protein
                       organism = synthetic construct
SEQUENCE: 221
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGGGSD SWQEEVIKLC GRELVRAQIA ICGKSTGGEG GGEEGGGEGG QLYSALANKC  300
CHVGCTKRSL ARFC                                                   314

SEQ ID NO: 222         moltype = AA  length = 315
FEATURE                Location/Qualifiers
source                 1..315
                       mol_type = protein
                       organism = synthetic construct
SEQUENCE: 222
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWKEEVIKL CGRELVRAQI AICGKSTASD AAGANANAGA RQLYSALANK  300
CCHVGCTKRS LAQFC                                                  315

SEQ ID NO: 223         moltype = AA  length = 315
FEATURE                Location/Qualifiers
source                 1..315
                       mol_type = protein
                       organism = synthetic construct
SEQUENCE: 223
METDTLLLWV LLLWVPGSTG DKTHTCPPCP APEAAGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALAA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVLHE ALHSHYTQKS  240
LSLSPGKGGS DSWKEEVIKL CGRELVRAQI AICGKSTASD AAGANANAGA RQLYSALANK  300
CCHVGCTKRS LAEFC                                                  315

SEQ ID NO: 224         moltype = AA  length = 309
FEATURE                Location/Qualifiers
source                 1..309
                       mol_type = protein
                       organism = synthetic construct
SEQUENCE: 224
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGKGGG GSGGGGSGGG  240
GSQLYSALAN KCCHVGCTKR SLARFCGGGG SGGGGSGGGG SSWMEEVIKL CGRELVRAQI  300
AICGMSTWS                                                         309

SEQ ID NO: 225         moltype = AA  length = 329
FEATURE                Location/Qualifiers
source                 1..329
                       mol_type = protein
                       organism = synthetic construct
SEQUENCE: 225
METDTLLLWV LLLWVPGSTG DKTHTCPPCP APELLGGPSV FLFPPKPKDT LMISRTPEVT  60
```

-continued

```
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSRDELTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGG GSGGGGSGGG GSQLYSALAN KCCHVGCTKR SLARFCGGGG SGGGGSGGGG  300
SSWMEEVIKL CGRELVRAQI AICGMSTWS                                    329
```

RELAXIN-2 FUSION PROTEIN ANALOGS AND METHODS OF USING SAME

RELATED APPLICATIONS

This application claims priority to U.S. Provisional Patent Application Ser. No. 63/263,917, filed Nov. 11, 2021, the entire disclosure of which is hereby incorporated herein by reference.

REFERENCE TO SEQUENCE LISTING

This application contains a sequence listing which has been submitted electronically in ASCII format and is hereby incorporated by reference in its entirety (said ASCII copy, created Nov. 11, 2022, is named "TECW-002_SL_ST26_2022-11-11" and is 284,217 bytes in size).

FIELD

This disclosure provides relaxin-2 fusion protein analogs with improved pharmacokinetic properties, methods for making these fusion proteins, and methods of using these fusion proteins to enhance relaxin-2 related activity in a subject and treat or prevent relaxin-2 related diseases.

BACKGROUND

Relaxin-2 exhibits strong antifibrotic activity. In injured tissues, fibroblast activation and proliferation cause increased collagen production and interstitial fibrosis. Fibrosis in the heart is increased by biomechanical overload, and influences ventricular dysfunction, remodeling, and arrhythmogenesis. However, due to the limited in vivo half-life of relaxin, treatment of patients has to be repeated every 14 to 21 days, whereby compound administration has to be performed as a continuous infusion for at least 48 hours. Further, the synthesis of relaxin-2 is difficult. Due to the low solubility of the B-chain and the requirement for the laborious, specific introduction of cysteine bridges between A and B-chains, yields of active peptide obtained by these methods are extremely low.

There is a need for an engineered relaxin-2 analog with greater half-life and greater ease in production.

SUMMARY

This disclosure provides fusion proteins that are engineered relaxin-2 analogs with improved pharmacokinetic properties. This disclosure also provides methods of using these fusion proteins to enhance relaxin-2 related activity in a subject and to treat or prevent relaxin-2 related diseases.

Provided herein is a fusion protein comprising, from N-terminus to C-terminus, a first peptide; a linker peptide; and a second peptide, wherein the first peptide comprises an amino acid sequence that differs at 0, 1, 2, 3, 4, or 5 amino acids when compared to the amino acid sequence of SEQ ID NO: 7 and the second peptide comprises an amino acid sequence that differs at 0, 1, 2, 3, 4, or 5 amino acids when compared to the amino acid sequence of SEQ ID NO: 9; or the first peptide comprises an amino acid sequence that differs at 0, 1, 2, 3, 4, or 5 amino acids when compared to the amino acid sequence of SEQ ID NO: 9 and the second peptide comprises an amino acid sequence that differs at 0, 1, 2, 3, 4, or 5 amino acids when compared to the amino acid sequence of SEQ ID NO: 7; the linker peptide comprises an amino acid sequence with 12-15 amino acids, comprising 2-5 acidic amino acids and 10-13 non-acidic amino acids; and the fusion protein has a pI from 6.0 to 8.2.

In some embodiments, the linker peptide comprises an amino acid sequence selected from the group consisting of $R_1R_1R_1R_2R_1R_1R_1R_2R_1R_1R_1R_2R_1$;
$R_1R_1R_1R_2R_1R_1R_1R_2R_1R_1R_1R_2R_1R_1R_1$;
$R_1R_1R_2R_1R_1R_1R_2R_2R_1R_1R_1R_2R_1R_1$;
$R_1R_1R_1R_2R_2R_1R_1R_1R_2R_2R_1R_1R_1$; and
$R_1R_1R_2R_1R_2R_1R_1R_2R_1R_2R_1R_1R_1$, wherein $R_1$ is a non-acidic amino acid and $R_2$ is an acidic amino acid.

In some embodiments, the acidic amino acid(s) are aspartate or glutamate. In some embodiments, the acidic amino acid(s) are glutamate. In some embodiments, the non-acidic amino acid(s) are glycine, proline, or serine. In some embodiments, the non-acidic amino acid(s) are glycine.

In some embodiments, the linker peptide comprises the amino acid sequence of one or more of SEQ ID NO: 14, 15, 16, 17, or 18. In some embodiments, the linker peptide comprises an amino acid sequence selected from the group consisting of SEQ ID NOs: 19-23.

In some embodiments, the first peptide comprises the amino acid sequence of DSW$X_3$EEVIKLCGRELVRAQIAICG$X_4$ST (SEQ ID NO: 3), wherein $X_3$ is methionine, lysine, or glutamine, and wherein $X_4$ is methionine or lysine. In some embodiments, the first peptide comprises the amino acid sequence of $X_5$Q$X_6$YSALANKCCHVGCTKRSLA$X_7$FC (SEQ ID NO: 4), wherein $X_5$ is arginine or absent, $X_6$ is leucine or aspartic acid, and wherein $X_7$ is arginine, glutamine, or glutamate.

In some embodiments, the second peptide comprises the amino acid sequence of DSW$X_3$EEVIKLCGRELVRAQIAICG$X_4$ST (SEQ ID NO: 3), wherein $X_3$ is methionine, lysine, or glutamine, and wherein $X_4$ is methionine or lysine. In some embodiments, the second peptide comprises the amino acid sequence of $X_5$Q$X_6$YSALANKCCHVGCTKRSLA$X_7$FC (SEQ ID NO: 4), wherein $X_5$ is arginine or absent, $X_6$ is leucine or aspartate, and wherein $X_7$ is arginine, glutamine or glutamate.

In some embodiments, the first peptide comprises an amino acid sequence selected from the group consisting of SEQ ID NOs: 5-7. In some embodiments, the second peptide comprises an amino acid sequence selected from the group consisting of SEQ ID NOs: 5-7. In some embodiments, the first peptide comprises an amino acid sequence selected from the group consisting of SEQ ID NOs: 8-13. In some embodiments, the second peptide comprises an amino acid sequence selected from the group consisting of SEQ ID NOs: 8-13.

In some embodiments, the first peptide comprises the amino acid sequence of SEQ ID NO: 5 and the second peptide comprises the amino acid sequence of SEQ ID NO: 8; the first peptide comprises the amino acid sequence of SEQ ID NO: 5 and the second peptide comprises the amino acid sequence of SEQ ID NO: 9; the first peptide comprises the amino acid sequence of SEQ ID NO: 5 and the second peptide comprises the amino acid sequence of SEQ ID NO: 10; the first peptide comprises the amino acid sequence of SEQ ID NO: 5 and the second peptide comprises the amino acid sequence of SEQ ID NO: 11; the first peptide comprises the amino acid sequence of SEQ ID NO: 5 and the second peptide comprises the amino acid sequence of SEQ ID NO: 12; the first peptide comprises the amino acid sequence of SEQ ID NO: 5 and the second peptide comprises the amino acid sequence of SEQ ID NO: 13; the first peptide comprises the amino acid sequence of SEQ ID NO: 6 and the second peptide comprises the amino acid sequence of SEQ ID NO: 8; the first peptide comprises the amino acid sequence of SEQ ID NO: 6 and the second peptide comprises the amino acid sequence of SEQ ID NO: 9; the first peptide comprises the amino acid sequence of SEQ ID NO: 6 and the second peptide comprises the amino acid sequence of SEQ ID NO: 10; the first peptide comprises the amino acid sequence of SEQ ID NO: 6 and the second peptide comprises the amino acid sequence of SEQ ID NO: 11; the first peptide comprises the amino acid sequence of SEQ ID NO: 6 and the second peptide comprises the amino acid sequence of SEQ ID NO: 12; the first peptide comprises the amino acid sequence of SEQ ID NO: 6 and the second peptide comprises the amino acid sequence of SEQ ID NO: 13; the first peptide comprises the amino acid sequence of SEQ ID NO: 7 and the second peptide comprises the amino acid sequence of SEQ ID NO: 8; the first peptide comprises the amino acid sequence of SEQ ID NO: 7 and the second peptide comprises the amino acid sequence of SEQ ID NO: 9; the first peptide comprises the amino acid sequence of SEQ ID NO: 7 and the second peptide comprises the amino acid sequence of SEQ ID NO: 10; the first peptide comprises the amino acid sequence of SEQ ID NO: 7 and the second peptide comprises the amino acid sequence of SEQ ID NO: 11; the first peptide comprises the amino acid sequence of SEQ ID NO: 7 and the second peptide comprises the amino acid sequence of SEQ ID NO: 12; or the first peptide comprises the amino acid sequence of SEQ ID NO: 7 and the second peptide comprises the amino acid sequence of SEQ ID NO: 13.

In some embodiments, the second peptide comprises the amino acid sequence of SEQ ID NO: 5 and the first peptide comprises the amino acid sequence of SEQ ID NO: 8; the second peptide comprises the amino acid sequence of SEQ ID NO: 5 and the first peptide comprises the amino acid sequence of SEQ ID NO: 9; the second peptide comprises the amino acid sequence of SEQ ID NO: 5 and the first peptide comprises the amino acid sequence of SEQ ID NO: 10; the second peptide comprises the amino acid sequence of SEQ ID NO: 5 and the first peptide comprises the amino acid sequence of SEQ ID NO: 11; the second peptide comprises the amino acid sequence of SEQ ID NO: 5 and the first peptide comprises the amino acid sequence of SEQ ID NO: 12; the second peptide comprises the amino acid sequence of SEQ ID NO: 5 and the first peptide comprises the amino acid sequence of SEQ ID NO: 13; the second peptide comprises the amino acid sequence of SEQ ID NO: 6 and the first peptide comprises the amino acid sequence of SEQ ID NO: 8; the second peptide comprises the amino acid sequence of SEQ ID NO: 6 and the first peptide comprises the amino acid sequence of SEQ ID NO: 9; the second peptide comprises the amino acid sequence of SEQ ID NO: 6 and the first peptide comprises the amino acid sequence of SEQ ID NO: 10; the second peptide comprises the amino acid sequence of SEQ ID NO: 6 and the first peptide comprises the amino acid sequence of SEQ ID NO: 11; the second peptide comprises the amino acid sequence of SEQ ID NO: 6 and the first peptide comprises the amino acid sequence of SEQ ID NO: 12; the second peptide comprises the amino acid sequence of SEQ ID NO: 6 and the first peptide comprises the amino acid sequence of SEQ ID NO: 13; the second peptide comprises the amino acid sequence of SEQ ID NO: 7 and the first peptide comprises the amino acid sequence of SEQ ID NO: 8; the second peptide comprises the amino acid sequence of SEQ ID NO: 7 and the first peptide comprises the amino acid sequence of SEQ ID NO: 9; the second peptide comprises the amino acid sequence of SEQ ID NO: 7 and the first peptide comprises the amino acid sequence of SEQ ID NO: 10; the second peptide comprises the amino acid sequence of SEQ ID NO: 7 and the first peptide comprises the amino acid sequence of SEQ ID NO: 11; the second peptide comprises the amino acid sequence of SEQ ID NO: 7 and the first peptide comprises the amino acid sequence of SEQ ID NO: 12; or the second peptide comprises the amino acid sequence of SEQ ID NO: 7 and the first peptide comprises the amino acid sequence of SEQ ID NO: 13.

In some embodiments, the fusion protein comprises an amino acid sequence selected from the group consisting of SEQ ID NOs: 25-48.

In some embodiments, the first peptide consists of an amino acid sequence selected from the group consisting of SEQ ID NOs: 5-7. In some embodiments, the second peptide consists of an amino acid sequence selected from the group consisting of SEQ ID NOs: 5-7. In some embodiments, the first peptide consists of an amino acid sequence selected from the group consisting of SEQ ID NOs: 8-13. In some embodiments, the second peptide consists of an amino acid sequence selected from the group consisting of SEQ ID NOs: 8-13.

In some embodiments, the first peptide consists of the amino acid sequence of SEQ ID NO: 5 and the second peptide consists of the amino acid sequence of SEQ ID NO: 8; the first peptide consists of the amino acid sequence of SEQ ID NO: 5 and the second peptide consists of the amino acid sequence of SEQ ID NO: 9; the first peptide consists of the amino acid sequence of SEQ ID NO: 5 and the second peptide consists of the amino acid sequence of SEQ ID NO: 10; the first peptide consists of the amino acid sequence of SEQ ID NO: 5 and the second peptide consists of the amino acid sequence of SEQ ID NO: 11; the first peptide consists of the amino acid sequence of SEQ ID NO: 5 and the second peptide consists of the amino acid sequence of SEQ ID NO: 12; the first peptide consists of the amino acid sequence of SEQ ID NO: 5 and the second peptide consists of the amino acid sequence of SEQ ID NO: 13; the first peptide consists of the amino acid sequence of SEQ ID NO: 6 and the second peptide consists of the amino acid sequence of SEQ ID NO: 8; the first peptide consists of the amino acid sequence of SEQ ID NO: 6 and the second peptide consists of the amino acid sequence of SEQ ID NO: 9; the first peptide consists of the amino acid sequence of SEQ ID NO: 6 and the second peptide consists of the amino acid sequence of SEQ ID NO: 10; the first peptide consists of the amino acid sequence of SEQ ID NO: 6 and the second peptide consists of the amino acid sequence of SEQ ID NO: 11; the first peptide consists of the amino acid sequence of SEQ ID NO: 6 and the second peptide consists of the amino acid sequence of SEQ ID NO: 12; the first peptide consists of the amino acid sequence of SEQ ID NO: 6 and the second peptide consists of the amino acid sequence of SEQ ID NO: 13; the first peptide consists of the amino acid sequence of SEQ ID NO: 7 and the second peptide consists of the amino acid sequence of SEQ ID NO: 8; the first peptide consists of the amino acid sequence of SEQ ID NO: 7 and the second peptide consists of the amino acid sequence of SEQ ID NO: 9; the first peptide consists of the amino acid sequence of SEQ ID NO: 7 and the second peptide consists of the amino acid sequence of SEQ ID NO: 10; the first peptide consists of the amino acid sequence of SEQ ID NO: 7 and the second peptide consists of the amino acid sequence of SEQ ID NO: 11; the first peptide consists of the amino acid sequence of SEQ ID NO: 7 and the second peptide consists of the amino acid sequence of SEQ ID NO: 12; or the first peptide consists of the amino acid sequence of SEQ ID NO: 7 and the second peptide consists of the amino acid sequence of SEQ ID NO: 13.

In some embodiments, the second peptide consists of the amino acid sequence of SEQ ID NO: 5 and the first peptide consists of the amino acid sequence of SEQ ID NO: 8; the second peptide consists of the amino acid sequence of SEQ ID NO: 5 and the first peptide consists of the amino acid sequence of SEQ ID NO: 9; the second peptide consists of the amino acid sequence of SEQ ID NO: 5 and the first peptide consists of the amino acid sequence of SEQ ID NO: 10; the second peptide consists of the amino acid sequence of SEQ ID NO: 5 and the first peptide consists of the amino acid sequence of SEQ ID NO: 11; the second peptide consists of the amino acid sequence of SEQ ID NO: 5 and the first peptide consists of the amino acid sequence of SEQ ID NO: 12; the second peptide consists of the amino acid sequence of SEQ ID NO: 5 and the first peptide consists of the amino acid sequence of SEQ ID NO: 13; the second peptide consists of the amino acid sequence of SEQ ID NO: 6 and the first peptide consists of the amino acid sequence of SEQ ID NO: 8; the second peptide consists of the amino acid sequence of SEQ ID NO: 6 and the first peptide consists of the amino acid sequence of SEQ ID NO: 9; the second peptide consists of the amino acid sequence of SEQ ID NO: 6 and the first peptide consists of the amino acid sequence of SEQ ID NO: 10; the second peptide consists of the amino acid sequence of SEQ ID NO: 6 and the first peptide consists of the amino acid sequence of SEQ ID NO: 11; the second peptide consists of the amino acid sequence of SEQ ID NO: 6 and the first peptide consists of the amino acid sequence of SEQ ID NO: 12; the second peptide consists of the amino acid sequence of SEQ ID NO: 6 and the first peptide consists of the amino acid sequence of SEQ ID NO: 13; the second peptide consists of the amino acid sequence of SEQ ID NO: 7 and the first peptide consists of the amino acid sequence of SEQ ID NO: 8; the second peptide consists of the amino acid sequence of SEQ ID NO: 7 and the first peptide consists of the amino acid sequence of SEQ ID NO: 9; the second peptide consists of the amino acid sequence of SEQ ID NO: 7 and the first peptide consists of the amino acid sequence of SEQ ID NO: 10; the second peptide consists of the amino acid sequence of SEQ ID NO: 7 and the first peptide consists of the amino acid sequence of SEQ ID NO: 11; the second peptide consists of the amino acid sequence of SEQ ID NO: 7 and the first peptide consists of the amino acid sequence of SEQ ID NO: 12; or the second peptide consists of the amino acid sequence of SEQ ID NO: 7 and the first peptide consists of the amino acid sequence of SEQ ID NO: 13.

In some embodiments, the fusion protein further comprises an IgG Fc. In some embodiments, the IgG Fc comprises the amino acid alanine at EU positions 234 and 235. In some embodiments, the IgG Fc comprises the amino acid alanine at EU position 329. In some embodiments, the IgG Fc comprises the amino acid alanine at EU positions 234, 235 and 329. In some embodiments, the IgG Fc comprises the amino acids alanine, alanine, alanine, leucine, and serine at EU positions 234, 235, 329, 428 and 434, respectively. In some embodiments, the IgG Fc comprises the amino acids lysine, phenylalanine, and tyrosine at EU positions 433, 434 and 436, respectively. In some embodiments, the IgG Fc comprises the amino acids tyrosine, threonine and glutamate at EU positions 252, 254 and 256, respectively. In some embodiments, the IgG Fc comprises the amino acids leucine and serine at EU positions 428 and 434, respectively.

In some embodiments, the IgG Fc comprises an amino acid sequence at least 85% identical to the amino acid sequence of a human IgG1 Fc. In some embodiments, the IgG Fc comprises the amino acid sequence of a human IgG1 Fc. In some embodiments, the IgG Fc comprises an amino acid sequence at least 95% identical to an amino acid sequence selected from the group consisting of SEQ ID NOs: 50-52 and 201-203. In some embodiments, the IgG Fc comprises an amino acid sequence selected from the group consisting of SEQ ID NOs: 50-52 and 201-203.

In some embodiments, the IgG Fc is linked to the N-terminus of the first peptide. In some embodiments, the IgG Fc is linked to the C-terminus of the second peptide.

In some embodiments, the fusion protein comprises an amino acid sequence selected from the group consisting of SEQ ID NOs: 53-85 and 204-211. In some embodiments, the fusion protein comprises an amino acid sequence selected from the group consisting of SEQ ID NOs: 86-118 and 214-221.

In some embodiments, the fusion protein consists of an amino acid sequence selected from the group consisting of SEQ ID NOs: 53-85 and 204-211. In some embodiments, the fusion protein consists of an amino acid sequence selected from the group consisting of SEQ ID NOs: 86-118 and 214-221.

In some embodiments, the first and second peptides do not comprise the amino acid sequence of a peptide selected from the group consisting of

DSWKEEVIKLCGRELVRAQIAICGKSTAS (SEQ ID NO: 187);

DSWKEEVIKLCGRELVRAQIAICGKSTWS (SEQ ID NO: 188);

DSWMEEVIKLCGRELVRAQIAICGKSTAS (SEQ ID NO: 189); and

DSWMEEVIKLCGRELVRAQIAICGKSTWS (SEQ ID NO: 190).

Also provided herein is a fusion protein comprising an amino acid sequence selected from the group consisting of SEQ ID NOs: 53-118 and 204-225. In some embodiments, the fusion protein consists of an amino acid sequence selected from the group consisting of SEQ ID NOs: 53-118 and 204-225.

Also provided herein is a polynucleotide comprising a nucleotide sequence encoding any of the fusion proteins provided above and herein. In some embodiments, the polynucleotide is an RNA molecule. In some embodiments, the polynucleotide is a DNA molecule.

Also provided herein is an expression vector comprising any polynucleotides described above and herein. In some embodiments, the expression vector is a plasmid. In some embodiments, the expression vector is a viral vector.

Also provided herein is a host cell comprising any polynucleotides or expression vectors described above and herein. In some embodiments, the host cell is a prokaryotic cell. In some embodiments, the host cell is a eukaryotic cell. In some embodiments, the prokaryotic cell an *E. coli* cell or a *Bacillus* cell. In some embodiments, the eukaryotic cell is selected from the group consisting of a yeast cell, an insect cell, and a mammalian cell. In some embodiments, the mammalian cell is selected from the group consisting of a CHO cell, a HeLa cell, and a 293 cell.

Also provided herein is a population of cells comprising two or more of any of the host cells described above and herein.

Also provided herein is a method of producing any of the fusion proteins described above and herein comprising culturing any of the host cells described above and herein under conditions such that the fusion protein is produced.

Also provided herein is a pharmaceutical composition comprising an effective amount of any of the fusion proteins described above and herein, or any polynucleotides described above and herein, or any expression vectors described above and herein.

Also provided herein is a method of enhancing a relaxin-2-related activity in a primary cell, comprising contacting the primary cell with any of the fusion proteins described above and herein, thereby enhancing relaxin-2-related activity in the cell. In some embodiments, the fusion protein activates the relaxin-2 receptor, RXFP1, on a cell surface. In some embodiments, the method elevates cAMP levels in the primary cell, inducing vasodilation, inducing the expression of angiogenic factors, inducing the expression of MMPs, and inducing collagen degradation. In some embodiments, the primary cell is selected from the group consisting of endothelial cells, vascular smooth muscle cells, other vascular cells, cardiomyocytes, other cardiac cells, and fibroblasts. In some embodiments, the primary cell is within a subject. In some embodiments, the subject has a relaxin-2-associated disorder. In some embodiments, the relaxin-2-associated disorder is selected from the group consisting of kidney diseases, fibrotic diseases, and cardiovascular diseases. In some embodiments, the disorder is selected from the group consisting of focal segmental glomerular sclerosis (FSGS), diabetic nephropathy, hepatorenal syndrome, scleroderma, idiopathic pulmonary fibrosis, renal fibrosis, cardiac fibrosis, NASH, dilated cardiomyopathy, diastolic heart failure, pulmonary arterial hypertension, chronic heart failure, acute heart failure, congestive heart failure, coronary artery disease, hypertension, and pre-eclampsia.

Also provided herein is a method of treating a relaxin-associated disorder in a subject in need thereof, comprising administering to the subject an effective amount of any of the fusion proteins described above and herein, any polynucleotides described above and herein, any expression vectors described above and herein, or any pharmaceutical composition described above and herein, thereby treating the relaxin-associated disorder. In some embodiments, the relaxin-2-associated disorder is selected from the group consisting of kidney diseases, fibrotic diseases, and cardiovascular diseases. In some embodiments, the disorder is selected from the group consisting of focal segmental glomerular sclerosis (FSGS), diabetic nephropathy, hepatorenal syndrome, scleroderma, idiopathic pulmonary fibrosis, renal fibrosis, cardiac fibrosis, NASH, dilated cardiomyopathy, diastolic heart failure, pulmonary arterial hypertension, chronic heart failure, acute heart failure, congestive heart failure, coronary artery disease, hypertension, and pre-eclampsia. In some embodiments, the method decreases arterial pressure, increases renal artery blood flow, increases cardiac filling at diastole, resolves established fibrosis, or suppresses new fibrosis development.

Also provided herein is a kit comprising an effective amount any of the fusion proteins described above and herein, any polynucleotides described above and herein, any expression vectors described above and herein, or any pharmaceutical composition described above and herein, and an instruction of use.

DETAILED DESCRIPTION

The disclosure provides fusion proteins comprising a human relaxin-2 B chain, or a derivative thereof, and a human relaxin-2 A chain, or a derivative thereof, joined by a peptide linker, wherein the fusion proteins have high in vivo circulating half-life when administered to mammals. In some embodiments, the in vivo circulating half-life of the fusion proteins provided in this disclosure is greater than 2 hours. In some embodiments, the fusion proteins provided in this disclosure have low pI. In some embodiments, the pI of the fusion proteins provided in this disclosure is less than 8.5. In some embodiments, the low pI of the fusion proteins provided in this disclosure is caused by acidic amino acid residues present in the peptide linker. In some embodiments, the peptide linker of the fusion protein comprises 2 or more acidic amino acids. In some embodiments, the peptide linker is 10-15 total amino acids in length.

Definitions

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an," and "the" include plural referents unless the context clearly dictates otherwise. In this application, the use of "or" means "and/or" unless stated otherwise. Furthermore, use of the term "including" as well as other forms, such as "include," "includes," and "included," is not limiting. The section headings used herein are for organizational purposes only and are not to be construed as limiting the subject matter described.

The term "polynucleotide" as used herein refers to a polymer of DNA or RNA. The polynucleotide sequence can be single-stranded or double-stranded; contain natural, non-natural, or altered nucleotides; and contain a natural, non-natural, or altered internucleotide linkage, such as a phosphoroamidate linkage or a phosphorothioate linkage, instead of the phosphodiester found between the nucleotides of an unmodified polynucleotide sequence. Polynucleotide sequences include, but are not limited to, all polynucleotide sequences which are obtained by any means available in the art, including, without limitation, recombinant means, e.g., the cloning of polynucleotide sequences from a recombinant library or a cell genome, using ordinary cloning technology and polymerase chain reaction, and the like, and by synthetic means.

The terms "protein" and "polypeptide" are used interchangeably herein and refer to a polymer of amino acids connected by one or more peptide bonds. As used herein, "amino acid sequence" refers to the information describing the relative order and identity of amino acid residues which make up a polypeptide.

As used herein, the term "an amino acid sequence that differs at 1 or more amino acids," with reference to an amino acid sequence, refers to an amino acid sequence that comprises at least one substitution, alteration, inversion, addition, or deletion of an amino acid residue compared to a reference amino acid sequence.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F, (1990) *PNAS* 87: 2264-2268, modified as in Karlin S & Altschul S F, (1993) *PNAS* 90: 5873-5877, each of which is herein incorporated by reference in its entirety. Such an algorithm is incorporated into the NBLAST and XBLAST programs of Altschul S F et al., (1990) *J Mol Biol* 215: 403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) *Nuc Acids Res* 25: 3389-3402, which is herein incorporated by reference in its entirety. Alternatively, PSI BLAST can be used to perform an iterated search which detects distant relationships between molecules. Id. When utilizing BLAST, Gapped BLAST, and PSI BLAST programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, (1988) *CABIOS* 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "linked to" refers to covalent or noncovalent binding between two molecules or moieties. The skilled worker will appreciate that when a first molecule or moiety is linked to a second molecule or moiety, the linkage need not be direct, but instead, can be via an intervening molecule or moiety.

As used herein, the terms "human relaxin-2 B chain" or "relaxin B chain" or "relaxin B" or "rel B" refer to a peptide comprising or consisting of the amino acid sequence as set forth in DSWMEEVIKLCGRELVRAQIAICGMSTWS (SEQ ID NO: 1) or derivatives thereof. In some embodiments, a derivative of a relaxin B chain comprises the amino acid sequence of SEQ ID NO: 1 with 1, 2, 3, 4, or 5 amino acid changes.

As used herein, the terms "human relaxin-2 A chain" or "relaxin A chain" or "relaxin A" or "rel A" refer to a peptide comprising or consisting of the amino acid sequence as set forth in QLYSALANKCCHVGCTKRSLARFC (SEQ ID NO: 2) or derivatives thereof. In some embodiments, a derivative of a relaxin A chain comprises the amino acid sequence of SEQ ID NO: 2 with 1, 2, 3, 4, or 5 amino acid changes.

As used herein, the term "linker peptide" refers to a peptide that links the relaxin A chain and the relaxin B chain in the fusion proteins described herein.

As used herein, the term "acidic amino acid" refers to an amino acid that has a carboxylic acid in its side chain. In some embodiments, the acidic amino acid is aspartate, glutamate, 2-aminoadipic acid, 2-aminobutyric acid or 2-aminopimelic acid. In some embodiments, acid amino acids include aspartate and glutamate.

As used herein, the term "non-acidic amino acid" refers to amino acids that are not acidic amino acids. In some embodiments, non-acidic amino acids include glycine, proline, and serine. In some embodiments, non-specific amino acids also include arginine, histidine, lysine, threonine, asparagine, glutamine, cysteine, alanine, valine, isoleucine, leucine, methionine, phenylalanine, tyrosine, and tryptophan.

As used herein, the term "IgG Fc" refers to the immunoglobulin G (IgG) fragment crystallizable (Fc) region. In some embodiments, the IgG Fc is the human IgG1, IgG2, IgG3, or IgG4 Fc region. In some embodiments, the IgG Fc is the IgG1 Fc region.

As used herein, the term "EU numbering system" refers to the EU numbering convention for the constant regions of an antibody, as described in Edelman, G. M. et al., Proc. Natl. Acad. USA, 63, 78-85 (1969) and Kabat et al., Sequences of Proteins of Immunological Interest, U.S. Dept. Health and Human Services, 5th edition, 1991, each of which is herein incorporated by reference in its entirety.

As used herein, the term "relaxin-2 receptor," "human relaxin-2 receptor," "human relaxin receptor 1," "RXFP1," or "LGR7" is the native receptor of relaxin-2 in humans. In some embodiments, RXFP1 comprises the amino acid sequence shown in NCBI Reference Sequence: NP_067647.2, NP_001240656.1, NP_001240657.1, NP_001240658.1, NP_001240659.1, NP_001240661.1, NP_001240662.1, or NP_001350705.1 incorporated herein by reference in its entirety.

As used herein, the terms "treat," "treating," and "treatment" refer to therapeutic or preventative measures described herein. In some embodiments, the methods of "treatment" employ administration of a fusion protein to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

As used herein, the term "pI" means the isoelectric point, i.e., the pH of a solution at which the next charge on a fusion protein is zero. In some embodiments, the pI is the calculated or theoretical pI. In some embodiments, the pI is measured experimentally by an instrument.

Fusion Proteins

The disclosure provides fusion proteins comprising a human relaxin-2 B chain, or a derivative thereof, and a human relaxin-2 A chain, or a derivative thereof, linked by a peptide linker, wherein the fusion proteins have high in vivo circulating half-life when administered to mammals. In some embodiments, the fusion protein comprises, from N-terminus to C-terminus, a human relaxin-2 B chain, or a derivative thereof, a peptide linker and a human relaxin-2 A chain, or a derivative thereof. In some embodiments, the fusion protein comprises, from N-terminus to C-terminus, a human relaxin-2 A chain, or a derivative thereof, a peptide linker and a human relaxin-2 B chain, or a derivative thereof. In some embodiments, the fusion protein further comprises an IgG Fc. The IgG Fc is linked to the N-terminus or C-terminus of the human relaxin B chain-linker protein-human relaxin A chain fusion protein or the human relaxin A chain-linker protein-human relaxin B chain fusion protein. In some embodiments, the IgG Fc described above is replaced with PEG.

Human Relaxin-2 B Chain Derivatives

The disclosure provides human relaxin-2 B chain derivatives, wherein the derivatives have 1, 2, 3, 4, or 5 amino acid changes when compared to the amino acid sequence of SEQ ID NO: 1. In some embodiments, the amino acid that corresponds with position 13 of SEQ ID NO: 1 must be arginine. In some embodiments, the amino acid that corresponds with position 17 of SEQ ID NO: 1 must be arginine. In some embodiments, the amino acid that corresponds with position 20 of SEQ ID NO: 1 must be isoleucine. In some embodiments, the amino acid that corresponds with position 13 of SEQ ID NO: 1 must be arginine; the amino acid that corresponds with position 17 of SEQ ID NO: 1 must be arginine; and the amino acid that corresponds with position 20 of SEQ ID NO: 1 must be isoleucine.

In some embodiments, the human relaxin-2 B chain derivatives comprise or consist of the following formula: DSW$X_3$EEVIKLCGRELVRAQIAICG$X_4$ST (SEQ ID NO: 3), wherein $X_3$ and $X_4$ are absent or any amino acid. In some embodiments, $X_3$ is methionine, lysine or glutamine, and $X_4$ is methionine or lysine. In some embodiments, $X_4$ is lysine.

In some embodiments, the human relaxin-2 B chain derivatives used in the fusion proteins described herein do not include the amino acid sequences of SEQ ID NOs: 187-190.

In some embodiments, the human relaxin-2 B chain derivatives are from 22, 23, 24, 25, 26, 27, 28, 29, 30, 31, or 32 amino acids in length. In some embodiments, the human relaxin-2 B chain derivatives are 25, 26, 27, 28, or 29 amino acids in length. In some embodiments, the human relaxin-2 B chain derivatives are 27 amino acids in length.

In some embodiments, the human relaxin-2 B chain derivatives comprise or consist of the amino acid sequences shown in Table 1, below.

TABLE 1

Human Relaxin-2 B Chain Derivative Sequences

| SEQ ID NO: | Amino Acid Sequence |
|---|---|
| 5 | DSWKEEVIKLCGRELVRAQIAICGKST |
| 6 | DSWMEEVIKLCGRELVRAQIAICGKST |
| 7 | DSWQEEVIKLCGRELVRAQIAICGKST |

Human Relaxin-2 A Chain Derivatives

The disclosure provides human relaxin-2 A chain derivatives, wherein the derivatives have 1, 2, 3, 4, or 5 amino acid changes when compared to the amino acid sequence of SEQ ID NO: 2. In some embodiments, the amino acid that corresponds with position 3 of SEQ ID NO: 2 must be lysine. In some embodiments, the amino acid that corresponds with position 23 of SEQ ID NO: 2 must be phenylalanine. In some embodiments, the amino acid that corresponds with position 3 of SEQ ID NO: 2 must be lysine; and the amino acid that corresponds with position 23 of SEQ ID NO: 2 must be phenylalanine.

In some embodiments, the human relaxin-2 A chain derivatives comprise or consist of the following formula: $X_5$Q$X_6$YSALANKCCHVGCTKRSLA$X_7$FC (SEQ ID NO: 4), wherein $X_5$, $X_6$, and $X_7$ are absent or any amino acid. In some embodiments, $X_5$ is arginine or absent, $X_6$ is leucine or aspartate, and $X_7$ is arginine, glutamine, or glutamate.

In some embodiments, the human relaxin-2 A chain derivatives are from 19, 20, 21, 22, 23, 24, 25, 26, 27, 28, 29, or 30 amino acids in length. In some embodiments, the human relaxin-2 A chain derivatives are 22, 23, 24, 25, or 26 amino acids in length. In some embodiments, the human relaxin-2 A chain derivatives are 24 amino acids in length. In some embodiments, the human relaxin-2 A chain derivatives are 25 amino acids in length.

In some embodiments, the human relaxin-2 A chain derivatives comprise or consist of the amino acid sequences shown in Table 2, below.

TABLE 2

Human Relaxin-2 A Chain Derivative Sequences

| SEQ ID NO: | Amino Acid Sequence |
|---|---|
| 8 | RQLYSALANKCCHVGCTKRSLARFC |
| 9 | QLYSALANKCCHVGCTKRSLARFC |
| 10 | RQLYSALANKCCHVGCTKRSLAQFC |
| 11 | RQLYSALANKCCHVGCTKRSLAEFC |
| 12 | RQDYSALANKCCHVGCTKRSLAQFC |
| 13 | RQDYSALANKCCHVGCTKRSLARFC |

Linker Peptides

The disclosure provides linker peptides, wherein the peptides have at least two acidic amino acids. In some embodiments, the acidic amino acid is glutamate. In some embodiments, the acidic amino acid is aspartate. In some embodiments, the acidic amino acid is a non-standard amino acid. In some embodiments, the acidic amino acid is 2-aminoadipic acid, 2-aminobutyric acid or 2-aminopimelic acid. In some embodiments, the linker peptide has 2, 3, 4, 5, 6, 7, 8, 9, or 10 acidic amino acids.

In some embodiments, the linker peptide is 8, 9, 10, 11, 12, 13, 14, or 15 amino acids in length. In some embodiments, the linker peptide is 12, 13, 14, or 15 amino acids in length. In some embodiments, the linker peptide has 2, 3, 4, or 5 acidic amino acids. In some embodiments, the linker peptide is 12, 13, 14, or 15 amino acids in length and has 2, 3, 4, or 5 acidic amino acids. In some embodiments, the remaining amino acids are non-acidic amino acids. In some embodiments, the non-acidic amino acids can be any standard amino acid that is not aspartate or glutamate. In some embodiments, non-acidic amino acids can be any amino acid that does not have a carboxylic acid in its side chain. In some embodiments, the non-acidic amino acid is glycine, proline, serine, arginine, histidine, lysine, threonine, asparagine, glutamine, cysteine, alanine, valine, isoleucine, leucine, methionine, phenylalanine, tyrosine, or tryptophan. In some embodiments, the non-acidic amino acid is glycine, proline, or cysteine. In some embodiments, the non-acidic amino acid is glycine.

In some embodiments, the linker peptide comprises acidic amino acids, wherein all the acidic amino acids are the same amino acids. In some embodiments, the acidic amino acids in the linker peptide are both/all glutamates. In some embodiments, the acidic amino acids in the linker peptide are both/all aspartates. In some embodiments, the linker peptide comprises amino acids that are a mixture of acidic amino acids. In some embodiments, the linker peptide comprises both glutamate and aspartate as acidic amino acids.

In some embodiments, the linker peptide comprises an amino acid sequence selected from the group consisting of $R_1R_1R_1R_2R_1R_1R_1R_2R_1R_1R_1R_2R_1$;

$R_1R_1R_1R_2R_1R_1R_1R_2R_1R_1R_1R_2R_1R_1R_1$;

$R_1R_1R_2R_1R_1R_1R_2R_2R_1R_1R_1R_2R_1R_1$;

$R_1R_1R_1R_2R_2R_1R_1R_1R_2R_2R_1R_1R_1$; and $R_1R_1R_2R_1R_2R_1R_1R_2R_1R_2R_1R_1R_1$, wherein $R_1$ is a non-acidic amino acid and $R_2$ is an acidic amino acid.

In some embodiments, the linker peptide comprises non-acidic amino acids, wherein all the non-acidic amino acids are the same amino acids. In some embodiments, the non-acidic amino acids in the linker peptide are all glycine. In some embodiments, the linker peptide comprises amino acids that are a mixture of non-acidic amino acids. In some embodiments, the linker peptide comprises 2, 3, 4, 5, 6, 7, 8, 9, or 10 different types of non-acidic amino acids.

In some embodiments, the linker peptide comprises or consists of the amino acid sequences shown in Table 3, below.

TABLE 3

| Linker Peptide Sequences | |
|---|---|
| SEQ ID NO: | Amino Acid Sequence |
| 14 | GGGE |
| 15 | GEGE |
| 16 | GGEG |
| 17 | GEGG |
| 18 | GGEE |
| 19 | GGGEGGGEGGGEG |
| 20 | GGGEGGGEGGGEGGG |
| 21 | GEGGGEEGGGEGG |

TABLE 3-continued

| Linker Peptide Sequences | |
|---|---|
| SEQ ID NO: | Amino Acid Sequence |
| 22 | GGGEEGGGEEGGG |
| 23 | GGEGEGGEGEGGS |

In some embodiments, the linker peptide comprises 2, 3, 4, or 5 repeats of SEQ ID NO: 14, 15, 16, 17, or 18. For example, 3 repeats of SEQ ID NO: 14 would be the amino acid sequence of GGGEGGGEGGGE (SEQ ID NO: 24).

Relaxin Linker Peptide Combinations for the Fusion Protein

In some embodiments, the fusion protein comprises an N-terminal or first peptide, a linker peptide, and a C-terminal or second peptide. In some embodiments, the N-terminal peptide comprises a human relaxin-2 A chain or a derivative thereof and the C-terminal peptide comprises a human relaxin-2 B chain or a derivative thereof. In some embodiments, the N-terminal peptide comprises a human relaxin-2 B chain or a derivative thereof and the C-terminal peptide comprises a human relaxin-2 A chain or a derivative thereof. Any combination of any of the embodiments of the human relaxin-2 A chain or a derivative thereof, with a human relaxin-2 A chain or a derivative thereof linked by any of the linker peptides disclosed herein can be used to construct embodiments of the fusion proteins described herein. In some embodiments, at least one of the N-terminal peptide and the C-terminal peptide is a derivative of a human relaxin-2 A chain or a human relaxin-2 B chain. In some embodiments, the N-terminal peptide comprises a human relaxin-2 A chain derivative and the C-terminal peptide comprises a human relaxin-2 B chain derivative. In some embodiments, the N-terminal peptide comprises a human relaxin-2 B chain derivative and the C-terminal peptide comprises a human relaxin-2 A chain derivative. Specific embodiments of the fusion proteins provided in this disclosure are shown below in Table 4.

TABLE 4

| Fusion Proteins | | | | | |
|---|---|---|---|---|---|
| B-SEQ ID NO: 19-A | | | B-SEQ ID NO: 20-A | | |
| SEQ ID NO of N-terminal Peptide | SEQ ID NO of linker peptide | SEQ ID NO of C-terminal Peptide | SEQ ID NO of N-terminal Peptide | SEQ ID NO of linker peptide | SEQ ID NO of C-terminal Peptide |
| 5 | 19 | 8 | 5 | 20 | 8 |
| 6 | 19 | 8 | 6 | 20 | 8 |
| 7 | 19 | 8 | 7 | 20 | 8 |
| 5 | 19 | 9 | 5 | 20 | 9 |
| 6 | 19 | 9 | 6 | 20 | 9 |
| 7 | 19 | 9 | 7 | 20 | 9 |
| 5 | 19 | 10 | 5 | 20 | 10 |
| 6 | 19 | 10 | 6 | 20 | 10 |
| 7 | 19 | 10 | 7 | 20 | 10 |
| 5 | 19 | 11 | 5 | 20 | 11 |
| 6 | 19 | 11 | 6 | 20 | 11 |
| 7 | 19 | 11 | 7 | 20 | 11 |
| 5 | 19 | 12 | 5 | 20 | 12 |
| 6 | 19 | 12 | 6 | 20 | 12 |
| 7 | 19 | 12 | 7 | 20 | 12 |

TABLE 4-continued

| Fusion Proteins | | | | | |
|---|---|---|---|---|---|
| 5 | 19 | 13 | 5 | 20 | 13 |
| 6 | 19 | 13 | 6 | 20 | 13 |
| 7 | 19 | 13 | 7 | 20 | 13 |

| B-SEQ ID NO: 21-A | | | B-SEQ ID NO: 22-A | | |
|---|---|---|---|---|---|
| SEQ ID NO of N-terminal Peptide | SEQ ID NO of linker peptide | SEQ ID NO of C-terminal Peptide | SEQ ID NO of N-terminal Peptide | SEQ ID NO of linker peptide | SEQ ID NO of C-terminal Peptide |
| 5 | 21 | 8 | 5 | 22 | 8 |
| 6 | 21 | 8 | 6 | 22 | 8 |
| 7 | 21 | 8 | 7 | 22 | 8 |
| 5 | 21 | 9 | 5 | 22 | 9 |
| 6 | 21 | 9 | 6 | 22 | 9 |
| 7 | 21 | 9 | 7 | 22 | 9 |
| 5 | 21 | 10 | 5 | 22 | 10 |
| 6 | 21 | 10 | 6 | 22 | 10 |
| 7 | 21 | 10 | 7 | 22 | 10 |
| 5 | 21 | 11 | 5 | 22 | 11 |
| 6 | 21 | 11 | 6 | 22 | 11 |
| 7 | 21 | 11 | 7 | 22 | 11 |
| 5 | 21 | 12 | 5 | 22 | 12 |
| 6 | 21 | 12 | 6 | 22 | 12 |
| 7 | 21 | 12 | 7 | 22 | 12 |
| 5 | 21 | 13 | 5 | 22 | 13 |
| 6 | 21 | 13 | 6 | 22 | 13 |
| 7 | 21 | 13 | 7 | 22 | 13 |

| B-SEQ ID NO: 23-A | | | A-SEQ ID NO: 19-B | | |
|---|---|---|---|---|---|
| SEQ ID NO of N-terminal Peptide | SEQ ID NO of linker peptide | SEQ ID NO of C-terminal Peptide | SEQ ID NO of N-terminal Peptide | SEQ ID NO of linker peptide | SEQ ID NO of C-terminal Peptide |
| 5 | 23 | 8 | 8 | 19 | 5 |
| 6 | 23 | 8 | 8 | 19 | 6 |
| 7 | 23 | 8 | 8 | 19 | 7 |
| 5 | 23 | 9 | 9 | 19 | 5 |
| 6 | 23 | 9 | 9 | 19 | 6 |
| 7 | 23 | 9 | 9 | 19 | 7 |
| 5 | 23 | 10 | 10 | 19 | 5 |
| 6 | 23 | 10 | 10 | 19 | 6 |
| 7 | 23 | 10 | 10 | 19 | 7 |
| 5 | 23 | 11 | 11 | 19 | 5 |
| 6 | 23 | 11 | 11 | 19 | 6 |
| 7 | 23 | 11 | 11 | 19 | 7 |
| 5 | 23 | 12 | 12 | 19 | 5 |
| 6 | 23 | 12 | 12 | 19 | 6 |
| 7 | 23 | 12 | 12 | 19 | 7 |
| 5 | 23 | 13 | 13 | 19 | 5 |
| 6 | 23 | 13 | 13 | 19 | 6 |
| 7 | 23 | 13 | 13 | 19 | 7 |

| A-SEQ ID NO: 20-B | | | A-SEQ ID NO: 21-B | | |
|---|---|---|---|---|---|
| SEQ ID NO of N-terminal Peptide | SEQ ID NO of linker peptide | SEQ ID NO of C-terminal Peptide | SEQ ID NO of N-terminal Peptide | SEQ ID NO of linker peptide | SEQ ID NO of C-terminal Peptide |
| 8 | 20 | 5 | 8 | 21 | 5 |
| 8 | 20 | 6 | 8 | 21 | 6 |
| 8 | 20 | 7 | 8 | 21 | 7 |
| 9 | 20 | 5 | 9 | 21 | 5 |
| 9 | 20 | 6 | 9 | 21 | 6 |
| 9 | 20 | 7 | 9 | 21 | 7 |
| 10 | 20 | 5 | 10 | 21 | 5 |
| 10 | 20 | 6 | 10 | 21 | 6 |
| 10 | 20 | 7 | 10 | 21 | 7 |
| 11 | 20 | 5 | 11 | 21 | 5 |
| 11 | 20 | 6 | 11 | 21 | 6 |
| 11 | 20 | 7 | 11 | 21 | 7 |
| 12 | 20 | 5 | 12 | 21 | 5 |
| 12 | 20 | 6 | 12 | 21 | 6 |

TABLE 4-continued

| Fusion Proteins | | | | | |
|---|---|---|---|---|---|
| 12 | 20 | 7 | 12 | 21 | 7 |
| 13 | 20 | 5 | 13 | 21 | 5 |
| 13 | 20 | 6 | 13 | 21 | 6 |
| 13 | 20 | 7 | 13 | 21 | 7 |
| A-SEQ ID NO: 22-B | | | A-SEQ ID NO: 23-B | | |
| SEQ ID NO of N-terminal Peptide | SEQ ID NO of linker peptide | SEQ ID NO of C-terminal Peptide | SEQ ID NO of N-terminal Peptide | SEQ ID NO of linker peptide | SEQ ID NO of C-terminal Peptide |
| 8 | 22 | 5 | 8 | 23 | 5 |
| 8 | 22 | 6 | 8 | 23 | 6 |
| 8 | 22 | 7 | 8 | 23 | 7 |
| 9 | 22 | 5 | 9 | 23 | 5 |
| 9 | 22 | 6 | 9 | 23 | 6 |
| 9 | 22 | 7 | 9 | 23 | 7 |
| 10 | 22 | 5 | 10 | 23 | 5 |
| 10 | 22 | 6 | 10 | 23 | 6 |
| 10 | 22 | 7 | 10 | 23 | 7 |
| 11 | 22 | 5 | 11 | 23 | 5 |
| 11 | 22 | 6 | 11 | 23 | 6 |
| 11 | 22 | 7 | 11 | 23 | 7 |
| 12 | 22 | 5 | 12 | 23 | 5 |
| 12 | 22 | 6 | 12 | 23 | 6 |
| 12 | 22 | 7 | 12 | 23 | 7 |
| 13 | 22 | 5 | 13 | 23 | 5 |
| 13 | 22 | 6 | 13 | 23 | 6 |
| 13 | 22 | 7 | 13 | 23 | 7 |

In some embodiments, there are additional amino acids between the N-terminal peptide and the linker peptide. In some embodiments, there are additional amino acids between the C-terminal peptide and the linker peptide. In some embodiments, there are no additional amino acids between the N-terminal peptide and the linker peptide. In some embodiments, there are no additional amino acids between the C-terminal peptide and the linker peptide.

In some embodiments, the portion of the fusion protein comprising the N-terminal peptide, the linker peptide, and the C-terminal peptide comprises or consists of the amino acid sequences shown in Table 5, below.

TABLE 5

| Peptide Combinations for the Fusion Protein | |
|---|---|
| SEQ ID NO: | Amino Acid Sequence |
| 25 | DSWKEEVIKLCGRELVRAQIAICGKSTGGGEGGGEGGGEGRQLYSALANKCCHVGCTKRSLARFC |
| 26 | DSWKEEVIKLCGRELVRAQIAICGKSTGGGEGGGEGGGEGGGQLYSALANKCCHVGCTKRSLARFC |
| 27 | DSWMEEVIKLCGRELVRAQIAICGKSTGGGEGGGEGGGEGRQLYSALANKCCHVGCTKRSLARFC |
| 28 | DSWQEEVIKLCGRELVRAQIAICGKSTGGGEGGGEGGGEGRQLYSALANKCCHVGCTKRSLARFC |
| 29 | DSWMEEVIKLCGRELVRAQIAICGKSTGGGEGGGEGGGEGGGQLYSALANKCCHVGCTKRSLARFC |
| 30 | DSWQEEVIKLCGRELVRAQIAICGKSTGGGEGGGEGGGEGGGQLYSALANKCCHVGCTKRSLARFC |
| 31 | DSWMEEVIKLCGRELVRAQIAICGKSTGGEGGGEEGGGEGGQLYSALANKCCHVGCTKRSLARFC |
| 32 | DSWQEEVIKLCGRELVRAQIAICGKSTGGEGGGEEGGGEGGQLYSALANKCCHVGCTKRSLARFC |
| 33 | DSWMEEVIKLCGRELVRAQIAICGKSTGGEGGGEEGGGEGGQLYSALANKCCHVGCTKRSLARFC |
| 34 | DSWQEEVIKLCGRELVRAQIAICGKSTGGEGGGEEGGGEGGQLYSALANKCCHVGCTKRSLARFC |

TABLE 5-continued

| Peptide Combinations for the Fusion Protein | |
|---|---|
| SEQ ID NO: | Amino Acid Sequence |
| 35 | DSWQEEVIKLCGRELVRAQIAICGKSTGGGEGGGEGGGEGRQLYSALANKCCHVGCTK RSLAQFC |
| 36 | DSWQEEVIKLCGRELVRAQIAICGKSTGGGEGGGEGGGEGRQLYSALANKCCHVGCTK RSLARFC |
| 37 | DSWQEEVIKLCGRELVRAQIAICGKSTGGGEGGGEGGGEGRQLYSALANKCCHVGCTK RSLAQFC |
| 38 | DSWQEEVIKLCGRELVRAQIAICGKSTGGGEEGGGEEGGGRQLYSALANKCCHVGCTK RSLARFC |
| 39 | DSWQEEVIKLCGRELVRAQIAICGKSTGGGEEGGGEEGGGRQLYSALANKCCHVGCTK RSLAQFC |
| 40 | DSWQEEVIKLCGRELVRAQIAICGKSTGGGEEGGGEEGGGRQLYSALANKCCHVGCTK RSLARFC |
| 41 | DSWQEEVIKLCGRELVRAQIAICGKSTGGGEEGGGEEGGGRQLYSALANKCCHVGCTK RSLAQFC |
| 42 | DSWQEEVIKLCGRELVRAQIAICGKSTGGGEGGGEGGGEGRQDYSALANKCCHVGCTK RSLAQFC |
| 43 | DSWQEEVIKLCGRELVRAQIAICGKSTGGGEGGGEGGGEGRQDYSALANKCCHVGCTK RSLARFC |
| 44 | DSWQEEVIKLCGRELVRAQIAICGKSTGGGEGGGEGGGEGRQDYSALANKCCHVGCTK RSLAQFC |
| 45 | DSWQEEVIKLCGRELVRAQIAICGKSTGGEGEGGEGEGGSRQLYSALANKCCHVGCTK RSLAQFC |
| 46 | DSWQEEVIKLCGRELVRAQIAICGKSTGGEGEGGEGEGGSRQLYSALANKCCHVGCTK RSLARFC |
| 47 | DSWQEEVIKLCGRELVRAQIAICGKSTGGEGEGGEGEGGSRQLYSALANKCCHVGCTK RSLAQFC |
| 48 | DSWQEEVIKLCGRELVRAQIAICGKSTGGEGEGGEGEGGSRQDYSALANKCCHVGCTK RSLAQFC |

In some embodiments, the fusion proteins provided herein further comprise an IgG Fe. The IgG Fe can be linked to the N-terminal end of the N-terminal peptide or the C-terminal end of the C-terminal peptide. The IgG Fe can be linked directly to the N-terminal peptide or the C-terminal peptide or they can be linked to the N-terminal peptide or the C-terminal peptide through an IgG Fc linker. In some embodiments, the IgG Fc linker comprises or consists of 1, 2, 3, 4, 5, 6, 7, 8, 9, or 10 amino acids. In some embodiments, the IgG Fc linker comprises or consists of 1, 2, 3, 4, or 5 amino acids. In some embodiments, the IgG Fc linker comprises or consists of 3 or 4 amino acids. In some embodiments, the IgG Fc linker comprises or consists of the amino acid sequence of GGS. It is known in the art that the C-terminal lysine (K) in many monoclonal antibodies is flexible, and is often clipped off during expression and purification with no known impairment in activity. In some embodiments, the IgG Fc comprises the amino acid sequence of one of SEQ ID NOs: 49-52 with GGS as the IgG Fc linker at the C-terminal end of the IgG Fc. In some embodiments, the IgG Fc comprises the amino acid sequence of one of SEQ ID NOs: 200-203 with GGS as the IgG Fc linker at the C-terminal end of the IgG Fc.

In some embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1)) and/or the hinge region, numbered according to the EU numbering system, to alter one or more functional properties of the antibody, such as serum half-life, complement fixation, Fc receptor binding, and/or antigen-dependent cellular cytotoxicity.

In certain embodiments, one, two, or more mutations (e.g., amino acid substitutions) are introduced into the hinge region of the Fc region (CH1 domain) such that the number of cysteine residues in the hinge region are altered (e.g., increased or decreased) as described in, e.g., U.S. Pat. No. 5,677,425, herein incorporated by reference in its entirety. The number of cysteine residues in the hinge region of the CH1 domain may be altered to, e.g., facilitate assembly of the light and heavy chains, or to alter (e.g., increase or decrease) the stability of the antibody.

In a specific embodiment, one, two, or more amino acid mutations (e.g., substitutions, insertions or deletions) are introduced into an IgG constant domain, or FcRn-binding fragment thereof (preferably an Fc or hinge-Fc domain fragment) to alter (e.g., decrease or increase) half-life of the antibody in vivo. See, e.g., International Publication Nos. WO 02/060919; WO 98/23289; and WO 97/34631; and U.S. Pat. Nos. 5,869,046, 6,121,022, 6,277,375, and 6,165,745, all of which are herein incorporated by reference in their entireties, for examples of mutations that will alter (e.g., decrease or increase) the half-life of an antibody in vivo. In certain embodiments, one, two, or more amino acid mutations (e.g., substitutions, insertions, or deletions) are introduced into an IgG constant domain, or FcRn-binding fragment thereof (preferably an Fe or hinge-Fc domain fragment) to decrease the half-life of the antibody in vivo. In other embodiments, one, two, or more amino acid mutations (e.g., substitutions, insertions, or deletions) are introduced into an IgG constant domain, or FcRn-binding fragment thereof (preferably an Fe or hinge-Fc domain fragment) to increase the half-life of the antibody in vivo. In a specific embodiment, the antibodies may have one or more amino acid mutations (e.g., substitutions) in the second constant (CH2) domain (residues 231-340 of human IgG1) and/or the third constant (CH3) domain (residues 341-447 of human IgG1), numbered according to the EU numbering system. In a specific embodiment, the constant region of the IgG1 of an antibody described herein comprises a methionine (M) to tyrosine (Y) substitution in position 252, a serine (S) to threonine (T) substitution in position 254, and a threonine (T) to glutamic acid (E) substitution in position 256, numbered according to the EU numbering system. See, U.S. Pat. No. 7,658,921, which is herein incorporated by reference in its entirety. This type of mutant IgG, referred to as "YTE mutant" has been shown to display fourfold increased half-life as compared to wild-type versions of the same antibody (see, Dall'Acqua W F et al., (2006) *J Biol Chem* 281: 23514-24, which is herein incorporated by reference in its entirety). In certain embodiments, an antibody comprises an IgG constant domain comprising one, two, three or more amino acid substitutions of amino acid residues at positions 251-257, 285-290, 308-314, 385-389, and 428-436, numbered according to the EU numbering system.

In certain embodiments, one, two, or more mutations (e.g., amino acid substitutions) are introduced into the Fc region of an antibody described herein (e.g., CH2 domain (residues 231-340 of human IgG1) and/or CH3 domain (residues 341-447 of human IgG1)) and/or the hinge region, numbered according to the EU numbering system, to increase or decrease the affinity of the antibody for an Fc receptor (e.g., an activated Fc receptor) on the surface of an effector cell. Mutations in the Fc region of an antibody that decrease or increase the affinity of an antibody for an Fc receptor and techniques for introducing such mutations into the Fc receptor or fragment thereof are known to one of skill in the art. Examples of mutations in the Fc receptor of an antibody that can be made to alter the affinity of the antibody for an Fc receptor are described in, e.g., Smith P et al., (2012) *PNAS* 109: 6181-6186, U.S. Pat. No. 6,737,056, and International Publication Nos. WO 02/060919; WO 98/23289; and WO 97/34631, all of which are herein incorporated by reference in their entireties.

In certain embodiments, the antibody comprises a heavy chain constant region that is a variant of a wild-type heavy chain constant region, wherein the variant heavy chain constant region binds to FcγRIIB with higher affinity than the wild-type heavy chain constant region binds to FcγRIIB. In certain embodiments, the variant heavy chain constant region is a variant human heavy chain constant region, e.g., a variant human IgG1, a variant human IgG2, or a variant human IgG4 heavy chain constant region. In certain embodiments, the variant human IgG heavy chain constant region comprises one or more of the following amino acid mutations, according to the EU numbering system: G236D, P238D, S239D, S267E, L328F, and L328E. In certain embodiments, the variant human IgG heavy chain constant region comprises a set of amino acid mutations selected from the group consisting of: S267E and L328F; P238D and L328E; P238D and one or more substitutions selected from the group consisting of E233D, G237D, H268D, P271G, and A330R; P238D, E233D, G237D, H268D, P271G, and A330R; G236D and S267E; S239D and S267E; V262E, S267E, and L328F; and V264E, S267E, and L328F, according to the EU numbering system. In certain embodiments, the FcγRIIB is expressed on a cell selected from the group consisting of macrophages, monocytes, B cells, dendritic cells, endothelial cells, and activated T cells.

In a further embodiment, one, two, or more amino acid substitutions are introduced into an IgG constant domain Fc region to alter the effector function(s) of the antibody. For example, one or more amino acids selected from amino acid residues 234, 235, 236, 237, 239, 243, 267, 292, 297, 300, 318, 320, 322, 328, 330, 332, and 396, numbered according to the EU numbering system, can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, each of which is herein incorporated by reference in its entirety. In certain embodiments, the deletion or inactivation (through point mutations or other means) of a constant region domain may reduce Fc receptor binding of the circulating antibody thereby increasing tumor localization. See, e.g., U.S. Pat. Nos. 5,585,097 and 8,591,886, each of which is herein incorporated by reference in its entirety, for a description of mutations that delete or inactivate the constant domain and thereby increase tumor localization. In certain embodiments, one or more amino acid substitutions may be introduced into the Fc region of an antibody described herein to remove potential glycosylation sites on the Fc region, which may reduce Fc receptor binding (see, e.g., Shields R L et al., (2001) *J Biol Chem* 276: 6591-604, which is herein incorporated by reference in its entirety). In various embodiments, one or more of the following mutations in the constant region of an antibody described herein may be made: an N297A substitution; an N297Q substitution; an L234A substitution; an L234F substitution; an L235A substitution; an L235F substitution; an L235V substitution; an L237A substitution; an S239D substitution; an E233P substitution; an L234V substitution; an L235A substitution; a C236 deletion; a P238A substitution; an S239D substitution; an F243L substitution; a D265A substitution; an S267E substitution; an L328F substitution; an R292P substitution; a Y300L substitution; an A327Q substitution; a P329A substitution (PA); an A332L substitution; an I332E substitution; or a P396L substitution, numbered according to the EU numbering system.

In certain embodiments, a mutation selected from the group consisting of D265A, P329A, and a combination thereof, numbered according to the EU numbering system, may be made in the constant region of an antibody described herein. In certain embodiments, a mutation selected from the group consisting of L235A, L237A, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein. In certain embodiments, a mutation selected from the group consisting of S239D, I332E, optionally A330L, and a combination thereof, numbered according to the EU numbering system, may be made in the constant region of an antibody described herein. In certain embodiments, a mutation selected from the group consisting of L235V, F243L, R292P, Y300L, P396L, and a combination thereof, numbered according to the EU numbering system, may be made in the constant region of an antibody described herein. In certain embodiments, a mutation selected from the group consisting of S267E, L328F, and a combination thereof, numbered according to the EU numbering system, may be made in the constant region of an antibody described herein.

In a specific embodiment, an antibody described herein comprises the constant domain of an IgG1 with an N297Q or N297A amino acid substitution, numbered according to the EU numbering system. In one embodiment, an antibody described herein comprises the constant domain of an IgG1 with a mutation selected from the group consisting of D265A, P329A, and a combination thereof, numbered according to the EU numbering system. In another embodiment, an antibody described herein comprises the constant domain of an IgG1 with a mutation selected from the group consisting of L234A, L235A (LALA), and a combination thereof, numbered according to the EU numbering system. In another embodiment, an antibody described herein comprises the constant domain of an IgG1 with a mutation selected from the group consisting of L234F, L235F, N297A, and a combination thereof, numbered according to the EU numbering system. In certain embodiments, amino acid residues in the constant region of an antibody described herein in the positions corresponding to positions L234, L235, and D265 in a human IgG1 heavy chain, numbered according to the EU numbering system, are not L, L, and D, respectively. This approach is described in detail in International Publication No. WO 14/108483, which is herein incorporated by reference in its entirety. In a particular embodiment, the amino acids corresponding to positions L234, L235, and D265 in a human IgG1 heavy chain are F, E, and A; or A, A, and A, respectively, numbered according to the EU numbering system.

In certain embodiments, one or more amino acids selected from amino acid residues 329, 331, and 322 in the constant region of an antibody described herein, numbered according to the EU numbering system, can be replaced with a different amino acid residue such that the antibody has altered C1q binding and/or reduced or abolished complement dependent cytotoxicity (CDC). This approach is described in further detail in U.S. Pat. No. 6,194,551 (Idusogie et al.), which is herein incorporated by reference in its entirety. In certain embodiments, one or more amino acid residues within amino acid positions 231 to 238 in the N-terminal region of the CH2 domain of an antibody described herein are altered to thereby alter the ability of the antibody to fix complement, numbered according to the EU numbering system. This approach is described further in International Publication No. WO 94/29351, which is herein incorporated by reference in its entirety. In certain embodiments, the Fc region of an antibody described herein is modified to increase the ability of the antibody to mediate antibody dependent cellular cytotoxicity (ADCC) and/or to increase the affinity of the antibody for an Fcγ receptor by mutating one or more amino acids (e.g., introducing amino acid substitutions) at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 328, 329, 330, 331, 333, 334, 335, 337, 338, 340, 360, 373, 376, 378, 382, 388, 389, 398, 414, 416, 419, 430, 434, 435, 437, 438, or 439, numbered according to the EU numbering system. This approach is described further in International Publication No. WO 00/42072, which is herein incorporated by reference in its entirety.

In some embodiments, the IgG Fc is an IgG1 Fc, or a derivative thereof. In some embodiments, the IgG Fc or IgG1 Fc comprises an amino acid sequence at least 85, 90, 95, 96, 97, 98, or 9900 identical to the amino acid sequence of IgG1 Fc. In some embodiments, the IgG Fc or IgG1 Fc comprises an amino acid sequence at least 85, 90, 95, 96, 97, 98, 99, or 10000 identical to an amino acid sequence provided below in Table 6.

TABLE 6

IgG Fc Amino Acid Sequences

| SEQ ID NO: | Description | Sequence |
|---|---|---|
| 49 | IgG1 Fc | DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 50 | IgG1 Fc LALA | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 51 | IgG1 Fc LALA PA | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPGK |
| 52 | IgG1 Fc LALA PA LS | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVLHEALHSHYTQKSLSLSPGK |

TABLE 6-continued

| IgG Fc Amino Acid Sequences | | |
|---|---|---|
| SEQ ID NO: | Description | Sequence |
| 200 | IgG1 Fc without C-terminal lysine | DKTHTCPPCPAPELLGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPG |
| 201 | IgG1 Fc LALA without C-terminal lysine | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALPAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPG |
| 202 | IgG1 Fc LALA PA without C-terminal lysine | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVMHEALHNHYTQKSLSLSPG |
| 203 | IgG1 Fc LALA PA LS without C-terminal lysine | DKTHTCPPCPAPEAAGGPSVFLFPPKPKDTLMISRTPEVTCVVVDV SHEDPEVKFNWYVDGVEVHNAKTKPREEQYNSTYRVVSVLTVLHQD WLNGKEYKCKVSNKALAAPIEKTISKAKGQPREPQVYTLPPSRDEL TKNQVSLTCLVKGFYPSDIAVEWESNGQPENNYKTTPPVLDSDGSF FLYSKLTVDKSRWQQGNVFSCSVLHEALHSHYTQKSLSLSPG |

In some embodiments, any IgG Fe, or derivative thereof, can be linked to the N-terminus or C-terminus of any of the embodiments described in Table 4 or 5 above with or without an IgG Fc linker. In some embodiments, human IgG1 Fc, or a derivative thereof, can be linked to the N-terminus or C-terminus of any of the embodiments described in Table 4 or 5 above with or without an IgG Fc linker. In some embodiments, the amino acid sequence of the human IgG1 Fc comprises or consists of the amino acid sequence of SEQ TD NO: 49 or 200. In some embodiments, the derivative if human IgG1 Fc comprises an amino acid sequence at least 85, 90, 95, 96, 97, 98, or 99% identical to the amino acid sequence of SEQ TD NO: 49 or 200.

In some embodiments, a human IgG1 Fc comprising a LALA mutation, or a derivative thereof, can be linked to the N-terminus or C-terminus of any of the embodiments described in Table 4 or 5 above with or without an IgG Fc linker. In some embodiments, the amino acid sequence of the human IgG1 Fc comprising a LALA mutation comprises or consists of the amino acid sequence of SEQ ID NO: 50 or 201. In some embodiments, the derivative if human IgG1 Fc comprising a LALA mutation comprises an amino acid sequence at least 85, 90, 95, 96, 97, 98, or 99% identical to the amino acid sequence of SEQ TD NO: 50 or 201.

In some embodiments, a human IgG1 Fc comprising a LALA PA mutation, or a derivative thereof, can be linked to the N-terminus or C-terminus of any of the embodiments described in Table 4 or 5 above with or without an IgG Fc linker. In some embodiments, the amino acid sequence of the human IgG1 Fc comprising a LALA PA mutation comprises or consists of the amino acid sequence of SEQ ID NO: 51 or 202. In some embodiments, the derivative if human IgG1 Fc comprising a LALA PA mutation comprises an amino acid sequence at least 85, 90, 95, 96, 97, 98, or 99% identical to the amino acid sequence of SEQ ID NO: 51 or 202.

In some embodiments, a human IgG1 Fc comprising a LALA PA LS mutation, or a derivative thereof, can be linked to the N-terminus or C-terminus of any of the embodiments described in Table 4 or 5 above with or without an IgG Fc linker. In some embodiments, the amino acid sequence of the human IgG1 Fc comprising a LALA PA LS mutation comprises or consists of the amino acid sequence of SEQ ID NO: 52 or 203. In some embodiments, the derivative if human IgG1 Fc comprising a LALA PA LS mutation comprises an amino acid sequence at least 85, 90, 95, 96, 97, 98, or 99% identical to the amino acid sequence of SEQ ID NO: 52 or 203.

In some embodiments, the fusion protein comprises or consists of the amino acid sequences shown in Table 7, below.

TABLE 7

| Fusion Protein Amino Acid Sequences | |
|---|---|
| SEQ ID NO: | Sequence |
| 53 | DKTHTCPPCPAPEAAGGPSVFLFPPKPKDTLMISRTPEVTCVVVDVSHEDPEVKFNWYVDGV EVHNAKTKPREEQYNSTYRVVSVLTVLHQDWLNGKEYKCKVSNKALPAPIEKTISKAKGQPR EPQVYTLPPSRDELTKNQVSLTCLVKGFYPSDIAVEWESNGQPENNYKTTPPVLDSDGSFFL YSKLTVDKSRWQQGNVFSCSVMHEALHNHYTQKSLSLSPGKGGSDSWKEEVIKLCGRELVRA QIAICGKSTGGGEGGGEGGGEGRQLYSALANKCCHVGCTKRSLARFC |

TABLE 7-continued

Fusion Protein Amino Acid Sequences

| SEQ ID NO: | Sequence |
|---|---|
| 54 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWKEEVIKLCGRELVRA<br>QIAICGKSTGGGEGGGEGGGEGGGQLYSALANKCCHVGCTKRSLARFC |
| 55 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWMEEVIKLCGRELVRA<br>QIAICGKSTGGGEGGGEGGGEGRQLYSALANKCCHVGCTKRSLARFC |
| 56 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWQEEVIKLCGRELVRA<br>QIAICGKSTGGGEGGGEGGGEGRQLYSALANKCCHVGCTKRSLARFC |
| 57 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGGEGGGEGGGEGRQLYSALANKCCHVGCTKRSLARFC |
| 58 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWMEEVIKLCGRELVRA<br>QIAICGKSTGGGEGGGEGGGEGGGQLYSALANKCCHVGCTKRSLARFC |
| 59 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWQEEVIKLCGRELVRA<br>QIAICGKSTGGGEGGGEGGGEGGGQLYSALANKCCHVGCTKRSLARFC |
| 60 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGGEGGGEGGGEGGGQLYSALANKCCHVGCTKRSLARFC |
| 61 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWMEEVIKLCGRELVRA<br>QIAICGKSTGGEGGGEEGGGEGGQLYSALANKCCHVGCTKRSLARFC |
| 62 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWQEEVIKLCGRELVRA<br>QIAICGKSTGGEGGGEEGGGEGGQLYSALANKCCHVGCTKRSLARFC |
| 63 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGGGSDSWMEEVIKLCGRELVRAQ<br>IAICGKSTGGEGGGEEGGGEGGQLYSALANKCCHVGCTKRSLARFC |
| 64 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGGGSDSWQEEVIKLCGRELVRAQ<br>IAICGKSTGGEGGGEEGGGEGGQLYSALANKCCHVGCTKRSLARFC |
| 65 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWQEEVIKLCGRELVRA<br>QIAICGKSTGGGEGGGEGGGEGRQLYSALANKCCHVGCTKRSLAQFC |
| 66 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL |

TABLE 7-continued

Fusion Protein Amino Acid Sequences

| SEQ ID NO: | Sequence |
|---|---|
| | YSKLTVDKSRWQQGNVFSCSVLHEALHSHYTQKSLSLSPGKGGSDSWQEEVIKLCGRELVRA<br>QIAICGKSTGGGEGGGEGGGEGRQLYSALANKCCHVGCTKRSLAQFC |
| 67 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGGGSDSWQEEVIKLCGRELVRAQ<br>IAICGKSTGGGEGGGEGGGEGRQLYSALANKCCHVGCTKRSLARFC |
| 68 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGGEGGGEGGGEGRQLYSALANKCCHVGCTKRSLARFC |
| 69 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGGGSDSWQEEVIKLCGRELVRAQ<br>IAICGKSTGGGEGGGEGGGEGRQLYSALANKCCHVGCTKRSLAQFC |
| 70 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGGEGGGEGGGEGRQLYSALANKCCHVGCTKRSLAQFC |
| 71 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWQEEVIKLCGRELVRA<br>QIAICGKSTGGGEEGGGEEGGGRQLYSALANKCCHVGCTKRSLARFC |
| 72 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGGEEGGGEEGGGRQLYSALANKCCHVGCTKRSLARFC |
| 73 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWQEEVIKLCGRELVRA<br>QIAICGKSTGGGEEGGGEEGGGRQLYSALANKCCHVGCTKRSLAQFC |
| 74 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGGEEGGGEEGGGRQLYSALANKCCHVGCTKRSLAQFC |
| 75 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGGGSDSWQEEVIKLCGRELVRAQ<br>IAICGKSTGGGEEGGGEEGGGRQLYSALANKCCHVGCTKRSLARFC |
| 76 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGGEEGGGEEGGGRQLYSALANKCCHVGCTKRSLARFC |
| 77 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGGGSDSWQEEVIKLCGRELVRAQ<br>IAICGKSTGGGEEGGGEEGGGRQLYSALANKCCHVGCTKRSLAQFC |
| 78 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGGEEGGGEEGGGRQLYSALANKCCHVGCTKRSLAQFC |

TABLE 7-continued

Fusion Protein Amino Acid Sequences

| SEQ ID NO: | Sequence |
|---|---|
| 79 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGGEGGGEGGGEGRQDYSALANKCCHVGCTKRSLAQFC |
| 80 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGGEGGGEGGGEGRQDYSALANKCCHVGCTKRSLARFC |
| 81 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGGEGGGEGGGEGRQDYSALANKCCHVGCTKRSLAQFC |
| 82 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGEGEGGEGEGGSRQLYSALANKCCHVGCTKRSLAQFC |
| 83 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGEGEGGEGEGGSRQLYSALANKCCHVGCTKRSLARFC |
| 84 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGGGSDSWQEEVIKLCGRELVRAQ<br>IAICGKSTGGEGEGGEGEGGSRQLYSALANKCCHVGCTKRSLAQFC |
| 85 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALAAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVLHEALHSHYTQKSLSLSPGKGGSDSWQEEVIKLCGRELVRA<br>QIAICGKSTGGEGEGGEGEGGSRQDYSALANKCCHVGCTKRSLAQFC |
| 191 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWKEEVIKLCGRELVRA<br>QIAICGKSTASDAAGANANAGARQLYSALANKCCHVGCTKRSLAQFC |
| 192 | DKTHTCPPCPAPEAAGGPSVFLFPPKPKDTLMISRTPEVTCVVVDVSHEDPEVKFNWYVDGV<br>EVHNAKTKPREEQYNSTYRVVSVLTVLHQDWLNGKEYKCKVSNKALPAPIEKTISKAKGQPR<br>EPQVYTLPPSRDELTKNQVSLTCLVKGFYPSDIAVEWESNGQPENNYKTTPPVLDSDGSFFL<br>YSKLTVDKSRWQQGNVFSCSVMHEALHNHYTQKSLSLSPGKGGSDSWKEEVIKLCGRELVRA<br>QIAICGKSTASDAAGANANAGARQLYSALANKCCHVGCTKRSLAEFC |
| 86 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALPAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGKG<br>GSDSWKEEVIKLCGRELVRAQIAICGKSTGGGEGGGEGGGEGRQLYSALANKCCHVGCTKRS<br>LARFC |
| 87 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALPAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGKG<br>GSDSWKEEVIKLCGRELVRAQIAICGKSTGGGEGGGEGGGEGGGQLYSALANKCCHVGCTKR<br>SLARFC |
| 88 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALPAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGKG<br>GSDSWMEEVIKLCGRELVRAQIAICGKSTGGGEGGGEGGGEGRQLYSALANKCCHVGCTKRS<br>LARFC |

TABLE 7-continued

| Fusion Protein Amino Acid Sequences | |
|---|---|
| SEQ ID NO: | Sequence |
| 89 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGKG GSDSWQEEVIKLCGRELVRAQIAICGKSTGGGEGGGEGGGEGRQLYSALANKCCHVGCTKRS LARFC |
| 90 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALAAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVLHEALHSHYTQKSLSLSPGKG GSDSWQEEVIKLCGRELVRAQIAICGKSTGGGEGGGEGGGEGRQLYSALANKCCHVGCTKRS LARFC |
| 91 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGKG GSDSWMEEVIKLCGRELVRAQIAICGKSTGGGEGGGEGGGEGGGQLYSALANKCCHVGCTKR SLARFC |
| 92 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGKG GSDSWQEEVIKLCGRELVRAQIAICGKSTGGGEGGGEGGGEGGGQLYSALANKCCHVGCTKR SLARFC |
| 93 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALAAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVLHEALHSHYTQKSLSLSPGKG GSDSWQEEVIKLCGRELVRAQIAICGKSTGGGEGGGEGGGEGGGQLYSALANKCCHVGCTKR SLARFC |
| 94 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGKG GSDSWMEEVIKLCGRELVRAQIAICGKSTGGEGGGEEGGGEGGQLYSALANKCCHVGCTKRS LARFC |
| 95 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGKG GSDSWQEEVIKLCGRELVRAQIAICGKSTGGEGGGEEGGGEGGQLYSALANKCCHVGCTKRS LARFC |
| 96 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGGG SDSWMEEVIKLCGRELVRAQIAICGKSTGGEGGGEEGGGEGGQLYSALANKCCHVGCTKRSL ARFC |
| 97 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGGG SDSWQEEVIKLCGRELVRAQIAICGKSTGGEGGGEEGGGEGGQLYSALANKCCHVGCTKRSL ARFC |
| 98 | METDTLLLWVLLLWVPGSTGDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNGKEYKCKVS NKALAAPIEKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQKSLSLSPGKG GSDSWQEEVIKLCGRELVRAQIAICGKSTGGGEGGGEGGGEGRQLYSALANKCCHVGCTKRS LAQFC |

TABLE 7-continued

| Fusion Protein Amino Acid Sequences | |
|---|---|
| SEQ ID NO: | Sequence |
| 99 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGKG<br>GSDSWQEEVIKLCGRELVRAQIAICGKSTGGGEGGGEGGGEGRQLYSALANKCCHVGCTKRS<br>LAQFC |
| 100 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGGG<br>SDSWQEEVIKLCGRELVRAQIAICGKSTGGGEGGGEGGGEGRQLYSALANKCCHVGCTKRSL<br>ARFC |
| 101 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGGEGGGEGGGEGRQLYSALANKCCHVGCTKRSL<br>ARFC |
| 102 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGGG<br>SDSWQEEVIKLCGRELVRAQIAICGKSTGGGEGGGEGGGEGRQLYSALANKCCHVGCTKRSL<br>AQFC |
| 103 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGGEGGGEGGGEGRQLYSALANKCCHVGCTKRSL<br>AQFC |
| 104 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGKG<br>GSDSWQEEVIKLCGRELVRAQIAICGKSTGGGEEGGGEEGGGRQLYSALANKCCHVGCTKRS<br>LARFC |
| 105 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGKG<br>GSDSWQEEVIKLCGRELVRAQIAICGKSTGGGEEGGGEEGGGRQLYSALANKCCHVGCTKRS<br>LARFC |
| 106 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGKG<br>GSDSWQEEVIKLCGRELVRAQIAICGKSTGGGEEGGGEEGGGRQLYSALANKCCHVGCTKRS<br>LAQFC |
| 107 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGKG<br>GSDSWQEEVIKLCGRELVRAQIAICGKSTGGGEEGGGEEGGGRQLYSALANKCCHVGCTKRS<br>LAQFC |
| 108 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGGG<br>SDSWQEEVIKLCGRELVRAQIAICGKSTGGGEEGGGEEGGGRQLYSALANKCCHVGCTKRSL<br>ARFC |

TABLE 7-continued

Fusion Protein Amino Acid Sequences

| SEQ ID NO: | Sequence |
|---|---|
| 109 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGGEEGGGEEGGGRQLYSALANKCCHVGCTKRSL<br>ARFC |
| 110 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSLSLSPGGG<br>SDSWQEEVIKLCGRELVRAQIAICGKSTGGGEEGGGEEGGGRQLYSALANKCCHVGCTKRSL<br>AQFC |
| 111 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGGEEGGGEEGGGRQLYSALANKCCHVGCTKRSL<br>AQFC |
| 112 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGKG<br>GSDSWQEEVIKLCGRELVRAQIAICGKSTGGGEGGGEGGGEGRQDYSALANKCCHVGCTKRS<br>LAQFC |
| 113 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGGEGGGEGGGEGRQDYSALANKCCHVGCTKRSL<br>ARFC |
| 114 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGGEGGGEGGGEGRQDYSALANKCCHVGCTKRSL<br>AQFC |
| 115 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGKG<br>GSDSWQEEVIKLCGRELVRAQIAICGKSTGGEGEGGEGEGGSRQLYSALANKCCHVGCTKRS<br>LAQFC |
| 116 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGEGEGGEGEGGSRQLYSALANKCCHVGCTKRSL<br>ARFC |
| 117 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGGG<br>SDSWQEEVIKLCGRELVRAQIAICGKSTGGEGEGGEGEGGSRQLYSALANKCCHVGCTKRSL<br>AQFC |
| 118 | METDTLLLWVLLLWVPGSTGDKTHTCPPCPAPEAAGGPSVFLFPPKPKDTLMISRTPEVTCV<br>VVDVSHEDPEVKFNWYVDGVEVHNAKTKPREEQYNSTYRVVSVLTVLHQDWLNGKEYKCKVS<br>NKALAAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVLHEALHSHYTQKSLSLSPGKG<br>GSDSWQEEVIKLCGRELVRAQIAICGKSTGGEGEGGEGEGGSRQDYSALANKCCHVGCTKRS<br>LAQFC |

As shown in Table 7, above, in some embodiments, the IgG Fc comprises a mouse IgG kappa signal sequence comprising the amino acid sequence of METDTLLLWVLLLWVPGSTG (SEQ ID NO: 194). In some embodiments a different signal sequence is used. In some embodiments, some shown in Table 7, no signal sequence is present on the fusion protein as produced.

Other Half-Life Extending Moieties

As used herein, the term "half-life extending moiety" includes non-proteinaceous, half-life extending moieties, such as PEG or HES, and proteinaceous half-life extending moieties such as Fc domain. In some embodiments, non-proteinaceous half-life extending moieties are linked to the fusion proteins described herein. In some embodiments, the non-proteinaceous half-life extending moieties are linked to the fusion proteins instead of IgG Fc. In some embodiments, the non-proteinaceous half-life extending moieties are linked to the fusion proteins in addition to IgG Fc.

Examples of suitable polymer molecules that act as non-proteinaceous half-life extending moieties include polymer molecules selected from the group consisting of polyalkylene oxide (PAO), including polyalkylene glycol (PAG), such as polyethylene glycol (PEG) and polypropylene glycol (PPG), branched PEGs, hydroxyalkyl starch (HAS), such as hydroxyethyl starch (HES), polysialic acid (PSA), polyvinyl alcohol (PVA), poly-carboxylate, poly-(vinylpyrrolidone), polyethylene-co-maleic acid anhydride, polystyrene-co-maleic acid anhydride, dextran, including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG has the advantage of having only few reactive groups capable of cross-linking compared to, e.g., polysaccharides such as dextran. In particular, monofunctional PEG, e.g., methoxypolyethylene glycol (mPEG), is of interest since its coupling chemistry is relatively simple (only one reactive group is available for conjugating with attachment groups on the polypeptide). Consequently, as the risk of cross-linking is eliminated, the resulting conjugated fusion proteins described herein are more homogeneous, and the reaction of the polymer molecules with the variant polypeptide is easier to control.

To effect covalent attachment of the polymer molecule(s) to the fusion proteins described herein, the hydroxyl end groups of the polymer molecule must be provided in activated form, i.e., with reactive functional groups (examples of which include primary amino groups, hydrazide (HZ), thiol, succinate (SUC), succinimidyl succinate (SS), succinimidyl succinamide (SSA), succinimidyl propionate (SPA), succinimidyl butyrate (SBA), succinimidyl carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g., from Shearwater Polymers, Inc., Huntsville, Ala., USA, or from PolyMASC Pharmaceuticals plc, UK.

Alternatively, the polymer molecules can be activated by conventional methods known in the art, e.g., as disclosed in WO 90/13540. Specific examples of activated linear or branched polymer molecules for use herein are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g., SPA-PEG, SSPA-PEG, SBA-PEG, SS-PEG, SSA-PEG, SC-PEG, SG-PEG, and SCM-PEG), and NOR-PEG, BTC-PEG, EPOXPEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. Nos. 5,932,462 and 5,643,575, both of which are incorporated herein by reference. Furthermore, the following publications disclose useful polymer molecules and/or PEGylation chemistries: U.S. Pat. Nos. 5,824,778, 5,476,653, WO 97/32607, EP 229,108, EP 402, 378, U.S. Pat. Nos. 4,902,502, 5,281,698, 5,122,614, 5,219, 564, WO 92/16555, WO 94/04193, WO 94/14758, WO 94/17039, WO 94/18247, WO 94/28024, WO 95/00162, WO 95/11924, WO 95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. Nos. 5,473,034, 5,516,673, EP 605 963, U.S. Pat. No. 5,382,657, EP 510 356, EP 400 472, EP 183 503, and EP 154 316.

Specific examples of activated PEG polymers particularly preferred for coupling to cysteine residues, include the following linear PEGs: vinylsulfone-PEG (VS-PEG), preferably vinylsulfone-mPEG (VS-mPEG); maleimide-PEG (MAL-PEG), preferably maleimide-mPEG (MAL-mPEG) and orthopyridyl-disulfide-PEG (OPSS-PEG), preferably orthopyridyl-disulfide-mPEG (OPSS-mPEG). Typically, such PEG or mPEG polymers will have a size of about 5 kDa, about 10 kDa, about 12 kDa or about 20 kDa.

The conjugation of the fusion proteins described herein and the activated polymer molecules is conducted by use of any conventional method, e.g., as described in the following references (which also describe suitable methods for activation of polymer molecules): Harris and Zalipsky, eds., Poly(ethylene glycol) *Chemistry and Biological Applications*, AZC Washington; R. F. Taylor, (1991), "Protein immobilisation. Fundamental and applications," Marcel Dekker, N.Y.; S. S. Wong, (1992), "Chemistry of Protein Conjugation and Crosslinking," CRC Press, Boca Raton; G. T. Hermanson et al., (1993), "Immobilized Affinity Ligand Techniques", Academic Press, N.Y.

The skilled person will be aware that the activation method and/or conjugation chemistry to be used depends on the attachment group(s) of the fusion protein (examples of which are given further above), as well as the functional groups of the polymer (e.g., being amine, hydroxyl, carboxyl, aldehyde, sulfhydryl, succinimidyl, maleimide, vinylsulfone or haloacetate). The PEGylation may be directed towards conjugation to all available attachment groups on the fusion protein (i.e., such attachment groups that are exposed at the surface of the polypeptide) or may be directed towards one or more specific attachment groups, e.g., the N-terminal amino group as described in U.S. Pat. No. 5,985,265 or to cysteine residues. Furthermore, the conjugation may be achieved in one step or in a stepwise manner (e.g., as described in WO 99/55377).

For PEGylation to cysteine residues (see above) the fusion protein is usually treated with a reducing agent, such as dithiothreitol (DDT) prior to PEGylation. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

It will be understood that the PEGylation is designed so as to produce the optimal molecule with respect to the number of PEG molecules attached, the size and form of such molecules (e.g., whether they are linear or branched), and the attachment site(s) in the fusion protein. The molecular weight of the polymer to be used may e.g., be chosen on the basis of the desired effect to be achieved.

In connection with conjugation to only a single attachment group on the fusion protein (e.g., the N-terminal amino group), it may be advantageous that the polymer molecule, which may be linear or branched, has a high molecular weight, preferably about 10-25 kDa, such as about 15-25 kDa, e.g., about 20 kDa.

Normally, the polymer conjugation is performed under conditions aimed at reacting as many of the available polymer attachment groups with polymer molecules. This is achieved by means of a suitable molar excess of the polymer relative to the polypeptide. Typically, the molar ratios of activated polymer molecules to polypeptide are up to about 1000-1, such as up to about 200-1, or up to about 100-1. In some cases the ratio may be somewhat lower, however, such as up to about 50-1, 10-1, 5-1, 2-1 or 1-1 in order to obtain optimal reaction.

It is also contemplated to couple the polymer molecules to the fusion protein through a linker. Suitable linkers are well known to the skilled person. A preferred example is cyanuric chloride (Abuchowski et al., (1977), *J Biol. Chem.,* 252, 3578-3581; U.S. Pat. No. 4,179,337; Shafer et al., (1986), *J. Polym. Sci. Polym. Chem. Ed.,* 24, 375-378).

Subsequent to the conjugation, residual activated polymer molecules are blocked according to methods known in the art, e.g., by addition of primary amine to the reaction mixture, and the resulting inactivated polymer molecules are removed by a suitable method.

It will be understood that depending on the circumstances, e.g., the amino acid sequence of the fusion protein, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to fusion protein. The PEGylated fusion proteins resulting from any given PEGylation process will, however, normally comprise a stochastic distribution of conjugated fusion protein having slightly different degrees of PEGylation.

For improvement of the biological half-life of the fusion proteins described herein, chemical modification such as PEGylation, or HESylation are applicable.

HAS and HES non-proteinaceous polymers, as well as methods of producing HAS or HES conjugates are disclosed for example in WO 02/080979, WO 03/070772, WO 057092391 and WO 057092390.

Polysialytion is another technology, which uses the natural polymer polysialic acid (PSA) to prolong the half-life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the fusion protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Biological Activity of the Relaxin-2 Fusion Proteins

In some embodiments, the relaxin-2 fusion proteins described herein have high levels of biological activity as compared to native relaxin-2. In some embodiments, any of the relaxin-2 fusion proteins described herein have from about 1% to about 200% of a biological activity as compared to native relaxin-2. In some embodiments, the relaxin-2 fusion protein has at least about 5%, about 10%, about 15%, about 20%, about 25%, about 30%, about 35%, about 40%, about 50%, about 60%, about 70%, about 80%, about 90%, about 100%, about 125% about 150%, about 175%, or about 200% of a biological activity as compared to native relaxin-2.

In some embodiments, any of the relaxin-2 fusion proteins described herein have from about 1% to about 200% of maximal biological activity as compared to native relaxin-2. In some embodiments, maximal biological activity is the maximum response ($E_{max}$) of relaxin-2 or relaxin-2 fusion protein. In some embodiments, the relaxin-2 fusion protein has at least about 5%, about 10%, about 15%, about 20%, about 25%, about 30%, about 35%, about 40%, about 50%, about 60%, about 70%, about 80%, about 90%, about 100%, about 125% about 150%, about 175%, or about 200% of a maximal biological activity as compared to native relaxin-2.

In some embodiments, any of the relaxin-2 fusion proteins described herein have about at least about 0.001-fold to about at least 1,000-fold enhanced potency as compared to native relaxin-2. In some embodiments, potency is the concentration of relaxin-2 or relaxin-2 fusion protein to elicit a half-maximal response ($EC_{50}$). In some embodiments, the relaxin-2 fusion protein has at least about 0.001-fold, about 0.01-fold, about 0.1-fold, about 1-fold, about 10-fold, about 100-fold, or about 1,000-fold of the potency as compared to native relaxin-2.

The biological activity can be any biological activity of native relaxin-2. For example, the biological activity can be the capacity to bind the receptor of native relaxin-2, RXFP1. The binding of relaxin-2 to RXFP1 can be measured by any well-known methods in the art, such as radioligand binding. In some embodiments, the fusion proteins described herein bind to RXFP1 when it is expressed on a cell surface.

In some embodiments, the biological activity can be the capacity to activate RXFP1 on a cell surface. The activation of RXFP1 by the relaxin-2 fusion proteins described herein can be determined by the increase of cAMP using any methods well known in the art, such as measuring the activity of a cAMP-driven reporter gene, e.g., β-galactosidase. The activation of RXFP1 by the relaxin-2 fusion proteins described herein in a cell may also be determined by using a biosensor such as the GloSensor biosensor. The activation of RXFP1 by the relaxin-2 fusion proteins described herein in a cell may also be determined by measuring the expression of certain genes, such as angiogenic factors, e.g., VEGF, or the expression of MMPs using well-known methods in the art. In some embodiments, the biological activity is a physiological, biochemical activity or any other effect-inducing activity of the relaxin-2. Exemplary biological activities include, but are not limited to, vasodilation, collagen degradation, angiogenesis, decreasing arterial blood pressure, increasing renal artery blood flow, increasing cardiac filling at diastole, resolving established fibrosis, and suppressing new fibrosis development.

In some embodiments, the fusion proteins described herein have improved pharmacokinetics profiles. Without wishing to be bound by any theory, the structure of the fusion proteins described herein is based upon, at least in part, the surprising discovery that reducing the pI of relaxin-2 fusion protein analogs increases their circulating half-life. In some embodiments, the circulating half-life is in a mammal. In some embodiments, the mammal is a rodent or a primate. In some embodiments, the rodent is a rat or a mouse. In some embodiments, the primate is a human or a monkey. In some embodiments, the monkey is a cynomolgus monkey. In some embodiments, the mammal is a human. In some embodiments, the fusion proteins described herein may have a circulating half-life of greater than about 5 hours, 10 hours, 20 hours, 50 hours, 75 hours, 100 hours, 125 hours, 150 hours, or more. In some embodiments, the fusion proteins described herein may have a circulating half-life of 5-10 hours, 10-20 hours, 20-50 hours, 50-75 hours, 75-100 hours, 100-125 hours, or 125-150 hours. Values and ranges intermediate to the recited values are also intended to be part of this disclosure. In some embodiments, the fusion proteins described herein have a longer circulating half-life than a native two chain relaxin-2. For example, the circulating half-life of a native two chain relaxin-2 may be less than about 5 hours. (See, e.g., Chen et al., The Pharmacokinetics of Recombinant Human Relaxin in Non-Pregnant Women after Intravenous, Intravaginal, and Intracervical Administration, Pharm. Res. 10: 834038 (1993), incorporated herein by reference).

This is increased half-life can be, at least in part, attributed to the reduced pI of the fusion proteins described herein. In some embodiments, the pI of the fusion protein is less than 9.4. In some embodiments, the pI of the fusion protein is less than 9.0, 8.9, 8.8, 8.7, 8.6, 8.5, 8.4, 8.3, 8.2, 8.1, or 8.0. In some embodiments, the pI of the fusion proteins described herein are between 6.0 and 9.4. In some embodiments, the pI of the fusion proteins described herein are 6.5-8.5, 6.6-8.4, 6.7-8.3, 6.8-8.2, 6.8-8.1, 6.8-8.0, or 6.8-7.9. In some embodiments, the pI referred to above is the calculated or theoretical pI. In some embodiments, the pI referred to above is the experimentally measured pI.

"Circulating half-life," as used herein, refers to the time it takes for the blood plasma concentration of a drug to halve its steady-state when circulating in the full blood of an organism. Circulating half-life of a particular agent may vary depending on a multitude of factors including, but not limited to, dosage, formulation, and/or administration route of the agent. One of ordinary skill in the art is able to determine the circulating half-life of an agent using well known methods in the art, such as the method described Chen supra.

Vectors

The disclosure also provides nucleic acid molecules that encode any of the fusion proteins or peptides described herein. In some embodiments, the nucleic acid molecules described herein are DNA molecules. In some embodiments, the nucleic acid molecules described herein are RNA molecules.

The nucleic acid molecules described herein can be transcribed from a promoter in an expression vector. In some embodiments, the vector is a non-viral vector. Exemplary non-viral vectors include, but are not limited to, plasmid DNA, transposons, episomal plasmids, minicircles, ministrings, and oligonucleotides (e.g., mRNA, naked DNA). In some embodiments, the vector is a DNA plasmid vector.

In some embodiments, the vector is a viral vector. Viral vectors can be replication competent or replication incompetent. Viral vectors can be integrating or non-integrating. A number of viral based systems have been developed for gene transfer into mammalian cells, and a suitable viral vector can be selected by a person of ordinary skill in the art. Exemplary viral vectors include, but are not limited to, adenovirus vectors (e.g., adenovirus 5), adeno-associated virus (AAV) vectors (e.g., AAV2, 3, 5, 6, 8, 9), retrovirus vectors (MMSV, MSCV), lentivirus vectors (e.g., HIV-1, HIV-2), gammaretrovirus vectors, herpes virus vectors (e.g., HSV1, HSV2), alphavirus vectors (e.g., SFV, SIN, VEE, M1), flavivirus (e.g., Kunjin, West Nile, Dengue virus), rhabdovirus vectors (e.g., rabies virus, VSV), measles virus vector (e.g., MV-Edm), Newcastle disease virus vectors, poxvirus vectors (e.g., VV), measles virus, and picornavirus vectors (e.g., Coxsackievirus).

In some embodiments, the vector or expression cassette comprises one or more additional elements. Additional elements include, but are not limited to, promoters, enhancers, polyadenylation (polyA) sequences, and selection genes.

In some embodiments, the vector comprises a polynucleotide sequence that encodes an amino acid sequence at least 90%, 95%, 96%, 97%, 98%, 99%, or 100% identical to an amino acid sequence recited in any of Tables 1-7. In some embodiments, the vector comprises or consists of a nucleotide sequence at least 75%, 80%, 85%, 90%, 95%, 96%, 97%, 98%, 99%, or 100% identical to any of the nucleotide sequence recited in Table 8, below.

TABLE 8

Nucleotide Sequences Encoding Fusion Proteins and Peptide Components

| SEQ ID NO: | Sequence |
|---|---|
| 119 | GATAAAACACACACGTGTCCCCCCTGCCCGGCTCCAGAGGCGGCTGGTGGTCCCAGCGTATT<br>CTTGTTTCCTCCCAAACCTAAGGATACGCTCATGATATCCCGCACCCCAGAAGTTACGTGTG<br>TAGTCGTCGACGTCAGTCACGAAGATCCAGAGGTCAAATTTAACTGGTATGTCGACGGAGTA<br>GAGGTCCACAATGCGAAAACCAAGCCCAGAGAAGAGCAGTACAACTCCACGTATCGCGTCGT<br>CTCCGTCCTCACCGTACTCCATCAAGATTGGCTGAATGGGAAAGAGTATAAATGCAAAGTAT<br>CTAACAAGGCTCTGCCAGCTCCGATAGAAAAGACTATATCAAAGGCCAAGGGGCAGCCAAGG<br>GAGCCTCAAGTCTATACTTTGCCCCCATCTCGGGATGAGCTTACGAAAAACCAGGTCAGCCT<br>TACCTGTCTTGTTAAAGGTTTTTATCCGAGTGACATCGCAGTGGAATGGGAATCTAATGGTC<br>AACCTGAAAACAATTACAAAACCACACCGCCAGTATTGGACAGCGATGGTAGTTTTTTTCTT<br>TACTCAAAACTGACTGTAGATAAAAGCAGATGGCAGCAGGGCAATGTCTTTTCATGTAGCGT<br>TATGCATGAGGCTCTTCACAACCACTATACCCAAAAGTCATTGTCTCTTAGTCCCGGAAAGG<br>GCGGAAGTGATTCTTGGAAGGAGGAGGTAATCAAGTTGTGCGGGCGAGAGTTGGTACGGGCA<br>CAGATCGCGATATGCGGAAAATCCACAGGTGGGGGCGAAGGAGGAGGTGAGGGTGGAGGTGA |

TABLE 8-continued

Nucleotide Sequences Encoding Fusion Proteins and Peptide Components

| SEQ ID NO: | Sequence |
|---|---|
| | AGGACGACAGTTGTATTCCGCCTTGGCAAACAAGTGTTGCCATGTGGGTTGCACAAAACGCA<br>GTCTTGCCCGCTTCTGT |
| 120 | GATAAGACACATACATGCCCTCCCTGTCCGGCTCCAGAGGCAGCCGGGGGTCCATCAGTCTT<br>CCTTTTTCCGCCTAAACCTAAGGATACACTGATGATCTCTCGAACACCGGAGGTCACTTGTG<br>TTGTCGTTGACGTATCACATGAGGATCCCGAAGTAAAGTTCAACTGGTATGTCGATGGTGTG<br>GAGGTTCATAATGCTAAAACTAAACCACGGGAGGAGCAATATAATTCCACATATAGGGTCGT<br>GAGCGTGTTGACGGTGCTTCATCAAGACTGGCTTAATGGGAAGGAATATAAATGCAAAGTGT<br>CAAATAAAGCACTTCCTGCGCCAATCGAGAAAACAATTAGTAAGGCAAAGGGGCAGCCGCGA<br>GAACCTCAGGTGTACACCTTGCCGCCTTCTAGAGACGAGCTCACAAAGAACCAAGTTTCCCT<br>GACTTGCCTCGTTAAGGGGTTTTATCCGTCCGATATAGCCGTGGAGTGGGAGTCAAACGGCC<br>AACCGGAAAATAATTACAAAACGACACCCCCAGTATTGGATAGTGACGGCTCTTTTTTCCTT<br>TATTCTAAGCTGACTGTGGACAAAAGCCGCTGGCAGCAGGGCAATGTCTTTTCATGCAGCGT<br>AATGCATGAAGCCCTGCACAACCACTACACGCAAAAATCCCTTTCCTTGTCACCCGGCAAGG<br>GCGGCTCTGACTCCTGGAAAGAGGAAGTTATAAAACTCTGTGGCCGAGAACTTGTTCGAGCT<br>CAAATCGCGATTTGTGGTAAGTCAACGGGTGGGGGCGAAGGTGGAGGCGAGGGTGGGGGAGA<br>AGGAGGAGGCCAGTTGTACTCAGCTCTTGCAAATAAGTGTTGCCACGTTGGTTGTACGAAGC<br>GGAGCCTTGCTCGCTTCTGC |
| 121 | GACAAAACACATACTTGTCCGCCTTGCCCGGCACCCGAAGCGGCCGGCGGACCCAGTGTCTT<br>TCTCTTCCCACCCAAACCGAAAGACACTCTGATGATTTCCAGGACGCCTGAAGTGACCTGCG<br>TTGTAGTTGATGTATCACACGAGGATCCCGAGGTCAAGTTCAATTGGTATGTAGATGGGGTG<br>GAGGTCCATAATGCAAAGACGAAGCCACGGGAGGAACAGTACAACTCTACGTACAGAGTTGT<br>CAGTGTTTTGACCGTCCTTCATCAGGATTGGCTGAACGGTAAAGAATATAAATGCAAGGTTA<br>GCAATAAAGCTTTGCCCGCCCCTATAGAGAAAACGATCAGTAAGGCGAAGGGGCAGCCTAGG<br>GAACCCCAGGTATATACCTTGCCGCCAAGTCGAGATGAGCTGACGAAGAACCAAGTGAGTCT<br>GACATGCCTCGTGAAGGGCTTCTATCCGAGCGATATCGCTGTCGAATGGGAGAGCAATGGGC<br>AGCCTGAGAATAACTATAAAACAACGCCACCCGTCCTCGACTCCGATGGCTCATTCTTCCTG<br>TACAGTAAACTTACAGTAGATAAGAGTAGATGGCAGCAGGGTAACGTCTTTAGTTGCTCCGT<br>GATGCACGAGGCATTGCACAATCATTACACTCAAAAATCTCTGTCCCTGAGTCCGGGCAAAG<br>GCGGTTCAGATAGCTGGATGGAGGAGGTCATAAAGCTTTGTGGACGAGAACTCGTTCGCGCC<br>CAGATAGCTATTTGTGGGAAATCAACCGGGGGTGGAGAAGGTGGCGGAGAAGGGGGAGGCGA<br>AGGGCGCCAACTGTATTCTGCATTGGCTAATAAGTGCTGTCACGTAGGATGTACAAAAAGGT<br>CTCTGGCGAGATTCTGC |
| 122 | GACAAGACGCACACTTGTCCACCTTGCCCTGCGCCGGAAGCTGCTGGAGGCCCCAGTGTCTT<br>TTTGTTCCCGCCCAAACCGAAGGACACTTTGATGATAAGTCGCACGCCCGAGGTTACCTGTG<br>TGGTTGTCGATGTCTCACACGAAGATCCGGAGGTGAAGTTTAATTGGTATGTAGATGGCGTG<br>GAGGTTCATAACGCCAAAACGAAACCCAGAGAAGAACAATATAACAGTACATATCGAGTAGT<br>ATCCGTTCTCACTGTCCTGCATCAAGACTGGTTGAACGGGAAGGAATATAAGTGCAAGGTGA<br>GCAATAAAGCACTCCCGGCCCCAATCGAAAAGACCATCAGCAAAGCGAAGGGGCAACCTCGA<br>GAACCCCAGGTATATACGCTCCCCCCTAGTCGGGATGAACTTACTAAAAATCAGGTTAGCCT<br>CACTTGCCTTGTTAAAGGGTTCTATCCCAGTGATATTGCCGTCGAATGGGAATCAAACGGGC<br>AGCCGGAAAATAACTACAAGACAACCCCTCCTGTGCTCGATAGCGATGGCTCTTTTTTCCTC<br>TACAGCAAACTTACCGTTGATAAGAGCCGGTGGCAACAAGGTAATGTTTTCTCCTGCTCCGT<br>TATGCATGAAGCACTCCATAACCATTATACCCAAAAAAGCCTGTCACTTAGTCCGGGTAAAG<br>GAGGTAGTGATTCTTGGCAGGAGGAGGTAATCAAACTTTGTGGGAGGGAGCTGGTACGAGCT<br>CAGATTGCTATATGTGGAAAAAGCACGGGCGGAGGAGAAGGAGGTGGCGAAGGCGGGGGTGA<br>AGGTCGGCAACTCTACTCCGCTCTCGCTAATAAGTGCTGCCACGTCGGGTGTACGAAGCGCT<br>CCCTGGCGCGATTCTGC |
| 123 | GATAAAACGCACACGTGTCCGCCCTGCCCAGCGCCTGAAGCCGCAGGCGGGCCGTCCGTCTT<br>CCTCTTTCCTCCAAAACCCAAAGACACACTTATGATCAGTAGGACCCCAGAGGTAACCTGCG<br>TCGTGGTCGACGTTTCCCATGAAGACCCAGAGGTCAAGTTCAACTGGTACGTCGACGGTGTC<br>GAAGTACATAATGCTAAAACGAAGCCTCGGGAAGAGCAGTACAACTCTACCTACCGCGTCGT<br>TTCCGTACTCACCGTACTTCACCAGGACTGGCTTAACGGTAAAGAGTATAAATGCAAAGTAT<br>CTAATAAGGCTCTCGCCGCGCCGATTGAGAAGACAATTTCAAAGGCCAAGGGGCAGCCGCGG<br>GAGCCCCAAGTGTATACCTTGCCCCCGTCCCGAGATGAGCTGACTAAAAACCAAGTAAGCTT<br>GACTTGCTTGGTCAAAGGCTTCTACCCTTCCGATATAGCTGTCGAATGGGAGTCAAATGGCC<br>AACCAGAGAACAATTATAAAACTACACCCCCGGTCTTGGATTCTGATGGCTCATTTTTTCTC<br>TATTCTAAACTGACCGTGGATAAGTCTCGCTGGCAGCAAGGTAACGTGTTCAGTTGCTCTGT<br>TCTTCACGAAGCACTGCACAGTCATTACACTCAGAAGAGTCTTAGCCTGAGCCCTGGTAAAG<br>GGGGTTCTGATTCCTGGCAGGAGGAAGTAATAAAACTCTGTGGCCGGGAGTTGGTACGGGCG<br>CAGATTGCGATATGCGGTAAGAGCACCGGCGGAGGCGAAGGCGGTGGGGAAGGAGGAGGAGA<br>AGGGAGACAACTCTATTCCGCATTGGCAAATAAGTGCTGCCACGTCGGGTGTACCAAACGAT<br>CCCTTGCACGGTTCTGT |
| 124 | GATAAGACCCATACGTGCCCCCCTTGCCCTGCGCCTGAGGCAGCGGGTGGCCCATCAGTCTT<br>TTTGTTCCCGCCCAAGCCAAAGGACACCCTCATGATTAGTAGAACACCGGAGGTTACGTGCG<br>TCGTAGTGGATGTCAGCCACGAGGATCCCGAGGTTAAGTTTAACTGGTACGTTGATGGGGTT<br>GAGGTCCATAATGCGAAGACTAAGCCGAGAGAGGAACAGTACAATTCCACGTATAGAGTTGT<br>CTCTGTACTGACTGTGCTGCATCAAGATTGGCTTAACGGTAAGGAGTACAAGTGCAAAGTCT<br>CTAATAAGGCTCTTCCTGCACCCATTGAGAAAACTATAAGCAAAGCAAAAGGTCAACCTCGC<br>GAACCTCAGGTGTACACACTGCCACCCTCTAGGGACGAGCTTACCAAAAATCAAGTATCTCT<br>TACCTGCCTTGTGAAAGGGTTTTATCCCTCAGATATTGCGGTTGAGTGGGAGTCTAACGGAC |

TABLE 8-continued

Nucleotide Sequences Encoding Fusion Proteins and Peptide Components

| SEQ ID NO: | Sequence |
|---|---|
| | AACCTGAGAACAACTATAAGACTACTCCCCCGGTGCTTGATTCAGACGGGAGTTTTTTTTTG<br>TATAGCAAACTTACCGTCGACAAAAGCCGGTGGCAACAGGGCAATGTATTCAGTTGTTCTGT<br>AATGCATGAAGCTTTGCATAATCATTACACCCAAAAGAGTCTTTCCCTGTCTCCTGGAAAAG<br>GGGGGTCAGACTCCTGGATGGAGGAGGTGATCAAACTGTGTGGGAGAGAGCTCGTCCGGGCT<br>CAGATAGCTATATGCGGCAAGTCTACGGGTGGGGGAGAGGGCGGAGGAGAGGGCGGTGGAGA<br>AGGAGGCGGCCAACTCTACAGCGCTCTGGCCAATAAATGTTGTCATGTCGGGTGTACTAAGC<br>GCTCACTGGCACGCTTTTGC |
| 125 | GACAAGACGCATACATGCCCGCCATGCCCGGCCCCCGAAGCTGCTGGGGGACCATCCGTATT<br>CCTCTTCCCTCCCAAACCAAAAGACACGTTGATGATAAGTAGAACACCAGAGGTAACGTGCG<br>TGGTTGTCGATGTTTCCCACGAAGATCCGGAGGTAAAATTCAATTGGTATGTAGATGGGGTG<br>GAAGTGCACAATGCCAAAACAAAGCCGCGAGAAGAACAATACAATAGTACTTACCGGGTTGT<br>GAGCGTGCTCACGGTGTTGCACCAAGACTGGCTCAACGGCAAGGAATACAAGTGCAAAGTAT<br>CTAATAAAGCTCTGCCTGCGCCGATAGAGAAGACCATCAGTAAGGCCAAAGGGCAGCCCCGA<br>GAGCCGCAAGTTTACACTCTTCCTCCGAGCAGAGATGAATTGACCAAGAACCAAGTAAGTTT<br>GACGTGCCTGGTGAAGGGCTTCTACCCCTCAGACATTGCGGTGGAGTGGGAAAGTAATGGTC<br>AACCGGAAAACAACTACAAGACCACGCCGCCCGTCCTCGACTCCGATGGGTCTTTCTTTCTT<br>TATTCAAAGTTGACAGTAGATAAGTCAAGGTGGCAGCAAGGTAACGTGTTTAGTTGTAGTGT<br>AATGCACGAGGCCCTGCATAATCATTATACCCAAAAGAGTTTGAGCCTCTCACCAGGAAAAG<br>GCGGATCAGACAGCTGGCAGGAGGAGGTAATTAAATTGTGTGGACGGGAGTTGGTCAGGGCG<br>CAAATAGCCATCTGCGGTAAGAGCACGGGTGGAGGAGAGGGTGGAGGGGAAGGTGGGGGAGA<br>AGGCGGCGGGCAGCTCTATTCTGCACTCGCCAACAAGTGTTGTCACGTCGGATGCACAAAGA<br>GATCTCTTGCTCGATTCTGC |
| 126 | GACAAAACACACACCTGTCCGCCTTGCCCGGCTCCTGAAGCCGCGGGTGGCCCTAGTGTGTT<br>TTTGTTTCCGCCGAAACCTAAGGATACCCTCATGATAAGCCGGACGCCCGAGGTTACCTGTG<br>TCGTGGTCGATGTTAGTCATGAGGATCCAGAAGTCAAGTTTAATTGGTACGTCGACGGCGTT<br>GAAGTCCACAATGCAAAAACTAAACCGCGAGAAGAACAGTACAACTCCACCTACAGAGTTGT<br>CTCAGTTTTGACAGTTCTCCATCAGGATTGGCTCAATGGAAAGGAATATAAGTGCAAGGTCA<br>GCAATAAAGCGCTTGCCGCCCCTATAGAGAAGACCATTAGCAAGGCGAAAGGACAGCCCCGC<br>GAGCCCCAGGTCTATACGCTGCCTCCTAGCAGAGATGAGCTCACGAAAAATCAGGTCAGCTT<br>GACATGCTTGGTGAAGGGCTTCTACCCCAGTGACATCGCAGTTGAATGGGAGAGCAACGGCC<br>AACCTGAGAACAACTACAAAACAACGCCCCCGGTTCTTGACAGCGATGGGTCCTTCTTTCTT<br>TACTCTAAGCTTACAGTTGATAAAAGCAGGTGGCAGCAGGGGAATGTGTTCTCATGTTCCGT<br>ACTGCATGAGGCTCTGCATTCTCACTACACCCAAAAAAGCCTTAGCCTGAGCCCCGGTAAGG<br>GAGGTAGTGACTCATGGCAAGAGGAAGTGATTAAGCTCTGCGGCCGGGAGTTGGTGAGAGCC<br>CAAATCGCCATTTGCGGTAAAAGTACCGGAGGGGGCGAGGGAGGAGGCGAAGGTGGAGGTGA<br>AGGAGGTGGACAGTTGTACTCAGCTCTTGCAAATAAATGTTGTCATGTTGGTTGCACGAAAA<br>GATCTCTTGCGAGGTTCTGT |
| 127 | GATAAGACGCATACTTGTCCACCGTGCCCCGCACCGGAAGCGGCTGGTGGTCCATCAGTTTT<br>TCTGTTCCCACCGAAACCTAAGGACACGTTGATGATATCACGGACACCAGAGGTTACGTGCG<br>TAGTGGTGGATGTGAGCCACGAGGATCCAGAAGTTAAATTTAATTGGTACGTAGATGGAGTG<br>GAGGTTCATAATGCGAAGACAAAGCCTCGCGAGGAACAGTATAATTCCACCTATCGCGTCGT<br>ATCTGTGCTTACGGTACTTCACCAAGACTGGTTGAACGGTAAGGAATATAAATGCAAGGTTT<br>CCAATAAAGCACTTCCTGCGCCAATTGAGAAGACAATATCCAAAGCTAAAGGTCAACCCAGG<br>GAACCGCAAGTCTACACTCTCCCCCCGTCTCGCGATGAATTGACGAAGAACCAGGTTAGTCT<br>CACCTGCCTGGTCAAGGGGTTTTACCCCTCTGACATAGCTGTAGAATGGGAGTCTAATGGAC<br>AGCCAGAGAACAATTACAAAACGACCCCCCCGGTCCTCGATTCTGATGGGAGTTTTTTTCTT<br>TATTCAAAATTGACTGTCGATAAGTCAAGATGGCAACAGGGTAACGTATTTTCTTGCAGTGT<br>TATGCATGAAGCATTGCACAACCACTATACACAAAAATCATTGAGTTTGAGTCCCGGTAAAG<br>GGGGAAGCGACTCATGGATGGAAGAAGTAATCAAGCTGTGCGGGCGAGAGCTTGTGCGAGCT<br>CAGATAGCAATCTGTGGTAAGTCTACAGGTGGAGAGGGTGGCGGTGAAGAAGGCGGGGGAGA<br>GGGAGGCCAGCTTTATTCTGCCCTGGCTAACAAGTGCTGTCACGTTGGATGCACGAAGCGCT<br>CCCTGGCCCGATTCTGC |
| 128 | GATAAGACGCATACTTGTCCCCCATGTCCCGCTCCGGAAGCCGCTGGCGGCCCCTCCGTTTT<br>TCTGTTCCCGCCGAAACCGAAAGACACCCTGATGATATCACGCACTCCCGAGGTCACTTGCG<br>TGGTAGTCGATGTTAGTCATGAAGATCCTGAGGTCAAATTCAATTGGTATGTAGATGGCGTT<br>GAGGTACACAACGCGAAGACAAAACCCCGAGAAGAACAGTATAACTCAACCTACCGCGTAGT<br>TTCAGTTCTTACCGTACTGCACCAAGACTGGTTGAACGGTAAAGAGTACAAATGTAAAGTCA<br>GCAATAAAGCTTTGCCAGCACCTATCGAAAAAACCATCAGTAAGGCCAAGGGTCAACCCAGG<br>GAGCCGCAAGTGTACACTCTTCCCCCTAGCAGGGATGAATTGACCAAGAATCAGGTCTCTTT<br>GACGTGCCTCGTTAAGGGTTTCTATCCCAGCGATATAGCCGTAGAATGGGAGTCTAACGGTC<br>AGCCAGAAAATAACTATAAGACAACCCCGCCTGTTTTGGATTCCGACGGCTCTTTTTTTCTC<br>TACTCTAAGTTGACCGTTGATAAGAGCAGATGGCAGCAGGGAAACGTATTTTCTTGTTCCGT<br>GATGCACGAAGCCCTGCACAATCACTATACGCAAAAGTCTCTGAGCTTGAGTCCGGGTAAAG<br>GCGGTTCTGACTCCTGGCAGGAGGAAGTCATAAAACTCTGCGGAAGAGAGCTCGTAAGGGCG<br>CAAATCGCTATTTGTGGTAAGAGCACCGGTGGGGAAGGAGGCGGTGAAGAGGGTGGCGGCGA<br>GGGTGGGCAATTGTATTCCGCGCTTGCCAATAAATGTTGTCACGTAGGCTGCACAAAGCGAA<br>GTCTCGCTAGGTTCTGC |
| 129 | GACAAGACCCACACATGTCCCCCGTGTCCGGCACCAGAAGCAGCGGGGGGACCGTCAGTATT<br>CTTGTTTCCACCGAAGCCCAAAGACACATTGATGATTTCACGAACTCCTGAAGTTACCTGTG<br>TGGTTGTAGATGTATCACACGAAGACCCAGAAGTCAAATTCAATTGGTATGTCGACGGGGTT |

TABLE 8-continued

| Nucleotide Sequences Encoding Fusion Proteins and Peptide Components | |
|---|---|
| SEQ ID NO: | Sequence |
| | GAAGTTCACAATGCGAAGACGAAGCCCCGGGAGGAACAGTACAACAGCACGTACAGGGTTGT<br>GAGCGTTCTTACTGTATTGCACCAGGATTGGCTCAACGGCAAGGAGTATAAATGTAAAGTTT<br>CTAATAAGGCTCTTCCTGCCCCAATTGAAAAGACGATATCTAAAGCGAAGGGCCAACCACGG<br>GAACCTCAGGTGTACACACTTCCGCCTAGCAGGGATGAGTTGACCAAGAATCAAGTCTCTTT<br>GACGTGCCTGGTCAAGGGGTTTTACCCATCAGATATCGCCGTCGAATGGGAGTCAAACGGAC<br>AACCCGAAAATAACTATAAAACTACTCCACCAGTTCTGGATAGCGACGGCTCATTTTTTCTG<br>TATTCAAAGCTCACTGTAGACAAGTCTAGGTGGCAGCAGGGTAATGTCTTCTCCTGCTCAGT<br>AATGCATGAGGCTCTTCACAACCACTATACTCAAAAGAGCCTTTCCCTGTCACCTGGCGGTG<br>GAAGCGACTCATGGATGGAGGAGGTAATAAAGCTCTGCGGAAGAGAACTGGTACGCGCACAA<br>ATCGCAATTTGTGGTAAGAGTACTGGCGGGGAAGGAGGTGGGGAAGAAGGGGGCGGTGAGGG<br>CGGACAGCTCTATTCTGCACTTGCAAACAAATGTTGCCACGTGGGATGTACTAAGCGAAGCC<br>TTGCAAGATTCTGC |
| 130 | GATAAAACCCACACATGCCCTCCATGCCCTGCTCCAGAGGCCGCCGGTGGGCCATCAGTTTT<br>CTTGTTTCCGCCTAAACCAAAGGACACGCTTATGATCTCCAGGACCCCCGAAGTTACGTGTG<br>TGGTGGTTGATGTTAGTCACGAGGACCCGGAAGTCAAGTTCAACTGGTACGTTGATGGTGTA<br>GAGGTGCACAATGCAAAGACGAAGCCACGCGAAGAACAATACAACAGCACATATCGAGTTGT<br>GAGCGTACTCACGGTACTGCATCAGGACTGGCTGAACGGTAAAGAATACAAATGTAAAGTCT<br>CCAATAAGGCACTTCCTGCGCCGATAGAAAAAACGATCAGTAAGGCCAAGGGCCAACCCCGA<br>GAACCACAGGTATATACGCTCCCACCGTCACGAGACGAGTTGACAAAAAATCAGGTCTCCCT<br>GACTTGCCTCGTGAAAGGTTTTTATCCCTCAGATATTGCTGTTGAGTGGGAAAGCAATGGGC<br>AGCCAGAGAATAATTATAAGACGACTCCTCCGGTTTTGGATTCCGACGGTAGTTTTTTCTTG<br>TATAGTAAGCTTACTGTAGACAAGTCAAGATGGCAACAAGGTAATGTGTTCTCTTGCTCAGT<br>TATGCATGAAGCTCTTCATAACCATTACACGCAAAAGAGTCTCAGTCTGAGCCCCGGTGGCG<br>GTAGCGACAGTTGGCAGGAAGAGGTGATTAAGTTGTGCGGTCGCGAGCTCGTTCGGGCCCAA<br>ATTGCAATCTGCGGAAAATCTACGGGCGGAGAGGGCGGGGGTGAGGAGGGTGGGGGTGAAGG<br>TGGGCAGCTCTATAGCGCCCTTGCGAATAAATGTTGTCACGTCGGATGCACAAAGAGGTCCC<br>TCGCCAGGTTCTGC |
| 131 | GATAAGACCCACACTTGCCCCCCTTGCCCTGCCCCCGAAGCGGCCGGAGGTCCTTCAGTATT<br>TTTGTTTCCACCGAAACCCAAAGATACTTTGATGATATCAAGAACTCCTGAAGTCACCTGCG<br>TGGTAGTTGACGTATCTCATGAGGATCCCGAGGTGAAGTTCAATTGGTACGTCGATGGCGTC<br>GAGGTTCATAACGCTAAGACTAAGCCGAGGGAAGAGCAATATAATTCCACTTATAGGGTGGT<br>GTCCGTCTTGACTGTTTTGCACCAGGATTGGTTGAACGGGAAAGAGTACAAATGTAAGGTGA<br>GTAATAAAGCTTTGGCTGCTCCCATCGAAAAGACAATAAGCAAGGCCAAGGGGCAACCTCGG<br>GAGCCGCAGGTGTACACCCTTCCTCCCAGTAGAGACGAACTGACAAAAAACCAGGTGTCCCT<br>GACCTGCCTTGTGAAGGGGTTTTACCCGAGCGACATAGCGGTTGAATGGGAGAGCAACGGGC<br>AACCCGAGAACAACTACAAAACTACACCGCCTGTCCTGGACTCCGATGGAAGCTTCTTCCTC<br>TACTCCAAACTGACCGTGGACAAAAGCAGATGGCAACAAGGAAACGTATTCTCATGCTCAGT<br>AATGCACGAAGCATTGCACAATCACTACACCCAAAAGTCCCTCTCACTCTCCCCTGGTAAGG<br>GCGGATCAGACTCATGGCAAGAGGAGGTAATTAAGTTGTGCGGGAGGGAGCTCGTCCGCGCG<br>CAAATAGCCATTTGTGGCAAGTCCACTGGAGGAGGCGAGGGTGGAGGAGAGGGTGGTGGGGA<br>GGGCAGGCAACTCTACAGTGCGCTCGCCAATAAATGCTGCCATGTTGGGTGCACGAAGCGCA<br>GTCTCGCACAATTCTGC |
| 132 | GATAAGACCCACACGTGTCCTCCATGTCCGGCACCGGAGGCTGCTGGCGGGCCTTCTGTATT<br>CCTCTTCCCACCCAAGCCAAAAGACACATTGATGATATCAAGGACGCCGGAAGTCACCTGTG<br>TTGTTGTGGACGTTTCCCATGAAGACCCAGAGGTAAAATTCAATTGGTATGTGGACGGCGTA<br>GAGGTTCACAACGCCAAAACCAAACCCCGAGAGGAACAGTATAATAGCACATATCGAGTAGT<br>ATCTGTTCTCACAGTGCTCCATCAAGACTGGCTTAATGGTAAAGAGTATAAATGCAAAGTTT<br>CCAATAAAGCCCTCGCTGCACCGATCGAGAAGACAATCAGTAAAGCGAAGGGCCAGCCTCGG<br>GAACCGCAGGTGTATACTCTTCCACCCTCAAGAGACGAGCTCACTAAAAACCAAGTTTCATT<br>GACATGCCTCGTCAAAGGTTTCTACCCATCAGACATCGCGGTCGAATGGGAAAGTAATGGGC<br>AGCCGGAAAACAACTATAAAACGACGCCGCCCGTCTTGGATTCTGATGGTTCATTTTTTCTT<br>TACTCTAAATTGACCGTCGATAAAAGTAGGTGGCAACAAGGAAATGTTTTTTCCTGCTCCGT<br>CCTGCATGAAGCGTTGCACAGTCACTATACCCAGAAGAGTCTTTCTTTGTCACCCGGAAAAG<br>GCGGTTCAGATTCATGGCAGGAAGAAGTAATTAAACTCTGTGGCCGCGAGCTTGTTAGGGCG<br>CAGATAGCCATATGTGGTAAAAGCACCGGAGGAGGTGAAGGCGGAGGCGAAGGAGGTGGGGA<br>AGGAAGACAATTGTATTCTGCACTTGCAAATAAATGCTGTCATGTGGGGTGCACGAAACGCA<br>GTCTTGCACAATTTTGT |
| 133 | GACAAAACCCATACCTGCCCCCCTTGCCCTGCACCAGAAGCGGCGGGAGGACCTAGCGTTTT<br>TCTTTTTCCTCCGAAACCGAAAGATACCCTCATGATATCAAGAACACCTGAGGTTACTTGCG<br>TTGTCGTGGACGTGAGTCACGAAGACCCCGAGGTGAAGTTCAACTGGTATGTAGATGGAGTG<br>GAGGTCCATAATGCAAAAACGAAACCGAGAGAAGAACAATACAACTCTACATATCGAGTCGT<br>GTCAGTACTCACGGTTTTGCATCAAGATTGGCTGAACGGTAAGGAGTACAAGTGTAAGGTTA<br>GCAACAAGGCTCTCGCGGCGCCGATAGAAAAGACTATAAGTAAAGCAAAAGGCCAGCCCAGA<br>GAACCTCAAGTTTACACTCTGCCTCCCAGCAGAGATGAACTGACTAAAAATCAGGTTTCATT<br>GACCTGTCTCGTCAAGGGTTTTTATCCAAGCGACATAGCAGTTGAATGGGAAAGCAACGGTC<br>AACCAGAAAATAATTACAAAACCACTCCACCAGTCTTGGACTCTGACGGATCCTTCTTTCTC<br>TATTCAAAATTGACGGTGGATAAATCTAGGTGGCAGCAAGGCAACGTCTTCTCTTGTAGCGT |

TABLE 8-continued

Nucleotide Sequences Encoding Fusion Proteins and Peptide Components

| SEQ ID NO: | Sequence |
|---|---|
| | TATGCATGAGGCGCTGCACAACCACTACACACAAAAGTCTCTTAGTTTGAGCCCGGGCGGCG<br>GAAGCGACTCTTGGCAAGAGGAAGTGATAAAACTCTGTGGTCGAGAATTGGTACGCGCGCAG<br>ATCGCTATCTGCGGCAAGTCCACAGGGGGAGGGGAAGGTGGCGGGGAAGGTGGTGGCGAGGG<br>CAGGCAGTTGTATAGTGCACTTGCCAACAAGTGCTGCCATGTGGGGTGCACCAAGCGCAGTT<br>TGGCACGGTTCTGC |
| 134 | GATAAAACTCACACTTGTCCCCCGTGTCCGGCACCAGAAGCCGCAGGAGGGCCATCTGTCTT<br>TCTTTTTCCCCCAAAACCCAAGGATACACTGATGATCTCCCGCACTCCCGAAGTTACTTGTG<br>TCGTAGTAGACGTTTCTCACGAGGACCCAGAGGTGAAATTCAATTGGTATGTTGACGGAGTA<br>GAGGTGCATAATGCCAAGACAAAGCCCCGAGAGGAACAATACAATTCAACCTACAGAGTAGT<br>GTCCGTTCTTACGGTTCTCCATCAGGATTGGCTCAACGGTAAGGAATATAAGTGCAAGGTAA<br>GCAACAAAGCGCTGGCCGCACCCATTGAGAAAACCATTTCAAAAGCTAAAGGCCAACCCCGC<br>GAACCACAAGTTTATACTCTCCCCCCAAGTCGCGATGAACTTACAAAAAATCAAGTCTCATT<br>GACGTGCTTGGTCAAAGGCTTCTACCCGAGCGATATCGCTGTTGAATGGGAGTCTAATGGAC<br>AACCGGAAAATAACTATAAAACTACACCCCCAGTCCTCGATTCAGACGGCAGCTTCTTCCTG<br>TATTCAAAACTGACGGTTGACAAATCACGCTGGCAACAGGGTAACGTTTTTTCCTGTAGCGT<br>TCTTCATGAAGCCTTGCACAGTCACTACACCCAGAAGTCCCTTAGCTTGTCACCTGGCGGGG<br>GTTCAGACTCTTGGCAGGAGGAGGTAATCAAACTGTGCGGAAGAGAACTGGTGAGGGCTCAG<br>ATTGCAATTTGTGGGAAGAGCACGGGTGGCGGTGAAGGAGGTGGCGAGGGCGGAGGAGAGGG<br>GAGGCAACTCTACAGTGCGTTGGCTAATAAATGCTGTCACGTCGGCTGTACTAAGAGAAGCC<br>TCGCCAGATTTTGC |
| 135 | GACAAGACGCATACTTGCCCTCCGTGCCCTGCACCAGAAGCCGCTGGTGGCCCATCTGTGTT<br>TTTGTTCCCCCCTAAGCCAAAAGACACATTGATGATTTCACGAACTCCAGAAGTGACTTGCG<br>TAGTTGTTGACGTATCACACGAAGACCCCGAGGTTAAATTTAATTGGTATGTGGACGGGGTC<br>GAGGTGCATAACGCCAAAACCAAACCCCGGGAGGAACAATATAACTCTACGTATCGGGTCGT<br>ATCTGTGTTGACCGTCCTTCACCAAGATTGGTTGAACGGCAAGGAATATAAGTGTAAAGTGT<br>CTAATAAAGCATTGGCTGCCCCGATAGAAAAGACGATCTCTAAAGCCAAGGGCCAACCCAGA<br>GAGCCTCAAGTATATACTCTCCCACCGAGTCGAGATGAGCTCACTAAGAACCAGGTGTCACT<br>CACGTGTCTGGTTAAAGGATTTTACCCTAGTGATATAGCCGTCGAGTGGGAATCAAATGGGC<br>AGCCGGAGAATAACTATAAGACCACGCCTCCAGTTCTCGATTCCGATGGTAGCTTTTTCCTT<br>TACTCTAAACTTACGGTCGACAAGTCCAGGTGGCAACAGGGCAATGTATTTTCTTGCTCCGT<br>CATGCACGAGGCTTTGCACAACCATTACACGCAAAAGTCACTGTCCCTGTCTCCTGGAGGCG<br>GTTCTGACAGTTGGCAGGAGGAGGTAATCAAATTGTGTGGGCGGGAGTTGGTTAGGGCGCAA<br>ATTGCTATTTGCGGCAAAAGTACTGGGGGCGGTGAAGGCGGAGGCGAGGGAGGAGGAGAAGG<br>TCGACAACTGTATTCTGCCTTGGCGAACAAATGCTGTCACGTCGGCTGTACGAAACGGTCTT<br>TGGCCCAGTTTTGT |
| 136 | GATAAGACACACACTTGTCCGCCATGCCCTGCGCCGGAAGCGGCGGGAGGACCGTCCGTTTT<br>CCTGTTCCCTCCCAAACCCAAAGACACGTTGATGATTAGTCGCACGCCAGAAGTTACGTGCG<br>TTGTCGTAGATGTATCCCACGAAGACCCCGAGGTGAAGTTCAATTGGTATGTAGATGGGGTG<br>GAGGTCCATAACGCTAAGACCAAACCACGCGAGGAACAATATAATTCTACGTACCGCGTAGT<br>GAGCGTTCTCACAGTTCTTCACCAGGATTGGCTTAACGGCAAGGAGTATAAGTGTAAGGTGT<br>CTAATAAGGCCTTGGCTGCCCCGATCGAAAAAACGATAAGTAAAGCAAAGGGTCAACCTAGA<br>GAACCCCAAGTGTACACTCTCCCGCCATCACGGGATGAATTGACTAAGAACCAAGTGTCACT<br>CACGTGTCTTGTAAAGGGCTTCTACCCATCCGATATAGCCGTTGAGTGGGAATCCAATGGTC<br>AGCCAGAGAACAACTATAAGACAACTCCGCCCGTACTTGATAGTGACGGTTCCTTTTTCCTT<br>TACAGTAAATTGACGGTAGATAAGTCTCGCTGGCAGCAAGGAAACGTCTTTTCTTGTTCAGT<br>GCTTCATGAGGCGCTTCACTCACACTATACTCAGAAGAGTTTGAGTTTGTCTCCAGGTGGAG<br>GCAGCGACTCATGGCAAGAGGAAGTAATCAAACTGTGTGGTCGCGAATTGGTACGAGCACAG<br>ATCGCGATCTGCGGGAAATCAACAGGTGGCGGCGAAGGCGGCGGGGAAGGCGGCGGCGAAGG<br>TAGGCAACTTTACTCAGCCCTTGCGAACAAATGTTGCCACGTAGGCTGTACTAAGAGAAGTC<br>TCGCCCAGTTTTGC |
| 137 | GACAAGACTCATACCTGCCCCCCTTGTCCAGCACCAGAAGCAGCTGGCGGGCCAAGCGTGTT<br>CCTGTTTCCACCTAAGCCCAAAGATACGTTGATGATCAGCCGCACCCCGGAAGTAACCTGTG<br>TAGTAGTAGATGTGTCCCACGAAGACCCCGAAGTAAAGTTTAATTGGTACGTCGATGGTGTC<br>GAAGTACATAACGCTAAAACGAAGCCCCGAGAAGAGCAGTACAACAGTACTTACAGAGTAGT<br>TTCTGTTCTTACAGTGCTGCATCAGGATTGGCTGAACGGGAAGGAGTATAAATGTAAAGTCT<br>CAAACAAGGCACTTGCGGCACCAATAGAGAAGACAATATCTAAGGCCAAAGGGCAGCCTAGA<br>GAGCCACAAGTATATACGCTGCCCCCCAGCAGGGACGAGCTGACAAAGAACCAAGTGTCACT<br>GACCTGCCTTGTTAAGGGCTTCTATCCGAGTGATATTGCTGTTGAATGGGAAAGTAACGGAC<br>AGCCGGAGAACAACTATAAAACTACTCCACCCGTGTTGGATAGTGACGGTAGCTTTTTTCTG<br>TACTCCAAGTTGACGGTAGACAAAAGTCGGTGGCAGCAGGGGAACGTATTTTCTTGTTCTGT<br>CATGCACGAAGCTCTTCACAATCACTATACGCAGAAGTCCCTCTCTCTCTCTCCTGGGAAGG<br>GTGGTTCCGACAGCTGGCAGGAGGAGGTCATTAAACTGTGTGGTAGAGAGCTGGTACGGGCT<br>CAAATTGCAATTTGTGGTAAGAGTACTGGCGGTGGCGAGGAAGGGGGTGGGGAGGAGGGCGG<br>AGGTAGGCAGCTCTACTCTGCTCTCGCCAACAAGTGTTGTCACGTCGGGTGTACTAAAAGAT<br>CACTTGCCCGCTTTTGT |
| 138 | GACAAAACACATACATGCCCGCCGTGTCCGGCGCCTGAAGCAGCAGGAGGCCCCAGTGTATT<br>CCTTTTCCCTCCAAAGCCAAAAGATACGTTGATGATATCTAGGACACCTGAGGTTACCTGCG<br>TCGTAGTGGACGTATCCCACGAAGACCCAGAAGTCAAGTTTAACTGGTATGTGGACGGAGTG<br>GAGGTACACAATGCAAAGACAAAGCCGCGAGAGGAACAATATAATTCCACCTATAGAGTCGT<br>GTCAGTCCTTACGGTCTTGCACCAGGACTGGCTCAATGGTAAGGAGTATAAGTGCAAAGTAT |

TABLE 8-continued

Nucleotide Sequences Encoding Fusion Proteins and Peptide Components

| SEQ ID NO: | Sequence |
|---|---|
| | CAAACAAAGCTCTCGCAGCGCCCATCGAAAAGACCATCAGCAAAGCTAAGGGCCAGCCAAGA<br>GAGCCTCAAGTGTACACGTTGCCGCCTTCAAGGGACGAGCTCACTAAAAATCAGGTATCACT<br>TACGTGTCTTGTCAAAGGGTTTTATCCTTCCGACATCGCGGTTGAATGGGAGAGCAATGGAC<br>AGCCGGAGAATAATTATAAAACGACGCCGCCGGTCCTTGACAGCGATGGTTCATTTTTCCTT<br>TACTCAAAGCTGACGGTTGATAAGTCTAGGTGGCAGCAGGGGAACGTCTTTTCCTGTAGTGT<br>ACTTCATGAGGCGCTCCATTCTCATTACACTCAGAAGTCACTGAGCCTTTCACCCGGCAAAG<br>GTGGATCAGACTCCTGGCAAGAAGAGGTAATCAAACTCTGTGGGAGGGAACTCGTTCGAGCC<br>CAGATTGCAATCTGTGGGAAAAGCACAGGCGGAGGGGAAGAAGGGGGTGGCGAAGAAGGTGG<br>GGGCAGGCAGCTCTATTCAGCTCTTGCCAACAAATGCTGTCATGTAGGCTGCACAAAGCGAT<br>CACTGGCGAGATTCTGT |
| 139 | GATAAAACTCATACTTGCCCACCCTGCCCGGCTCCCGAGGCAGCAGGTGGACCCTCAGTATT<br>TTTGTTCCCTCCGAAACCTAAAGATACACTTATGATTAGCCGGACCCCTGAGGTAACGTGTG<br>TGGTGGTTGACGTAAGTCATGAAGATCCAGAAGTAAAGTTTAACTGGTACGTAGACGGTGTG<br>GAGGTACATAATGCGAAGACAAAACCACGAGAGGAACAGTATAACTCTACCTACCGCGTAGT<br>AAGCGTACTTACTGTGCTCCACCAAGACTGGCTTAACGGGAAAGAGTATAAGTGTAAAGTCA<br>GTAATAAAGCACTGGCCGCCCCGATCGAAAAAACAATCAGCAAGGCCAAAGGACAACCAAGG<br>GAGCCTCAGGTCTATACTCTTCCCCCGAGTAGGGATGAGCTTACCAAGAACCAGGTGTCTCT<br>GACATGCCTTGTCAAGGGATTTTACCCGAGTGACATAGCCGTAGAATGGGAGTCAAACGGCC<br>AACCTGAAAACAACTATAAGACCACGCCTCCCGTACTCGACTCAGATGGAAGCTTTTTCCTC<br>TATAGCAAGCTGACCGTCGACAAAAGTAGGTGGCAACAGGGAAACGTCTTTAGTTGTTCCGT<br>CATGCACGAAGCTTTGCATAACCATTACACCCAGAAGAGTCTTTCCCTTTCCCCTGGCAAGG<br>GGGGCTCCGACTCCTGGCAAGAGGAAGTAATCAAACTGTGTGGGCGCGAGCTTGTCCGCGCG<br>CAAATAGCCATTTGCGGAAAAAGTACTGGAGGAGGAGAGGAAGGCGGCGGCGAGGAAGGTGG<br>GGGCAGGCAGCTGTACAGTGCCTTGGCTAACAAGTGCTGCCATGTCGGCTGTACGAAAAGGT<br>CTCTTGCTCAATTCTGT |
| 140 | GATAAGACACATACCTGTCCACCCTGCCCAGCACCTGAAGCTGCAGGCGGCCCCAGCGTATT<br>CCTGTTTCCTCCGAAGCCGAAAGACACACTTATGATTTCCCGGACGCCTGAGGTAACTTGCG<br>TCGTAGTAGATGTGTCTCACGAAGACCCCGAGGTGAAATTCAACTGGTACGTTGATGGTGTG<br>GAAGTTCATAATGCGAAAACTAAACCACGAGAGGAGCAATATAACTCAACTTATAGAGTTGT<br>GAGCGTCTTGACGGTACTGCACCAGGACTGGCTGAATGGCAAAGAGTACAAATGCAAAGTCT<br>CAAATAAGGCGTTGGCGGCTCCCATAGAGAAAACTATCAGCAAAGCCAAGGGTCAACCTCGG<br>GAGCCACAAGTGTATACTCTTCCGCCTAGTCGCGACGAGCTCACAAAGAATCAGGTGAGTCT<br>TACTTGTTTGGTTAAGGGTTTCTACCCCAGTGACATTGCGGTCGAGTGGGAAAGTAACGGAC<br>AGCCTGAAAACAACTATAAAACAACGCCTCCAGTACTCGATTCAGATGGTTCATTCTTTCTT<br>TATTCCAAACTCACAGTCGACAAGAGTAGATGGCAACAAGGGAACGTGTTTAGCTGTAGCGT<br>ACTCCATGAGGCACTCCACTCTCACTATACCCAAAAGTCTCTCAGCTTGTCACCCGGAAAAG<br>GCGGTTCTGACAGTTGGCAAGAGGAAGTGATTAAATTGTGTGGGCGGGAACTTGTGAGGGCT<br>CAAATCGCGATTTGCGGCAAGTCCACTGGTGGCGGCGAGGAAGGAGGAGGTGAAGAAGGAGG<br>AGGTAGGCAACTGTATTCAGCGTTGGCGAATAAATGCTGCCATGTTGGATGTACTAAACGGA<br>GCCTTGCTCAGTTCTGC |
| 141 | GATAAAACGCATACTTGCCCTCCTTGCCCGGCACCTGAAGCTGCCGGAGGTCCTTCCGTGTT<br>CCTGTTCCCACCTAAGCCAAAAGACACACTTATGATTTCTCGCACACCAGAAGTAACGTGCG<br>TCGTAGTTGACGTCTCCCATGAAGACCCGGAGGTAAAATTTAATTGGTACGTCGACGGGGTA<br>GAAGTTCATAACGCAAAGACTAAACCACGAGAAGAGCAATACAACTCTACATACAGAGTAGT<br>AAGCGTTCTCACCGTTCTTCATCAAGATTGGCTCAACGGAAAGGAGTATAAGTGTAAGGTGT<br>CCAATAAAGCGTTGGCCGCACCAATCGAAAAGACCATAAGCAAAGCCAAAGGCCAACCCCGC<br>GAACCGCAGGTGTACACACTTCCCCCGTCCAGGGATGAATTGACAAAAAACCAAGTTTCCCT<br>CACGTGTCTCGTCAAGGGATTCTACCCGAGTGATATCGCAGTTGAATGGGAAAGCAATGGTC<br>AGCCCGAGAATAACTACAAGACTACTCCCCCTGTGTTGGACTCAGACGGCTCATTCTTCCTC<br>TACAGTAAGTTGACTGTGGACAAAAGTCGGTGGCAGCAAGGCAATGTCTTCAGTTGTAGTGT<br>AATGCATGAAGCACTCCACAATCATTACACCCAAAAATCCCTGAGCCTGTCCCCGGGCGGAG<br>GTTCAGATTCATGGCAGGAGGAAGTTATAAAACTGTGCGGGCGCGAGTTGGTGAGGGCGCAG<br>ATCGCAATCTGTGGAAAGAGTACGGGAGGTGGCGAAGAGGGTGGTGGAGAAGAGGGAGGAGG<br>TCGACAACTGTATTCCGCGCTCGCGAACAAGTGTTGCCACGTTGGCTGCACCAAACGAAGCC<br>TGGCTCGATTTTGC |
| 142 | GACAAGACACACACTTGTCCACCTTGCCCGGCTCCCGAGGCGGCAGGAGGACCAAGCGTTTT<br>TCTGTTCCCTCCCAAACCAAAGGATACGCTTATGATCTCTCGAACGCCGGAAGTTACTTGCG<br>TAGTAGTTGATGTCTCCCATGAAGATCCCGAAGTGAAGTTCAACTGGTATGTAGATGGTGTG<br>GAAGTTCATAACGCGAAAACCAAACCACGCGAAGAACAGTATAACAGTACTTATCGGGTTGT<br>TTCAGTACTCACGGTGCTCCATCAAGACTGGCTTAATGGAAAGGAGTATAAATGTAAGGTAA<br>GTAACAAGGCATTGGCGGCTCCCATCGAGAAGACAATCTCCAAAGCAAAAGGGCAACCACGG<br>GAGCCTCAGGTGTATACGTTGCCGCCCAGCAGAGATGAACTTACTAAGAATCAGGTGAGTCT<br>CACTTGTCTCGTCAAGGGCTTCTATCCCAGCGATATAGCCGTAGAATGGGAGAGTAACGGTC<br>AGCCGGAGAACAACTACAAAACAACCCCGCCTGTTTTGGACTCCGATGGGAGTTTTTTTCTC<br>TACAGCAAACTCACGGTAGACAAAAGCAGGTGGCAGCAGGGCAATGTTTTCAGTTGCTCTGT<br>TCTCCACGAAGCCCTCCACTCCCACTATACTCAGAAGTCTCTGAGTCTCTCACCAGGGGGAG<br>GTAGCGATAGCTGGCAGGAGGAAGTGATCAAGTTGTGCGGGCGCGAACTCGTGCGGGCACAA<br>ATTGCTATATGCGGTAAAAGTACGGGAGGTGGAGAGGAGGGTGGAGGTGAAGAAGGCGGTGG<br>TAGACAATTGTATAGTGCGCTCGCCAACAAGTGTTGTCATGTCGGGTGTACGAAACGGTCCT<br>TGGCGCGGTTTTGC |

TABLE 8-continued

Nucleotide Sequences Encoding Fusion Proteins and Peptide Components

| SEQ ID NO: | Sequence |
|---|---|
| 143 | GACAAGACACATACTTGTCCACCATGTCCCGCCCCAGAAGCTGCGGGAGGACCATCAGTTTT<br>TTTGTTCCCCCCGAAACCGAAGGATACCCTCATGATAAGTCGAACGCCCGAAGTCACTTGCG<br>TGGTGGTTGATGTTAGCCACGAGGACCCAGAAGTGAAGTTCAACTGGTACGTGGACGGGGTC<br>GAAGTTCATAATGCGAAAACAAAGCCTCGCGAGGAACAGTACAACTCTACATACAGGGTTGT<br>GTCTGTTTTGACAGTCTTGCACCAAGATTGGCTCAACGGGAAGGAATATAAGTGTAAGGTAA<br>GCAATAAAGCACTGGCGGCCCCGATCGAAAAAACGATATCCAAGGCCAAGGGCCAGCCCCGA<br>GAGCCTCAGGTATATACTCTGCCGCCAAGCCGGGATGAACTGACTAAAAACCAGGTCTCTTT<br>GACTTGTCTTGTCAAGGGATTTTACCCAAGTGACATTGCGGTAGAGTGGGAAAGCAACGGTC<br>AACCAGAAAACAATTACAAGACGACACCGCCGGTACTCGACTCAGATGGATCCTTTTTCCTG<br>TATAGCAAGCTGACAGTGGACAAGTCCCGGTGGCAGCAAGGGAACGTATTTTCATGCAGCGT<br>GATGCATGAGGCTCTTCACAACCATTACACACAGAAAAGTCTGTCATTGAGCCCTGGCGGCG<br>GGAGCGATTCTTGGCAAGAAGAAGTTATAAAACTTTGCGGTCGAGAGCTGGTTCGGGCACAA<br>ATTGCTATCTGCGGAAAATCTACAGGAGGAGGCGAGGAGGGAGGGGGCGAAGAAGGCGGGGG<br>GAGACAGTTGTACAGTGCGCTCGCTAACAAGTGTTGCCACGTCGGTTGCACAAAGAGATCCC<br>TGGCTCAATTCTGT |
| 144 | GATAAAACTCACACCTGTCCCCCGTGTCCCGCACCAGAAGCGGCCGGTGGTCCCTCCGTTTT<br>TCTCTTCCCTCCTAAACCTAAGGACACACTTATGATTAGCAGAACTCCAGAAGTTACGTGCG<br>TAGTCGTTGACGTTAGTCATGAAGATCCTGAGGTTAAGTTCAACTGGTACGTAGACGGAGTA<br>GAGGTCCACAACGCCAAGACGAAACCCCGAGAAGAGCAGTATAATTCTACCTATCGAGTTGT<br>TTCAGTATTGACGGTGCTTCACCAAGATTGGCTGAATGGCAAAGAGTATAAGTGCAAGGTAA<br>GCAACAAAGCACTCGCGGCTCCTATCGAGAAAACTATTTCCAAAGCTAAGGGCCAGCCTCGC<br>GAACCACAAGTCTATACCCTGCCACCGAGTCGGGACGAACTCACCAAGAACCAAGTGTCTCT<br>TACTTGCCTCGTTAAAGGTTTTTATCCCAGCGACATAGCCGTCGAATGGGAGTCCAATGGCC<br>AACCTGAGAACAACTATAAAACTACCCCTCCTGTACTTGATAGCGACGGAAGTTTTTTCCTC<br>TATTCAAAACTCACAGTTGATAAGTCTCGATGGCAACAGGGCAACGTCTTCTCTTGCAGTGT<br>GTTGCATGAAGCTCTGCACTCTCATTACACACAGAAGAGTTTGTCTCTCAGTCCAGGTGGCG<br>GCTCAGATAGCTGGCAGGAAGAAGTAATCAAGTTGTGCGGCAGGGAACTGGTAAGGGCACAG<br>ATAGCCATTTGTGGAAAATCTACGGGTGGCGGTGAGGAAGGCGGCGGAGAAGAAGGGGGAGG<br>TCGGCAGCTGTATAGTGCACTCGCAAACAAGTGCTGCCATGTCGGGTGCACCAAGCGATCCC<br>TTGCCCAGTTTTGC |
| 145 | GACAAAACGCACACCTGTCCACCGTGTCCTGCTCCAGAGGCGGCCGGGGGACCGTCCGTTTT<br>CCTTTTTCCTCCCAAACCTAAGGATACCCTTATGATCTCTCGCACGCCCGAGGTTACCTGTG<br>TTGTGGTTGACGTGTCCCATGAAGACCCGGAAGTAAAATTTAATTGGTACGTGGACGGGGTC<br>GAGGTTCATAACGCAAAGACCAAGCCACGAGAGGAGCAATATAATTCCACCTATCGCGTAGT<br>CTCCGTCCTCACCGTGCTTCACCAGGATTGGCTCAACGGGAAGGAATACAAATGTAAAGTCA<br>GTAATAAGGCTTTGGCGGCCCCGATTGAGAAGACTATAAGTAAGGCTAAGGGACAGCCACGA<br>GAACCGCAAGTTTATACATTGCCCCCCTCTAGGGATGAGTTGACTAAGAATCAGGTGTCACT<br>CACTTGTCTGGTAAAAGGGTTCTACCCGTCCGACATCGCTGTGGAATGGGAAAGCAATGGGC<br>AACCTGAAAATAATTATAAGACAACCCCTCCGGTGCTTGATAGCGACGGATCATTCTTTCTC<br>TATTCCAAGCTTACTGTAGATAAGAGTCGATGGCAACAGGGGAACGTATTCAGTTGCTCTGT<br>TCTCCATGAGGCCCTGCATAGTCACTACACCCAAAAAAGCCTTAGTTTGAGTCCCGGGAAAG<br>GAGGCTCCGATTCTTGGCAAGAAGAGGTAATAAAGCTGTGTGGACGAGAACTTGTCCGAGCA<br>CAAATTGCGATTTGTGGCAAATCTACAGGAGGGGGAGAAGGAGGCGGCGAAGGGGGAGGCGA<br>GGGCAGGCAGGATTATTCCGCTCTGGCGAACAAATGTTGCCATGTTGGATGCACGAAACGAA<br>GCCTGGCTCAGTTTTGC |
| 146 | GATAAAACGCATACCTGCCCACCGTGTCCTGCACCTGAGGCCGCTGGAGGACCTTCCGTCTT<br>CCTCTTTCCACCCAAGCCGAAAGACACACTCATGATTAGTAGAACTCCAGAGGTCACGTGTG<br>TTGTGGTGGACGTCAGTCACGAGGACCCTGAGGTTAAGTTCAACTGGTACGTTGATGGCGTA<br>GAAGTCCACAATGCAAAGACCAAACCGAGAGAGGAGCAATATAACAGTACATATAGGGTTGT<br>TAGCGTACTTACTGTTTTGCATCAAGACTGGTTGAATGGGAAGGAATATAAATGTAAAGTCT<br>CCAACAAGGCTCTGGCTGCACCAATAGAAAAAACTATTTCTAAGGCAAAGGGTCAGCCTAGA<br>GAGCCTCAAGTCTATACCTTGCCACCGTCAAGAGACGAGCTCACTAAAAATCAGGTGAGCCT<br>GACCTGTCTTGTGAAGGGCTTTTACCCGTCAGATATTGCCGTGGAGTGGGAATCAAACGGTC<br>AGCCGGAGAATAACTACAAGACGACCCCACCAGTACTCGATAGCGATGGGTCTTTCTTTCTG<br>TACTCCAAGCTCACCGTGGACAAATCACGCTGGCAACAGGGCAACGTCTTTAGTTGCAGCGT<br>ACTGCACGAGGCACTGCACAGCCACTACACACAAAAGAGTCTTTCTCTGTCTCCCGGTGGTG<br>GCTCCGATAGTTGGCAGGAAGAAGTCATAAAGCTTTGTGGAAGAGAGCTTGTACGAGCGCAG<br>ATTGCAATCTGCGGGAAGAGCACTGGAGGAGGTGAGGGAGGGGGTGAGGGCGGGGGCGAAGG<br>ACGCCAGGACTATTCAGCACTTGCAAACAAATGCTGCCATGTAGGGTGTACGAAGCGCTCAC<br>TGGCCCGGTTTTGC |
| 147 | GATAAAACACATACCTGCCCCCCATGCCCAGCCCCCGAAGCTGCAGGGGGGCCCTCTGTTTT<br>CCTTTTTCCACCCAAACCTAAAGATACTCTGATGATTAGTCGGACTCCGGAAGTGACTTGCG<br>TCGTTGTCGACGTCTCTCATGAGGATCCAGAAGTTAAGTTTAACTGGTATGTCGACGGGGTT<br>GAGGTTCATAATGCAAAAACTAAACCGAGAGAAGAACAGTACAACTCTACTTATAGGGTTGT<br>CAGTGTACTGACCGTCCTGCACCAGGATTGGCTTAACGGTAAGGAGTATAAGTGTAAAGTGT<br>CCAATAAAGCCCTTGCCGCACCCATCGAGAAAACCATCTCCAAGGCAAAAGGACAGCCAAGG<br>GAACCGCAGGTATATACACTTCCGCCAAGCCGAGACGAACTTACGAAGAACCAGGTGTCTCT<br>CACGTGTCTCGTAAAAGGGTTTTATCCCAGCGATATCGCAGTTGAGTGGGAGAGCAATGGGC<br>AGCCAGAGAATAATTATAAGACAACCCCTCCCGTGCTGGATTCAGACGGGAGTTTTTTTCTT<br>TACTCTAAGCTGACCGTAGACAAAAGTCGATGGCAGCAAGGCAACGTCTTTTCCTGCTCCGT<br>TCTCCATGAAGCACTGCATAGCCATTATACCCAGAAGTCACTGAGCCTCTCTCCAGGGGGCG |

TABLE 8-continued

Nucleotide Sequences Encoding Fusion Proteins and Peptide Components

| SEQ ID NO: | Sequence |
|---|---|
| | GGTCCGATTCATGGCAGGAAGAGGTAATCAAACTCTGTGGACGCGAACTGGTTCGCGCGCAG<br>ATAGCGATTTGCGGCAAAAGCACAGGCGGTGGGGAAGGCGGTGGCGAGGGCGGTGGTGAAGG<br>TCGACAAGATTATTCTGCTCTCGCTAACAAGTGTTGTCATGTAGGATGTACTAAAAGGAGTC<br>TTGCGCAGTTCTGT |
| 148 | GATAAGACGCACACATGCCCACCCTGTCCTGCGCCTGAAGCCGCGGGGGGACCCAGCGTTTT<br>TCTCTTCCCGCCGAAACCGAAAGACACACTTATGATCAGCCGGACTCCCGAGGTTACCTGCG<br>TGGTGGTAGATGTATCTCACGAGGATCCCGAGGTCAAATTCAACTGGTACGTTGATGGGGTT<br>GAAGTTCATAATGCCAAAACGAAGCCAAGAGAAGAGCAGTATAACTCCACATATAGAGTTGT<br>TTCCGTCTTGACTGTTCTTCACCAAGATTGGCTGAATGGGAAGGAGTACAAATGTAAAGTTA<br>GCAACAAGGCACTCGCCGCTCCCATTGAAAAAACTATAAGCAAAGCTAAGGGCCAACCGCGC<br>GAACCACAGGTCTACACGTTGCCGCCCTCTAGGGACGAACTCACGAAGAATCAGGTTTCCCT<br>TACCTGCCTCGTTAAAGGATTCTACCCCTCTGACATAGCGGTTGAATGGGAGAGCAACGGTC<br>AGCCTGAGAACAACTACAAAACGACGCCTCCGGTGTTGGATTCCGACGGTAGTTTTTTCCTC<br>TATAGTAAGCTGACAGTGGATAAATCTCGGTGGCAGCAAGGGAATGTATTCTCCTGTTCAGT<br>CCTGCATGAAGCCCTCCACTCCCATTATACACAGAAATCTCTTTCTCTGAGTCCCGGTAAAG<br>GTGGGAGTGACTCTTGGCAGGAAGAGGTAATTAAGTTGTGTGGAAGGGAGCTGGTAAGAGCA<br>CAGATTGCCATCTGTGGCAAATCCACGGGCGGCGAAGGTGAGGGGGGTGAGGGGGAAGGGGG<br>GTCCAGACAACTGTATTCTGCTCTGGCGAATAAGTGTTGCCATGTAGGGTGCACTAAACGGT<br>CCTTGGCGCAGTTCTGT |
| 149 | GATAAAACTCATACGTGCCCACCTTGCCCCGCACCGGAGGCTGCTGGAGGACCCTCTGTCTT<br>CCTGTTCCCGCCGAAGCCTAAAGACACATTGATGATCAGTCGAACACCGGAAGTCACCTGTG<br>TAGTGGTTGATGTGAGCCATGAGGACCCTGAAGTAAAATTTAACTGGTATGTTGATGGCGTA<br>GAAGTACACAACGCGAAGACTAAACCAAGGGAAGAGCAATACAACTCTACCTATAGGGTCGT<br>TAGCGTACTGACTGTGCTTCACCAAGACTGGCTTAACGGGAAGGAGTACAAGTGCAAAGTGA<br>GCAATAAGGCCCTCGCCGCGCCTATCGAGAAAACCATTTCCAAAGCCAAGGGTCAACCAAGG<br>GAGCCTCAGGTTTACACCCTGCCCCCTTCAAGGGATGAGTTGACAAAAAACCAGGTAAGTCT<br>GACGTGTCTCGTTAAGGGATTCTACCCGTCAGATATCGCGGTAGAGTGGGAGAGCAACGGTC<br>AGCCAGAAAATAATTACAAAACAACACCTCCAGTTTTGGACTCTGATGGGAGTTTTTTTCTT<br>TATTCTAAGTTGACAGTGGATAAGTCACGCTGGCAACAGGGGAACGTATTTAGCTGCTCAGT<br>ACTTCATGAAGCGTTGCATTCTCACTACACACAGAAGAGCCTCTCCTTGAGTCCCGGAGGTG<br>GCTCTGATTCTTGGCAGGAGGAGGTAATAAAACTTTGTGGTAGAGAACTGGTTCGCGCTCAG<br>ATAGCTATTTGTGGAAAATCCACTGGCGGTGAAGGTGAAGGTGGAGAAGGAGAGGGCGGAAG<br>CCGGCAGTTGTACTCTGCCCTGGCTAATAAGTGCTGTCACGTGGGCTGCACTAAGCGGAGCT<br>TGGCAAGATTTTGC |
| 150 | GATAAAACTCATACCTGTCCACCTTGTCCTGCGCCTGAGGCAGCTGGAGGGCCTAGCGTGTT<br>CCTGTTCCCCCCCAAACCCAAAGACACGCTCATGATTAGCCGAACCCCTGAAGTGACCTGCG<br>TTGTTGTGGACGTAAGCCACGAAGACCCCGAAGTTAAGTTTAATTGGTACGTCGACGGTGTT<br>GAGGTTCATAACGCGAAGACTAAGCCGAGAGAGGAGCAATATAACAGCACCTACCGCGTAGT<br>CTCAGTTCTTACCGTGCTCCACCAGGACTGGCTTAACGGGAAGGAATACAAATGCAAAGTTT<br>CCAACAAAGCCTTGGCAGCCCCAATAGAGAAGACAATATCTAAGGCGAAAGGCCAACCGCGG<br>GAACCGCAAGTTTATACCCTCCCACCGAGCAGGGATGAGCTGACAAAAAATCAGGTTTCCCT<br>CACTTGTCTGGTCAAGGGATTTTATCCTTCAGACATAGCCGTTGAATGGGAGAGTAATGGGC<br>AGCCGGAGAATAATTACAAGACCACCCCCCCGGTGTTGGACAGCGACGGTTCCTTCTTTCTC<br>TATTCTAAACTTACCGTCGACAAATCACGGTGGCAACAAGGAAATGTATTCTCATGCAGTGT<br>ATTGCACGAAGCTCTGCACTCTCATTACACCCAAAAATCCCTCTCTCTCAGCCCTGGCGGTG<br>GATCTGATTCTTGGCAGGAAGAGGTGATTAAACTGTGTGGGCGAGAGCTTGTCCGAGCTCAG<br>ATCGCTATTTGTGGCAAGAGTACCGGAGGCGAGGGTGAGGGAGGCGAAGGCGAGGGCGGAAG<br>CCGGCAACTCTATAGCGCACTCGCTAATAAATGTTGTCATGTCGGCTGCACGAAGCGCTCAC<br>TGGCGCAGTTCTGC |
| 151 | GACAAAACGCATACCTGTCCTCCATGCCCCGCTCCCGAGGCTGCCGGCGGACCAAGCGTATT<br>TCTCTTCCCCCCTAAACCTAAAGACACATTGATGATAAGTAGGACGCCTGAAGTAACGTGTG<br>TTGTCGTTGATGTAAGCCATGAAGATCCTGAAGTAAAGTTTAATTGGTATGTTGATGGCGTA<br>GAAGTACATAACGCTAAGACGAAGCCACGGGAAGAGCAGTATAACTCAACTTACCGCGTTGT<br>AAGCGTGCTTACCGTCCTGCATCAGGATTGGCTGAATGGTAAGGAATATAAGTGCAAAGTAA<br>GCAACAAAGCATTGGCCGCACCAATAGAGAAGACGATTAGTAAAGCAAAAGGCCAGCCCAGA<br>GAGCCGCAGGTTTATACACTTCCACCAAGCAGAGATGAACTTACGAAGAACCAGGTGTCTCT<br>GACTTGTCTGGTCAAGGGTTTCTATCCTTCCGACATTGCAGTGGAGTGGGAAAGCAATGGGC<br>AGCCCGAAAACAATTATAAGACGACACCTCCAGTGTTGGACTCAGACGGTTCCTTTTTCTTG<br>TATTCCAAACTTACAGTGGATAAGTCAAGGTGGCAGCAAGGCAACGTATTTTCTTGTAGTGT<br>TTTGCACGAAGCCCTGCATTCCCACTATACTCAAAAGAGCCTCAGTCTGTCCCCAGGAAAGG<br>GAGGGAGTGACAGTTGGCAAGAGGAGGTAATAAAATTGTGTGGCAGAGAGCTTGTGCGCGCT<br>CAGATCGCAATATGCGGGAAATCTACTGGGGGTGAGGGTGAGGGCGGCGAGGGAGAGGGGGG<br>CAGTCGCCAAGATTATTCCGCCCTTGCGAATAAGTGTTGTCACGTCGGATGTACTAAGAGAT<br>CATTGGCTCAGTTTTGT |
| 152 | ATGGAGACGGACACTTTGCTGCTTTGGGTACTGCTGCTTTGGGTTCCTGGATCTACTGGCGA<br>TAAAACACACACGTGTCCCCCCTGCCCGGCTCCAGAGGCGGCTGGTGGTCCCAGCGTATTCT<br>TGTTTCCTCCCAAACCTAAGGATACGCTCATGATATCCCGCACCCCAGAAGTTACGTGTGTA<br>GTCGTCGACGTCAGTCACGAAGATCCAGAGGTCAAATTTAACTGGTATGTCGACGGAGTAGA<br>GGTCCACAATGCGAAAACCAAGCCCAGAGAAGAGCAGTACAACTCCACGTATCGCGTCGTCT<br>CCGTCCTCACCGTACTCCATCAAGATTGGCTGAATGGGAAAGAGTATAAATGCAAAGTATCT |

TABLE 8-continued

Nucleotide Sequences Encoding Fusion Proteins and Peptide Components

| SEQ ID NO: | Sequence |
|---|---|
| | AACAAGGCTCTGCCAGCTCCGATAGAAAAGACTATATCAAAGGCCAAGGGGCAGCCAAGGGA |
| | GCCTCAAGTCTATACTTTGCCCCCATCTCGGGATGAGCTTACGAAAAACCAGGTCAGCCTTA |
| | CCTGTCTTGTTAAAGGTTTTTATCCGAGTGACATCGCAGTGGAATGGGAATCTAATGGTCAA |
| | CCTGAAAACAATTACAAAACCACACCGCCAGTATTGGACAGCGATGGTAGTTTTTTTCTTTA |
| | CTCAAAACTGACTGTAGATAAAAGCAGATGGCAGCAGGGCAATGTCTTTTCATGTAGCGTTA |
| | TGCATGAGGCTCTTCACAACCACTATACCCAAAAGTCATTGTCTCTTAGTCCCGGAAAGGGC |
| | GGAAGTGATTCTTGGAAGGAGGAGGTAATCAAGTTGTGCGGGCGAGAGTTGGTACGGGCACA |
| | GATCGCGATATGCGGAAAATCCACAGGTGGGGGCGAAGGAGGAGGTGAGGGTGGAGGTGAAG |
| | GACGACAGTTGTATTCCGCCTTGGCAAACAAGTGTTGCCATGTGGGTTGCACAAAACGCAGT |
| | CTTGCCCGCTTCTGT |
| 153 | ATGGAGACCGATACGCTGTTGCTGTGGGTATTGCTTCTCTGGGTGCCCGGCTCAACTGGGGA |
| | TAAGACACATACATGCCCTCCCTGTCCGGCTCCAGAGGCAGCCGGGGGTCCATCAGTCTTCC |
| | TTTTTCCGCCTAAACCTAAGGATACACTGATGATCTCTCGAACACCGGAGGTCACTTGTGTT |
| | GTCGTTGACGTATCACATGAGGATCCCGAAGTAAAGTTCAACTGGTATGTCGATGGTGTGGA |
| | GGTTCATAATGCTAAAACTAAACCACGGGAGGAGCAATATAATTCCACATATAGGGTCGTGA |
| | GCGTGTTGACGGTGCTTCATCAAGACTGGCTTAATGGGAAGGAATATAAATGCAAAGTGTCA |
| | AATAAAGCACTTCCTGCGCCAATCGAGAAAACAATTAGTAAGGCAAAGGGGCAGCCGCGAGA |
| | ACCTCAGGTGTACACCTTGCCGCCTTCTAGAGACGAGCTCACAAAGAACCAAGTTTCCCTGA |
| | CTTGCCTCGTTAAGGGGTTTTATCCGTCCGATATAGCCGTGGAGTGGGAGTCAAACGGCCAA |
| | CCGGAAAATAATTACAAAACGACACCCCCAGTATTGGATAGTGACGGCTCTTTTTTCCTTTA |
| | TTCTAAGCTGACTGTGGACAAAAGCCGCTGGCAGCAGGGCAATGTCTTTTCATGCAGCGTAA |
| | TGCATGAAGCCCTGCACAACCACTACACGCAAAAATCCCTTTCCTTGTCACCCGGCAAGGGC |
| | GGCTCTGACTCCTGGAAAGAGGAAGTTATAAAACTCTGTGGCCGAGAACTTGTTCGAGCTCA |
| | AATCGCGATTTGTGGTAAGTCAACGGGTGGGGGCGAAGGTGGAGGCGAGGGTGGGGGAGAAG |
| | GAGGAGGCCAGTTGTACTCAGCTCTTGCAAATAAGTGTTGCCACGTTGGTTGTACGAAGCGG |
| | AGCCTTGCTCGCTTCTGC |
| 154 | ATGGAAACTGATACTCTTCTGCTGTGGGTCCTGCTGCTGTGGGTTCCAGGATCTACTGGAGA |
| | CAAAACACATACTTGTCCGCCTTGCCCGGCACCCGAAGCGGCCGGCGGACCCAGTGTCTTTC |
| | TCTTCCCACCCAAACCGAAAGACACTCTGATGATTTCCAGGACGCCTGAAGTGACCTGCGTT |
| | GTAGTTGATGTATCACACGAGGATCCCGAGGTCAAGTTCAATTGGTATGTAGATGGGGTGGA |
| | GGTCCATAATGCAAAGACGAAGCCACGGGAGGAACAGTACAACTCTACGTACAGAGTTGTCA |
| | GTGTTTTGACCGTCCTTCATCAGGATTGGCTGAACGGTAAAGAATATAAATGCAAGGTTAGC |
| | AATAAAGCTTTGCCCGCCCCTATAGAGAAAACGATCAGTAAGGCGAAGGGGCAGCCTAGGGA |
| | ACCCCAGGTATATACCTTGCCGCCAAGTCGAGATGAGCTGACGAAGAACCAAGTGAGTCTGA |
| | CATGCCTCGTGAAGGGCTTCTATCCGAGCGATATCGCTGTCGAATGGGAGAGCAATGGGCAG |
| | CCTGAGAATAACTATAAAACAACGCCACCCGTCCTCGACTCCGATGGCTCATTCTTCCTGTA |
| | CAGTAAACTTACAGTAGATAAGAGTAGATGGCAGCAGGGTAACGTCTTTAGTTGCTCCGTGA |
| | TGCACGAGGCATTGCACAATCATTACACTCAAAAATCTCTGTCCCTGAGTCCGGGCAAAGGC |
| | GGTTCAGATAGCTGGATGGAGGAGGTCATAAAGCTTTGTGGACGAGAACTCGTTCGCGCCCA |
| | GATAGCTATTTGTGGGAAATCAACCGGGGGTGGAGAAGGTGGCGGAGAAGGGGGAGGCGAAG |
| | GGCGCCAACTGTATTCTGCATTGGCTAATAAGTGCTGTCACGTAGGATGTACAAAAAGGTCT |
| | CTGGCGAGATTCTGC |
| 155 | ATGGAGACCGACACCCTCTTGTTGTGGGTTCTCCTCTTGTGGGTGCCCGGCAGTACTGGAGA |
| | CAAGACGCACACTTGTCCACCTTGCCCTGCGCCGGAAGCTGCTGGAGGCCCCAGTGTCTTTT |
| | TGTTCCCGCCCAAACCGAAGGACACTTTGATGATAAGTCGCACGCCCGAGGTTACCTGTGTG |
| | GTTGTCGATGTCTCACACGAAGATCCGGAGGTGAAGTTTAATTGGTATGTAGATGGCGTGGA |
| | GGTTCATAACGCCAAAACGAAACCCAGAGAAGAACAATATAACAGTACATATCGAGTAGTAT |
| | CCGTTCTCACTGTCCTGCATCAAGACTGGTTGAACGGGAAGGAATATAAGTGCAAGGTGAGC |
| | AATAAAGCACTCCCGGCCCCAATCGAAAAGACCATCAGCAAAGCGAAGGGGCAACCTCGAGA |
| | ACCCCAGGTATATACGCTCCCCCCTAGTCGGGATGAACTTACTAAAAATCAGGTTAGCCTCA |
| | CTTGCCTTGTTAAAGGGTTCTATCCCAGTGATATTGCCGTCGAATGGGAATCAAACGGGCAG |
| | CCGGAAAATAACTACAAGACAACCCCTCCTGTGCTCGATAGCGATGGCTCTTTTTTCCTCTA |
| | CAGCAAACTTACCGTTGATAAGAGCCGGTGGCAACAAGGTAATGTTTTCTCCTGCTCCGTTA |
| | TGCATGAAGCACTCCATAACCATTATACCCAAAAAAGCCTGTCACTTAGTCCGGGTAAAGGA |
| | GGTAGTGATTCTTGGCAGGAGGAGGTAATCAAACTTTGTGGGAGGGAGCTGGTACGAGCTCA |
| | GATTGCTATATGTGGAAAAAGCACGGGCGGAGGAGAAGGAGGTGGCGAAGGCGGGGGTGAAG |
| | GTCGGCAACTCTACTCCGCTCTCGCTAATAAGTGCTGCCACGTCGGGTGTACGAAGCGCTCC |
| | CTGGCGCGATTCTGC |
| 156 | ATGGAAACAGATACCCTCCTCCTCTGGGTCCTTCTTCTTTGGGTGCCTGGCTCAACTGGAGA |
| | TAAAACGCACACGTGTCCGCCCTGCCCAGCGCCTGAAGCCGCAGGCGGGCCGTCCGTCTTCC |
| | TCTTTCCTCCAAAACCCAAAGACACACTTATGATCAGTAGGACCCCAGAGGTAACCTGCGTC |
| | GTGGTCGACGTTTCCCATGAAGACCCAGAGGTCAAGTTCAACTGGTACGTCGACGGTGTCGA |
| | AGTACATAATGCTAAAACGAAGCCTCGGGAAGAGCAGTACAACTCTACCTACCGCGTCGTTT |
| | CCGTACTCACCGTACTTCACCAGGACTGGCTTAACGGTAAAGAGTATAAATGCAAAGTATCT |
| | AATAAGGCTCTCGCCGCGCCGATTGAGAAGACAATTTCAAAGGCCAAGGGGCAGCCGCGGGA |
| | GCCCCAAGTGTATACCTTGCCCCCGTCCCGAGATGAGCTGACTAAAAACCAAGTAAGCTTGA |
| | CTTGCTTGGTCAAAGGCTTCTACCCTTCCGATATAGCTGTCGAATGGGAGTCAAATGGCCAA |
| | CCAGAGAACAATTATAAAACTACACCCCCGGTCTTGGATTCTGATGGCTCATTTTTTCTCTA |
| | TTCTAAACTGACCGTGGATAAGTCTCGCTGGCAGCAAGGTAACGTGTTCAGTTGCTCTGTTC |
| | TTCACGAAGCACTGCACAGTCATTACACTCAGAAGAGTCTTAGCCTGAGCCCTGGTAAAGGG |
| | GGTTCTGATTCCTGGCAGGAGGAAGTAATAAAACTCTGTGGCCGGGAGTTGGTACGGGCGCA |

TABLE 8-continued

Nucleotide Sequences Encoding Fusion Proteins and Peptide Components

| SEQ ID NO: | Sequence |
|---|---|
| | GATTGCGATATGCGGTAAGAGCACCGGCGGAGGCGAAGGCGGTGGGGAAGGAGGAGGAGAAG<br>GGAGACAACTCTATTCCGCATTGGCAAATAAGTGCTGCCACGTCGGGTGTACCAAACGATCC<br>CTTGCACGGTTCTGT |
| 157 | ATGGAGACGGACACCCTCCTTCTCTGGGTTTTGCTCCTTTGGGTCCCTGGTTCCACTGGAGA<br>TAAGACCCATACGTGCCCCCCTTGCCCTGCGCCTGAGGCAGCGGGTGGCCCATCAGTCTTTT<br>TGTTCCCGCCCAAGCCAAAGGACACCCTCATGATTAGTAGAACACCGGAGGTTACGTGCGTC<br>GTAGTGGATGTCAGCCACGAGGATCCCGAGGTTAAGTTTAACTGGTACGTTGATGGGGTTGA<br>GGTCCATAATGCGAAGACTAAGCCGAGAGAGGAACAGTACAATTCCACGTATAGAGTTGTCT<br>CTGTACTGACTGTGCTGCATCAAGATTGGCTTAACGGTAAGGAGTACAAGTGCAAAGTCTCT<br>AATAAGGCTCTTCCTGCACCCATTGAGAAAACTATAAGCAAAGCAAAAGGTCAACCTCGCGA<br>ACCTCAGGTGTACACACTGCCACCCTCTAGGGACGAGCTTACCAAAAATCAAGTATCTCTTA<br>CCTGCCTTGTGAAAGGGTTTTATCCCTCAGATATTGCGGTTGAGTGGGAGTCTAACGGACAA<br>CCTGAGAACAACTATAAGACTACTCCCCCGGTGCTTGATTCAGACGGGAGTTTTTTTTTGTA<br>TAGCAAACTTACCGTCGACAAAAGCCGGTGGCAACAGGGCAATGTATTCAGTTGTTCTGTAA<br>TGCATGAAGCTTTGCATAATCATTACACCCAAAAGAGTCTTTCCCTGTCTCCTGGAAAAGGG<br>GGGTCAGACTCCTGGATGGAGGAGGTGATCAAACTGTGTGGGAGAGAGCTCGTCCGGGCTCA<br>GATAGCTATATGCGGCAAGTCTACGGGTGGGGGAGAGGGCGGAGGAGAGGGCGGTGGAGAAG<br>GAGGCGGCCAACTCTACAGCGCTCTGGCCAATAAATGTTGTCATGTCGGGTGTACTAAGCGC<br>TCACTGGCACGCTTTTGC |
| 158 | ATGGAAACCGACACCCTTTTGTTGTGGGTATTGCTGTTGTGGGTTCCCGGTAGCACGGGGGA<br>CAAGACGCATACATGCCCGCCATGCCCGGCCCCCGAAGCTGCTGGGGGACCATCCGTATTCC<br>TCTTCCCTCCCAAACCAAAAGACACGTTGATGATAAGTAGAACACCAGAGGTAACGTGCGTG<br>GTTGTCGATGTTTCCCACGAAGATCCGGAGGTAAAATTCAATTGGTATGTAGATGGGGTGGA<br>AGTGCACAATGCCAAAACAAAGCCGCGAGAAGAACAATACAATAGTACTTACCGGGTTGTGA<br>GCGTGCTCACGGTGTTGCACCAAGACTGGCTCAACGGCAAGGAATACAAGTGCAAAGTATCT<br>AATAAAGCTCTGCCTGCGCCGATAGAGAAGACCATCAGTAAGGCCAAAGGGCAGCCCCGAGA<br>GCCGCAAGTTTACACTCTTCCTCCGAGCAGAGATGAATTGACCAAGAACCAAGTAAGTTTGA<br>CGTGCCTGGTGAAGGGCTTCTACCCCTCAGACATTGCGGTGGAGTGGGAAAGTAATGGTCAA<br>CCGGAAAACAACTACAAGACCACGCCGCCCGTCCTCGACTCCGATGGGTCTTTCTTTCTTTA<br>TTCAAAGTTGACAGTAGATAAGTCAAGGTGGCAGCAAGGTAACGTGTTTAGTTGTAGTGTAA<br>TGCACGAGGCCCTGCATAATCATTATACCCAAAAGAGTTTGAGCCTCTCACCAGGAAAAGGC<br>GGATCAGACAGCTGGCAGGAGGAGGTAATTAAATTGTGTGGACGGGAGTTGGTCAGGGCGCA<br>AATAGCCATCTGCGGTAAGAGCACGGGTGGAGGAGAGGGTGGAGGGGAAGGTGGGGGAGAAG<br>GCGGCGGGCAGCTCTATTCTGCACTCGCCAACAAGTGTTGTCACGTCGGATGCACAAAGAGA<br>TCTCTTGCTCGATTCTGC |
| 159 | ATGGAGACTGATACTCTTTTGTTGTGGGTACTGCTCCTGTGGGTTCCAGGCTCCACAGGAGA<br>CAAAACACACACCTGTCCGCCTTGCCCGGCTCCTGAAGCCGCGGGTGGCCCTAGTGTGTTTT<br>TGTTTCCGCCGAAACCTAAGGATACCCTCATGATAAGCCGGACGCCCGAGGTTACCTGTGTC<br>GTGGTCGATGTTAGTCATGAGGATCCAGAAGTCAAGTTTAATTGGTACGTCGACGGCGTTGA<br>AGTCCACAATGCAAAAACTAAACCGCGAGAAGAACAGTACAACTCCACCTACAGAGTTGTCT<br>CAGTTTTGACAGTTCTCCATCAGGATTGGCTCAATGGAAAGGAATATAAGTGCAAGGTCAGC<br>AATAAAGCGCTTGCCGCCCCTATAGAGAAGACCATTAGCAAGGCGAAAGGACAGCCCCGCGA<br>GCCCCAGGTCTATACGCTGCCTCCTAGCAGAGATGAGCTCACGAAAAATCAGGTCAGCTTGA<br>CATGCTTGGTGAAGGGCTTCTACCCCAGTGACATCGCAGTTGAATGGGAGAGCAACGGCCAA<br>CCTGAGAACAACTACAAAACAACGCCCCCGGTTCTTGACAGCGATGGGTCCTTCTTTCTTTA<br>CTCTAAGCTTACAGTTGATAAAAGCAGGTGGCAGCAGGGGAATGTGTTCTCATGTTCCGTAC<br>TGCATGAGGCTCTGCATTCTCACTACACCCAAAAAAGCCTTAGCCTGAGCCCCGGTAAGGGA<br>GGTAGTGACTCATGGCAAGAGGAAGTGATTAAGCTCTGCGGCCGGGAGTTGGTGAGAGCCCA<br>AATCGCCATTTGCGGTAAAAGTACCGGAGGGGGCGAGGGAGGAGGCGAAGGTGGAGGTGAAG<br>GAGGTGGACAGTTGTACTCAGCTCTTGCAAATAAATGTTGTCATGTTGGTTGCACGAAAAGA<br>TCTCTTGCGAGGTTCTGT |
| 160 | ATGGAGACTGACACTCTTTTGTTGTGGGTGCTTCTTCTGTGGGTACCTGGATCCACTGGGGA<br>TAAGACGCATACTTGTCCACCGTGCCCCGCACCGGAAGCGGCTGGTGGTCCATCAGTTTTTC<br>TGTTCCCACCGAAACCTAAGGACACGTTGATGATATCACGGACACCAGAGGTTACGTGCGTA<br>GTGGTGGATGTGAGCCACGAGGATCCAGAAGTTAAATTTAATTGGTACGTAGATGGAGTGGA<br>GGTTCATAATGCGAAGACAAAGCCTCGCGAGGAACAGTATAATTCCACCTATCGCGTCGTAT<br>CTGTGCTTACGGTACTTCACCAAGACTGGTTGAACGGTAAGGAATATAAATGCAAGGTTTCC<br>AATAAAGCACTTCCTGCGCCAATTGAGAAGACAATATCCAAAGCTAAAGGTCAACCCAGGGA<br>ACCGCAAGTCTACACTCTCCCCCCGTCTCGCGATGAATTGACGAAGAACCAGGTTAGTCTCA<br>CCTGCCTGGTCAAGGGGTTTTACCCCTCTGACATAGCTGTAGAATGGGAGTCTAATGGACAG<br>CCAGAGAACAATTACAAAACGACCCCCCCGGTCCTCGATTCTGATGGGAGTTTTTTTCTTTA<br>TTCAAAATTGACTGTCGATAAGTCAAGATGGCAACAGGGTAACGTATTTTCTTGCAGTGTTA<br>TGCATGAAGCATTGCACAACCACTATACACAAAAATCATTGAGTTTGAGTCCCGGTAAAGGG<br>GGAAGCGACTCATGGATGGAAGAAGTAATCAAGCTGTGCGGGCGAGAGCTTGTGCGAGCTCA<br>GATAGCAATCTGTGGTAAGTCTACAGGTGGAGAGGGTGGCGGTGAAGAAGGCGGGGGAGAGG<br>GAGGCCAGCTTTATTCTGCCCTGGCTAACAAGTGCTGTCACGTTGGATGCACGAAGCGCTCC<br>CTGGCCCGATTCTGC |
| 161 | ATGGAAACCGATACATTGCTTTTGTGGGTCCTCCTTCTTTGGGTTCCTGGCTCTACAGGCGA<br>TAAGACGCATACTTGTCCCCCATGTCCCGCTCCGGAAGCCGCTGGCGGCCCCTCCGTTTTTC<br>TGTTCCCGCCGAAACCGAAAGACACCCTGATGATATCACGCACTCCCGAGGTCACTTGCGTG |

TABLE 8-continued

Nucleotide Sequences Encoding Fusion Proteins and Peptide Components

| SEQ ID NO: | Sequence |
|---|---|
| | GTAGTCGATGTTAGTCATGAAGATCCTGAGGTCAAATTCAATTGGTATGTAGATGGCGTTGA<br>GGTACACAACGCGAAGACAAAACCCCGAGAAGAACAGTATAACTCAACCTACCGCGTAGTTT<br>CAGTTCTTACCGTACTGCACCAAGACTGGTTGAACGGTAAAGAGTACAAATGTAAAGTCAGC<br>AATAAAGCTTTGCCAGCACCTATCGAAAAAACCATCAGTAAGGCCAAGGGTCAACCCAGGGA<br>GCCGCAAGTGTACACTCTTCCCCCTAGCAGGGATGAATTGACCAAGAATCAGGTCTCTTTGA<br>CGTGCCTCGTTAAGGGTTTCTATCCCAGCGATATAGCCGTAGAATGGGAGTCTAACGGTCAG<br>CCAGAAAATAACTATAAGACAACCCCGCCTGTTTTGGATTCCGACGGCTCTTTTTTTCTCTA<br>CTCTAAGTTGACCGTTGATAAGAGCAGATGGCAGCAGGGAAACGTATTTTCTTGTTCCGTGA<br>TGCACGAAGCCCTGCACAATCACTATACGCAAAAGTCTCTGAGCTTGAGTCCGGGTAAAGGC<br>GGTTCTGACTCCTGGCAGGAGGAAGTCATAAAACTCTGCGGAAGAGAGCTCGTAAGGGCGCA<br>AATCGCTATTTGTGGTAAGAGCACCGGTGGGGAAGGAGGCGGTGAAGAGGGTGGCGGCGAGG<br>GTGGGCAATTGTATTCCGCGCTTGCCAATAAATGTTGTCACGTAGGCTGCACAAAGCGAAGT<br>CTCGCTAGGTTCTGC |
| 162 | ATGGAAACCGACACCTTGCTTTTGTGGGTGCTCTTGCTGTGGGTTCCGGGGAGCACTGGCGA<br>CAAGACCCACACATGTCCCCCGTGTCCGGCACCAGAAGCAGCGGGGGGACCGTCAGTATTCT<br>TGTTTCCACCGAAGCCCAAAGACACATTGATGATTTCACGAACTCCTGAAGTTACCTGTGTG<br>GTTGTAGATGTATCACACGAAGACCCAGAAGTCAAATTCAATTGGTATGTCGACGGGGTTGA<br>AGTTCACAATGCGAAGACGAAGCCCCGGGAGGAACAGTACAACAGCACGTACAGGGTTGTGA<br>GCGTTCTTACTGTATTGCACCAGGATTGGCTCAACGGCAAGGAGTATAAATGTAAAGTTTCT<br>AATAAGGCTCTTCCTGCCCCAATTGAAAAGACGATATCTAAAGCGAAGGGCCAACCACGGGA<br>ACCTCAGGTGTACACACTTCCGCCTAGCAGGGATGAGTTGACCAAGAATCAAGTCTCTTTGA<br>CGTGCCTGGTCAAGGGGTTTTACCCATCAGATATCGCCGTCGAATGGGAGTCAAACGGACAA<br>CCCGAAAATAACTATAAAACTACTCCACCAGTTCTGGATAGCGACGGCTCATTTTTTCTGTA<br>TTCAAAGCTCACTGTAGACAAGTCTAGGTGGCAGCAGGGTAATGTCTTCTCCTGCTCAGTAA<br>TGCATGAGGCTCTTCACAACCACTATACTCAAAAGAGCCTTTCCCTGTCACCTGGCGGTGGA<br>AGCGACTCATGGATGGAGGAGGTAATAAAGCTCTGCGGAAGAGAACTGGTACGCGCACAAAT<br>CGCAATTTGTGGTAAGAGTACTGGCGGGGAAGGAGGTGGGGAAGAAGGGGGCGGTGAGGGCG<br>GACAGCTCTATTCTGCACTTGCAAACAAATGTTGCCACGTGGGATGTACTAAGCGAAGCCTT<br>GCAAGATTCTGC |
| 163 | ATGGAGACCGACACACTGTTGCTGTGGGTACTCCTCCTGTGGGTGCCAGGAAGCACGGGCGA<br>TAAAACCCACACATGCCCTCCATGCCCTGCTCCAGAGGCCGCCGGTGGGCCATCAGTTTTCT<br>TGTTTCCGCCTAAACCAAAGGACACGCTTATGATCTCCAGGACCCCCGAAGTTACGTGTGTG<br>GTGGTTGATGTTAGTCACGAGGACCCGGAAGTCAAGTTCAACTGGTACGTTGATGGTGTAGA<br>GGTGCACAATGCAAAGACGAAGCCACGCGAAGAACAATACAACAGCACATATCGAGTTGTGA<br>GCGTACTCACGGTACTGCATCAGGACTGGCTGAACGGTAAAGAATACAAATGTAAAGTCTCC<br>AATAAGGCACTTCCTGCGCCGATAGAAAAAACGATCAGTAAGGCCAAGGGCCAACCCCGAGA<br>ACCACAGGTATATACGCTCCCACCGTCACGAGACGAGTTGACAAAAAATCAGGTCTCCCTGA<br>CTTGCCTCGTGAAAGGTTTTTATCCCTCAGATATTGCTGTTGAGTGGGAAAGCAATGGGCAG<br>CCAGAGAATAATTATAAGACGACTCCTCCGGTTTTGGATTCCGACGGTAGTTTTTTCTTGTA<br>TAGTAAGCTTACTGTAGACAAGTCAAGATGGCAACAAGGTAATGTGTTCTCTTGCTCAGTTA<br>TGCATGAAGCTCTTCATAACCATTACACGCAAAAGAGTCTCAGTCTGAGCCCCGGTGGCGGT<br>AGCGACAGTTGGCAGGAAGAGGTGATTAAGTTGTGCGGTCGCGAGCTCGTTCGGGCCCAAAT<br>TGCAATCTGCGGAAAATCTACGGGCGGAGAGGGCGGGGGTGAGGAGGGTGGGGGTGAAGGTG<br>GGCAGCTCTATAGCGCCCTTGCGAATAAATGTTGTCACGTCGGATGCACAAAGAGGTCCCTC<br>GCCAGGTTCTGC |
| 164 | ATGGAAACTGACACACTGTTGCTGTGGGTGCTGCTCCTTTGGGTACCCGGATCAACCGGGGA<br>TAAGACCCACACTTGCCCCCCTTGCCCTGCCCCCGAAGCGGCCGGAGGTCCTTCAGTATTTT<br>TGTTTCCACCGAAACCCAAAGATACTTTGATGATATCAAGAACTCCTGAAGTCACCTGCGTG<br>GTAGTTGACGTATCTCATGAGGATCCCGAGGTGAAGTTCAATTGGTACGTCGATGGCGTCGA<br>GGTTCATAACGCTAAGACTAAGCCGAGGGAAGAGCAATATAATTCCACTTATAGGGTGGTGT<br>CCGTCTTGACTGTTTTGCACCAGGATTGGTTGAACGGGAAAGAGTACAAATGTAAGGTGAGT<br>AATAAAGCTTTGGCTGCTCCCATCGAAAAGACAATAAGCAAGGCCAAGGGGCAACCTCGGGA<br>GCCGCAGGTGTACACCCTTCCTCCCAGTAGAGACGAACTGACAAAAAACCAGGTGTCCCTGA<br>CCTGCCTTGTGAAGGGGTTTTACCCGAGCGACATAGCGGTTGAATGGGAGAGCAACGGGCAA<br>CCCGAGAACAACTACAAAACTACACCGCCTGTCCTGGACTCCGATGGAAGCTTCTTCCTCTA<br>CTCCAAACTGACCGTGGACAAAAGCAGATGGCAACAAGGAAACGTATTCTCATGCTCAGTAA<br>TGCACGAAGCATTGCACAATCACTACACCCAAAAGTCCCTCTCACTCTCCCCTGGTAAGGGC<br>GGATCAGACTCATGGCAAGAGGAGGTAATTAAGTTGTGCGGGAGGGAGCTCGTCCGCGCGCA<br>AATAGCCATTTGTGGCAAGTCCACTGGAGGAGGCGAGGGTGGAGGAGAGGGTGGTGGGGAGG<br>GCAGGCAACTCTACAGTGCGCTCGCCAATAAATGCTGCCATGTTGGGTGCACGAAGCGCAGT<br>CTCGCACAATTCTGC |
| 165 | ATGGAGACCGACACTCTGCTGCTCTGGGTACTCTTGCTGTGGGTGCCTGGGTCTACTGGGGA<br>TAAGACCCACACGTGTCCTCCATGTCCGGCACCGGAGGCTGCTGGCGGGCCTTCTGTATTCC<br>TCTTCCCACCCAAGCCAAAAGACACATTGATGATATCAAGGACGCCGGAAGTCACCTGTGTT<br>GTTGTGGACGTTTCCCATGAAGACCCAGAGGTAAAATTCAATTGGTATGTGGACGGCGTAGA<br>GGTTCACAACGCCAAAACCAAACCCCGAGAGGAACAGTATAATAGCACATATCGAGTAGTAT<br>CTGTTCTCACAGTGCTCCATCAAGACTGGCTTAATGGTAAAGAGTATAAATGCAAAGTTTCC<br>AATAAAGCCCTCGCTGCACCGATCGAGAAGACAATCAGTAAAGCGAAGGGCCAGCCTCGGGA<br>ACCGCAGGTGTATACTCTTCCACCCTCAAGAGACGAGCTCACTAAAAACCAAGTTTCATTGA<br>CATGCCTCGTCAAAGGTTTCTACCCATCAGACATCGCGGTCGAATGGGAAAGTAATGGGCAG<br>CCGGAAAACAACTATAAAACGACGCCGCCCGTCTTGGATTCTGATGGTTCATTTTTTCTTTA |

TABLE 8-continued

Nucleotide Sequences Encoding Fusion Proteins and Peptide Components

| SEQ ID NO: | Sequence |
|---|---|
| | CTCTAAATTGACCGTCGATAAAAGTAGGTGGCAACAAGGAAATGTTTTTTCCTGCTCCGTCC<br>TGCATGAAGCGTTGCACAGTCACTATACCCAGAAGAGTCTTTCTTTGTCACCCGGAAAAGGC<br>GGTTCAGATTCATGGCAGGAAGAAGTAATTAAACTCTGTGGCCGCGAGCTTGTTAGGGCGCA<br>GATAGCCATATGTGGTAAAAGCACCGGAGGAGGTGAAGGCGGAGGCGAAGGAGGTGGGGAAG<br>GAAGACAATTGTATTCTGCACTTGCAAATAAATGCTGTCATGTGGGGTGCACGAAACGCAGT<br>CTTGCACAATTTTGT |
| 166 | ATGGAAACCGATACGCTGCTTCTTTGGGTTCTTCTCCTCTGGGTTCCAGGGTCCACCGGCGA<br>CAAAACCCATACCTGCCCCCCTTGCCCTGCACCAGAAGCGGCGGGAGGACCTAGCGTTTTTC<br>TTTTTCCTCCGAAACCGAAAGATACCCTCATGATATCAAGAACACCTGAGGTTACTTGCGTT<br>GTCGTGGACGTGAGTCACGAAGACCCCGAGGTGAAGTTCAACTGGTATGTAGATGGAGTGGA<br>GGTCCATAATGCAAAAACGAAACCGAGAGAAGAACAATACAACTCTACATATCGAGTCGTGT<br>CAGTACTCACGGTTTTGCATCAAGATTGGCTGAACGGTAAGGAGTACAAGTGTAAGGTTAGC<br>AACAAGGCTCTCGCGGCGCCGATAGAAAAGACTATAAGTAAAGCAAAAGGCCAGCCCAGAGA<br>ACCTCAAGTTTACACTCTGCCTCCCAGCAGAGATGAACTGACTAAAAATCAGGTTTCATTGA<br>CCTGTCTCGTCAAGGGTTTTTATCCAAGCGACATAGCAGTTGAATGGGAAAGCAACGGTCAA<br>CCAGAAAATAATTACAAAACCACTCCACCAGTCTTGGACTCTGACGGATCCTTCTTTCTCTA<br>TTCAAAATTGACGGTGGATAAATCTAGGTGGCAGCAAGGCAACGTCTTCTCTTGTAGCGTTA<br>TGCATGAGGCGCTGCACAACCACTACACACAAAAGTCTCTTAGTTTGAGCCCGGGCGGCGGA<br>AGCGACTCTTGGCAAGAGGAAGTGATAAAACTCTGTGGTCGAGAATTGGTACGCGCGCAGAT<br>CGCTATCTGCGGCAAGTCCACAGGGGGAGGGGAAGGTGGCGGGGAAGGTGGTGGCGAGGGCA<br>GGCAGTTGTATAGTGCACTTGCCAACAAGTGCTGCCATGTGGGGTGCACCAAGCGCAGTTTG<br>GCACGGTTCTGC |
| 167 | ATGGAAACGGACACCCTTCTGCTCTGGGTACTGCTGCTCTGGGTTCCTGGTTCTACCGGTGA<br>TAAAACTCACACTTGTCCCCCGTGTCCGGCACCAGAAGCCGCAGGAGGGCCATCTGTCTTTC<br>TTTTTCCCCCAAAACCCAAGGATACACTGATGATCTCCCGCACTCCCGAAGTTACTTGTGTC<br>GTAGTAGACGTTTCTCACGAGGACCCAGAGGTGAAATTCAATTGGTATGTTGACGGAGTAGA<br>GGTGCATAATGCCAAGACAAAGCCCCGAGAGGAACAATACAATTCAACCTACAGAGTAGTGT<br>CCGTTCTTACGGTTCTCCATCAGGATTGGCTCAACGGTAAGGAATATAAGTGCAAGGTAAGC<br>AACAAAGCGCTGGCCGCACCCATTGAGAAAACCATTTCAAAAGCTAAAGGCCAACCCCGCGA<br>ACCACAAGTTTATACTCTCCCCCCAAGTCGCGATGAACTTACAAAAAATCAAGTCTCATTGA<br>CGTGCTTGGTCAAAGGCTTCTACCCGAGCGATATCGCTGTTGAATGGGAGTCTAATGGACAA<br>CCGGAAAATAACTATAAAACTACACCCCCAGTCCTCGATTCAGACGGCAGCTTCTTCCTGTA<br>TTCAAAACTGACGGTTGACAAATCACGCTGGCAACAGGGTAACGTTTTTTCCTGTAGCGTTC<br>TTCATGAAGCCTTGCACAGTCACTACACCCAGAAGTCCCTTAGCTTGTCACCTGGCGGGGGT<br>TCAGACTCTTGGCAGGAGGAGGTAATCAAACTGTGCGGAAGAGAACTGGTGAGGGCTCAGAT<br>TGCAATTTGTGGGAAGAGCACGGGTGGCGGTGAAGGAGGTGGCGAGGGCGGAGGAGAGGGGA<br>GGCAACTCTACAGTGCGTTGGCTAATAAATGCTGTCACGTCGGCTGTACTAAGAGAAGCCTC<br>GCCAGATTTTGC |
| 168 | ATGGAAACAGATACTTTGTTGCTGTGGGTACTCCTCCTCTGGGTACCTGGGAGCACCGGGGA<br>CAAGACGCATACTTGCCCTCCGTGCCCTGCACCAGAAGCCGCTGGTGGCCCATCTGTGTTTT<br>TGTTCCCCCCTAAGCCAAAAGACACATTGATGATTTCACGAACTCCAGAAGTGACTTGCGTA<br>GTTGTTGACGTATCACACGAAGACCCCGAGGTTAAATTTAATTGGTATGTGGACGGGGTCGA<br>GGTGCATAACGCCAAAACCAAACCCCGGGAGGAACAATATAACTCTACGTATCGGGTCGTAT<br>CTGTGTTGACCGTCCTTCACCAAGATTGGTTGAACGGCAAGGAATATAAGTGTAAAGTGTCT<br>AATAAAGCATTGGCTGCCCCGATAGAAAAGACGATCTCTAAAGCCAAGGGCCAACCCAGAGA<br>GCCTCAAGTATATACTCTCCCACCGAGTCGAGATGAGCTCACTAAGAACCAGGTGTCACTCA<br>CGTGTCTGGTTAAAGGATTTTACCCTAGTGATATAGCCGTCGAGTGGGAATCAAATGGGCAG<br>CCGGAGAATAACTATAAGACCACGCCTCCAGTTCTCGATTCCGATGGTAGCTTTTTCCTTTA<br>CTCTAAACTTACGGTCGACAAGTCCAGGTGGCAACAGGGCAATGTATTTTCTTGCTCCGTCA<br>TGCACGAGGCTTTGCACAACCATTACACGCAAAAGTCACTGTCCCTGTCTCCTGGAGGCGGT<br>TCTGACAGTTGGCAGGAGGAGGTAATCAAATTGTGTGGGCGGGAGTTGGTTAGGGCGCAAAT<br>TGCTATTTGCGGCAAAAGTACTGGGGGCGGTGAAGGCGGAGGCGAGGGAGGAGGAGAAGGTC<br>GACAACTGTATTCTGCCTTGGCGAACAAATGCTGTCACGTCGGCTGTACGAAACGGTCTTTG<br>GCCCAGTTTTGT |
| 169 | ATGGAAACTGACACTCTTCTGTTGTGGGTCCTTCTGCTGTGGGTTCCTGGCTCTACTGGAGA<br>TAAGACACACACTTGTCCGCCATGCCCTGCGCCGGAAGCGGCGGGAGGACCGTCCGTTTTCC<br>TGTTCCCTCCCAAACCCAAAGACACGTTGATGATTAGTCGCACGCCAGAAGTTACGTGCGTT<br>GTCGTAGATGTATCCCACGAAGACCCCGAGGTGAAGTTCAATTGGTATGTAGATGGGGTGGA<br>GGTCCATAACGCTAAGACCAAACCACGCGAGGAACAATATAATTCTACGTACCGCGTAGTGA<br>GCGTTCTCACAGTTCTTCACCAGGATTGGCTTAACGGCAAGGAGTATAAGTGTAAGGTGTCT<br>AATAAGGCCTTGGCTGCCCCGATCGAAAAAACGATAAGTAAAGCAAAGGGTCAACCTAGAGA<br>ACCCCAAGTGTACACTCTCCCGCCATCACGGGATGAATTGACTAAGAACCAAGTGTCACTCA<br>CGTGTCTTGTAAAGGGCTTCTACCCATCCGATATAGCCGTTGAGTGGGAATCCAATGGTCAG<br>CCAGAGAACAACTATAAGACAACTCCGCCCGTACTTGATAGTGACGGTTCCTTTTTCCTTTA<br>CAGTAAATTGACGGTAGATAAGTCTCGCTGGCAGCAAGGAAACGTCTTTTCTTGTTCAGTGC<br>TTCATGAGGCGCTTCACTCACACTATACTCAGAAGAGTTTGAGTTTGTCTCCAGGTGGAGGC<br>AGCGACTCATGGCAAGAGGAAGTAATCAAACTGTGTGGTCGCGAATTGGTACGAGCACAGAT<br>CGCGATCTGCGGGAAATCAACAGGTGGCGGCGAAGGCGGCGGGGAAGGCGGCGGCGAAGGTA<br>GGCAACTTTACTCAGCCCTTGCGAACAAATGTTGCCACGTAGGCTGTACTAAGAGAAGTCTC<br>GCCCAGTTTTGC |

TABLE 8-continued

Nucleotide Sequences Encoding Fusion Proteins and Peptide Components

| SEQ ID NO: | Sequence |
|---|---|
| 170 | ATGGAGACAGATACCCTTCTGTTGTGGGTCCTTCTGCTTTGGGTGCCGGGAAGTACAGGCGA CAAGACTCATACCTGCCCCCCTTGTCCAGCACCAGAAGCAGCTGGCGGGCCAAGCGTGTTCC TGTTTCCACCTAAGCCCAAAGATACGTTGATGATCAGCCGCACCCCGGAAGTAACCTGTGTA GTAGTAGATGTGTCCCACGAAGACCCCGAAGTAAAGTTTAATTGGTACGTCGATGGTGTCGA AGTACATAACGCTAAAACGAAGCCCCGAGAAGAGCAGTACAACAGTACTTACAGAGTAGTTT CTGTTCTTACAGTGCTGCATCAGGATTGGCTGAACGGGAAGGAGTATAAATGTAAAGTCTCA AACAAGGCACTTGCGGCACCAATAGAGAAGACAATATCTAAGGCCAAAGGGCAGCCTAGAGA GCCACAAGTATATACGCTGCCCCCCAGCAGGGACGAGCTGACAAAGAACCAAGTGTCACTGA CCTGCCTTGTTAAGGGCTTCTATCCGAGTGATATTGCTGTTGAATGGGAAAGTAACGGACAG CCGGAGAACAACTATAAAACTACTCCACCCGTGTTGGATAGTGACGGTAGCTTTTTTCTGTA CTCCAAGTTGACGGTAGACAAAAGTCGGTGGCAGCAGGGGAACGTATTTTCTTGTTCTGTCA TGCACGAAGCTCTTCACAATCACTATACGCAGAAGTCCCTCTCTCTCTCTCCTGGGAAGGGT GGTTCCGACAGCTGGCAGGAGGAGGTCATTAAACTGTGTGGTAGAGAGCTGGTACGGGCTCA AATTGCAATTTGTGGTAAGAGTACTGGCGGTGGCGAGGAAGGGGGTGGGGAGGAGGGCGGAG GTAGGCAGCTCTACTCTGCTCTCGCCAACAAGTGTTGTCACGTCGGGTGTACTAAAAGATCA CTTGCCCGCTTTTGT |
| 171 | ATGGAAACCGATACCCTGCTCTTGTGGGTCCTCCTGCTTTGGGTCCCAGGTTCCACAGGCGA CAAAACACATACATGCCCGCCGTGTCCGGCGCCTGAAGCAGCAGGAGGCCCCAGTGTATTCC TTTTCCCTCCAAAGCCAAAAGATACGTTGATGATATCTAGGACACCTGAGGTTACCTGCGTC GTAGTGGACGTATCCCACGAAGACCCAGAAGTCAAGTTTAACTGGTATGTGGACGGAGTGGA GGTACACAATGCAAAGACAAAGCCGCGAGAGGAACAATATAATTCCACCTATAGAGTCGTGT CAGTCCTTACGGTCTTGCACCAGGACTGGCTCAATGGTAAGGAGTATAAGTGCAAAGTATCA AACAAAGCTCTCGCAGCGCCCATCGAAAAGACCATCAGCAAAGCTAAGGGCCAGCCAAGAGA GCCTCAAGTGTACACGTTGCCGCCTTCAAGGGACGAGCTCACTAAAAATCAGGTATCACTTA CGTGTCTTGTCAAAGGGTTTTATCCTTCCGACATCGCGGTTGAATGGGAGAGCAATGGACAG CCGGAGAATAATTATAAAACGACGCCGCCGGTCCTTGACAGCGATGGTTCATTTTTCCTTTA CTCAAAGCTGACGGTTGATAAGTCTAGGTGGCAGCAGGGGAACGTCTTTTCCTGTAGTGTAC TTCATGAGGCGCTCCATTCTCATTACACTCAGAAGTCACTGAGCCTTTCACCCGGCAAAGGT GGATCAGACTCCTGGCAAGAAGAGGTAATCAAACTCTGTGGGAGGGAACTCGTTCGAGCCCA GATTGCAATCTGTGGGAAAAGCACAGGCGGAGGGGAAGAAGGGGGTGGCGAAGAAGGTGGGG GCAGGCAGCTCTATTCAGCTCTTGCCAACAAATGCTGTCATGTAGGCTGCACAAAGCGATCA CTGGCGAGATTCTGT |
| 172 | ATGGAAACCGACACCCTGCTGCTCTGGGTTCTTCTCCTCTGGGTTCCCGGCTCAACCGGAGA TAAAACTCATACTTGCCCACCCTGCCCGGCTCCCGAGGCAGCAGGTGGACCCTCAGTATTTT TGTTCCCTCCGAAACCTAAAGATACACTTATGATTAGCCGGACCCCTGAGGTAACGTGTGTG GTGGTTGACGTAAGTCATGAAGATCCAGAAGTAAAGTTTAACTGGTACGTAGACGGTGTGGA GGTACATAATGCGAAGACAAAACCACGAGAGGAACAGTATAACTCTACCTACCGCGTAGTAA GCGTACTTACTGTGCTCCACCAAGACTGGCTTAACGGGAAAGAGTATAAGTGTAAAGTCAGT AATAAAGCACTGGCCGCCCCGATCGAAAAAACAATCAGCAAGGCCAAAGGACAACCAAGGGA GCCTCAGGTCTATACTCTTCCCCCGAGTAGGGATGAGCTTACCAAGAACCAGGTGTCTCTGA CATGCCTTGTCAAGGGATTTTACCCGAGTGACATAGCCGTAGAATGGGAGTCAAACGGCCAA CCTGAAAACAACTATAAGACCACGCCTCCCGTACTCGACTCAGATGGAAGCTTTTTCCTCTA TAGCAAGCTGACCGTCGACAAAAGTAGGTGGCAACAGGGAAACGTCTTTAGTTGTTCCGTCA TGCACGAAGCTTTGCATAACCATTACACCCAGAAGAGTCTTTCCCTTTCCCCTGGCAAGGGG GGCTCCGACTCCTGGCAAGAGGAAGTAATCAAACTGTGTGGGCGCGAGCTTGTCCGCGCGCA AATAGCCATTTGCGGAAAAAGTACTGGAGGAGGAGAGGAAGGCGGCGGCGAGGAAGGTGGGG GCAGGCAGCTGTACAGTGCCTTGGCTAACAAGTGCTGCCATGTCGGCTGTACGAAAAGGTCT CTTGCTCAATTCTGT |
| 173 | ATGGAAACTGATACTCTTCTCCTTTGGGTGCTCCTCCTCTGGGTTCCCGGGTCCACAGGCGA TAAGACACATACCTGTCCACCCTGCCCAGCACCTGAAGCTGCAGGCGGCCCCAGCGTATTCC TGTTTCCTCCGAAGCCGAAAGACACACTTATGATTTCCCGGACGCCTGAGGTAACTTGCGTC GTAGTAGATGTGTCTCACGAAGACCCCGAGGTGAAATTCAACTGGTACGTTGATGGTGTGGA AGTTCATAATGCGAAAACTAAACCACGAGAGGAGCAATATAACTCAACTTATAGAGTTGTGA GCGTCTTGACGGTACTGCACCAGGACTGGCTGAATGGCAAAGAGTACAAATGCAAAGTCTCA AATAAGGCGTTGGCGGCTCCCATAGAGAAAACTATCAGCAAAGCCAAGGGTCAACCTCGGGA GCCACAAGTGTATACTCTTCCGCCTAGTCGCGACGAGCTCACAAAGAATCAGGTGAGTCTTA CTTGTTTGGTTAAGGGTTTCTACCCCAGTGACATTGCGGTCGAGTGGGAAAGTAACGGACAG CCTGAAAACAACTATAAAACAACGCCTCCAGTACTCGATTCAGATGGTTCATTCTTTCTTTA TTCCAAACTCACAGTCGACAAGAGTAGATGGCAACAAGGGAACGTGTTTAGCTGTAGCGTAC TCCATGAGGCACTCCACTCTCACTATACCCAAAAGTCTCTCAGCTTGTCACCCGGAAAAGGC GGTTCTGACAGTTGGCAAGAGGAAGTGATTAAATTGTGTGGGCGGGAACTTGTGAGGGCTCA AATCGCGATTTGCGGCAAGTCCACTGGTGGCGGCGAGGAAGGAGGAGGTGAAGAAGGAGGAG GTAGGCAACTGTATTCAGCGTTGGCGAATAAATGCTGCCATGTTGGATGTACTAAACGGAGC CTTGCTCAGTTCTGC |
| 174 | ATGGAAACTGACACCTTGTTGCTTTGGGTATTGCTTCTGTGGGTTCCGGGTAGCACGGGTGA TAAAACGCATACTTGCCCTCCTTGCCCGGCACCTGAAGCTGCCGGAGGTCCTTCCGTGTTCC TGTTCCCACCTAAGCCAAAAGACACACTTATGATTTCTCGCACACCAGAAGTAACGTGCGTC GTAGTTGACGTCTCCCATGAAGACCCGGAGGTAAAATTTAATTGGTACGTCGACGGGGTAGA AGTTCATAACGCAAAGACTAAACCACGAGAAGAGCAATACAACTCTACATACAGAGTAGTAA GCGTTCTCACCGTTCTTCATCAAGATTGGCTCAACGGAAAGGAGTATAAGTGTAAGGTGTCC AATAAAGCGTTGGCCGCACCAATCGAAAAGACCATAAGCAAAGCCAAAGGCCAACCCCGCGA |

TABLE 8-continued

Nucleotide Sequences Encoding Fusion Proteins and Peptide Components

| SEQ ID NO: | Sequence |
|---|---|
| | ACCGCAGGTGTACACACTTCCCCCGTCCAGGGATGAATTGACAAAAAACCAAGTTTCCCTCA<br>CGTGTCTCGTCAAGGGATTCTACCCGAGTGATATCGCAGTTGAATGGGAAAGCAATGGTCAG<br>CCCGAGAATAACTACAAGACTACTCCCCCTGTGTTGGACTCAGACGGCTCATTCTTCCTCTA<br>CAGTAAGTTGACTGTGGACAAAAGTCGGTGGCAGCAAGGCAATGTCTTCAGTTGTAGTGTAA<br>TGCATGAAGCACTCCACAATCATTACACCCAAAAATCCCTGAGCCTGTCCCCGGGCGGAGGT<br>TCAGATTCATGGCAGGAGGAAGTTATAAAACTGTGCGGGCGCGAGTTGGTGAGGGCGCAGAT<br>CGCAATCTGTGGAAAGAGTACGGGAGGTGGCGAAGAGGGTGGTGGAGAAGAGGGAGGAGGTC<br>GACAACTGTATTCCGCGCTCGCGAACAAGTGTTGCCACGTTGGCTGCACCAAACGAAGCCTG<br>GCTCGATTTTGC |
| 175 | ATGGAGACTGACACCCTTCTCCTCTGGGTCCTCTTGCTTTGGGTCCCTGGCTCTACTGGTGA<br>CAAGACACACACTTGTCCACCTTGCCCGGCTCCCGAGGCGGCAGGAGGACCAAGCGTTTTTC<br>TGTTCCCTCCCAAACCAAAGGATACGCTTATGATCTCTCGAACGCCGGAAGTTACTTGCGTA<br>GTAGTTGATGTCTCCCATGAAGATCCCGAAGTGAAGTTCAACTGGTATGTAGATGGTGTGGA<br>AGTTCATAACGCGAAAACCAAACCACGCGAAGAACAGTATAACAGTACTTATCGGGTTGTTT<br>CAGTACTCACGGTGCTCCATCAAGACTGGCTTAATGGAAAGGAGTATAAATGTAAGGTAAGT<br>AACAAGGCATTGGCGGCTCCCATCGAGAAGACAATCTCCAAAGCAAAAGGGCAACCACGGGA<br>GCCTCAGGTGTATACGTTGCCGCCCAGCAGAGATGAACTTACTAAGAATCAGGTGAGTCTCA<br>CTTGTCTCGTCAAGGGCTTCTATCCCAGCGATATAGCCGTAGAATGGGAGAGTAACGGTCAG<br>CCGGAGAACAACTACAAAACAACCCCGCCTGTTTTGGACTCCGATGGGAGTTTTTTTCTCTA<br>CAGCAAACTCACGGTAGACAAAAGCAGGTGGCAGCAGGGCAATGTTTTCAGTTGCTCTGTTC<br>TCCACGAAGCCCTCCACTCCCACTATACTCAGAAGTCTCTGAGTCTCTCACCAGGGGGAGGT<br>AGCGATAGCTGGCAGGAGGAAGTGATCAAGTTGTGCGGGCGCGAACTCGTGCGGGCACAAAT<br>TGCTATATGCGGTAAAAGTACGGGAGGTGGAGAGGAGGGTGGAGGTGAAGAAGGCGGTGGTA<br>GACAATTGTATAGTGCGCTCGCCAACAAGTGTTGTCATGTCGGGTGTACGAAACGGTCCTTG<br>GCGCGGTTTTGC |
| 176 | ATGGAAACTGACACACTTCTTCTGTGGGTACTCTTGTTGTGGGTTCCGGGCTCAACGGGTGA<br>CAAGACACATACTTGTCCACCATGTCCCGCCCCAGAAGCTGCGGGAGGACCATCAGTTTTTT<br>TGTTCCCCCCGAAACCGAAGGATACCCTCATGATAAGTCGAACGCCCGAAGTCACTTGCGTG<br>GTGGTTGATGTTAGCCACGAGGACCCAGAAGTGAAGTTCAACTGGTACGTGGACGGGGTCGA<br>AGTTCATAATGCGAAAACAAAGCCTCGCGAGGAACAGTACAACTCTACATACAGGGTTGTGT<br>CTGTTTTGACAGTCTTGCACCAAGATTGGCTCAACGGGAAGGAATATAAGTGTAAGGTAAGC<br>AATAAAGCACTGGCGGCCCCGATCGAAAAAACGATATCCAAGGCCAAGGGCCAGCCCCGAGA<br>GCCTCAGGTATATACTCTGCCGCCAAGCCGGGATGAACTGACTAAAAACCAGGTCTCTTTGA<br>CTTGTCTTGTCAAGGGATTTTACCCAAGTGACATTGCGGTAGAGTGGGAAAGCAACGGTCAA<br>CCAGAAAACAATTACAAGACGACACCGCCGGTACTCGACTCAGATGGATCCTTTTTCCTGTA<br>TAGCAAGCTGACAGTGGACAAGTCCCGGTGGCAGCAAGGGAACGTATTTTCATGCAGCGTGA<br>TGCATGAGGCTCTTCACAACCATTACACACAGAAAAGTCTGTCATTGAGCCCTGGCGGCGGG<br>AGCGATTCTTGGCAAGAAGAAGTTATAAAACTTTGCGGTCGAGAGCTGGTTCGGGCACAAAT<br>TGCTATCTGCGGAAAATCTACAGGAGGAGGCGAGGAGGGAGGGGGCGAAGAAGGCGGGGGGA<br>GACAGTTGTACAGTGCGCTCGCTAACAAGTGTTGCCACGTCGGTTGCACAAAGAGATCCCTG<br>GCTCAATTCTGT |
| 177 | ATGGAGACAGATACTCTCTTGCTGTGGGTGCTGCTCTTGTGGGTTCCTGGAAGTACCGGTGA<br>TAAAACTCACACCTGTCCCCCGTGTCCCGCACCAGAAGCGGCCGGTGGTCCCTCCGTTTTTC<br>TCTTCCCTCCTAAACCTAAGGACACACTTATGATTAGCAGAACTCCAGAAGTTACGTGCGTA<br>GTCGTTGACGTTAGTCATGAAGATCCTGAGGTTAAGTTCAACTGGTACGTAGACGGAGTAGA<br>GGTCCACAACGCCAAGACGAAACCCCGAGAAGAGCAGTATAATTCTACCTATCGAGTTGTTT<br>CAGTATTGACGGTGCTTCACCAAGATTGGCTGAATGGCAAAGAGTATAAGTGCAAGGTAAGC<br>AACAAAGCACTCGCGGCTCCTATCGAGAAAACTATTTCCAAAGCTAAGGGCCAGCCTCGCGA<br>ACCACAAGTCTATACCCTGCCACCGAGTCGGGACGAACTCACCAAGAACCAAGTGTCTCTTA<br>CTTGCCTCGTTAAAGGTTTTTATCCCAGCGACATAGCCGTCGAATGGGAGTCCAATGGCCAA<br>CCTGAGAACAACTATAAAACTACCCCTCCTGTACTTGATAGCGACGGAAGTTTTTTCCTCTA<br>TTCAAAACTCACAGTTGATAAGTCTCGATGGCAACAGGGCAACGTCTTCTCTTGCAGTGTGT<br>TGCATGAAGCTCTGCACTCTCATTACACACAGAAGAGTTTGTCTCTCAGTCCAGGTGGCGGC<br>TCAGATAGCTGGCAGGAAGAAGTAATCAAGTTGTGCGGCAGGGAACTGGTAAGGGCACAGAT<br>AGCCATTTGTGGAAAATCTACGGGTGGCGGTGAGGAAGGCGGCGGAGAAGAAGGGGGAGGTC<br>GGCAGCTGTATAGTGCACTCGCAAACAAGTGCTGCCATGTCGGGTGCACCAAGCGATCCCTT<br>GCCCAGTTTTGC |
| 178 | ATGGAAACTGATACGCTCCTCCTTTGGGTTCTTCTCCTCTGGGTACCCGGAAGCACTGGTGA<br>CAAAACGCACACCTGTCCACCGTGTCCTGCTCCAGAGGCGGCCGGGGGACCGTCCGTTTTCC<br>TTTTTCCTCCCAAACCTAAGGATACCCTTATGATCTCTCGCACGCCCGAGGTTACCTGTGTT<br>GTGGTTGACGTGTCCCATGAAGACCCGGAAGTAAAATTTAATTGGTACGTGGACGGGGTCGA<br>GGTTCATAACGCAAAGACCAAGCCACGAGAGGAGCAATATAATTCCACCTATCGCGTAGTCT<br>CCGTCCTCACCGTGCTTCACCAGGATTGGCTCAACGGGAAGGAATACAAATGTAAAGTCAGT<br>AATAAGGCTTTGGCGGCCCCGATTGAGAAGACTATAAGTAAGGCTAAGGGACAGCCACGAGA<br>ACCGCAAGTTTATACATTGCCCCCCTCTAGGGATGAGTTGACTAAGAATCAGGTGTCACTCA<br>CTTGTCTGGTAAAAGGGTTCTACCCGTCCGACATCGCTGTGGAATGGGAAAGCAATGGGCAA<br>CCTGAAAATAATTATAAGACAACCCCTCCGGTGCTTGATAGCGACGGATCATTCTTTCTCTA<br>TTCCAAGCTTACTGTAGATAAGAGTCGATGGCAACAGGGGAACGTATTCAGTTGCTCTGTTC<br>TCCATGAGGCCCTGCATAGTCACTACACCCAAAAAAGCCTTAGTTTGAGTCCCGGGAAAGGA |

TABLE 8-continued

Nucleotide Sequences Encoding Fusion Proteins and Peptide Components

| SEQ ID NO: | Sequence |
|---|---|
| | GGCTCCGATTCTTGGCAAGAAGAGGTAATAAAGCTGTGTGGACGAGAACTTGTCCGAGCACA<br>AATTGCGATTTGTGGCAAATCTACAGGAGGGGGAGAAGGAGGCGGCGAAGGGGGAGGCGAGG<br>GCAGGCAGGATTATTCCGCTCTGGCGAACAAATGTTGCCATGTTGGATGCACGAAACGAAGC<br>CTGGCTCAGTTTTGC |
| 179 | ATGGAAACCGACACCCTCCTCCTTTGGGTACTTCTTCTCTGGGTTCCGGGTAGTACAGGAGA<br>TAAAACGCATACCTGCCCACCGTGTCCTGCACCTGAGGCCGCTGGAGGACCTTCCGTCTTCC<br>TCTTTCCACCCAAGCCGAAAGACACACTCATGATTAGTAGAACTCCAGAGGTCACGTGTGTT<br>GTGGTGGACGTCAGTCACGAGGACCCTGAGGTTAAGTTCAACTGGTACGTTGATGGCGTAGA<br>AGTCCACAATGCAAAGACCAAACCGAGAGAGGAGCAATATAACAGTACATATAGGGTTGTTA<br>GCGTACTTACTGTTTTGCATCAAGACTGGTTGAATGGGAAGGAATATAAATGTAAAGTCTCC<br>AACAAGGCTCTGGCTGCACCAATAGAAAAAACTATTTCTAAGGCAAAGGGTCAGCCTAGAGA<br>GCCTCAAGTCTATACCTTGCCACCGTCAAGAGACGAGCTCACTAAAAATCAGGTGAGCCTGA<br>CCTGTCTTGTGAAGGGCTTTTACCCGTCAGATATTGCCGTGGAGTGGGAATCAAACGGTCAG<br>CCGGAGAATAACTACAAGACGACCCCACCAGTACTCGATAGCGATGGGTCTTTCTTTCTGTA<br>CTCCAAGCTCACCGTGGACAAATCACGCTGGCAACAGGGCAACGTCTTTAGTTGCAGCGTAC<br>TGCACGAGGCACTGCACAGCCACTACACACAAAAGAGTCTTTCTCTGTCTCCCGGTGGTGGC<br>TCCGATAGTTGGCAGGAAGAAGTCATAAAGCTTTGTGGAAGAGAGCTTGTACGAGCGCAGAT<br>TGCAATCTGCGGGAAGAGCACTGGAGGAGGTGAGGGAGGGGGTGAGGGCGGGGGCGAAGGAC<br>GCCAGGACTATTCAGCACTTGCAAACAAATGCTGCCATGTAGGGTGTACGAAGCGCTCACTG<br>GCCCGGTTTTGC |
| 180 | ATGGAGACCGACACTTTGCTGCTTTGGGTGTTGCTGCTGTGGGTCCCCGGTAGTACGGGAGA<br>TAAAACACATACCTGCCCCCCATGCCCAGCCCCCGAAGCTGCAGGGGGGCCCTCTGTTTTCC<br>TTTTTCCACCCAAACCTAAAGATACTCTGATGATTAGTCGGACTCCGGAAGTGACTTGCGTC<br>GTTGTCGACGTCTCTCATGAGGATCCAGAAGTTAAGTTTAACTGGTATGTCGACGGGGTTGA<br>GGTTCATAATGCAAAAACTAAACCGAGAGAAGAACAGTACAACTCTACTTATAGGGTTGTCA<br>GTGTACTGACCGTCCTGCACCAGGATTGGCTTAACGGTAAGGAGTATAAGTGTAAAGTGTCC<br>AATAAAGCCCTTGCCGCACCCATCGAGAAAACCATCTCCAAGGCAAAAGGACAGCCAAGGGA<br>ACCGCAGGTATATACACTTCCGCCAAGCCGAGACGAACTTACGAAGAACCAGGTGTCTCTCA<br>CGTGTCTCGTAAAAGGGTTTTATCCCAGCGATATCGCAGTTGAGTGGGAGAGCAATGGGCAG<br>CCAGAGAATAATTATAAGACAACCCCTCCCGTGCTGGATTCAGACGGGAGTTTTTTTCTTTA<br>CTCTAAGCTGACCGTAGACAAAAGTCGATGGCAGCAAGGCAACGTCTTTTCCTGCTCCGTTC<br>TCCATGAAGCACTGCATAGCCATTATACCCAGAAGTCACTGAGCCTCTCTCCAGGGGGCGGG<br>TCCGATTCATGGCAGGAAGAGGTAATCAAACTCTGTGGACGCGAACTGGTTCGCGCGCAGAT<br>AGCGATTTGCGGCAAAAGCACAGGCGGTGGGGAAGGCGGTGGCGAGGGCGGTGGTGAAGGTC<br>GACAAGATTATTCTGCTCTCGCTAACAAGTGTTGTCATGTAGGATGTACTAAAAGGAGTCTT<br>GCGCAGTTCTGT |
| 181 | ATGGAGACGGACACTCTTCTCCTGTGGGTTCTCCTCTTGTGGGTTCCAGGATCTACCGGCGA<br>TAAGACGCACACATGCCCACCCTGTCCTGCGCCTGAAGCCGCGGGGGGACCCAGCGTTTTTC<br>TCTTCCCGCCGAAACCGAAAGACACACTTATGATCAGCCGGACTCCCGAGGTTACCTGCGTG<br>GTGGTAGATGTATCTCACGAGGATCCCGAGGTCAAATTCAACTGGTACGTTGATGGGGTTGA<br>AGTTCATAATGCCAAAACGAAGCCAAGAGAAGAGCAGTATAACTCCACATATAGAGTTGTTT<br>CCGTCTTGACTGTTCTTCACCAAGATTGGCTGAATGGGAAGGAGTACAAATGTAAAGTTAGC<br>AACAAGGCACTCGCCGCTCCCATTGAAAAAACTATAAGCAAAGCTAAGGGCCAACCGCGCGA<br>ACCACAGGTCTACACGTTGCCGCCCTCTAGGGACGAACTCACGAAGAATCAGGTTTCCCTTA<br>CCTGCCTCGTTAAAGGATTCTACCCCTCTGACATAGCGGTTGAATGGGAGAGCAACGGTCAG<br>CCTGAGAACAACTACAAAACGACGCCTCCGGTGTTGGATTCCGACGGTAGTTTTTTCCTCTA<br>TAGTAAGCTGACAGTGGATAAATCTCGGTGGCAGCAAGGGAATGTATTCTCCTGTTCAGTCC<br>TGCATGAAGCCCTCCACTCCCATTATACACAGAAATCTCTTTCTCTGAGTCCCGGTAAAGGT<br>GGGAGTGACTCTTGGCAGGAAGAGGTAATTAAGTTGTGTGGAAGGGAGCTGGTAAGAGCACA<br>GATTGCCATCTGTGGCAAATCCACGGGCGGCGAAGGTGAGGGGGGTGAGGGGGAAGGGGGGT<br>CCAGACAACTGTATTCTGCTCTGGCGAATAAGTGTTGCCATGTAGGGTGCACTAAACGGTCC<br>TTGGCGCAGTTCTGT |
| 182 | ATGGAGACTGACACACTGCTCCTCTGGGTCCTTTTGCTCTGGGTTCCGGGGTCCACCGGTGA<br>TAAAACTCATACGTGCCCACCTTGCCCCGCACCGGAGGCTGCTGGAGGACCCTCTGTCTTCC<br>TGTTCCCGCCGAAGCCTAAAGACACATTGATGATCAGTCGAACACCGGAAGTCACCTGTGTA<br>GTGGTTGATGTGAGCCATGAGGACCCTGAAGTAAAATTTAACTGGTATGTTGATGGCGTAGA<br>AGTACACAACGCGAAGACTAAACCAAGGGAAGAGCAATACAACTCTACCTATAGGGTCGTTA<br>GCGTACTGACTGTGCTTCACCAAGACTGGCTTAACGGGAAGGAGTACAAGTGCAAAGTGAGC<br>AATAAGGCCCTCGCCGCGCCTATCGAGAAAACCATTTCCAAAGCCAAGGGTCAACCAAGGGA<br>GCCTCAGGTTTACACCCTGCCCCCTTCAAGGGATGAGTTGACAAAAAACCAGGTAAGTCTGA<br>CGTGTCTCGTTAAGGGATTCTACCCGTCAGATATCGCGGTAGAGTGGGAGAGCAACGGTCAG<br>CCAGAAAATAATTACAAAACAACACCTCCAGTTTTGGACTCTGATGGGAGTTTTTTTCTTTA<br>TTCTAAGTTGACAGTGGATAAGTCACGCTGGCAACAGGGGAACGTATTTAGCTGCTCAGTAC<br>TTCATGAAGCGTTGCATTCTCACTACACACAGAAGAGCCTCTCCTTGAGTCCCGGAGGTGGC<br>TCTGATTCTTGGCAGGAGGAGGTAATAAAACTTTGTGGTAGAGAACTGGTTCGCGCTCAGAT<br>AGCTATTTGTGGAAAATCCACTGGCGGTGAAGGTGAAGGTGGAGAAGGAGAGGGCGGAAGCC<br>GGCAGTTGTACTCTGCCCTGGCTAATAAGTGCTGTCACGTGGGCTGCACTAAGCGGAGCTTG<br>GCAAGATTTTGC |
| 183 | ATGGAAACCGACACGCTGCTGCTGTGGGTGCTGTTGTTGTGGGTTCCAGGCTCAACTGGCGA<br>TAAAACTCATACCTGTCCACCTTGTCCTGCGCCTGAGGCAGCTGGAGGGCCTAGCGTGTTCC |

TABLE 8-continued

Nucleotide Sequences Encoding Fusion Proteins and Peptide Components

| SEQ ID NO: | Sequence |
|---|---|
| | TGTTCCCCCCCAAACCCAAAGACACGCTCATGATTAGCCGAACCCCTGAAGTGACCTGCGTT<br>GTTGTGGACGTAAGCCACGAAGACCCCGAAGTTAAGTTTAATTGGTACGTCGACGGTGTTGA<br>GGTTCATAACGCGAAGACTAAGCCGAGAGAGGAGCAATATAACAGCACCTACCGCGTAGTCT<br>CAGTTCTTACCGTGCTCCACCAGGACTGGCTTAACGGGAAGGAATACAAATGCAAAGTTTCC<br>AACAAAGCCTTGGCAGCCCCAATAGAGAAGACAATATCTAAGGCGAAAGGCCAACCGCGGGA<br>ACCGCAAGTTTATACCCTCCCACCGAGCAGGGATGAGCTGACAAAAAATCAGGTTTCCCTCA<br>CTTGTCTGGTCAAGGGATTTTATCCTTCAGACATAGCCGTTGAATGGGAGAGTAATGGGCAG<br>CCGGAGAATAATTACAAGACCACCCCCCCGGTGTTGGACAGCGACGGTTCCTTCTTTCTCTA<br>TTCTAAACTTACCGTCGACAAATCACGGTGGCAACAAGGAAATGTATTCTCATGCAGTGTAT<br>TGCACGAAGCTCTGCACTCTCATTACACCCAAAAATCCCTCTCTCTCAGCCCTGGCGGTGGA<br>TCTGATTCTTGGCAGGAAGAGGTGATTAAACTGTGTGGGCGAGAGCTTGTCCGAGCTCAGAT<br>CGCTATTTGTGGCAAGAGTACCGGAGGCGAGGGTGAGGGAGGCGAAGGCGAGGGCGGAAGCC<br>GGCAACTCTATAGCGCACTCGCTAATAAATGTTGTCATGTCGGCTGCACGAAGCGCTCACTG<br>GCGCAGTTCTGC |
| 184 | ATGGAGACGGACACACTGCTCTTGTGGGTACTGCTCCTTTGGGTGCCAGGAAGTACAGGAGA<br>CAAAACGCATACCTGTCCTCCATGCCCCGCTCCCGAGGCTGCCGGCGGACCAAGCGTATTTC<br>TCTTCCCCCCTAAACCTAAAGACACATTGATGATAAGTAGGACGCCTGAAGTAACGTGTGTT<br>GTCGTTGATGTAAGCCATGAAGATCCTGAAGTAAAGTTTAATTGGTATGTTGATGGCGTAGA<br>AGTACATAACGCTAAGACGAAGCCACGGGAAGAGCAGTATAACTCAACTTACCGCGTTGTAA<br>GCGTGCTTACCGTCCTGCATCAGGATTGGCTGAATGGTAAGGAATATAAGTGCAAAGTAAGC<br>AACAAAGCATTGGCCGCACCAATAGAGAAGACGATTAGTAAAGCAAAAGGCCAGCCCAGAGA<br>GCCGCAGGTTTATACACTTCCACCAAGCAGAGATGAACTTACGAAGAACCAGGTGTCTCTGA<br>CTTGTCTGGTCAAGGGTTTCTATCCTTCCGACATTGCAGTGGAGTGGGAAAGCAATGGGCAG<br>CCCGAAAACAATTATAAGACGACACCTCCAGTGTTGGACTCAGACGGTTCCTTTTTCTTGTA<br>TTCCAAACTTACAGTGGATAAGTCAAGGTGGCAGCAAGGCAACGTATTTTCTTGTAGTGTTT<br>TGCACGAAGCCCTGCATTCCCACTATACTCAAAAGAGCCTCAGTCTGTCCCCAGGAAAGGGA<br>GGGAGTGACAGTTGGCAAGAGGAGGTAATAAAATTGTGTGGCAGAGAGCTTGTGCGCGCTCA<br>GATCGCAATATGCGGGAAATCTACTGGGGGTGAGGGTGAGGGCGGCGAGGGAGAGGGGGGCA<br>GTCGCCAAGATTATTCCGCCCTTGCGAATAAGTGTTGTCACGTCGGATGTACTAAGAGATCA<br>TTGGCTCAGTTTTGT |

In some embodiments, any of the nucleotide sequences shown in Table 8 further comprise additional nucleotide sequence on their 5' and/or 3' ends. In some embodiments, any of the nucleotide sequences shown in Table 8 further comprise the nucleotide sequence ACGGGACC-GATCCAGCCTCCGGACTCTAGAGCCACC (SEQ ID NO: 185) on their 5' ends and/or any of the nucleotide sequences shown in Table 8 further comprise the nucleotide sequence TGATAAACCGGTTAGTAATGAGTTTGA-TATCTCGAC (SEQ ID NO: 186) on their 3' ends.

Pharmaceutical Compositions

The present disclosure provides pharmaceutical compositions comprising the fusion proteins or component peptides described herein or the nucleic acid molecules, or the expression vectors that encode them. The pharmaceutical compositions described herein are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also, Powell et al., "Compendium of excipients for parenteral formulations" PDA (1998) *J Pharm Sci Technol* 52:238-311.

The dose of the fusion proteins or component peptides described herein or the nucleic acid molecules, or the expression vectors that encode them administered to a patient may vary depending upon the age and the size of the patient, target disease, conditions, route of administration, and the like. The preferred dose is typically calculated according to body weight or body surface area. Depending on the severity of the condition, the frequency and the duration of the treatment can be adjusted. Effective dosages and schedules for administering the fusion proteins or component peptides described herein or the nucleic acid molecules, or the expression vectors that encode them may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition disclosed herein, e.g., encapsulation in liposomes, microparticles, microcapsules, recombinant cells capable of expressing the mutant viruses, receptor mediated endocytosis (see, e.g., Wu et al., 1987, *J. Biol. Chem.* 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

Any pharmaceutical composition described herein can be delivered subcutaneously or intravenously with a standard needle and syringe. In addition, with respect to subcutaneous delivery, a pen delivery device readily has applications in delivering a pharmaceutical composition disclosed herein.

Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used (see, Langer, supra; Sefton, 1987, *CRC Crit. Ref Biomed.* Eng. 14:201). In another embodiment, polymeric materials can be used; see, *Medical Applications of Controlled Release*, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in *Medical Applications of Controlled Release*, supra, vol. 2, pp. 115-138). Other controlled release systems are discussed in the review by Langer, 1990, *Science* 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending, or emulsifying any of the fusion proteins described herein in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid fusion protein contained is generally about 5 to about 500 mg per dosage form in a unit dose; especially in the form of injection, it is preferred that the aforesaid fusion protein is contained in about 5 to about 100 mg and in about 10 to about 250 mg for the other dosage forms.

Therapeutic Uses

Monotherapy

The present disclosure provides methods comprising administering to a subject in need thereof a therapeutic composition comprising the fusion proteins or component peptides described herein or the nucleic acid molecules, or the expression vectors that encode them. The therapeutic composition can comprise any of the fusion proteins or component peptides as disclosed herein and a pharmaceutically acceptable carrier or diluent. As used herein, the expression "a subject in need thereof" means a human or non-human animal that exhibits one or more symptoms or indicia of a relaxin-2 associated disorder or disease, or who otherwise would benefit an increase or decrease in relaxin-2 activity. The fusion proteins or component peptides described herein and the expression vectors that encode them (and therapeutic compositions comprising the same) are useful, inter alia, for treating any disease or disorder in which activation or deactivation of RXFP1 is beneficial.

In certain embodiments, the present disclosure provides methods for activating RXFP1 on a cell surface, comprising administering an effective amount of the fusion proteins or component peptides described herein or the nucleic acid molecules, or the expression vectors that encode them to a subject in need thereof, thereby activating RXFP1 on the surface of the cell. Activation of RXFP1 on the cell surface can lead to cellular responses, including but not limited to, the elevation of cAMP levels, vasodilation, the expression of angiogenic factors, including VEGF, the expression of MMPs, and collagen degradation. In some embodiments, the cell is selected from the group consisting of endothelial cells, vascular smooth muscle cells, other vascular cells, cardiomyocytes, other cardiac cells, and fibroblasts.

This disclosure also provides methods for treating various relaxin-2 associated diseases. As used herein, the term "relaxin-2-associated disease," is a disease or disorder that is caused by, or associated with, relaxin-2 protein production or relaxin-2 protein activity. The term "relaxin-2-associated disease" includes a disease, disorder or condition that would benefit from an increase in relaxin-2 protein activity. Non-limiting examples of relaxin-2-associated diseases include, for example, kidney diseases, including but not limited to, focal segmental glomerular sclerosis (FSGS), diabetic nephropathy, hepatorenal syndrome; fibrotic diseases, including but not limited to, scleroderma, idiopathic pulmonary fibrosis, renal fibrosis, cardiac fibrosis, NASH; cardiovascular diseases, including dilated cardiomyopathy, diastolic heart failure, pulmonary arterial hypertension, chronic heart failure, acute heart failure, congestive heart failure, coronary artery disease, hypertension, pre-eclampsia. Further details regarding signs and symptoms of the various diseases or conditions are provided herein and are well known in the art.

Administration of the compositions according to the methods described herein may result in a reduction of the severity, signs, symptoms, or markers of a relaxin-2-associated disease or disorder in a patient with a relaxin-2-associated disease or disorder. By "reduction" in this context is meant a statistically significant decrease in such level. The reduction (absolute reduction or reduction of the difference between the elevated level in the subject and a normal level) can be, for example, at least about 20%, 25%, 30%, 35%, 40%, 45%, 50%, 55%, 60%, 65%, 70%, 75%, 80%, 85%, 90%, or 95%, or to below the level of detection of the assay used.

Combination Therapies and Formulations

The present disclosure also provides compositions and therapeutic formulations comprising the fusion proteins or component peptides described herein or the nucleic acid molecules, or the expression vectors that encode them in combination with one or more additional therapeutically active components, and methods of treatment comprising administering such combinations to subjects in need thereof.

Exemplary additional therapeutic agents include any therapeutic agents that may be used for the treatment of any relaxin-2-related disorders described herein. Exemplary additional therapeutic agents that may be combined with or administered in combination with the fusion proteins or component peptides described herein or the nucleic acid molecules, or the expression vectors that encode them include, but are not limited to, angiotensin II receptor blockers, e.g., azilsartan, candesartan, eprosartan, losartan, ACE inhibitors, e.g., lisinopril, benazepril, captopril, enalapril, moexipril, perindopril, quinapril, trandolapril, calcium channel blockers, e.g., amlodipine, amlodipine and benazepril, amlodipine and valsartan, diltiazem, felodipine, isradipine, nicardipine, nimodipine, nisoldipine, verapamil, or diuretics, e.g., chlorthalidone, hydrochlorothiazide, metolazone, indapamide, torsemide, furosemide, bumetanide, amiloride, triamterene, spironolactone, eplerenone, aldosterone antagonist, e.g., spironolactone, eplerenone, digoxin, e.g., lanoxin, beta blockers, e.g., carvedilol, metoprolol, bisoprolol.

In some embodiments, the additional therapeutic agents are drugs effective in treating fibrosis, including but not limited to, small molecule drugs and antibodies. Exemplary anti-fibrosis drugs include, but are not limited to, TGF-β inhibitors, e.g., small molecules such as hydronidone, distiertide, or antibodies such as fresolimumab, PDGF or VEGF antagonist, e.g., small molecules such as imatinib, nilotinib, or any drugs that target extracellular factors that are involved in the pathogenesis of fibrosis. The description of exemplary drugs for fibrosis can be found, e.g., Li et al., "Drugs and Targets in Fibrosis, Frontiers in Pharm." 8: Article 855 (2007), incorporated herein by reference.

The additional therapeutically active component(s) may be administered just prior to, concurrent with, or shortly after the administration of the fusion proteins or component peptides described herein or the nucleic acid molecules, or the expression vectors that encode them.

The present disclosure provides pharmaceutical compositions in which the fusion proteins or component peptides described herein or the nucleic acid molecules, or the expression vectors that encode them is co-formulated with one or more of the additional therapeutically active component(s) as described elsewhere herein.

Administration Regimens

In some embodiments, multiple doses of the fusion proteins or component peptides described herein or the nucleic acid molecules, or the expression vectors that encode them may be administered to a subject over a defined time course. The methods according to this aspect of the disclosure comprise sequentially administering to a subject multiple doses of the fusion proteins or component peptides described herein or the nucleic acid molecules, or the expression vectors that encode them. As used herein, "sequentially administering" means that each dose of the fusion proteins or component peptides described herein or the nucleic acid molecules, or the expression vectors that encode them is administered to the subject at a different point in time, e.g., on different days separated by a predetermined interval (e.g., hours, days, weeks, or months). The present disclosure provides methods which comprise sequentially administering to the patient a single initial dose of a fusion proteins or component peptides described herein or the nucleic acid molecules, or the expression vectors that encode them, followed by one or more secondary doses of the fusion proteins or component peptides described herein or the nucleic acid molecules, or the expression vectors that encode them, and optionally followed by one or more tertiary doses of the fusion proteins or component peptides described herein or the nucleic acid molecules, or the expression vectors that encode them.

The terms "initial dose," "secondary doses," and "tertiary doses," refer to the temporal sequence of administration of the fusion proteins or component peptides described herein or the nucleic acid molecules, or the expression vectors that encode them. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the fusion proteins or component peptides described herein or the nucleic acid molecules, or the expression vectors that encode them, but generally may differ from one another in terms of frequency of administration. In certain embodiments, however, the amounts of fusion proteins or component peptides described herein or the nucleic acid molecules, or the expression vectors that encode them contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of fusion proteins or component peptides described herein or the nucleic acid molecules, or the expression vectors that encode them, which is administered to a patient prior to the administration of the very next dose in the sequence with no intervening doses.

The methods according to this aspect of the disclosure may comprise administering to a patient any number of secondary and/or tertiary doses of fusion proteins or component peptides described herein or the nucleic acid molecules, or the expression vectors that encode them. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

In one embodiment, one or more of the fusion proteins or component peptides described herein or the nucleic acid molecules, or the expression vectors that encode them are administered to a subject as a weight-based dose. A "weight-based dose" (e.g., a dose in mg/kg) is a dose of the protein or peptides that will change depending on the subject's weight.

In another embodiment, one or more of the fusion proteins or component peptides described herein or the nucleic acid molecules, or the expression vectors that encode them, is administered to a subject as a fixed dose. A "fixed dose" (e.g., a dose in mg) means that one dose of the fusion proteins or component peptides described herein or the nucleic acid molecules, or the expression vectors that encode them is used for all subjects regardless of any specific subject-related factors, such as weight. In one particular embodiment, a fixed dose of fusion proteins or component peptides described herein or the nucleic acid molecules, or the expression vectors that encode them is based on a predetermined weight or age.

In general, a suitable dose of the fusion proteins or component peptides described herein or the nucleic acid molecules, or the expression vectors that encode them can be in the range of about 0.001 to about 200.0 milligram per kilogram body weight of the recipient, generally in the range of about 1 to 50 mg per kilogram body weight. For example, the fusion proteins or component peptides described herein or the nucleic acid molecules, or the expression vectors that encode them can be administered at about 0.1 mg/kg, about 0.2 mg/kg, about 0.5 mg/kg, about 1 mg/kg, about 1.5 mg/kg, about 2 mg/kg, about 3 mg/kg, about 5 mg/kg, about 10 mg/kg, about 15 mg/kg, about 20 mg/kg, about 25 mg/kg, about 30 mg/kg, about 40 mg/kg, about 50 mg/kg per single dose. Values and ranges intermediate to the recited values are also intended to be part of this disclosure.

In some embodiments, one or more of the fusion proteins or component peptides described herein or the nucleic acid molecules, or the expression vectors that encode them is administered as a fixed dose of between about 10 mg to about 2500 mg. In some embodiments, the fusion proteins or component peptides described herein or the nucleic acid molecules, or the expression vectors that encode them are administered as a fixed dose of about 10 mg, about 15 mg, about 20 mg, 25 mg, about 30 mg, about 50 mg, about 75 mg, about 100 mg, about 125 mg, about 150 mg, about 175 mg, 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1500 mg, about 2000 mg, or about 2500 mg. Values and ranges intermediate to the recited values are also intended to be part of this disclosure.

Kits

Any of the compositions described herein may be comprised in a kit. In a non-limiting example, the kit comprises one or more of the fusion proteins or component peptides described herein or the nucleic acid molecules, or the expression vectors that encode them.

The kit may further include reagents or instructions for using the fusion proteins or component peptides described herein or the nucleic acid molecules, or the expression vectors that encode them in a subject. It may also include one or more buffers.

The components of the kits may be packaged either in aqueous media or in lyophilized form. The container means of the kits will generally include at least one vial, test tube, flask, bottle, syringe, or other container means, into which a component may be placed, and preferably, suitably aliquoted. Where there is more than one component in the kit (labeling reagent and label may be packaged together), the kit also will generally contain a second, third, or other additional container into which the additional components may be separately placed. The kits may also comprise a second container means for containing a sterile, pharmaceutically acceptable buffer and/or other diluent. However, various combinations of components may be comprised in a vial. The kits of the present disclosure also typically include a means for containing the fusion proteins or component peptides described herein or the nucleic acid molecules, or the expression vectors that encode them, and any other reagent containers in close confinement for commercial sale.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

EXAMPLES

The examples of the present disclosure are offered by way of illustration and explanation, and are not intended to limit the scope of the present disclosure.

Example 1. Heparin Chromatography for Relaxin-2 Fusion Protein Analogs

Introduction

Heparin chromatography is a method commonly employed at early candidate screening to better understand a molecule's propensity to interact with elements of the vasculature when dosed in patients. Heparin and heparin sulfate proteoglycans are negatively charged polysaccharides present in vasculature and in tissues, of which positively charged molecules may bind at physiological pH (i.e., pI>7.4). Here, heparin chromatography was employed to screen for candidates/variants with reduced heparin binding, which is predictive of good PK properties. Materials used for the heparin chromatography are provided in Table 9.

TABLE 9

Materials

| Item | Vendor | Cat No. |
|---|---|---|
| POROS ™ Heparin 2.1 × 30 mm Column | Thermo Fisher | 4333411 |

Methods

Mobile Phase A (Binding): 20 mM Tris pH 7.4 Mobile Phase B (Elution): 20 mM Tris pH 7.4+1M NaCl Injection: 10 μg Detection: 220 nm 1. Equilibrated heparin column using mobile phase A for 10 minutes at 0.5 mL/min prior to analysis.
2. Diluted samples for analysis to 1 mg/mL with 20 mM Tris pH 7.4 to minimize ionic strength.

3. Ran the Heparin Chromatography method on the Agilent HPLC, using gradient shown in Table 10, below:

TABLE 10

| HPLC Gradient | | | |
|---|---|---|---|
| Time (min) | Flow (mL/min) | % A | % B |
| 0 | 0.5 | 100 | 0 |
| 1 | 0.5 | 100 | 0 |
| 6 | 0.5 | 50 | 50 |
| 6.5 | 0.5 | 50 | 50 |
| 7 | 0.5 | 0 | 100 |
| 8 | 0.5 | 0 | 100 |
| 8.5 | 0.5 | 100 | 0 |
| 10 | 0.5 | 100 | 0 |

4. Included a positive control (no Heparin binding, Human IgG pool) and negative control (SE301 or AT1R).
5. Analyzed samples for retention time and reported relative retention time compared to the positive control (i.e., RT sample/RT positive control).
6. Calculated the approximate concentration of NaCl needed to elute using the following calculation:

[NaCl]=(RT sample−1)*100

The results of the calculation are shown in Table 11.

TABLE 11

| Retention Time, Relative Retention Time, and NaCl Concentration for Samples | | | |
|---|---|---|---|
| Sample | RT | RRT | [NaCl] |
| Positive Control | 1.5 | N/A | 50 |
| Negative Control | 3.5 | 2.3 | 250 |
| Sample | 2.0 | 1.3 | 100 |

Results

Table 12 shows the results of the heparin chromatography for a variety of relaxin-2 analog fusion proteins.

TABLE 12

| Heparin Chromatography | | | |
|---|---|---|---|
| | | Heparin Chromatography | |
| Sample | Theoretical pI | RT | ~[NaCl] (mM) at elution |
| IgG | N/A | 2.0 | 20 |
| Prior fusion protein | 8.5 (9.4*) | 4.6 | 278 |
| SEQ ID NO: 53 | 8.2 | 3.9 | 208 |
| SEQ ID NO: 55 | 7.9 | 3.3 | 152 |
| SEQ ID NO: 56 | 7.9 | 3.4 | 163 |
| SEQ ID NO: 58 | 7.6 | 2.7 | 91 |
| SEQ ID NO: 59 | 7.6 | 2.8 | 99 |
| SEQ ID NO: 61 | 7.2 | 2.4 | 62 |
| SEQ ID NO: 62 | 7.2 | 2.5 | 70 |
| SEQ ID NO: 63 | 6.8 | 2.2 | 39 |
| SEQ ID NO: 64 | 6.8 | 2.2 | 43 |
| SEQ ID NO: 191 | 8.4 | 3.6 | 183 |
| SEQ ID NO: 192 | 8.3 | 3.2 | 140 |

*Experimentally determined using imaged capillary isoelectric focusing.

IgG is from Jackson ImmunoResearch (Catalog #009-000-003). The "Prior fusion protein" is a LALA IgG-RelB-Linker-RelA fusion with a theoretical pI of 8.5, but an experimentally determined pI of 9.4. Its linker protein comprises only one acidic amino acid. SEQ ID NOs: 53, 56, 58, 59, and 61-64 have linker proteins comprising at least two acidic amino acids as well as LALA IgG (SEQ TD NO: 50 or 201). The final two fusion proteins have linker proteins comprising only one acidic amino acid and have higher theoretical pI's. As shown in Table 12, above, there is a correlation between lower pI and lower non-specific binding found through heparin chromatography.

Example 2. Low pI Relaxin-2 Fusion Protein Analogs Tend to have Decreased Self Association as Measured by Affinity-Capture Self-Interaction Nanoparticle Spectroscopy (AC-SINS)

Introduction

Understanding a molecule's propensity to self-associate is critical when evaluating biophysical properties of a development candidate. There are numerous ways to evaluate a molecule's propensity to self-associate, concentrating the molecule to high concentrations and evaluating by SEC (% Monomer) or measuring changes in turbidity (OD 340 nm), using DLS to calculate the second virial coefficient ($B_{22}$) or self-interaction coefficient ($k_d$), or using AC-SINS ($\Delta\lambda_{max}$). All three of these methods provide useful information but use different amounts of material to perform the evaluation. AC-SINS has emerged as a high throughput method for evaluating self-association using minimal material but still giving locally high concentrations by using affinity capture on gold nanoparticles. In short, gold nanoparticles are pre-coated with anti-human antibodies (Fc, Fab and H+L), which when incubated with target antibodies in dilute solutions, capture and concentrate in solution the antibody of interest. When the immobilized molecules of interest interact, the inter-particle distances decrease between gold nanoparticles, leading to increased plasmon wavelengths (i.e., red shift) that can be quantified using UV-VIS spectroscopy. Materials used for the spectroscopy are provided in Table 13.

TABLE 13

| Materials | | |
|---|---|---|
| Item | Vendor | Cat No. |
| 1M sodium acetate pH 4.3 | Molecular Dimensions | MD2-019-PH |
| 1× DPBS | Gibco | 14190-136 |
| Panitumumab (Low Assoc Ctrl) | MyBioSource | MBS156169 |
| Ipilimumab (Med Assoc Ctrl) | MyBioSource | MBS156153 |
| Ganitumab (High Assoc Ctrl) | MyBioSource | MBS156142 |
| 20 nm gold nanoparticles | Ted Pella | 15705 |
| PEG methyl ether thiol (2 kDa) | Sigma | 729140 |
| Goat anti-Human IgG, Fcγ | Jackson ImmunoResearch | 109-005-098 |
| Goat non-specific mAb | Jackson ImmunoResearch | 005-000-003 |
| Zeba Desalting Columns 40K 5 mL | Thermo Fisher | 87770 |
| Zeba Desalting Columns 40K 2 mL | Thermo Fisher | 87768 |
| Zeba Desalting Columns 40K 0.5 mL | Thermo Fisher | 87766 |
| Costar 384-well Polystyrene plates | Fisher Scientific | 12-565-506 |
| 96-well Polypropylene plates | Grenier Bio-One | 652230P |

Methods

Preparing Buffer Solutions

To prepare 20 mM sodium acetate pH 4.3, 2 mL 1M sodium acetate pH 4.3 stock was diluted to 100 mL with MilliQ water. pH was measured 4.3±0.1 and the solution was sterile filtered. The solution remained stable at room temperature for 1 month.

To 1 g PEG methyl ether thiol, was added 10 mL MilliQ water. This was vortexed briefly to suspend solids, making a 50 mM solution. To prepare a 10 μM solution for final dilution, the dilution scheme below was followed:

a. Dilute 50 mM stock to 1 mM (20 μL 50 mM stock+980 μL MilliQ water)
b. Dilute 1 mM step to 100 μM (10 μL 1 mM stock+90 μL MilliQ water)
c. Dilute 100 μM step to 10 μM (100 μL 100 μM stock+900 μL MilliQ water)
d. Volumes can be scaled according to number of samples to assay
e. Remaining 50 mM stock should be aliquoted and kept at −20° C. until needed Preparing Gold NanoParticle Solution Goat anti-human Fc IgG antibody (capture) and goat IgG antibody (non-capture) were buffer exchanged into 20 mM sodium acetate, pH 4.3. After buffer exchange, concentrations were normalized to 0.4 mg/mL for both antibodies.

A 4:1 volume ratio mixture of capture (anti-Fc):non-capture (Goat IgG) solution was prepared for 80% capture capacity coating solution to be used to incubate gold nanoparticles (AuNPs).

A 9:1 volume ratio of AuNPs:coating solution was made. The solution was incubated at room temperature, overnight in the dark.

After incubation, thiolated PEG was added to 0.1 μM final concentration from the diluted M stock to block empty sites on the AuNPs (i.e., 5 mL solution of AuNPs, add 50 μL 10 μM stock) and incubated at RT for one hour in the dark.

Preparing AuNP Solution 2 mL of coated AuNP solution was centrifuged at 20,000×g for 15 minutes to sediment the AuNPs and 1800 μL supernatant was carefully removed using a 1 mL pipette. The pelleted AuNPs were gently resuspended using a 200 μL pipette to generate a 10× concentrated stock of coated AuNPs.

Preparing Target Antibody Solution (Either Method Follows this)

For each sample analyzed, 10 μL of AuNP concentrate was incubated with 100 μL antibody test solution (normalize to 0.05 mg/mL) at room temperature in the dark for 2 hours in a 96-well polypropylene plate. Two blank solutions were prepared with 10 μL 10× AuNP concentrated to 100 μL PBS for purposes of blanking the assay and determining wavelength shift upon addition of test antibody. Ganitumab was included as a positive control (high association, red shift) and Panitumumab as a negative control (no association, no UV shift). Each sample was prepared in duplicate for analysis.

After the 2-hour incubation, 100 μL of resulting solution was transferred to a UV transparent polystyrene plate (384-well format). Two blank solutions were transferred to properly assess wavelength shift, then add duplicate standards and samples for analysis. The plate was then centrifuged for 1 minute at 1000×g to level the solutions in the wells.

Absorbance data are collected from 510 to 570 nm in 2 nm steps to determine wavelength shifts for each sample relative to AuNPs alone.

Results

The results from ASCINS are shown below in Table 14.

TABLE 14 pI Variants Have Decreased Self-Association Propensity

| Sample | Isoelectric Point (Calculated) | $\Delta\lambda_{max}$ |
|---|---|---|
| Prior fusion protein (Control) | 8.5 | 15.2 |
| Prior fusion protein (LALA) | 8.5 | 15.9 |
| SEQ ID NO: 53 | 8.2 | 7.5 |
| SEQ ID NO: 54 | 7.9 | 1.2 |
| SEQ ID NO: 55 | 7.9 | 7.0 |
| SEQ ID NO: 56 | 7.9 | 6.7 |
| SEQ ID NO: 58 | 7.6 | 1.8 |
| SEQ ID NO: 59 | 7.6 | 1.9 |
| SEQ ID NO: 61 | 7.2 | −0.6 |
| SEQ ID NO: 62 | 7.2 | −0.4 |
| SEQ ID NO: 63 | 6.8 | 0.4 |
| Prior fusion protein (Control) | 8.5 | 15.2 |
| SEQ ID NO: 64 | 6.8 | 0.4 |
| SEQ ID NO: 191 | 8.4 | 10.1 |
| SEQ ID NO: 192 | 8.3 | 6.1 |

As shown in Table 14, above, fusion proteins with low pI also have a tendency to show low self-aggregation.

Example 3. Relaxin-2 Fusion Protein Analogs Induce cAMP Response in RXFP1 Transfected Cells Methods HEK293 cells were seeded into a 96-well tissue culture plate followed by transient co-transfection with a human RXFP1 and a pGloSensor-22F plasmid. Transfected cells were stimulated by relaxin-2 or fusion protein analogs thereof, inducing Gs-mediated cAMP signaling. cAMP is assayed using the activity of the GloSensor biosensor, which is a mutant luciferase fused to a cAMP binding domain, leading to a production of light in the presence of its substrate luciferin. This readout of relative luminescent units (RLU) is used a proxy for cAMP response.

Reagents 96-well tissue-culture treated plates. White with clear bottom. (Corning #3610)

HEK293 cells (ATCC CRL-1573)

Poly-D-lysine (Gibco A3890401)

DPBS (No calcium, no magnesium; Gibco 14190250)

DMEM (High glucose with L-glutamine and Sodium Pyruvate; Gibco 11995065)

TrypLE Express (Gibco 12605010)

FBS (HyClone™, Australian origin; Cytiva SH30084)

Penicillin-Streptomycin (Gibco 15140122)

$CO_2$-independent media (Gibco 18045088)

Opti-MEM™ I Reduced Serum media (Gibco 31985062)

pGloSensor™-22F cAMP plasmid (Promega Cat. #E2301)

D-luciferin, Potassium Salt (GoldBio LUCK-1G)

FuGENE HD transfection reagent (Promega #E2311)

Reservoirs (Corning/Axygen RES-V-25-SI)

Relaxin-2 (R&D Biosystems 6586-RN-025)

RXFP1-containing plasmid (pcDNA5/FRT/TO-human RXFP1, full-length)

Forskolin (Sigma F6886)

Plate reader capable of reading luminescence (CLARIOstar Plus)

Reagent Preparation

D-Luciferin, Potassium Salt:

D-luciferin was reconstituted in 10 mM HEPES, pH 7.5 at 25 mg/mL (78.5 mM; MW=318.4). This was aliquoted into single-use aliquots of ~200-500 μL in sterile microfuge tubes and stored at −80° C.

Relaxin-2 Peptide:

Relaxin-2 peptides or relaxin-2 fusion protein analogs were reconstituted at 0.1 mg/mL in sterile DPBS (MW=5, 986 Da, ε=12,865 $M^{-1}$ $cm^{-1}$) and measured at $A_{280}$ to determine final concentration. Aliquots were stored at −20° C.

Forskolin:

Forskolin was reconstituted in 100% DMSO at 5 mM (2.05 mg/mL, MW=410.5). Aliquots were stored at −20° C.

cAMP Assay Media:

$CO_2$-independent media was pre-warmed to 37° C. using the bead bath. A single aliquot of D-luciferin was thawed and added at 5% final concentration (e.g., 4.75 mL cAMP assay media+250 μL of D-luciferin stock; gives 1.25 mg/mL or 3.93 mM final D-luciferin). This was used within the same day or discarded.

Cell Culture and Maintenance

HEK293 cells (ATCC CRL-1573) were cultured in DMEM+100 FBS, (1× or 10 U/mL) Pen-Strep in a humidified $CO_2$ incubator at 37 C, 500 $CO_2$ until 80-100%0 confluency. Cells were typically split 1:6 for 3 days and maintained in a sterile T-75 tissue culture flask.

cAMVP Signaling Assay Protocol

This protocol is adapted from the GloSensor cAMVP assay by Promega.

Raw data was exported to Excel using the MARS data analysis software that is opened following a run on the CLARIOstar plate reader. These values are measured in RLU, or relative luminescence units.

As shown in Table 15, all of the low pI relaxin-2 fusion protein analogs were able to induce a cAMP response in RXFP1 transfected cells.

TABLE 15 cAMP Response in RXFP1 Transfected HEK293 Cells

| Agonist | $PEC_{50}$ | $EC_{50}$ in nM |
|---|---|---|
| Relaxin | 10.38 | 0.042 |
| Prior fusion protein (Control) | 9.51 | 0.31 |
| Prior fusion protein (LALA) | 9.49 | 0.33 |
| SEQ ID NO: 53 | 8.66 | 2.17 |
| SEQ ID NO: 54 | 8.10 | 7.87 |
| SEQ ID NO: 55 | 8.62 | 2.41 |
| SEQ ID NO: 56 | 8.72 | 1.90 |
| SEQ ID NO: 58 | 7.83 | 14.7 |
| SEQ ID NO: 59 | 7.75 | 17.7 |
| SEQ ID NO: 61 | 7.25 | 56.7 |
| SEQ ID NO: 62 | 7.18 | 65.8 |
| SEQ ID NO: 63 | 6.76 | 173.3 |
| SEQ ID NO: 64 | 7.02 | 96.2 |
| SEQ ID NO: 191 | 9.37 | 0.42 |
| SEQ ID NO: 192 | 8.84 | 1.46 |

Example 4. In Vitro Characteristics of Relaxin-2 Fusion Protein Analogs

Methods

Heparin Chromatography:

Heparin chromatography was performed to understand the propensity of a relaxin-2 fusion protein analog to interact with elements of the vasculature and/or rapidly distribute into tissues when dosed in patients. Analogs that were found to bind heparin weakly may be predictive of good pharmacokinetic properties. Briefly, a heparin column was equilibrated using mobile phase A (20 mM Tris pH 7.4) for 10 minutes at 0.5 mL/min prior to analysis. 10 g per sample was run using the Heparin Chromatography method on an Agilent HPLC using 280 nm detection, using gradient shown in Table 16, below (mobile phase B: 20 mM Tris pH 7.4, 1 M NaCl):

TABLE 16

HPLC Gradient

| Time (min) | Flow (mL/min) | % A | % B |
|---|---|---|---|
| 0 | 0.5 | 100 | 0 |
| 6 | 0.5 | 50 | 50 |
| 7 | 0.5 | 0 | 100 |
| 8 | 0.5 | 0 | 100 |
| 8.5 | 0.5 | 100 | 0 |
| 10 | 0.5 | 100 | 0 |

A positive control (no Heparin binding, pembrolizumab) and negative control (mild Heparin binding, adalimumab) was included, and samples were analyzed for retention time and relative retention time compared to the positive control (i.e., RT sample/RT positive control). The approximate concentration of NaCl needed to elute was calculated using the following calculation:

$$[NaCl]=(RT\ sample)*100$$

The results of the calculation are shown in Table 17:

TABLE 17

Retention Time and NaCl Concentration for Samples

| Sample | RT | [NaCl] |
|---|---|---|
| Positive Control | 1.5 | 150 |
| Negative Control | 3.5 | 350 |
| Sample | 2.0 | 200 |

Capillary Isoelectric Focusing (cIEF)

Imaged capillary isoelectric focusing (cIEF) was used to separate differentially charged molecules (i.e., relaxin-2 fusion protein analogs) using electrophoretic mobility in an ampholyte solution to determine their isoelectric points (pI). Molecules were loaded to a capillary and separated based on their pI by allowing molecules to migrate along an electrical field until the molecules reached the pH corresponding to their pI. UV absorption of the whole capillary was measured throughout the separation, which allowed for real-time observation as well as final quantification.

Baculovirus Particle (BVP) ELISA

BVP ELISA was employed to understand the propensity of a relaxin-2 fusion protein analog for non-specific or non-target interactions. BVPs are empty viral capsids with no viral genome, but in the process of production, budding off from the cell membrane allows them to take components of the cell membrane along with them. Thus, the BVPs possess a highly diverse cell surface with many moieties present, which mimic what the molecule of interest (i.e., relaxin-2 fusion protein analog) may encounter in vivo. Briefly, BVPs are coated on a plate by adding 25 L of BVP solution to each well. BVP solution was made by diluting BVP stock (Medna Scientific; Cat. No. E3001) to $1\times10^6$ PFU/mL with 0.1 M carbonate buffer, pH 9.6. Following overnight incubation at 5° C., BVP solution was blotted from wells and wells were washed three times with PBST. Plates were blocked with 100 L/well of 1×BSA in PBS blocking buffer (Cepham Life Sciences; Cat. No. 10615). Plates were incubated at 25° C. on a plate shaker for 1 hour. Blocking solution was blotted from wells and wells were washed three times with PBST. Samples (i.e., relaxin-2 fusion protein analogs) were prepared in duplicate to cover dilution range from 3 µM to 0.1 nM and added to plates. Plates were incubated at 25° C. for 1 hour, after which the wells were blotted and washed three times with PBST. 25 µL/well of 1:10,000 diluted detection monoclonal antibody (Peroxidase AffiniPure Goat Anti-Human IgG, Fcγ fragment specific; Jackson ImmunoResearch; Cat. No. 50-194-1564) was added, and plates were incubated at 25° C. for 1 hour, after which the wells were blotted and washed three times with PBST. 1-Step™ Ultra TMB-ELISA Substrate Solution (Life Technologies; Cat. No. 34029) was then added. After about 2 minutes, 25 L 2N HCl was added to quench the reaction, and a plate reader was used to analyze the plate at 450 nm with correction at 570 nm.

Potency Assay

A transient hRXFP1 assay was performed substantially as described in Example 3.

Affinity-Capture Self-Interaction Nanoparticle Spectroscopy (AC-SINS)

AC-SINS was performed to understand the propensity of a molecule (i.e., relaxin-2 fusion protein analog) to self-associate. The methodology performed was similar to the method described in Example 2. AuNP solution was prepared as follows: 1.5 mL of coated AuNP solution was centrifuged at 20,000×g for 5 minutes to sediment the AuNPs and 1,350 µL was carefully removed using a 1 mL pipette. The pelleted AuNPs were gently resuspended using a 200 µL pipette to generate a 10× concentrated stock of coated AuNPs. For each sample analyzed, 5 µL of AuNP concentrate was incubated with 45 µL antibody test solution (normalized to 0.05 mg/mL) at room temperature in the dark for 2 hours in a 384-well polypropylene plate. After the 2-hour incubation, absorbance data was collected from 450 nm to 650 nm in 1 nm steps to determine wavelength shifts for each sample relative to AuNPs alone.

Nanoscale Differential Scanning Fluorimetry (NanoDSF)

NanoDSF was performed using the NanoTemper Prometheus Panta to investigate the conformational stability of a relaxin-2 protein fusion analog. Conformational stability was measured by applying a thermal ramp to a solution containing the molecule of interest, measuring the intrinsic fluorescence, backscattering, and using dynamic light scattering (DLS) to provide various thermal stability parameters.

Results

The results are shown below in Table 18:

TABLE 18

In vitro Characteristics of Relaxin-2 Fusion Protein Analogs

| | Heparin Binding | | cIEF | BVP ELISA | Potency Assay | AC- | NanoDSF | |
|---|---|---|---|---|---|---|---|---|
| Sample | RT | [NaCl] (mM) | Isoelectric point (pI) | Normalized Score | EC50 (nM) | SINS Δλmax | $T_{onset}$ (° C.) | $T_m1$ (° C.) |
| Relaxin-2 | ND | ND | 9.4 | N/A | 0.1 | N/A | N/A | N/A |
| Prior fusion (SEQ ID NO: 224) | ND | ND | 9.0 | 28 | 0.3 | 7 | 61.4 | 68.9 |
| SEQ ID NO: 204 | 3.88 | 330 | 8.9 | 2 | 2.5 | 8 | 60.5 | 70.4 |
| SEQ ID NO: 205 | NT | NT | ND | ND | 12.3 | 1 | 63.3 | 70.7 |
| SEQ ID NO: 206 | 3.32 | 280 | 8.5 | 1 | 2.9 | 7 | 62.8 | 70.6 |
| SEQ ID NO: 57 | 3.43 | 290 | 8.5 | 1 | 2.5 | 7 | 61.6 | 70.6 |
| SEQ ID NO: 207 | 2.71 | 230 | 7.9 | 1 | 16.0 | 2 | 62.9 | 70.9 |
| SEQ ID NO: 60 | 2.79 | 240 | 7.9 | 1 | 15.8 | 2 | 63.0 | 71.0 |
| SEQ ID NO: 208 | 2.42 | 210 | 7.5 | 1 | 60.3 | 0 | 63.9 | 71.1 |
| SEQ ID NO: 209 | 2.5 | 210 | 7.1 | 1 | 62.8 | 0 | 63.6 | 71.2 |
| SEQ ID NO: 210 | 2.19 | 190 | 7.1 | 1 | 140.0 | 0 | 62.4 | 71.0 |
| SEQ ID NO: 211 | 2.23 | 190 | ND | 1 | 101.2 | 0 | 62.8 | 70.8 |
| SEQ ID NO: 212 | 3.63 | 310 | ND | 1 | 0.5 | 10 | 62.9 | 70.8 |
| SEQ ID NO: 213 | 3.2 | 270 | ND | 1 | 1.8 | 6 | 63.0 | 71.2 |
| SEQ ID NO: 66 | 2.7 | 230 | 8.0 | 1 | 4.2 | 5 | 63.0 | 69.9 |
| SEQ ID NO: 68 | 3 | 250 | 8.0 | 1 | 3.3 | 11 | 61.9 | 69.3 |
| SEQ ID NO: 70 | 2.5 | 210 | 7.5 | 1 | 8.0 | 7 | 61.9 | 69.7 |

TABLE 18-continued

In vitro Characteristics of Relaxin-2 Fusion Protein Analogs

| | Heparin Binding | | cIEF | BVP ELISA | Potency Assay | AC- | NanoDSF | |
|---|---|---|---|---|---|---|---|---|
| Sample | RT | [NaCl] (mM) | Isoelectric point (pI) | Normalized Score | EC50 (nM) | SINS Δλmax | $T_{onset}$ (° C.) | $T_m1$ (° C.) |
| SEQ ID NO: 72 | 3.1 | 260 | 8.0 | 1 | 5.8 | 4 | 62.6 | 69.6 |
| SEQ ID NO: 74 | 2.6 | 220 | 7.4 | 1 | 10.2 | 3 | 62.3 | 69.9 |
| SEQ ID NO: 76 | 3 | 250 | 7.4 | ND | ND | ND | ND | ND |
| SEQ ID NO: 78 | 2.3 | 200 | 7.1 | 1 | 23.4 | 4 | 60.9 | 69.9 |
| SEQ ID NO: 79 | 2.3 | 200 | 7.5 | 1 | 117.0 | 0 | 61.9 | 70.0 |
| SEQ ID NO: 80 | 2.6 | 220 | 7.4 | 1 | 162.0 | 0 | 62.6 | 69.8 |
| SEQ ID NO: 81 | 2 | 170 | 7.1 | 1 | 426.0 | 0 | 62.8 | 70.2 |
| SEQ ID NO: 82 | 2.6 | 220 | 7.5 | 1 | 18.9 | 4 | 62.3 | 70.1 |
| SEQ ID NO: 83 | 2.8 | 240 | 7.5 | ND | 9.3 | 7 | 60.9 | 69.2 |
| SEQ ID NO: 84 | 2.3 | 200 | 7.1 | 1 | 41.9 | 5 | 61.4 | 69.9 |
| SEQ ID NO: 85 | 2.1 | 180 | 7.2 | 1 | 54.4 | 0 | 62.8 | 70.2 |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

The invention claimed is:

1. A fusion protein comprising, from N-terminus to C-terminus, a first peptide;

a linker peptide; and a second peptide, wherein:

(a) the first peptide comprises an amino acid sequence that differs at 0, 1, 2, 3, 4, or 5 amino acids when compared to the amino acid sequence of SEQ ID NO: 7, and the second peptide comprises an amino acid sequence that differs at 0, 1, 2, 3, 4, or 5 amino acids when compared to the amino acid sequence of SEQ ID NO: 9; or the first peptide comprises an amino acid sequence that differs at 0, 1, 2, 3, 4, or 5 amino acids when compared to the amino acid sequence of SEQ ID NO: 9; and the second peptide comprises an amino acid sequence that differs at 0, 1, 2, 3, 4, or 5 amino acids when compared to the amino acid sequence of SEQ ID NO: 7; and (b) the linker peptide comprises an amino acid sequence with 12-15 amino acids, comprising 2-5 acidic amino acids and 10-13 non-acidic amino acids, wherein:

(i) the linker peptide comprises an amino acid sequence selected from the group consisting of:

$R_1R_1R_1R_2R_1R_1R_1R_2R_1R_1R_1R_2R_1$;

$R_1R_1R_1R_2R_1R_1R_1R_2R_1R_1R_1R_2R_1R_1R_1$;

$R_1R_1R_2R_1R_1R_1R_2R_2R_1R_1R_1R_2R_1R_1$;

$R_1R_1R_1R_2R_2R_1R_1R_1R_2R_2R_1R_1R_1$; and $R_1R_1R_2R_1R_2R_1R_1R_2R_1R_2R_1R_1R_1$, wherein $R_1$ is a non-acidic amino acid and $R_2$ is an acidic amino acid;

(ii) each of the acidic amino acids in the linker peptide is aspartate; or (iii) each of the acidic amino acids in the linker peptide is glutamate.

2. The fusion protein of claim 1, wherein the linker peptide comprises an amino acid sequence selected from the group consisting of SEQ ID NOs: 14-23.

3. The fusion protein of claim 1, wherein one or more of the non-acidic amino acid(s) are glycine, proline, or serine.

4. The fusion protein of claim 1, wherein:

the first peptide comprises the amino acid sequence of $DSWX_3EEVIKLCGRELVRAQIAICGX_4ST$ (SEQ ID NO: 3), wherein $X_3$ is methionine, lysine, or glutamine, and wherein $X_4$ is methionine or lysine;

the first peptide comprises the amino acid sequence of $X_5QX_6YSALANKCCHVGCTKRSLAX_7FC$ (SEQ ID NO: 4), wherein $X_5$ is arginine or absent, wherein $X_6$ is leucine or aspartate, and wherein $X_7$ is arginine, glutamine, or glutamate;

the first peptide comprises an amino acid sequence selected from the group consisting of SEQ ID NOs: 5-7;

the first peptide comprises an amino acid sequence selected from the group consisting of SEQ ID NOs: 8-13;

the second peptide comprises the amino acid sequence of $DSWX_3EEVIKLCGRELVRAQIAICGX_4ST$ (SEQ ID NO: 3), wherein $X_3$ is methionine, lysine, or glutamine, and wherein $X_4$ is methionine or lysine;

the second peptide comprises the amino acid sequence of $X_5QX_6YSALANKCCHVGCTKRSLAX_7FC$ (SEQ ID NO: 4), wherein $X_5$ is arginine or absent, wherein $X_6$ is leucine or aspartate, and wherein $X_7$ is arginine, glutamine, or glutamate;

the second peptide comprises an amino acid sequence selected from the group consisting of SEQ ID NOs: 5-7; and/or the second peptide comprises an amino acid sequence selected from the group consisting of SEQ ID NOs: 8-13.

5. The fusion protein of claim 1, wherein:

the first peptide comprises the amino acid sequence of SEQ ID NO: 5 and the second peptide comprises the amino acid sequence of SEQ ID NO: 8;

the first peptide comprises the amino acid sequence of SEQ ID NO: 5 and the second peptide comprises the amino acid sequence of SEQ ID NO: 9;

the first peptide comprises the amino acid sequence of SEQ ID NO: 5 and the second peptide comprises the amino acid sequence of SEQ ID NO: 10;

the first peptide comprises the amino acid sequence of SEQ ID NO: 5 and the second peptide comprises the amino acid sequence of SEQ ID NO: 11;

the first peptide comprises the amino acid sequence of SEQ ID NO: 5 and the second peptide comprises the amino acid sequence of SEQ ID NO: 12;

the first peptide comprises the amino acid sequence of SEQ ID NO: 5 and the second peptide comprises the amino acid sequence of SEQ ID NO: 13;

the first peptide comprises the amino acid sequence of SEQ ID NO: 6 and the second peptide comprises the amino acid sequence of SEQ ID NO: 8;

the first peptide comprises the amino acid sequence of SEQ ID NO: 6 and the second peptide comprises the amino acid sequence of SEQ ID NO: 9;

the first peptide comprises the amino acid sequence of SEQ ID NO: 6 and the second peptide comprises the amino acid sequence of SEQ ID NO: 10;

the first peptide comprises the amino acid sequence of SEQ ID NO: 6 and the second peptide comprises the amino acid sequence of SEQ ID NO: 11;

the first peptide comprises the amino acid sequence of SEQ ID NO: 6 and the second peptide comprises the amino acid sequence of SEQ ID NO: 12;

the first peptide comprises the amino acid sequence of SEQ ID NO: 6 and the second peptide comprises the amino acid sequence of SEQ ID NO: 13;

the first peptide comprises the amino acid sequence of SEQ ID NO: 7 and the second peptide comprises the amino acid sequence of SEQ ID NO: 8;

the first peptide comprises the amino acid sequence of SEQ ID NO: 7 and the second peptide comprises the amino acid sequence of SEQ ID NO: 9;

the first peptide comprises the amino acid sequence of SEQ ID NO: 7 and the second peptide comprises the amino acid sequence of SEQ ID NO: 10;

the first peptide comprises the amino acid sequence of SEQ ID NO: 7 and the second peptide comprises the amino acid sequence of SEQ ID NO: 11;

the first peptide comprises the amino acid sequence of SEQ ID NO: 7 and the second peptide comprises the amino acid sequence of SEQ ID NO: 12;

the first peptide comprises the amino acid sequence of SEQ ID NO: 7 and the second peptide comprises the amino acid sequence of SEQ ID NO: 13;

the second peptide comprises the amino acid sequence of SEQ ID NO: 5 and the first peptide comprises the amino acid sequence of SEQ ID NO: 8;

the second peptide comprises the amino acid sequence of SEQ ID NO: 5 and the first peptide comprises the amino acid sequence of SEQ ID NO: 9;

the second peptide comprises the amino acid sequence of SEQ ID NO: 5 and the first peptide comprises the amino acid sequence of SEQ ID NO: 10;

the second peptide comprises the amino acid sequence of SEQ ID NO: 5 and the first peptide comprises the amino acid sequence of SEQ ID NO: 11;

the second peptide comprises the amino acid sequence of SEQ ID NO: 5 and the first peptide comprises the amino acid sequence of SEQ ID NO: 12;

the second peptide comprises the amino acid sequence of SEQ ID NO: 5 and the first peptide comprises the amino acid sequence of SEQ ID NO: 13;

the second peptide comprises the amino acid sequence of SEQ ID NO: 6 and the first peptide comprises the amino acid sequence of SEQ ID NO: 8;

the second peptide comprises the amino acid sequence of SEQ ID NO: 6 and the first peptide comprises the amino acid sequence of SEQ ID NO: 9;

the second peptide comprises the amino acid sequence of SEQ ID NO: 6 and the first peptide comprises the amino acid sequence of SEQ ID NO: 10;

the second peptide comprises the amino acid sequence of SEQ ID NO: 6 and the first peptide comprises the amino acid sequence of SEQ ID NO: 11;

the second peptide comprises the amino acid sequence of SEQ ID NO: 6 and the first peptide comprises the amino acid sequence of SEQ ID NO: 12;

the second peptide comprises the amino acid sequence of SEQ ID NO: 6 and the first peptide comprises the amino acid sequence of SEQ ID NO: 13;

the second peptide comprises the amino acid sequence of SEQ ID NO: 7 and the first peptide comprises the amino acid sequence of SEQ ID NO: 8;

the second peptide comprises the amino acid sequence of SEQ ID NO: 7 and the first peptide comprises the amino acid sequence of SEQ ID NO: 9;

the second peptide comprises the amino acid sequence of SEQ ID NO: 7 and the first peptide comprises the amino acid sequence of SEQ ID NO: 10;

the second peptide comprises the amino acid sequence of SEQ ID NO: 7 and the first peptide comprises the amino acid sequence of SEQ ID NO: 11;

the second peptide comprises the amino acid sequence of SEQ ID NO: 7 and the first peptide comprises the amino acid sequence of SEQ ID NO: 12; or the second peptide comprises the amino acid sequence of SEQ ID NO: 7 and the first peptide comprises the amino acid sequence of SEQ ID NO: 13.

6. The fusion protein of claim 1, wherein the fusion protein comprises an amino acid sequence selected from the group consisting of SEQ ID NOs: 25-48, optionally wherein the fusion protein further comprises an IgG Fc, optionally wherein:

the IgG Fc comprises the amino acid alanine at EU positions 234 and 235;

the IgG Fc comprises the amino acid alanine at EU position 329;

the IgG Fc comprises the amino acid alanine at EU positions 234, 235, and 329;

the IgG Fc comprises the amino acids alanine, alanine, alanine, leucine, and serine at EU positions 234, 235, 329, 428, and 434, respectively;

the IgG Fc comprises the amino acids lysine, phenylalanine, and tyrosine at EU positions 433, 434, and 436, respectively;

the IgG Fc comprises the amino acids tyrosine, threonine, and glutamate at EU positions 252, 254, and 256, respectively;

the IgG Fc comprises the amino acids leucine and serine at EU positions 428 and 434, respectively;

the IgG Fc comprises an amino acid sequence at least 85% identical to the amino acid sequence of the human IgG1 Fc set forth in SEQ ID NO: 49;

the IgG Fc comprises the amino acid sequence of the human IgG1 Fc set forth in SEQ ID NO: 49;

the IgG Fc comprises an amino acid sequence at least 95% identical to an amino acid sequence selected from the group consisting of SEQ ID NOs: 50-52 and 201-203; and/or the IgG Fc comprises an amino acid sequence selected from the group consisting of SEQ ID NOs: 50-52 and 201-203.

7. The fusion protein of claim 6, wherein the IgG Fc is linked to the N-terminus of the first peptide or to the C-terminus of the second peptide.

8. The fusion protein of claim 1, wherein the first and second peptides do not comprise the amino acid sequence of a peptide selected from the group consisting of SEQ ID NOs:187-190.

9. A fusion protein comprising an amino acid sequence selected from the group consisting of SEQ ID NOs: 53-118, 204-211, and 214-221.

10. A pharmaceutical composition comprising an effective amount of the fusion protein of claim 1.

11. A kit comprising an effective amount of the fusion protein of claim 1, and an instruction of use.

12. The fusion protein of claim 1, wherein the fusion protein has a pI from 6.0 to 8.2.

* * * * *